(12) United States Patent
Clennan et al.

(10) Patent No.: US 11,319,266 B2
(45) Date of Patent: May 3, 2022

(54) SYNTHESES, CHARACTERIZATIONS, AND APPLICATIONS OF HELI-ACENES

(71) Applicant: University of Wyoming, Laramie, WY (US)

(72) Inventors: Edward L. Clennan, Laramie, WY (US); Jacob Weber, Laramie, WY (US)

(73) Assignee: University of Wyoming-Office of Research & Economic Development, Laramie, WY (US)

( * ) Notice: Subject to any disclaimer, the term of this patent is extended or adjusted under 35 U.S.C. 154(b) by 0 days.

(21) Appl. No.: 16/867,931

(22) Filed: May 6, 2020

(65) Prior Publication Data

US 2020/0354294 A1  Nov. 12, 2020

Related U.S. Application Data

(60) Provisional application No. 62/843,829, filed on May 6, 2019.

(51) Int. Cl.

| | | |
|---|---|---|
| C07C 15/20 | (2006.01) | |
| C07C 15/28 | (2006.01) | |
| C07C 15/30 | (2006.01) | |
| C07C 15/56 | (2006.01) | |
| C07C 45/00 | (2006.01) | |
| C07C 49/665 | (2006.01) | |
| C07C 253/30 | (2006.01) | |
| C07C 255/52 | (2006.01) | |
| C09K 11/06 | (2006.01) | |
| H01L 51/00 | (2006.01) | |
| H01L 51/50 | (2006.01) | |
| H01L 51/52 | (2006.01) | |
| C07C 5/31 | (2006.01) | |
| C07C 45/51 | (2006.01) | |

(52) U.S. Cl.
CPC ............... *C07C 15/20* (2013.01); *C07C 5/31* (2013.01); *C07C 45/513* (2013.01); *C07C 49/665* (2013.01); *C07C 253/30* (2013.01); *C07C 255/52* (2013.01); *C09K 11/06* (2013.01); *H01L 51/0056* (2013.01); *C07B 2200/09* (2013.01); *C07C 2603/54* (2017.05); *C09K 2211/1011* (2013.01); *H01L 51/5028* (2013.01); *H01L 51/5056* (2013.01); *H01L 51/5293* (2013.01)

(58) Field of Classification Search
CPC ..... C07C 15/20; C07C 255/52; C07C 253/30; C07C 49/665; C07C 5/31; C07C 45/513; C07C 2603/54; C09K 11/06; C09K 2211/1011; C07B 2200/09
See application file for complete search history.

(56) References Cited

PUBLICATIONS

Weber et al. J. Org. Chem. 2019, 84, 817-830 (pub. Dec. 12, 2018). (Year: 2018).*
Chemical Abstract Service STNext Database, Registry No. 191-69-5 [Entered STN: Nov. 16, 1984], (Year: 1984).*

* cited by examiner

*Primary Examiner* — Amanda L. Aguirre
(74) *Attorney, Agent, or Firm* — Blue Filament Law PLLC

(57) ABSTRACT

A method is provided for using twisted acenes, and more particularly to configurationally stable twisted acenes that are imbedded into the structure of [7]helicene at the fulcrum ring to form useable material structures. The helicene propagates its chiral nature into the acene, while acting as a locking mechanism to thermal racemization. These doubly-helical compounds are part of a new homologous series of polycyclic aromatic hydrocarbons, namely the [7]helitwistacenes. Such [7]helitwistacenes have utility as materials suitable for forming a circularly polarized organic light emitting diode (CP-OLED) for direct emission of circularly polarized (CP) light for the fabrication of high efficiency electronic displays.

13 Claims, 51 Drawing Sheets

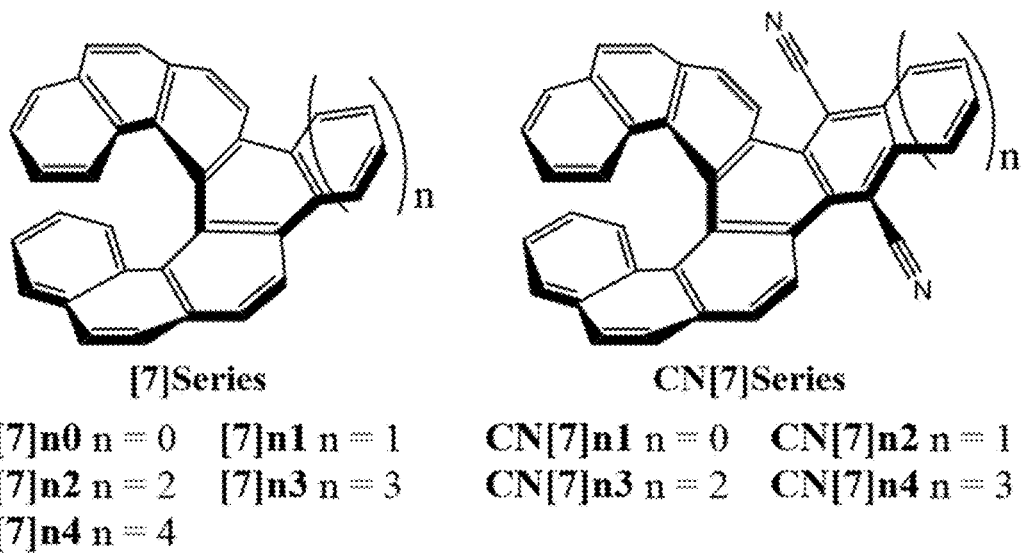
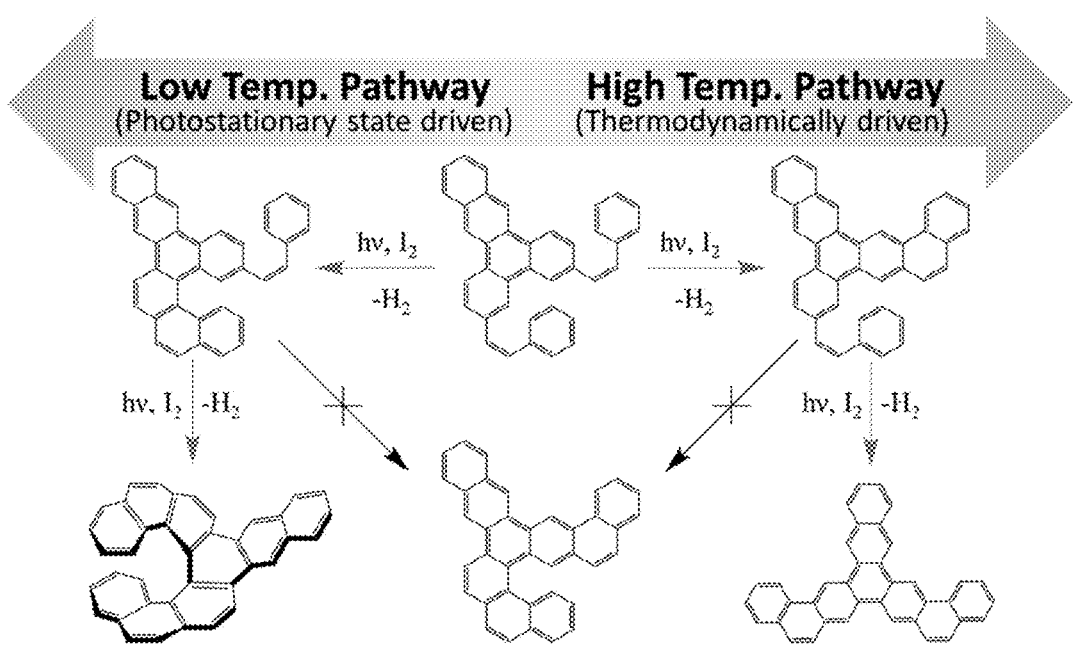
FIG. 4

CN[7]n4, X = CN; Me[7]n4, X = Me; Ph[7]n4, X= Ph tetraCN[7]n4, X = CN; tetraMe[7]n4, X = Me; tetraPh[7]n4, X= Ph hexaCN[7]n4, X = CN; octaMe[7]n4, X = Me; octaPh[7]n4, X= Ph octaCN[7]n4, X = CN; octaMe[7]n4, X = Me; octaPh[7]n4, X= Ph

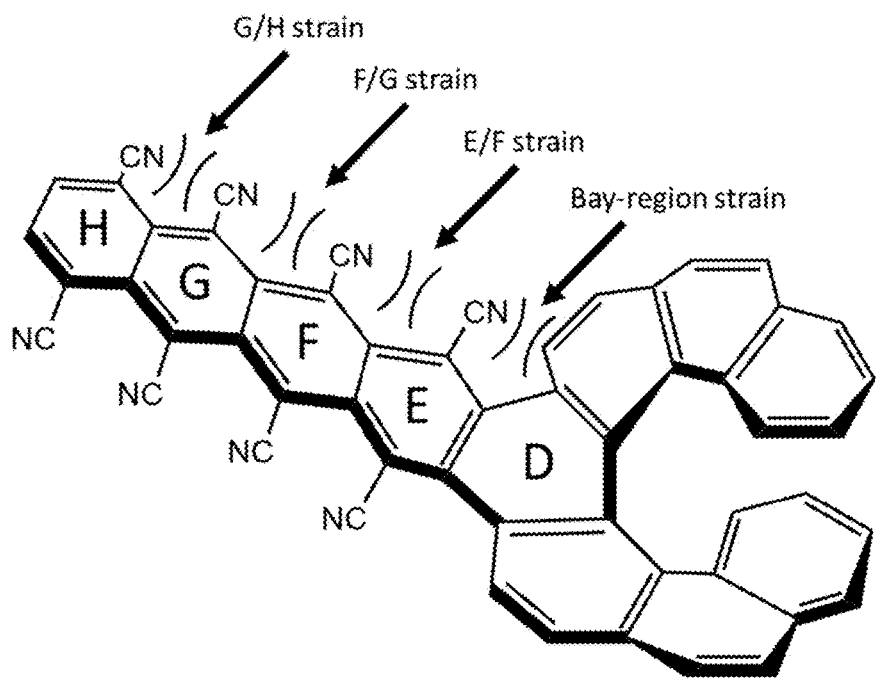
FIG. 12
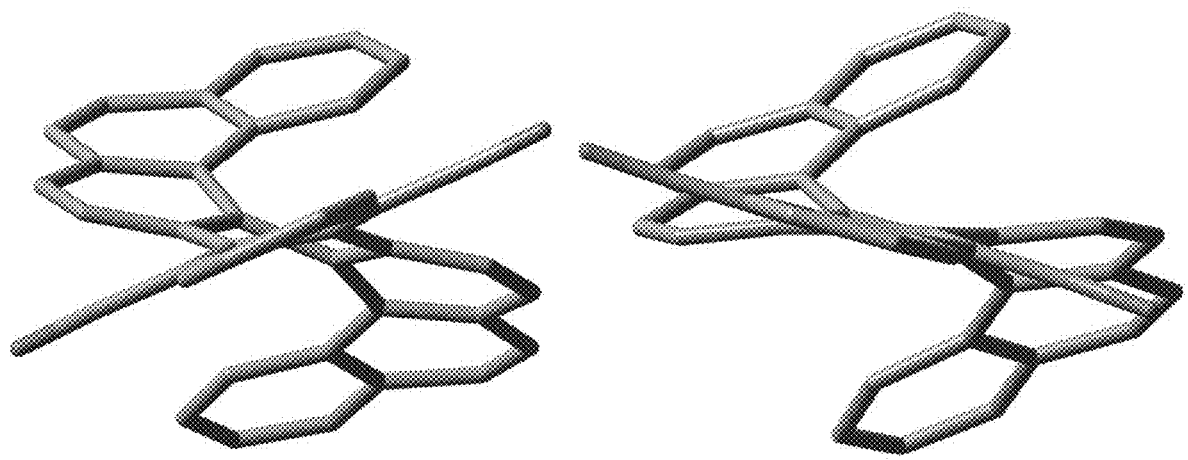
FIG. 13A                    FIG. 13B

[7]n2

CN[7]n2

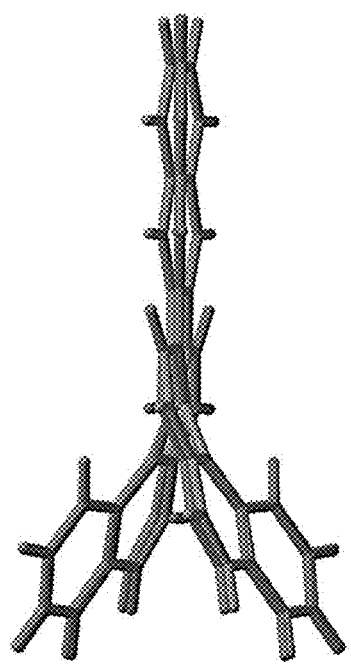
[7]n2
FIG. 48A
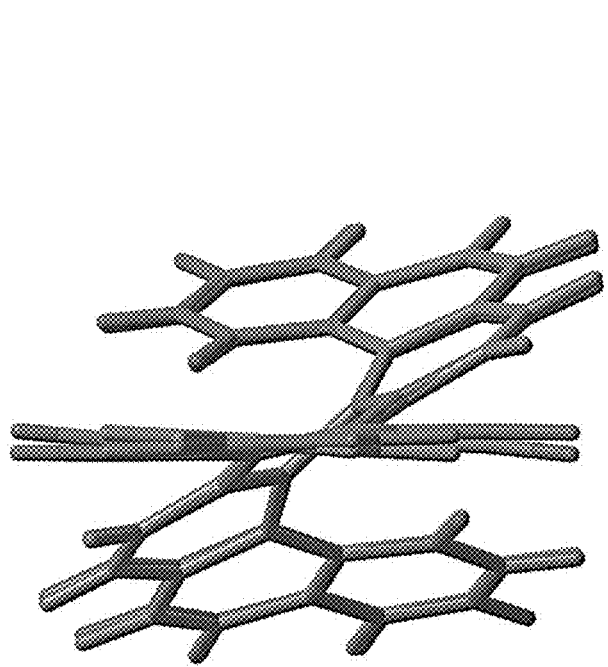
CN[7]n2
FIG. 48B
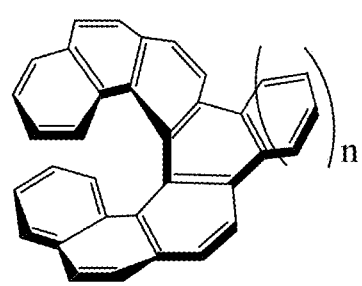
[7]Series
[7]n0 n = 0   [7]n1 n = 1
[7]n2 n = 2   [7]n3 n = 3
[7]n4 n = 4
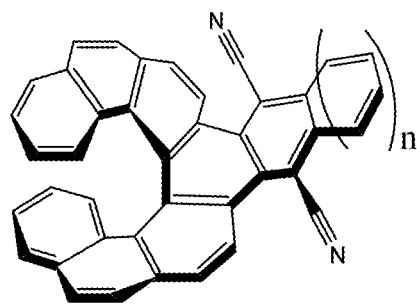
CN[7]Series
CN[7]n1 n = 0   CN[7]n2 n = 1
CN[7]n3 n = 2   CN[7]n4 n = 3
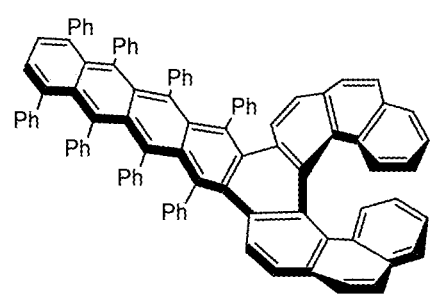
octaPh[7]n4
FIG. 49

SYNTHESES, CHARACTERIZATIONS, AND APPLICATIONS OF HELI-ACENES

RELATED APPLICATIONS

This application is a non-provisional application that claims priority benefit of U.S. Provisional Application Ser. No. 62/843,829 filed May 6, 2019; the contents of which are hereby incorporated by reference.

FIELD OF INVENTION

The present invention generally relates to twisted acenes, and more particularly to configurationally stable twisted acenes that are imbedded into the structure of [7]helicene at the fulcrum ring. The helicene propagates its chiral nature into the acene, while acting as a locking mechanism to thermal racemization. These doubly-helical compounds are part of a new homologous series of polycyclic aromatic hydrocarbons, namely the [7]helitwistacenes. Such [7]helitwistacenes have utility as materials suitable for forming a circularly polarized organic light emitting diode (CP-OLED) for direct emission of circularly polarized (CP) light for the fabrication of high efficiency electronic displays.

BACKGROUND

Sensitizers can be regarded as energy transfer or electron transfer catalysts. Return electron transfer in the radical-cation/radical-anion ion pair intermediates diminishes the efficiency of many electron-transfer sensitizers. Photophysical and electrochemical properties of a series of novel dicationic sensitizers have been reported.[1,2] These doubly-charged sensitizers were designed to prevent energy wasting return electron transfer by promoting a competitive rapid repulsive separation of an initially formed sensitizer-radical-cation/substrate-radical-cation pair. Indeed, very efficient electron-transfer catalyzed sulfide and alkene photooxygenations, Diels-Alder reactions, and retro-(2+2) cycloadditions were observed. A detailed computational study of a large number of structurally diverse dications led to the suggestion of desirable properties in an optimally designed sensitizer.[3] The dications previously reported[1,2] are plagued by rapid reaction with water that makes them difficult to use. However, viologens are nitrogen centered dications that are impervious to reaction with water. Consequently, they would be ideal electron transfer sensitizers if one could increase the singlet excited lifetime of the parent viologen (N, N'-dimethyl-4,4'-bipyridinum dication) which unfortunately is less than a nanosecond. In an effort to generate an improved polyaromatic dicationic sensitizer with a substantially longer lifetime a heli-viologen as shown in FIG. 3A has been synthesized.[3] This heli-viologen has several unique and electronically beneficial characteristics one of which is the fact that it is the most easily reduced redox-active helicene known. This heli-viologen also has sufficiently long singlet ($E_{S1}$=59±0.1 kcal/mol; 5.8±0.6 ns) and triplet (54±1 kcal/mol; 40.6±0.4 ms) lifetimes to allow bimolecular electron transfer reactions to occur. A published[4] Stern Volmer study of the quenching of the heli-viologen of FIG. 3A by a series of sulfides has verified its substantial singlet ($S_1$) lifetime and illustrates the potent oxidizing character of $S_1$. Furthermore, additional publications[5,6] contain a massive amount of material that directly bear on the topic of the present disclosure and are accompanied by over 160 pages of supporting information. These new viologens also form charge transfer complexes and can be used in molecular recognition devices.

Polyaromatic hydrocarbons (PAHs) have fascinated organic chemists since they were first isolated in the 19$^{th}$ century.[7] This fascination at first was related to their unusual reactivity in comparison to simple alkenes and to less carbon rich materials. In the early 20$^{th}$ century chemical giants such as Erik Hückel, Eric Clar, and Linus Pauling expanded on August Kekulé's ideas to provide a theoretical framework that is still used to this day to help understand the structure and reactivity of these amazing molecules.[8] The Kekulé valence structure,[9] the Hückel (4n+2)π electron rule, the Pauling bond orders,[10] and the Clar aromatic sextet[11] are concepts that are familiar to all PAH scholars. Interest in PAHs was re-invigorated in the late 20$^{th}$ and early 21$^{st}$ century by the discovery of fullerenes[12,13] and graphene[14] and by the realization that these beautiful molecules have important applications in electronic and optical devices.[15] Through combinatorial arrangements of ortho- and peri-fused benzene, a seemingly endless array of these compounds can be imagined, and this vastness necessitates the categorization of PAHs into subclasses.

Classes of PAHs are organized based on structural similarities forming homologous series, within which, compounds deviate from one another only by the number of rings that make up the structure. Certain trends of photochemical, electronic, and thermodynamic properties may be expressed in one class that greatly deviates from other classes. Two such classes are centrally important to this disclosure, namely the linear acenes and the chiral helicenes. A detailed discussion of the properties, preparation, and applications of these two classes will follow. A defining feature of all PAHs is aromaticity and although many of the unique properties of these compounds are explained through this intrinsic trait, it remains true that there is no single accepted definition for the term aromatic. However, as used herein aromaticity refers to PAHs that contain a conduit of conjugated electrons upon a planar skeleton of sp2 hybridized carbons. Resultant of this ensemble, is a property called aromaticity.

The most elementary unit of PAHs is benzene and the most well-known representation of this compound is the Kekulé structure which is composed of a six-membered ring with six equivalent sp$^2$ hybridized carbon atoms having six completely delocalized electrons in its π-system.[3] The next largest PAH is naphthalene having two fused benzene rings. Upon addition of more benzene units the number of possible isomers greatly increases. Three or more annulated aromatic rings can generate different structural peripheries that cause a change in the stability, optical absorption spectra, and electronic properties of the PAHs.[4] These two available peripheries are called arm-chair (FIG. 1A) and zig-zag (FIG. 1B). In PAHs with five or more aromatic rings the arm-chair periphery lays the foundation for periphery elements such as the bay, cove and fjord regions (FIG. 1C).

Experimental and theoretical methods have increased the palpability of aromaticity by quantizing the aromatic resonance energy of benzene and other systems and now local indices are available that enumerate the extent of aromaticity of each ring within a PAH system. These values can be quite telling when it comes to structure and reactivity. The Mallory reaction is one of only a few synthetic tactics for accessing the larger helicenes, warranting an exclusive section for this vital reaction.

FIGS. 2A-2G illustrate the remarkable structural diversity of PAHs and includes fully aromatic PAHs in which all electrons reside in a Clar sextet, as shown in prior art FIG. 2A,[16] K-region PAHs, prior art FIG. 2B, generated for example by annealing that of FIG. 2A with an additional ring in the bay region, phenacenes, prior art FIG. 2C, that are characterized by a zig-zag fused structure with alternating Clar sextets, rylenes, prior art FIG. 2D, that are constructed by peri-annulation of naphthylenes, non-planar PAHs such as the bowl shaped corannulene, prior art FIG. 2E, or helical [5]helicene, prior art FIG. 2F, and acenes, prior art FIG. 2G, that are linearly fused benzoid hydrocarbons.

Helicenes (e.g., that shown in prior art FIG. 2F) are ortho-fused PAHs that are well over 100 years old but have recently experienced a renaissance because of their demonstrated applications in enantioselective catalysis, in molecular recognition, in sensing, and in chiroptical, optical, and supramolecular materials.[17-26] These applications take advantage of their enhanced optical rotations and circular dichroism features that are a direct result of their helical architectures.

Acenes or polyacenes are a class of organic compounds and polycyclic aromatic hydrocarbons made up of linearly fused benzene rings. The larger representatives have potential interest in optoelectronic applications and are actively researched in chemistry and electrical engineering.

While aromatic compounds are often thought of as flat, rigid structures. This notion however, is quickly shattered with the mere existence of some PAHs such as the DNA-like helicenes, which are an extreme example of the structural distortions that can arise when strain is introduced into an aromatic system. The helicenes however are not the only spiral class of PAHs. Surprisingly, the acenes can also be twisted forming a subclass of spiral PAHs called the twistacenes. Like the helicenes, these compounds form a helix, but the twist is propagated parallel to the ring plane (longitudinal twist) rather than perpendicular to it. These compounds have a surprisingly high propensity to flex as demonstrated by the mere energetic cost of 3.2 kcal/mol to twist naphthalene by 20° as predicted by quantum chemical calculations.[42] The chiral nature of the twistacenes coupled with their impressive electronic properties are an exciting forefront of research with a wide array of potential applications.

The unique twisted structure of acenes combined with the electronic characteristics of the acenes yields their application as components in electronic devices. Several twistacenes have been successfully employed in OLEDs[27-29] with the electroluminescent twistacene 6,8,15,17-tetraphenyltetrabenzoheptacene (ta4) as a specific example, having a quantum yield of fluorescence of 15%.[30] Because of the minimal response of the electronic properties of acenes to twisting distortions, non-planar polyacenes can be fabricated that are resistant to photooxidation, insolubility, and dimerization that often plague the higher acenes.

Circularly polarized (CP) light is of interest in the fabrication of high efficiency electronic displays. The current method of generating CP light in high efficiency electronic displays is to pass plane averaged emission through a series of filters. These filters generate unwanted bulk and reduce the throughput of the CP light. These inadequacies would be immediately resolved with the realization of direct emission of CP light from a circularly polarized organic light emitting diode (CP-OLED). The remarkable electronic properties of acenes have been exploited in the fabrication of high efficiency OLEDs and naturally, twisted acenes are ideal candidates for the fabrication of CP-OLEDs. However, most twisted acenes synthesized to date exhibit half-lives of specific rotation decay no greater than several hours at room temperature, excluding their viability as components in CP-OLED devices.

While there has been previous development of homologous series of polycyclic aromatic hydrocarbons, there continues to be a need for new PAH molecular structures that have utility as materials suitable for forming a circularly polarized organic light emitting diode (CP-OLED) for direct emission of circularly polarized (CP) light for the fabrication of high efficiency electronic displays.

SUMMARY

A new homologous series of polycyclic aromatic hydrocarbons are provided, namely the [7]helitwistacenes. Embodiments of the inventive [7]helitwistacenes have utility as materials suitable for forming a circularly polarized organic light emitting diode (CP-OLED) for direct emission of circularly polarized (CP) light for the fabrication of high efficiency electronic displays. Embodiments of the present invention provide configurationally stable twisted acenes that are imbedded into the structure of [7]helicene at the fulcrum ring. The helicene propagates its chiral nature into the acene, while acting as a locking mechanism to thermal racemization.

BRIEF DESCRIPTION OF THE DRAWINGS

The present invention is further detailed with respect to the following drawings that are intended to show certain aspects of the present of invention, but should not be construed as limit on the practice of the invention, wherein:

FIG. 4 is a schematic diagram that illustrates the use of temperature in the Mallory photocyclization dehydrogenation of four different bis-styrenyl substrates to switch between exclusive formation of two of the three possible isomeric products, providing an explanation for the counterintuitive regioselectivity of the Mallory reaction to form the more sterically strained helical isomers when access to more than one product is possible;

FIG. 12 illustrates steric interactions in CN[7]n4 that govern twistomer formation;

FIGS. 13A and 13B illustrate B3LYP/6-31G(d) optimized CN[7]n2 and its twistomer, respectively, with hydrogens omitted for clarity;

FIGS. 48A and 48B show the optimized structures of the ground and $S_1$ states of [7]n2 and CN[7]n2, respectively, overlaid for comparison, where green structures are ground states, red structures are $S_1$ states (B3LYP/6-31G(d));

FIG. 49 illustrates example embodiments of heliacenes;

DETAILED DESCRIPTION

Figure 1A:
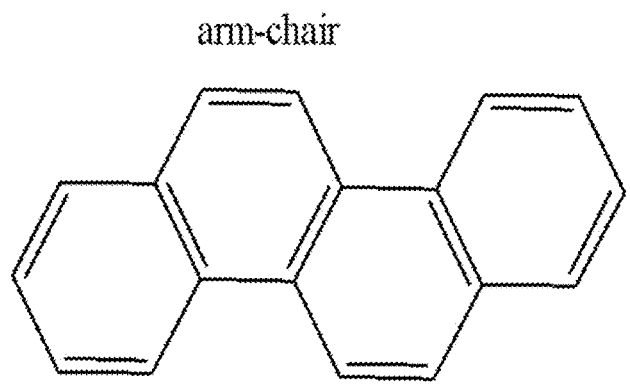
FIGS. 1A-1C show prior art arrangements of three or more annulated aromatic rings that can generate different structural peripheries that cause a change in the stability, optical absorption spectra, and electronic properties of PAHs.
Figure 1B:
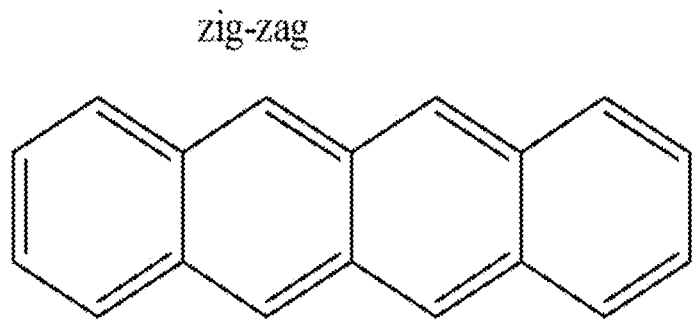
Figure 1C:
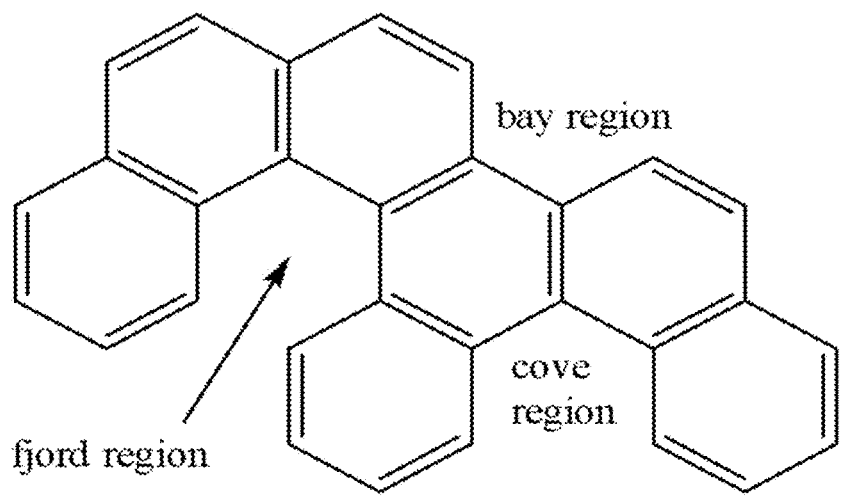
Figure 2A:
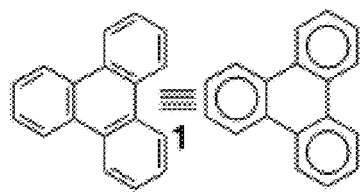
FIG. 2A shows a prior art fully aromatic PAH in which all electrons reside in a Clar sextet.
Figure 2B:
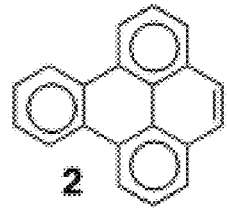
FIG. 2B shows a prior art K-region PAH generated by annealing that of FIG. 1A with an additional ring in the bay region.
Figure 2C:
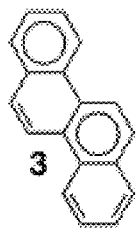
FIG. 2C shows a prior art phenacene that is characterized by a zig-zag fused structure with alternating Clar sextets.
Figure 2D:
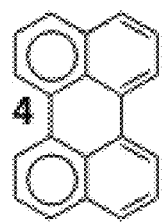
FIG. 2D shows a prior art rylene that is constructed by peri-annulation of naphthylenes.
Figure 2E:
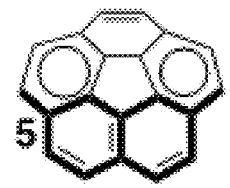
FIG. 2E shows a prior art non-planar PAH such as the bowl shaped corannulene.
Figure 2F:
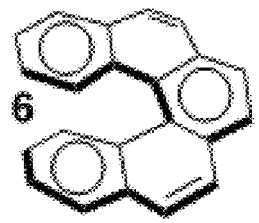
FIG. 2F shows a helical [5]helicene.
Figure 2G:
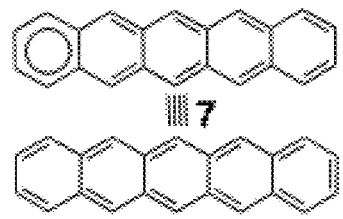
FIG. 2G shows prior art acenes that are linearly fused benzoid hydrocarbons.
Figure 3A:
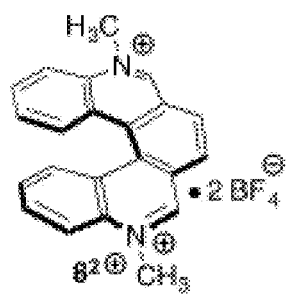
FIGS. 3A-3E show a number of prior art Heli-viologens.
Figure 3B:
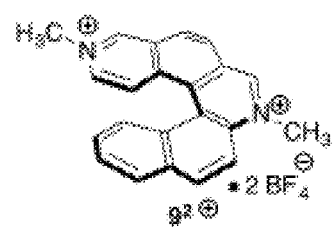
Figure 3C:
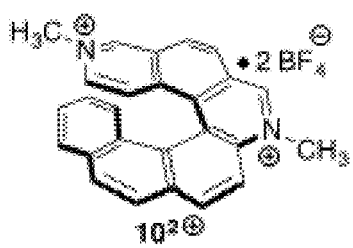
Figure 3D:
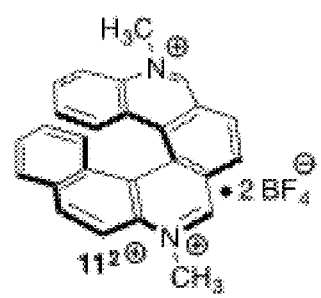
Figure 3E:
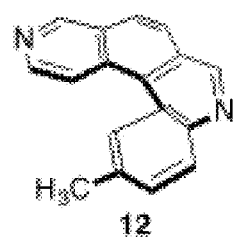

The present invention has utility as a new homologous series of polycyclic aromatic hydrocarbons, namely the [7]helitwistacenes. Embodiments of the inventive [7]helitwistacenes have utility as materials suitable for forming a circularly polarized organic light emitting diode (CP-OLED) for direct emission of circularly polarized (CP) light for the fabrication of high efficiency electronic displays. Embodiments of the present invention provide configurationally stable twisted acenes that are imbedded into the structure of [7]helicene at the fulcrum ring. The helicene propagates its chiral nature into the acene, while acting as a locking mechanism to thermal racemization.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

A dissertation of Jacob Weber entitled "[7]HELIACENES: CONFIGURATIONALLY STABLE TWISTED ACENES & THE ORIGIN OF THE PREFERENTIAL FORMATION OF HELICENES IN MALLORY PHOTOCYCLIZATIONS (University of Wyoming) and all references cited therein which are hereby incorporated by reference in their entireties provides a comprehensive discussion of PAHs, helicenes, acenes, twisted acenes, photochemical properties of PAHs, aromaticity, experimental approaches and theory related to measurement of resonance energy of PAHs, chiral resolution and application of helicenes, and Mallory reactions. The dissertation also discloses a wide array of computational studies as a function of acene elongation for these [7]helitwistacenes. Furthermore, it was discovered that temperature, as shown in FIG. 4, may be used in the Mallory photocyclization dehydrogenation of four different bis-styrenyl substrates to switch between exclusive formation of two of the three possible isomeric products, providing an explanation for the counterintuitive regioselectivity of the Mallory reaction to form the more sterically strained helical isomers when access to more than one product is possible. The Mallory reaction is invaluable for accessing the higher helicenes and other large strained PAH systems.

Acenes are graphene nanoribbons with the closest approach to zigzag-edged one-dimensionality compared to any other class of polycyclic aromatic hydrocarbon (PAHs). Acenes unique linear annulation dictates that only one resonating Clar sextet be present regardless of length[31] and in turn, a vanishing band-gap and dramatic loss in stability is observed throughout the series. With their impressive scaled electronic properties, acenes have been used as organic semiconductor components in field effect transistors, photovoltaic cells, and light emitting diodes.[32] However, solution based processing of these planar species is vexed by low solubility, having strong van der Waals interactions, and decomposition through dimerization and oxidation.[33]

Configurationally stable twisted acenes have been synthesized with the use of aliphatic bridging groups causing them to deviate from true polycyclic aromatic hydrocarbon (PAH) character. The synthesis and characterization of two novel configurationally stable twisted acenes that are imbedded into the structure of [7]helicene at the fulcrum ring are reported herein. The helicene propagates its chiral nature into the acene, while acting as a locking mechanism to thermal racemization. These doubly-helical compounds are part of a new homologous series of polycyclic aromatic hydrocarbons, namely the [7]helitwistacenes.

Specifically, acenes of different lengths are attached onto the base-structure of [7]helicene at the fulcrum ring creating a new polycyclic aromatic hydrocarbon (PAH) series called the [7]heliacenes. The function of the helical domain in these molecules is multifaceted, acting to: (i) generate the twist and dictate the direction of twist (right or left handed) in the acene through steric interactions at the helicene/acene junction, (ii) lock in the configuration/handedness of the twisted acene by correlating it with a high barrier of racemization of the helical domain, and (iii) impart added solubility and stability. In addition, in order to enhance the chiroptical properties of the heliacene, the ability of substituents to maximize and propagate the twist down the longitudinal axis of the acene appendage are studied.

Figure 5A:
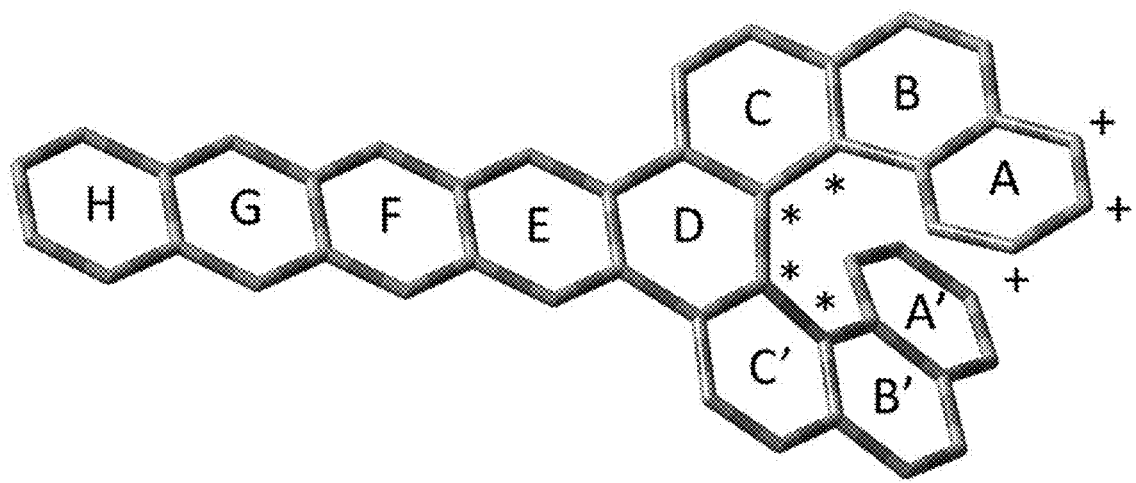
FIG. 5A illustrates the B3LYP/6-31G(d) calculated structure of [7]n4 (hydrogens omitted for clarity) showing the labeling of the rings, the helical core dihedral angle (*'s), and outer rim carbons (+'s)
Figure 5B:
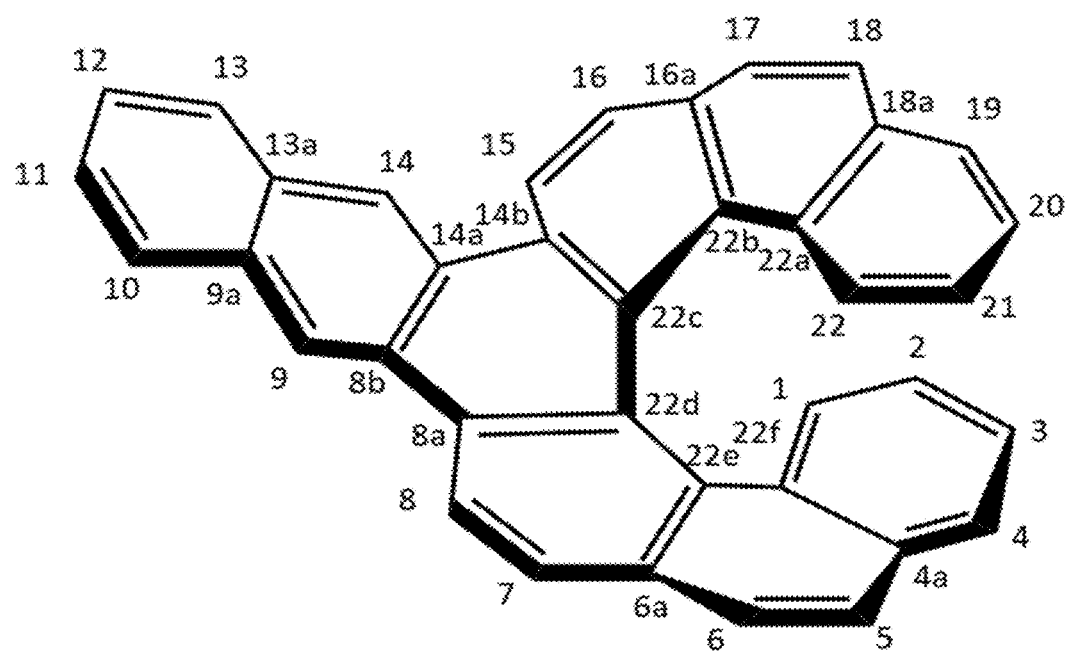
FIG. 5B illustrates a numbering system of the [7]heliacenes using [7]n2 as a specific example.

The geometries of the [7]Series are optimized using the B3LYP/6-31G(d) computational model. The optimized structure of [7]n4 is shown in FIG. 5A illustrating the labels of each ring in the [7]heliacenes. In FIG. 5B illustrates the numbering system used for the [7]heliacenes with [7]n2 as a specific example. In order to facilitate the discussion on the structural features of the [7]heliacenes, some geometric parameters must be defined. The helical pitch is the average distance between the three outer-rim carbons (denoted by +'s in FIG. 5A) and the corresponding opposing carbons in the two terminal helicene rings (ring A and A' FIG. 5A). The pitch is an estimate of the height of one complete helical turn along the direction parallel to the helical axis and indicates how open the helical jaws are. The helical core dihedral angle is the dihedral angle formed by the four carbons denoted with *'s in FIG. 5A and is an indication of the extent of helical strain in the system. Finally, the acene twist is the dihedral angle generated by the four outermost carbons in the acene motif. For example, in [7]n2 the acene twist is the dihedral angle formed by carbons 11, 12, 22c, and 22d in FIG. 5B. This term gives the magnitude of longitudinal twisting in the embedded acene as defined by Pascal.[38] Adhering to these definitions, the geometric parameters of the [7]Series are presented in Table 1 including the twist angle of each acene ring.

TABLE 1

| B3LYP/6-31G(d) Optimized geometric parameters of the [7]Series. | | | | | | | | | |
|---|---|---|---|---|---|---|---|---|---|
| | Helical pitch (Å) | Helical core dihedral* | Acene twist | Ring twist (D)* | Ring twist (E)* | Ring twist (F)* | Ring twist (G)* | Ring twist (H)* | [7]Helicene configuration | Twisted acene configuration |
| [7]n0 | 4.67 | −28.2° | 16.3° | 16.3° | | | | | M | P |
| [7]n1 | 4.81 | −32.5° | 22.4° | 20.2° | 2.1° | | | | M | P |
| [7]n2 | 4.84 | −33.8° | 24.6° | 21.7° | 2.7° | 0.1° | | | M | P |
| [7]n3 | 4.87 | −34.6° | 26.2° | 22.6° | 3.3° | 0.1° | 0° | | M | P |
| [7]n4 | 4.88 | −35.0° | 27.2° | 23.2° | 3.6° | 0.2° | 0° | 0° | M | P |

Longitudinally twisting the acenes out of planarity, as introduced by Pascal,[34] has been shown to produce only marginal changes to their electronic properties,[35] while introducing an avenue for the fabrication of polyacenes with resistance to insolubility, dimerization, and photooxidation.[36] These twisted compounds also have utility as circularly polarized fluorescent materials, but most twisted acenes have prohibitively low barriers of racemization,[37] precluding their use as enantiopure components in emissive devices.

This problem is addressed by fusing a chiral domain onto twisted acenes, which alone has a substantial barrier to racemization, to lock in the configuration of the twistacene. This allows for the isolation of enantiopure twisted acenes.

Calculations predict a moderate twist for all embedded acenes in the [7]Series ranging from 22.4° for naphthalene in [7]n1 up to 27.2° for pentacene in [7]n4. As these values indicate, the acene twist increases through the series with the greatest change of 6.1° observed upon the initial annulation of ring E. As more rings are added completing the series, the twist continues to increase by an average value of 1° per ring. The acene twist is not equally distributed in each ring, with an approximate 90% and 10% expression in rings D and E, respectively, and little to no twist observed in rings F through H.

The geometric parameters that monitor the helical domain also increase through the series, with the greatest change observed going from [7]n0 to [7]n1. Annulation of ring E corresponds to an increase of 0.14 Å and 4.3° for the helical pitch and the absolute value of the helical core dihedral angle, respectively. Subsequent annulations of rings E through F bring about little change to the overall helical core geometry (0.01-0.03 Å for the helical pitch and 0.4°-1.3° for the helical core dihedral angle).

Figure 6:
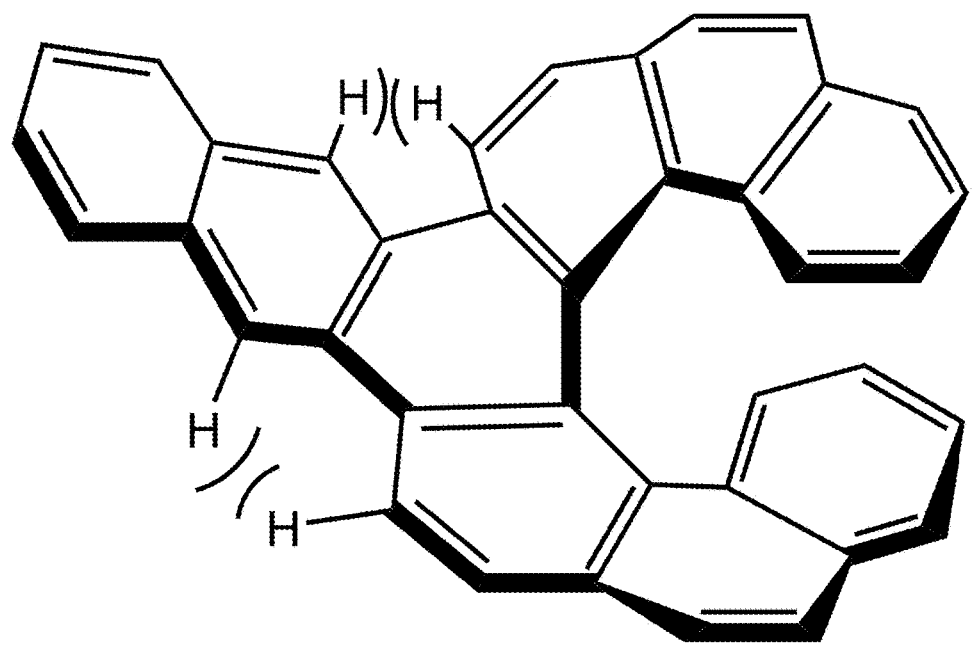
FIG. 6 illustrates [7]n2 showing the steric interactions in the two bay-regions.
Figure 7:
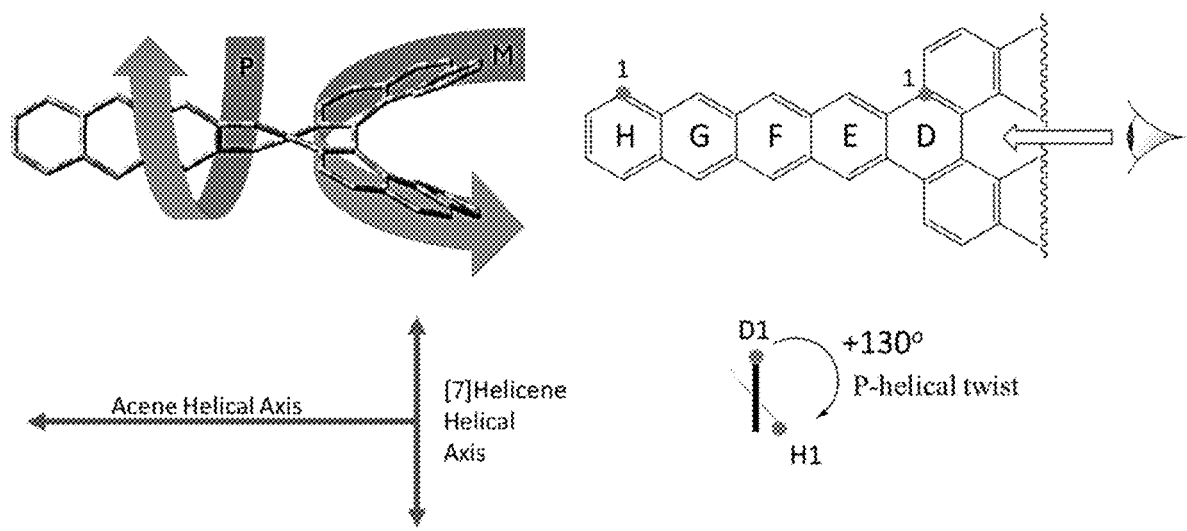
FIG. 7 illustrates configurations and axes of the acene and helicene domains of the [7]heliacenes.

Addition of ring E on [7]n0, forming [7]n1, generates two bay-regions at the helicene/acene juncture. These bay regions are represented in FIG. 6 for [7]n2. The intra H—H distance between bay-region hydrogens is approximately 1.95 Å for all members in the [7]Series, well within twice the Van der Waals radius of hydrogen (2.4 Å) as determined by Bondi.[39] Steric crowding in the helicene/acene bay regions facilitate geometric "communication" between the two domains, allowing [7]helicene to propagate its chiral nature into the acene domain. This results in an acene twist that is both orthogonal and of the opposite configuration to that of the [7]helicene core helix (FIG. 7). The initial formation of the dual bay-regions going from [7]n0 to [7]n1 also explains the relatively large change in geometric parameters between these two species.

The geometric parameters of the acene and [7]helicene structural motifs of the [7]Series continue to change when rings F through H are added, despite these rings being sterically removed from the system (i.e., $H_9$ and $H_{10}$ closest approach >2.4 Å). This alludes to electronic "communication" between the acene and helicene domain and is described further below this disclosure.

Figure 8:
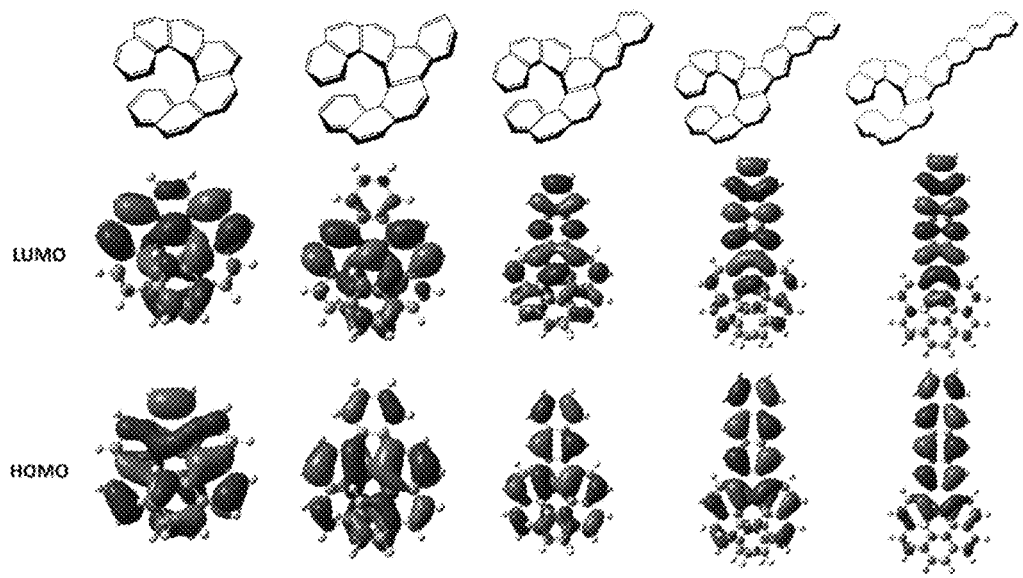
FIG. 8 is a visual representation of HOMO/LUMO orbitals of the [7]Series.

Population analysis at the B3LYP/6-311+G(2d,p) computational level was used to calculate the highest occupied molecular orbital (HOMO) and lowest unoccupied molecular orbital (LUMO) and their orbital energies for each member of the [7]Series. The HOMO/LUMO orbitals of the [7]Series are visually presented in FIG. 8. The band-gaps of each species was calculated by taking the difference between the LUMO and HOMO orbital energies. These values are listed in Table 2, along with the calculated band-gaps of some representative acenes.

TABLE 2

B3LYP/6-311 + G(2d,p) band-gaps of the [7]Series and select acenes. Calculated by taking the difference of the LUMO and HOMO orbital energies.
Calculated band-gap
ΔE LUMO-HOMO (eV)

| [7]Heliacenes | | | |
|---|---|---|---|
| [7]n0 | 3.81 | | |
| [7]n2 | 3.78 | Acenes | |
| [7]n2 | 3.44 | Anthracene | 3.55 |
| [7]n3 | 2.86 | Tetracene | 2.75 |
| [7]n4 | 2.33 | Pentacene | 2.19 |

As progression is made through the [7]Series (left to right FIG. 8) the frontier orbitals become more localized on the acene domain. In fact, the HOMO and LUMO of the pentacene embedded species, [7]n4, resides almost entirely on the acene with very little orbital leakage onto the helicene. Furthermore, the band-gap steadily decreases through the series, dropping from 3.81 eV in [7]n0 to 2.33 eV in [7]n4, reaching values that are comparable to those of the free acenes. For instance, the anthracene embedded species [7]n2 has a lower band-gap than free anthracene, while the band-gaps of [7]n3 and [7]n4 are only 0.11 and 0.14 eV higher than those of their free acene counterparts, respectively. The frontier orbital residency of the higher [7]heliacenes coupled with their relatively low bad-gaps, indicates that these compounds are viable surrogates endowed with the electronic characteristics of the corresponding planar acene.

Figure 9A:
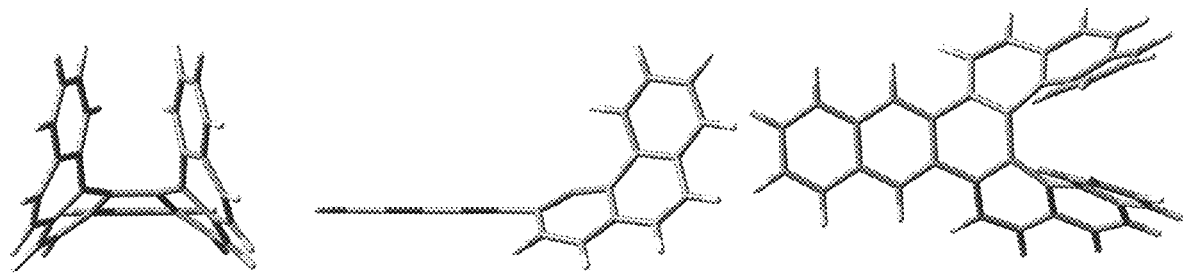
FIG. 9A is a visual representation of B3LYP/6-31G(d) optimized geometry for the TS structure viewed from three different vantage points.
Figure 9B:
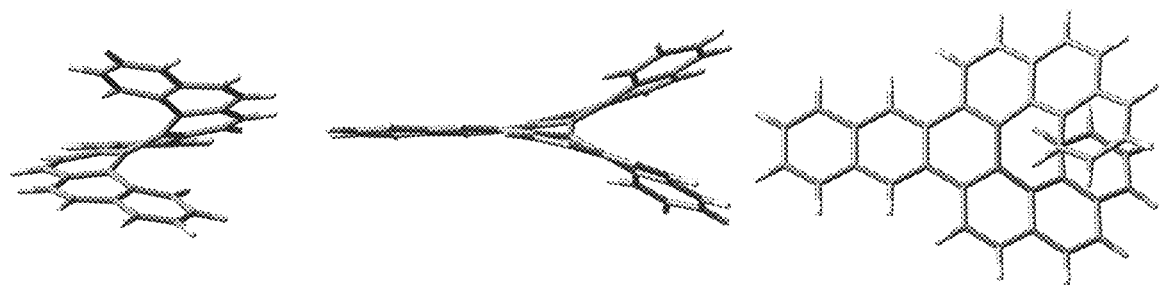
FIG. 9B is a visual representation of the B3LYP/6-31G(d) optimized geometry of [7]n2 structure viewed from three different vantage points.

The transition state (TS) structures for the racemization process of each compound in the [7]Series are located at the B3LYP/6-31G(d) computational level. The racemization TS for [7]n2 is shown in FIG. 9A from three different perspectives. The corresponding perspectives of the lowest energy conformation of the starting material (SM) [7]n2 is shown for each TS perspective in FIG. 9B. Frequency calculations are performed on each TS and SM in the [7]Series and the racemization barriers are calculated using the sum of the electronic and thermal free energies of each structure. All calculated TSs had a single imaginary frequency. The racemization barriers extracted using these calculations are presented in Table 3.

TABLE 3

B3LYP/6-31G(d) calculated barriers
of racemization for the [7]Series using the
sum of the electronic and thermal free energies.

| | ΔG≠ (kcal/mol) |
|---|---|
| [7]n0 | 42.0 |
| [7]n1 | 39.4 |
| [7]n2 | 39.2 |
| [7]n3 | 39.2 |
| [7]n4 | 39.1 |

The thermal racemization of [7]helicene has been studied both experimentally (ΔG≠#=41.7 kcal/mol)[40] and theoretically[41] and its TS is determined to adopt a saddle-like structure. The TS for racemization of the inventive [7]heliacenes also adopt a saddle-like structure in their TS (FIG. 9A). These structures have no $C_2$ symmetry and no helical axis. In turn, the acene twist angle is 0° and there is a $\sigma_v$ mirror plane, giving these saddle-like structures $C_s$ symmetry. These findings are in accordance with the Hammond postulate and provide a satisfying rationale for the sign inversion of the acene twist angle that must occur during interconversion between enantiomers.

The calculated barrier of racemization for [7]helicene ([7]n0, 42 kcal/mol) is very close to what is experimentally found by Martin (41.7 kcal/mol)[40], lending confidence to the accuracy of the values calculated for the other members of the [7]Series. Extension of the acene corresponds with a decrease in the racemization barrier, with the largest decrease of 2.6 kcal/mol observed with the annulation of ring E. Addition of rings F through H had little to no effect on the racemization barrier. The bay-region hydrogens (FIG. 6) are further apart in the racemization transition structure (2.28 Å) than in the chiral heliacene (1.95 Å). In addition, the acene domain in the TS is not twisted and has a twist angle of 0° consistent with its assignment to the achiral $C_s$ point group. This is in contrast to the chiral heliacenes that have twist angles of 22° to 27°. The dramatic decrease in the racemization barrier upon addition of ring E and much smaller decreases upon annulation of additional rings suggest that relief of steric strain rather than an increase in orbital overlap in the transition structure is responsible for this phenomenon. This is consistent with Pascal's calculation that reveals that it only costs 20 kcal/mol to twist naphthalene by 20°.[42]

Lowering the racemization barrier from 41.7 kcal/mol to 39.1 kcal/mol is not expected to adversely affect the configurational stability of the [7]heliacenes at room temperature. This can be demonstrated by using $\Delta G^{\neq}=39$ kcal/mol as the lower limit to the racemization barrier. Using this value in the Eyring equation, the rate constant for racemization is calculated at room temperature and at 100° C. The half-life for a first order racemization with a barrier of 39 kcal/mol is estimated to be over 100 million years at room temperature and 200 years at 100° C. Needless to say, all of the [7]Series up to [7]n4 are expected to be configurationally stable both at room temperature and at moderately high temperatures.

As previously suggested, steric interactions between hydrogens in the bay-regions of the [7]heliacenes play an important role in dictating the twist of the appended acene. Consequently, it is reasonable to replace these hydrogens with different sized substituents in order to modulate the magnitude of the acene twist. The viability of this approach was verified by computationally studying heliacenes with substituents of varying sizes in a para-relationship on ring E, at the acene/helicene juncture. Specifically, this approach has studied the methyl, cyano, phenyl, iso-propyl, and t-butyl substituted [7]heliacenes to create the Me[7]Series, CN[7]Series, Ph[7]Series, iPr[7]Series, and t-Bu[7]Series, respectfully. The geometric parameters and racemization barriers were studied for all series, while the electronic properties were only looked at for the CN[7]Series. The effect of multiple substitutions of different groups were also computationally studied along the longitudinal axis of [7]n4 in order to determine if the magnitude of twist can be increased and its direction faithfully propagated down the acene axis.

Figure 10:
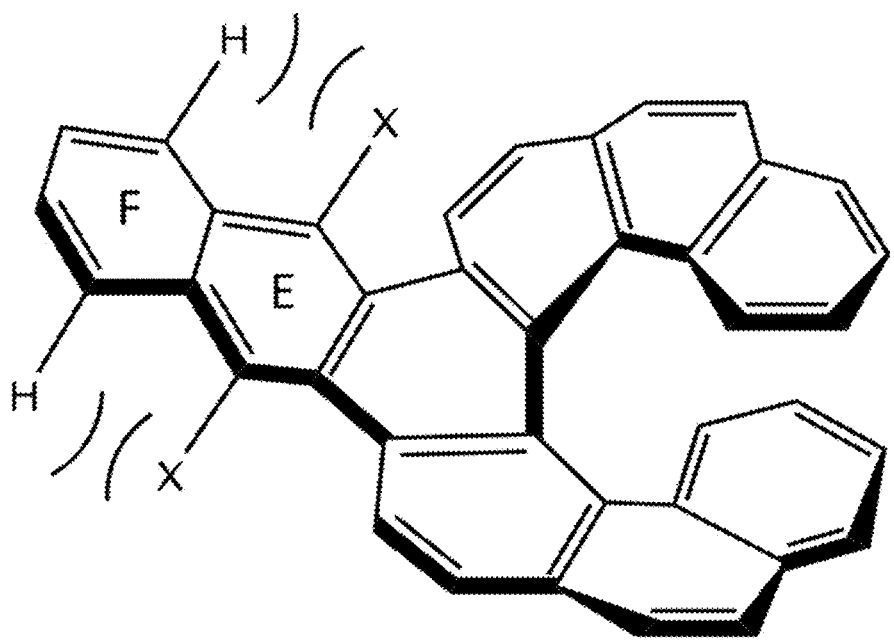
FIG. 10 shows a new steric interaction that is introduced between the substituents on ring E and the hydrogens on ring F of the [7]helicene that illustrates E/F strain.
Figure 11A:
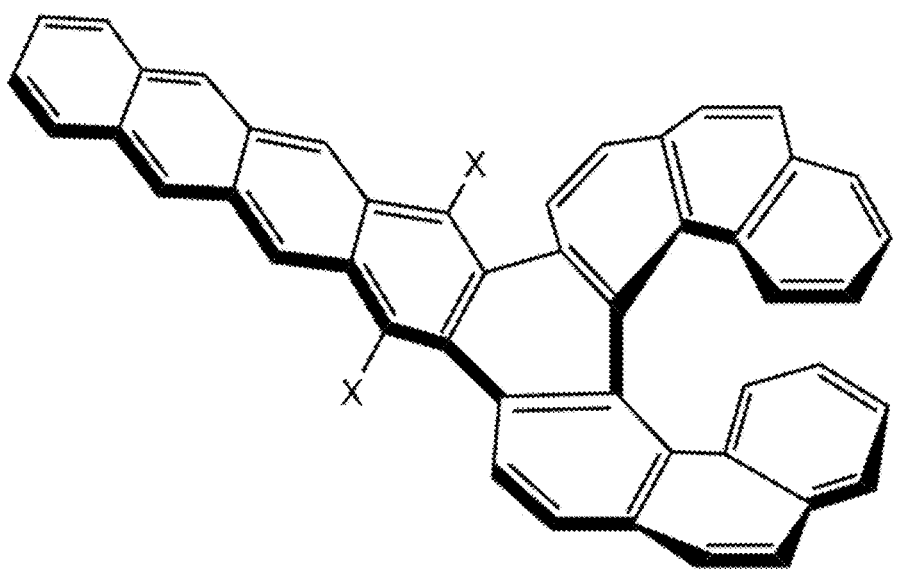
FIGS. 11A-11D illustrate examples of multi-substituted [7]heliacenes.
Figure 11B:
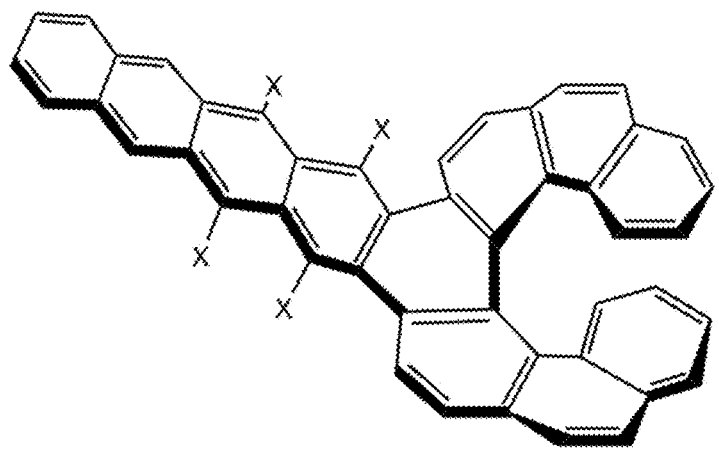
Figure 11C:
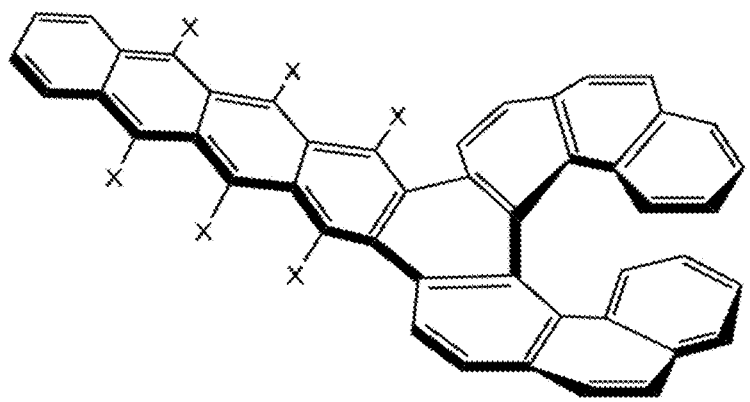
Figure 11D:
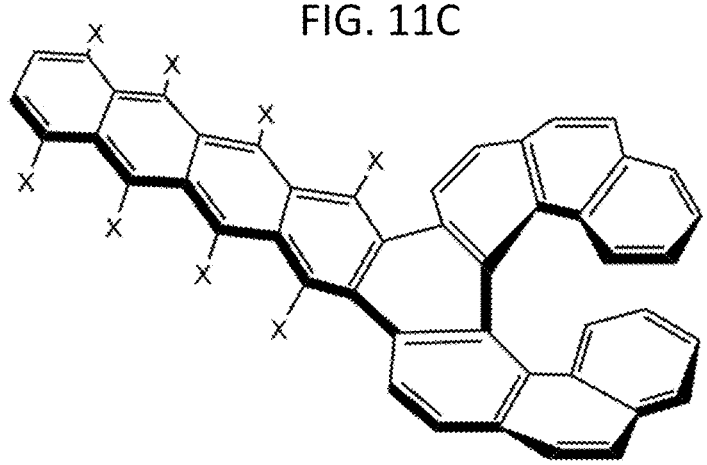

All of the ring-E di-substituted [7]heliacenes were optimized at the B3LYP/6-31G(d) computational level. The geometric parameters of these compounds are listed in Table 4 using the same definitions as used in Table 1.

roughly correlate to the size of the substituents. With larger groups in the bay-regions, there is enhanced steric "communication" between the two domains in the [7]heliacenes, thus allowing the [7]helicene motif to more effectively impart its chiral nature into the imbedded acene. Also, a new steric interaction is introduced between the substituents on ring E and the hydrogens on ring F (FIG. 10). This so called "E/F strain" propagates the twist further away from the helicine core producing a large twist in ring E and a non-trivial twist in ring F. Both the increased bay-region steric interactions, and the introduction of E/F strain accounts for the large increase in the acene twist of the functionalized [7]heliacenes. E-ring substituents increase the pitch and the internal dihedral angle of the helical core of the [7]heliacenes. (columns 2 and 3 in Table 4)

Most, but not all, the acene rings are twisted in the same direction in the substituted [7]heliacenes. In the t-Bu[7] Series the bulk of the two t-butyl substituents are such that the E/F steric interaction twists ring F against the overall torsional direction imparted by the CDE/C'DE bay region interactions. Consequently, the twist in rings F, G, and H have the opposite sign compared to that of rings D and E, diminishing the overall acene twist in these species.

Additional steric interactions were introduced in the [7]heliacenes when substituents were placed on rings F, G, and H, further propagating the steric "communication" between the helicene and the acene domain. This was computationally studied by incrementally substituting the acene rings of [7]n4 in a para-related fashion with nitrile, methyl, and phenyl substituents to create three different series as illustrated in FIGS. 11A-11D. Multi-substitution of the acene domain greatly complicates the potential energy surface, opening up access to twistomers (twisted-isomers) in which steric interactions generate multiple geometric

TABLE 4

Optimized geometric parameters of the E-ring di-substituted [7]heliacenes.
Calculated at the B3LYP/6-31G(d) computational level.

| | Helical pitch (Å) | Helical core dihedral | Acene twist | Ring twist (D) | Ring twist (E) | Ring twist (F) | Ring twist (G) | Ring twist (H) | [7]Helicene configuration | Twisted acene configuration |
|---|---|---|---|---|---|---|---|---|---|---|
| [7]n0 | 4.67 | −28.2° | 16.3° | 16.3° | | | | | | |
| CN[7]n1 | 4.93 | −37.6° | 39.8° | 29.1° | 10.5° | | | | M | P |
| CN[7]n2 | 4.94 | −39.6° | 46.2° | 31.9° | 12.5° | 1.5° | | | M | P |
| CN[7]n3 | 4.95 | −40.2° | 47.6° | 32.7° | 13.1° | 1.4° | 0° | | M | P |
| CN[7]n4 | 4.97 | −40.7° | 48.4° | 33.2° | 13.4° | 1.4° | −0.1° | 0° | M | P |
| Ph[7]n1 | 4.96 | −40.4° | 45.1° | 33.0° | 11.9° | | | | M | P |
| Ph[7]n2 | 5.03 | −42.6° | 57.8° | 35.9° | 16.0° | 5.6° | | | M | P |
| Ph[7]n3 | 5.05 | −43.4° | 60.5° | 36.9° | 16.8° | 5.5° | 0.6° | | M | P |
| Ph[7]n4 | 5.06 | −43.7° | 61.9° | 37.5° | 17.4° | 5.7° | 0.7° | 0° | M | P |
| Me[7]n1 | 4.94 | −40.0° | 45.1° | 32.2° | 12.8° | | | | M | P |
| Me[7]n2 | 4.96 | −42.8° | 51.6° | 36.1° | 14.1° | 0.9° | | | M | P |
| Me[7]n3 | 4.98 | −43.5° | 53.4° | 37.0° | 14.9° | 1.0° | −0.1° | | M | P |
| Me[7]n4 | 4.98 | −43.7° | 54.6° | 37.4° | 15.4° | 1.2° | 0° | 0° | M | P |
| iPr[7]n1 | 4.94 | −41.6° | 49.0° | 34.7° | 14.1° | | | | M | P |
| iPr[7]n2 | 4.98 | −44.1° | 59.8° | 38.5° | 17.6° | 3.2° | | | M | P |
| iPr[7]n3 | 4.99 | −44.6° | 61.9° | 39.4° | 18.4° | 3.2° | 0.2° | | M | P |
| iPr[7]n4 | 5.00 | −44.8° | 62.9° | 39.9° | 19.0° | 3.2° | 0.1° | 0° | M | P |
| t-Bu[7]n1 | 4.96 | −45.5° | 57.3° | 40.7° | 16.1° | | | | M | P |
| t-Bu[7]n2 | 5.00 | −47.9° | 60.5° | 44.5° | 16.8° | −1.7° | | | M | P |
| t-Bu[7]n3 | 5.03 | −48.6° | 62.6° | 45.6° | 17.7° | −1.4° | −0.4° | | M | P |
| t-Bu[7]n4 | 5.05 | −48.9° | 63.6° | 46.0° | 18.2° | −1.4° | −0.4° | 0° | M | P |

Figure 14:
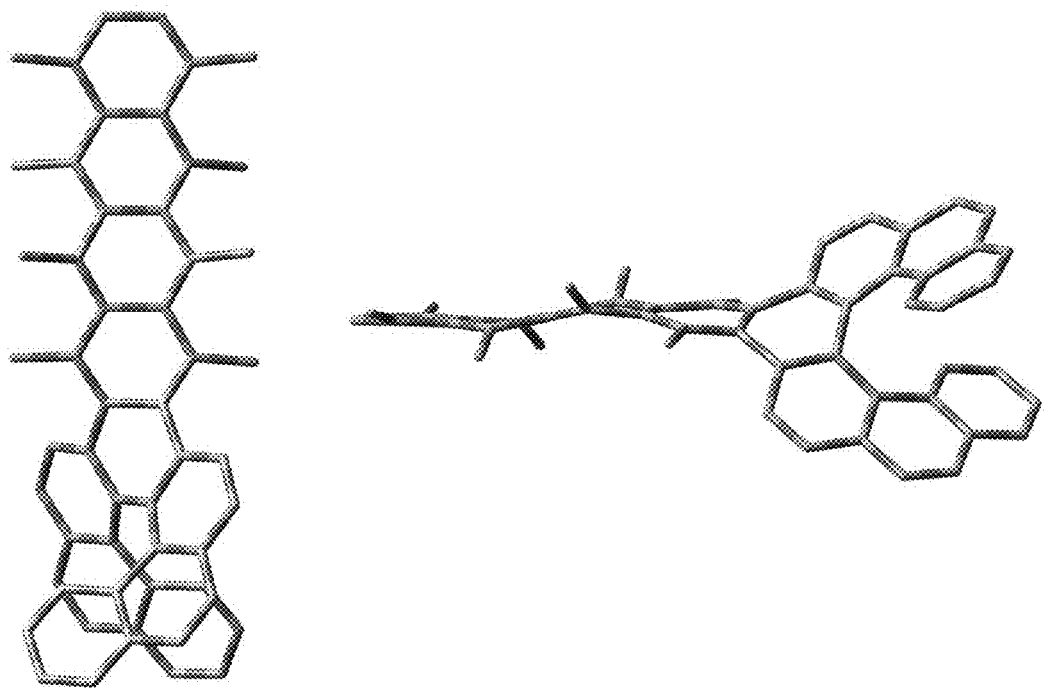
FIG. 14 illustrate a Class 2 twistomer of octaMe[7]n4 (hydrogens omitted for clarity) that are optimized at the B3LYP/6-31G(d) computational level.

The acene twist of the E-ring di-substituted [7]heliacenes are all dramatically enhanced relative to their non-substituted counterpart (Table 1 vs. Table 4). For example, the acene twist of the pentacene embedded species of the CN[7]Series, Me[7]Series, Ph[7]Series, iPr[7]Series, and t-Bu[7]Series are 48.4°, 54.6°, 61.9°, 62.9°, and 63.6°, respectively, compared to 27.2° for [7]n4. These values minima for a single [7]heliacene. An example of these steric interactions for octaCN[7]n4 is presented in FIG. 12. Two broad classes of twistomers are discovered for the [7]heliacenes. In the first class of twistomers (class-a twistomers) a $C_2$-axis of symmetry exists perpendicular to the helical-axis of [7]helicene. The $C_2$-axis of symmetry in these compounds is shared with the helical axis of the acene domain and exists in the parent compound, [7]helicene. FIGS. 13A and 13B are an example of two class-a twistomers of CN[7]n2. The second class of twistomers (class-b twistomers) have no $C_2$-axis of symmetry. The structure in FIG. 14 is an example of a class-b twistomer. Each class-b twistomer has para-related substituents that are puckered in toward one another causing them to reside on the same face of the acene plane. This puckering pattern of para-related substituents alternates as one traverses from the [7]helicene core, causing substituents on neighboring rings to reside on the opposite face of the acene. For ease of discussion, the class-a twistomers are named by preceding the compounds established name by the ring juncture at which the acene twist originating from the [7]helicene core is opposed. Under this context, the twistomer of FIG. 13B is called D/E-CN[7]n2. The directional change of the acene twist is not limited to a single event within one species. For example, the helicity of the acene in a D/E,G/H twistomer changes direction twice and in the extreme example a D/E,E/F,F/G,G/H twistomer has a longitudinal acene twist that changes direction at each ring juncture in the appended acene. A twistomer that has a longitudinal acene twist that is not opposed down the entire length of the appended acene has no modification made to its name and is referred to as "fully twisted". For instance, the fully twisted species of FIG. 13A is CN[7]n2. Since only one form of class-b twistomers have been located, these twistomers are designated by preceding the compounds name with CB. Under this context, the twistomer in FIG. 14 is called CB-octaMe[7]n4. All twistomers located were optimized at the B3LYP/6-31G(d) computational level. The geometric parameters of the appended acenes of these species are presented in Table 5.

CN[7]Series were predicted to be negligible, ranging from 0.7° in D/E-CN[7]n2 to −0.6° in D/E-CN[7]n4. This is true despite a 10° twist in ring D, which is counteracted by an approximate −10° combined twist of rings E and F. The population of the higher energy twistomers in the CN[7] Series is interesting from a scholarly viewpoint, however, they are not expected to have significant impact on the chiroptical properties of the heliacenes. They are much higher in energy (4.17 kcal/mol to 4.85 kcal/mol) and consequently are only 0.1% of the total heliacene population.

An enthalpic transition state for interconversion of the two CN[7]n2 twistomers is located 0.57 kcal/mol above the highest energy twistomer. The negative frequency associated with this transition state involves vibrations of the cyano groups and a twisting vibration of the acene tail of the heliacene. Relaxed scan calculations seem to suggest that a second transition state very close to the lower energy twistomer also exists. However, despite several efforts this second transition state was not located, probably due to the shallow nature of the potential energy surface surrounding this structure.

Multi-substituted twistomers are listed in rows 7-18 of Table 5. In addition to the steric interactions in the dual bay-region and at the E/F juncture, the multi-substituted [7]helipentacenes in Table 5 have steric interactions at the F/G and G/H junctures. These additional interactions greatly enhance the value of the acene longitudinal twist for the fully twisted species. As an example, hexaCN[7]n4, octaMe[7]n4, and octaPh[7]n4 have impressive acene twist values of 97.1°, 134.1°, and 157.7°, respectively. Notice however, that only the phenylated species, octaPh[7]n4, has a fully twisted form that is also the lowest energy isomer. This is not

TABLE 5

Geometric parameters of the appended acenes of the substituted [7]heliacene twistomers. B3LYP/6-31G(d)

| | Acene twist | Ring twist (D) | Ring twist (E) | Ring twist (F) | Ring twist (G) | Ring twist (H) | Relative energy (kcal/mol) | Relative pentacene SP energies* |
|---|---|---|---|---|---|---|---|---|
| CN[7]n2 | 46.2° | 31.9° | 12.5° | 1.5° | | | 0 | NA |
| D/E-CN[7]n2 | 0.7° | 10.6° | −8.7° | −1.3° | | | 4.17 | NA |
| CN[7]n3 | 47.6° | 32.7° | 13.1° | 1.4° | 0° | | 0 | NA |
| D/E-CN[7]n3 | −0.1° | 10.4° | −9.2° | −1.3° | 0° | | 4.62 | NA |
| CN[7]n4 | 48.4° | 33.2° | 13.4° | 1.4° | 0° | 0° | 0 | NA |
| D/E-CN[7]n4 | −0.6° | 10.2° | −9.5° | −1.3° | 0° | 0° | 4.85 | NA |
| hexaCN[7]n4 | 97.1° | 36.9° | 27.9° | 20.8° | 9.3° | 1.3° | 1.9 | 7.7 |
| CB-hexaCN[7]n4 | 58.4° | 34.3° | 17.2° | 5.1° | 1.4° | 0.2° | 0 | 0 |
| G/H-octaCN[7]n4 | 93.1° | 36.8° | 27.9° | 22.8° | 8.2° | −3.6° | 3.7 | 8.7 |
| E/F,G/H-octaCN[7]n4 | 68.6° | 36.9° | 23.8° | 3.4° | −1.6° | 5.4° | 2.9 | 2 |
| CB-octaCN[7]n4 | 58.2° | 34.4° | 17.1° | 4.5° | 1.3° | 0.5° | 0 | 0 |
| hexaMe[7]n4 | 118.1° | 41.0° | 28.5° | 27.6° | 17.4° | 2.3° | 4.5 | 12.1 |
| CB-hexaMe[7]n4 | 61.0° | 38.1° | 17.6° | 3.3° | 0.9° | 0.3° | 0 | 0 |
| octaMe[7]n4 | 134.1° | 40.5° | 27.7° | 28.7° | 25.6° | 10.2° | 8.1 | 15.3 |
| G/H-octaMe[7]n4 | 102.6° | 40.8° | 28.0° | 26.3° | 11.9° | −5.6° | 7.8 | 9.4 |
| CB-octaMe[7]n4 | 62.0° | 38.3° | 18.0° | 3.5° | 1.0° | 0.5° | 0 | 0 |
| octaPh[7]n4 | 157.7° | 41.0° | 33.2° | 32.9° | 30.8° | 17.8° | 0 | 4.6 |
| E/F-octaMe[7]n4 | −64.9° | 31.3° | −11.3° | −33.5° | −32.2° | −18.5° | 23.6 | 0 |

*Relative energies of the isolated pentacene of each twistomer, obtained by cutting the pentacene out of each species and adding hydrogens, followed by single point calculations. (kcal/mol)

CN[7]Series twistomers are listed in rows 1-6 of Table 5. The difference between the two structures in FIGS. 13A and 13B is evident by looking at the positions of the cyano groups. The cyano-groups and the helical arms are staggered in the lower energy conformation but eclipsed in the higher energy conformation. The twist of the acene is also visibly diminished in the higher energy twistomer, D/E-CN[7]n2. In fact, the acene twist in all of the D/E-twistomers of the the case for the multi-methylated and cyanated species and shines a light on a trend for these compounds. The lowest energy twistomers of the multi-methyl and -cyano substituted [7]helipentacenes are the twistomers with the smallest pentacene twist. Since the acene twist is lowest for the class-b twistomers, these species have the lowest relative energy compared to all other twistomers. The acene twist of class-a twistomers decreases with an increasing number of junctures that the acene twist is opposed from that established by the fulcrum ring in the [7]helicene core. Therefore, a higher number of these oppositions correlates to a lower relative energy in the class-a twistomers. The multi-phenylated [7]heliacenes are behaving fundamentally different. Specifically, the fully twisted species are the lowest energy twistomers. To help understand the origin of this difference, the closest approach distance between sterically interacting groups in the bay-region and ring junctures are measured. These values are listed in Table 6 along with the total atomic overlap, using an atomic radius of 1.20 and 1.70 Å for hydrogen and carbon, respectively.

HPLC. However, the encouraging results with the phenyl-substituted heliacenes suggest that they might form with high diastereoselectivity. In addition, the phenyl-substituted heliacenes are synthetically readily accessible, and are the focus of future work in this area.

Frequency calculations were performed for the starting materials and TS of each member of the disubstituted [7]heliacenes and their barriers of racemization were extracted using the sum of their electronic and thermal free energies. These barriers are listed in Table 7. The calculations were performed at the B31YP/6-31G(d) computational level.

TABLE 6

Closest atomic approach distance of substituents in the bay-regions and at each ring juncture of the functionalized [7]n4 species. Structures optimized at the B3LYP/6-31G(d) computational level.

| | Closest approach distance (Å) | | | | Total atomic overlap (Å)* |
|---|---|---|---|---|---|
| | Bay-region | E/F | F/G | G/H | |
| hexaCN[7]n4 | 2.34(CH) | 2.79(CC) | 2.73(CC) | 2.43(CH) | 2.31 |
| C2-hexaCN[7]n4 | 2.33(CH) | 2.76(CC) | 2.76(CC) | 2.45(CH) | 2.30 |
| G/H-octaCN[7]n4 | 2.35(CH) | 2.80(CC) | 2.77(CC) | 2.76(CC) | 2.42 |
| E/F,G/H-octaCN[7]n4 | 2.34(CH) | 2.77(CC) | 2.72(CC) | 2.76(CC) | 2.51 |
| c2-octaCN[7]n4 | 2.33(CH) | 2.76(CC) | 2.77(CC) | 2.78(CC) | 2.46 |
| hexaMe[7]n4 | 2.16(HH) | 2.10(HH) | 2.20(HH) | 2.19(HH) | 0.95 |
| C2-hexaMe[7]n4 | 2.16(HH) | 2.10(HH) | 2.16(HH) | 2.14(HH) | 1.04 |
| octaMe[7]n4 | 2.16(HH) | 2.11(HH) | 2.22(HH) | 2.05(HH) | 1.06 |
| G/H-octaMe[7]n4 | 2.16(HH) | 2.09(HH) | 2.12(HH) | 2.14(HH) | 1.09 |
| C2-octaMe[7]n4 | 2.16(HH) | 2.06(HH) | 2.30(HH) | 2.12(HH) | 0.96 |
| octaPh[7]n4 | 2.44(CH) | 3.03(CC) | 3.03(CC) | 3.05(CC) | 1.55 |
| E/F-octaPh[7]n4 | 2.36(CH), 2.41(CH) | 2.48(CH) | 3.02(CC) | 3.05(CC) | 2.18 |

*Sum of the atomic overlap from the values in columns 2 through 5, using the atomic radii of hydrogen and carbon determined by Bondi.[39]

There are two governing factors that determine the relative energy of a given twistomer. (i) The energy of the free pentacene (far-right column, Table 5) has a higher energy when it is twisted. This is most dramatically demonstrated by the 15 kcal/mol energy increase in the free pentacene of octaMe[7]n4 compared to the free pentacene of CB-octaMe [7]n4 that is 72 less twisted. (ii) The relative amount of steric strain between isomers plays a role in determining the relative energies between twistomers. The final column in Table 6 is an approximation of the overall steric strain contained in a twistomer. For the cyanated and methylated [7]n4 species the steric contributions to the overall energy between isomers are predicted to be very similar with total atomic overlap values deviating by no more than 0.1 Å. For the twistomers of octa-phenylated species however, the total atomic overlap is 0.63 Å higher in the less twisted E/F-octaPh[7]n4 species compared to the fully twisted octaPh [7]n4 isomer. Therefore, steric contributions to the total energy of the non-twisted E/F-octaPh[7]n4 species are expected to be much higher than in the fully twisted isomer, octaPh[7]n4. This is due in part to an additional steric interaction in the bay-regions of the E/F twistomer.

The population of twistomers can potentially complicate the use of substituted heliacenes for chiroptical applications. The twistomers are diastereomers and can be separated by conventional chromatography methods if their interconversions are not rapid. Interconversion is slower with the larger substituents. Consequently, to get an enantiopure heliacene it might require as a first step separation of diastereomers by HPLC followed by separation of enantiomers by chiral

TABLE 7

Calculated barriers of racemization for the substituted E-ring disubstituted [7]heliacenes.

| | $\Delta G^{\neq}$ (kcal/mol) |
|---|---|
| [7]n0 | 42.0 |
| CN[7]n1 | 34.5 |
| CN[7]n2 | 34.1 |
| CN[7]n3 | 34.4 |
| CN[7]n4 | 34.5 |
| Ph[7]n1 | 34.0 |
| Ph[7]n2 | 33.4 |
| Ph[7]n3 | 33.9 |
| Ph[7]n4 | 34.0 |
| tetraPh[7]n4 | 44.6 |
| Me[7]n1 | 31.6 |
| Me[7]n2 | 32.3 |
| Me[7]n3 | 32.6 |
| Me[7]n4 | 32.9 |
| iPr[7]n1 | 31.2 |
| t-Bu[7]n1 | 33.8 |

The barriers of racemization for the di-substituted species are 7.7 to 10 kcal/mol lower in energy than the barrier calculated for [7]helicene. The transition states (TS) adopt a butterfly geometry as illustrated for CN[7]n2 in FIG. 15. Important structural differences between the starting materials and the TS in CN[7]n4 include: (i) the acene twist angle is 48.4° in the starting material and 0° in the TS; (i) the fulcrum ring twist angle decreases from 33.2° in the starting material to 0° in the TS; (iii) the closest approach of two carbons in the terminal rings of the helicene domain decreases from 3.50 Å in the starting material to 2.89 Å in the TS; and (iv) the distance between the bay region hydrogen (red hydrogen in the CN[7]n2 TS in FIGS. 16B and 16C) and the cyano carbon increases from 2.26 Å in the starting material to 2.51 Å in the TS. The energetic cost of increasing the fulcrum ring (ring D) twist from 16.3° in [7]n0 (Table 4) to 33.2° in CN[7]n4, raising the energy of the starting material, and the diminished bay region strain in the TS state of CN[7]n4 in comparison to its starting material both contributes to the 7.5 kcal/mol decrease in the racemization barrier observed in CN[7]n4 in comparison to [7]n0.

Figure 15:
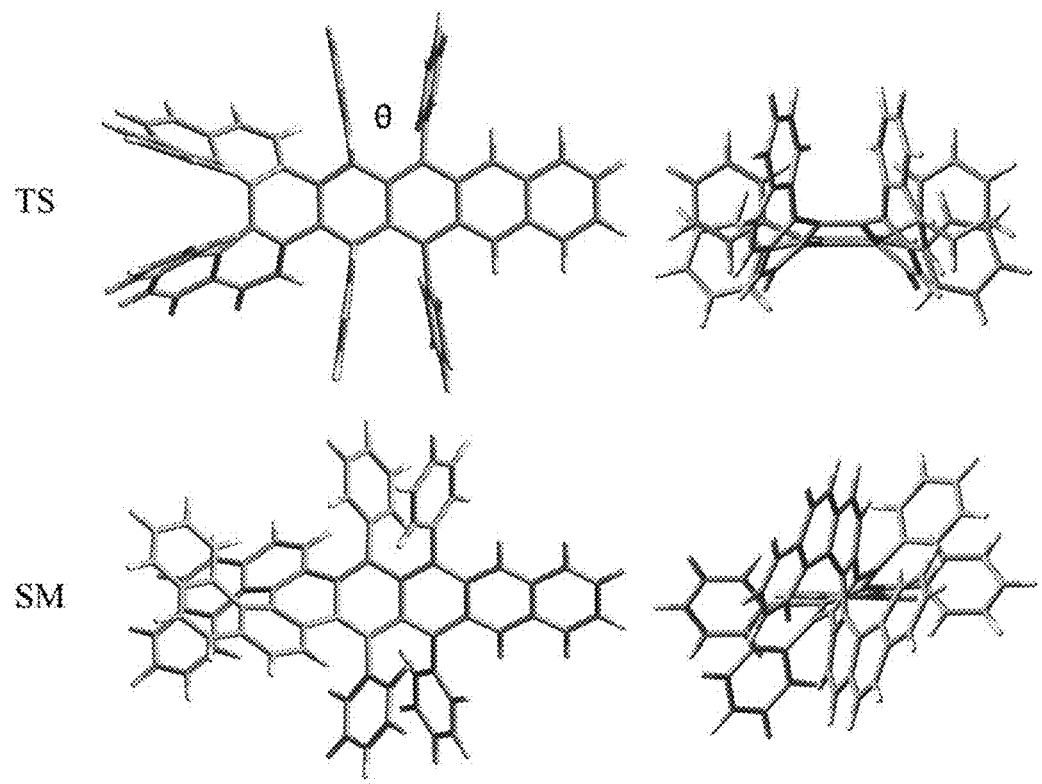
FIG. 15 illustrates the starting material and TS of tetraPh[7]n4 optimized at the B3LYP/6-31G(d) computational level.
Figures 16A, 16B, 16C:
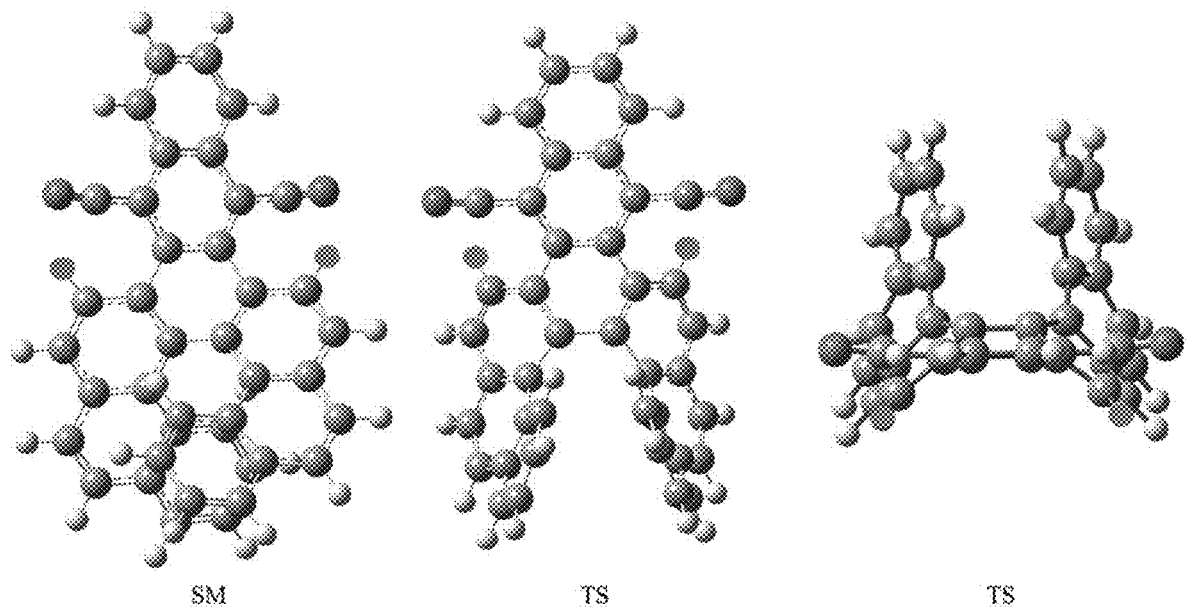
FIGS. 16A-16C show the B3LYP/6-31G(d) minimized structure of CN[7]n2 (16A) and its TS (16B and 16C) with the bay region hydrogens color coded red.

The starting material and TS for racemization of tetraPh[7]n4 are presented in FIG. 15. In contrast to the di-substituted [7]heliacenes, tetraPh[7]n4 has a racemization barrier that is 3.6 kcal/mol higher in energy than that of [7]helicene. This increase appears to be primarily a result of increased cost of the phenyl-phenyl peri-interactions in the TS ($\theta$=34.4°) in comparison to the starting material ($\theta$=40.9°). The peri-interactions in tetraPh[7]n4 TS lead to a boat-cyclohexane-like deformation that forces the peri carbons in ring E 12.7° and in ring F 4.8° out of the plane of the acene. In addition, the 33.4° increase in the twist angle and the 10.6 kcal/mol higher barrier for racemization in tetraPh[7]n4 in comparison to Ph[7]n4 show that the second pair of phenyl groups serves to simultaneously increase the acene twist and to provide additional protection from increases in the rates of racemization.

Figure 17:
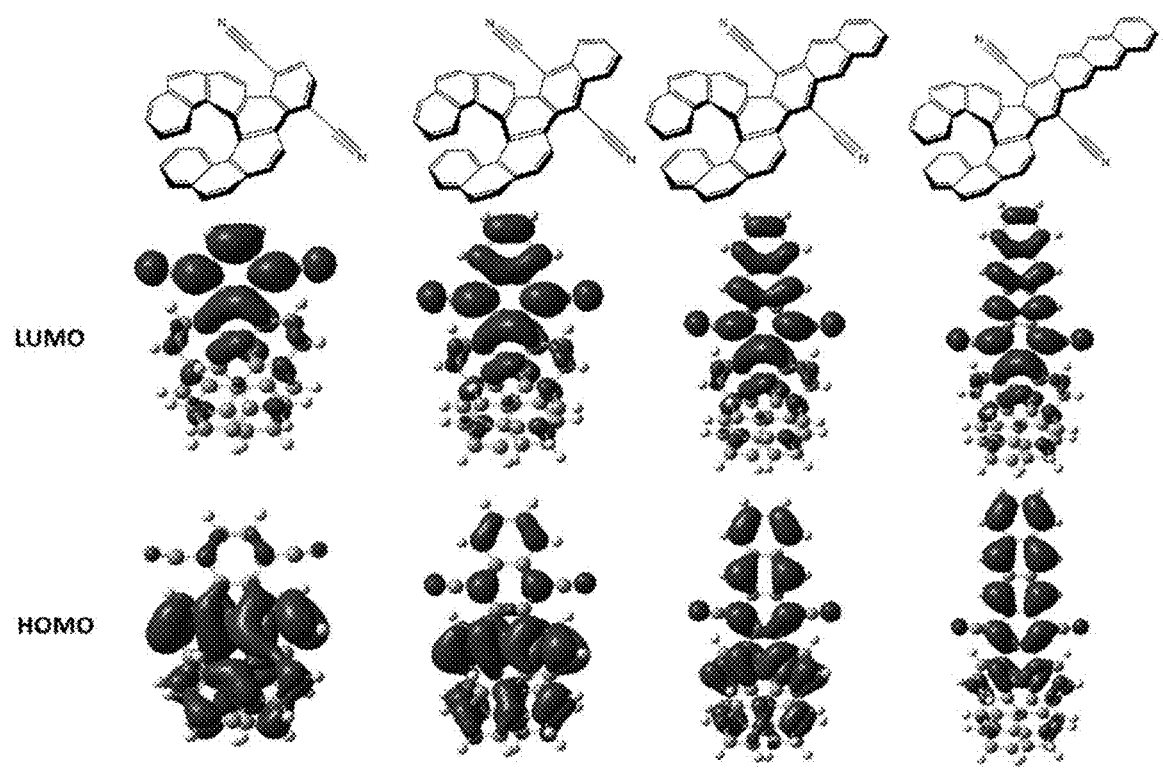
FIG. 17 show HOMOs and LUMOs of the CN[7]Series calculated at the B3LYP/6-311+G(2d,p) computational level.

The geometries of the CN[7]Series were optimized at the B3LYP/6-311+G(2d,p) computational level and population analysis was performed to obtain their orbital energy levels. The HOMOs and LUMOs of these compounds are illustrated in FIG. 17. The band-gap values of the CN[7]Series, [7]Series, and some representative free acenes are graphically represented in FIG. 18.

The CN[7]Series heliacenes have a lower band-gap than their non-cyanated ([7]Series) analogue. This is unexpected since in general the effect of substituting electron-withdrawing groups on aromatic systems is to lower the HOMO and LUMO energy levels, with the HOMO energy level loared to a greater extent. This would cause an increase in the band-gap. However, the opposite effect is observed. This can be explained by realizing that the HOMO and LUMO orbitals in the heliacenes have little spatial overlap which is easily seen by looking at the residency of the HOMOs and LUMOs in the CN[7]series (FIG. 17). The HOMO of CN[7]n1 resides primarily on the helicene, but as the length of the acene is extended, it becomes increasingly localized on the acene domain. In contrast, the LUMO is highly localization on the acene domain for all members of the CN[7]Series. Because the LUMOs reside primarily on the acene domain where the nitrile groups are substituted, their orbital energy levels are loared by the para-cyano groups more compared to the helicene based HOMOs. Consequently, the HOMO energy in CN[7]n1 where the HOMO resides nearly completely on the helicene (FIG. 18) is not perturbed extensively by the cyano-groups while the LUMO energy is loared dramatically leading to a substantial decrease in the band gap in comparison to [7]n1 (a-b=0.56 eV in FIG. 18). At the other end of the series (FIG. 18), in CN[7]n4, the HOMO and LUMO orbitals have nearly perfect spatial overlap. Consequently, the additions of the cyano-groups to [7]n4 perturb the energies of the HOMO and LUMO to nearly the same extent and have a diminished effect on the band gap (c-d=0.2 eV in FIG. 18). It is worth pointing out that the decrease in the disjoint character of the HOMO and LUMO orbitals in CN[7]Series coincides with a decrease in the charge transfer nature of the excited state as depicted in FIG. 17.

Two novel [7]heliacenes, [7]n2 and CN[7]n2, have been successfully synthesized and fully characterized. Single crystal X-ray diffraction was used to unequivocally establish their structures and to provide insight into their geometries. Chiral resolution was performed for CN[7]n2 and its CD spectra and barrier of racemization are measured. Also, the photophysical and electrochemical properties of these compounds were studied.

Figure 18:
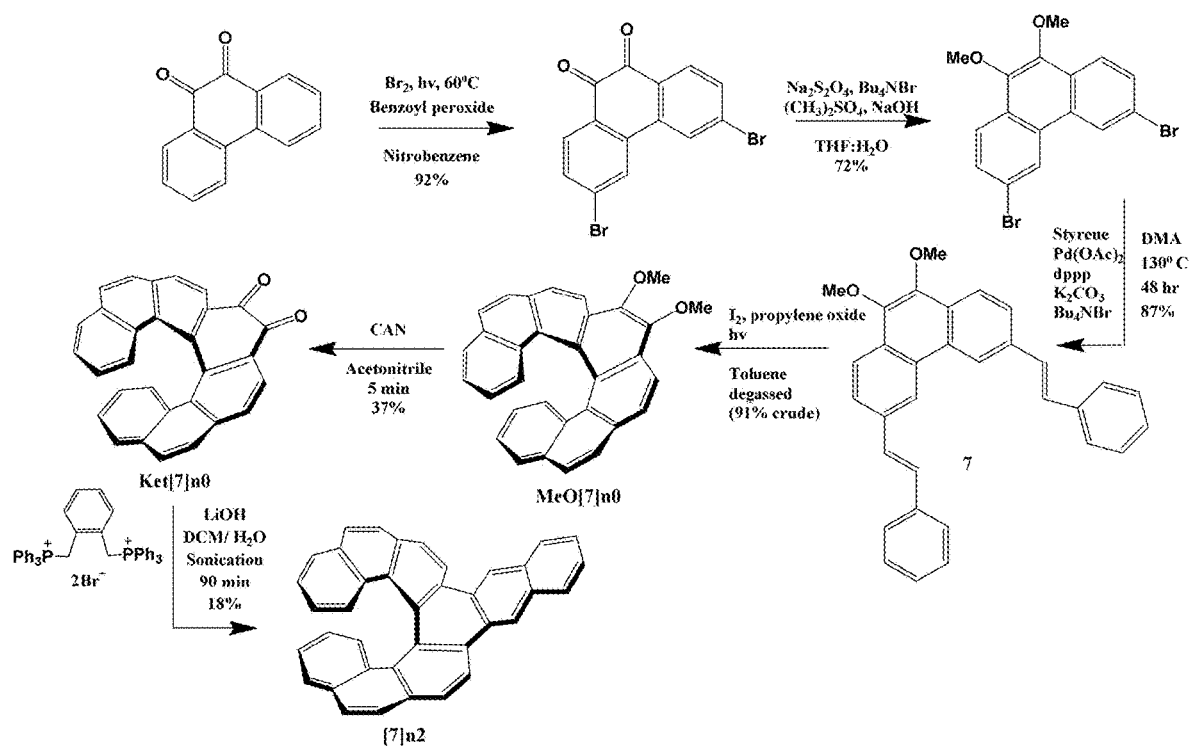
FIG. 18 illustrates an embodiment of a convergent synthetic pathway to [7]n2.

Two different synthetic pathways were devised to make [7]n2. One is a more convergent pathway and is depicted in FIG. 18. It is convergent because intermediate Ket[7]n0 can be converted to several different heliacenes. The other is a more linear approach and is presented in FIG. 20.

The convergent pathway (FIG. 18) began with the radical bromination of phenanthrene quinone to give 3,6-dibromophenanthrene quinone in high yield. This was followed by conversion of the dione to the dimethoxy functionality with dimethylsulfate followed by a Heck coupling to make the bis-styrenyl substrate 7, both in moderate to good yield. Following this, a bis-photocyclization dehydrogenation under Mallory conditions gave the [7]helicene, MeO[7]n0. The dimethoxy functionality was then converted to the dione using a low yielding ceric ammonium nitrate (CAN) oxidation, giving the key intermediate Ket[7]n0. Finally, a sonication assisted bis-Wittig reaction gave the [7]heliacene, [7]n2 in low yield.

Four major problems were encountered during the synthesis of [7]n2 whose solution finally resulted in the partially optimized synthesis shown in FIG. 18. These included: (i) The 9,10-dione analogue of 7 (21) was completely unreactive under the bis-Mallory photocyclization conditions used. This necessitated the replacement of the 9,10-dione functionality with methoxy groups prior to the bis-Mallory step, creating two additional synthetic steps in the final synthetic procedure (FIG. 19) including the low yielding CAN oxidation that reestablishes the 9,10-dione functionality to give Ket[7]n0. (ii) In the Mallory photochemical closure of 7, the mono-closed [5]helicene precursor is susceptible to self-sensitized singlet oxygen formation. Once formed, singlet oxygen cleaves the styrenyl arm of the mono-styrenyl precursor to MeO[7]n0 forming the aldehyde 15b (Chart 2-3) as a major by-product at about 36% relative yield. This problem was easily corrected by careful exclusion of oxygen in the reaction mixture. 15b is a new compound and is fully characterized. (iii) Ket[7]n0 slowly decomposes to the diester, 16, when concentrated in the presence of light. This decomposition is followed via $^1$H NMR as a function of time in ambient light. To minimize this decomposition, Ket[7]n0 was used in its semi-crude state in the CAN oxidation step. (iv) The planar dibenzopentaphene isomer, 12b, is formed as a major by-product in the bis-photocyclization dehydrogenation of substrate 7. However, this is not detrimental to the formation of the [7]helicene, as lower reaction temperatures effectively excludes the formation of 12b. This temperature control of regioisomeric distributions in Mallory photocyclizations is described later in this disclosure.

Figure 19:
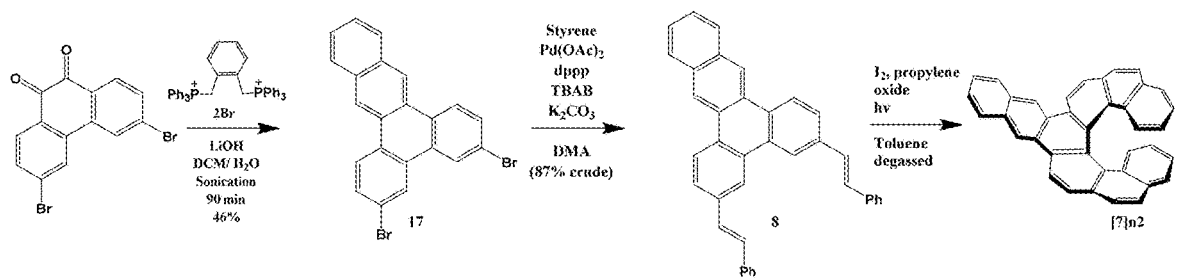
FIG. 19 Illustrates an embodiment of a linear synthetic pathway to [7]n2.

The linear synthetic pathway in FIG. 19 began with the bis-Wittig reaction of 3,6-dibromophenanthrene quinone with o-(bis-triphenylphosphonium)xylene to form 3,6-dibromobenzo[f]tetraphene 17 in 46% yield. This was followed by a Heck coupling to give the bis-styrenyl substrate 8. Finally, irradiation of 8 under Mallory conditions gave [7]n2.

Figure 20:
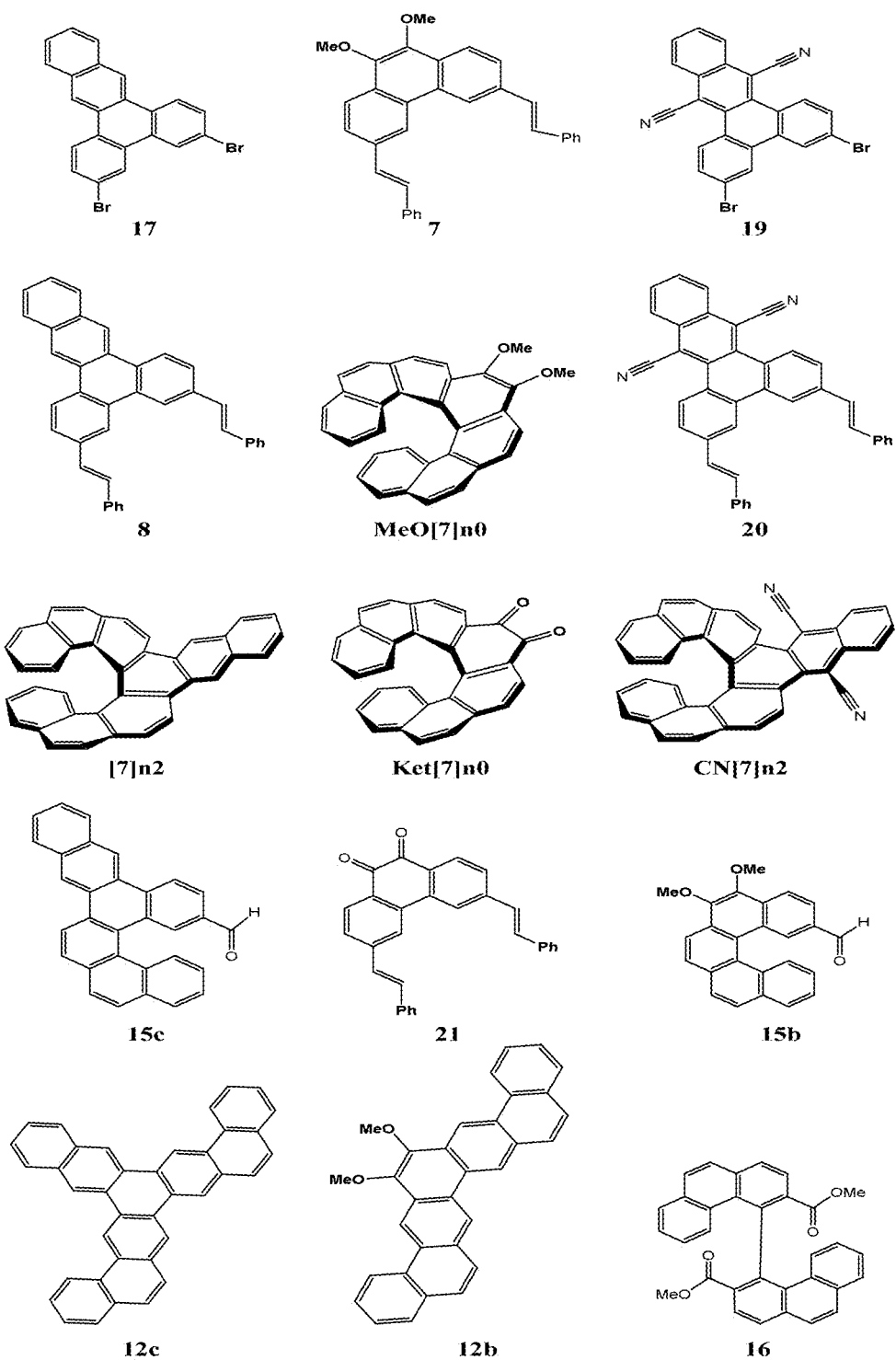
FIG. 20 is a chart showing various compounds referred to in the disclosure.

Two major problems were encountered in the synthetic pathway to [7]n2 presented in FIG. 19. (i) In the bis-Mallory reaction of substrate 8 singlet oxygen was generated forming the aldehyde 15c as a major oxygenated side-product in 42% relative yield. This was corrected by exclusion of oxygen from the reaction mixture prior to irradiation. 15c is a new compound and was fully characterized. (ii) Analytically pure samples of [7]n2 could not be obtained. This is due to the formation of the planar regio-isomeric by-product 12c. Despite best efforts, a trace amount of this compound would always accompany [7]n2, even after flash column chromatography. However, as discussed in further below in this disclosure, running the Mallory reaction at reduced temperatures prevents formation of 12c (FIG. 20). FIG. 20, despite its linear construction, is an attractive pathway for the formation of [7]n2, because it is two steps shorter than that of FIG. 18.

Figure 21:
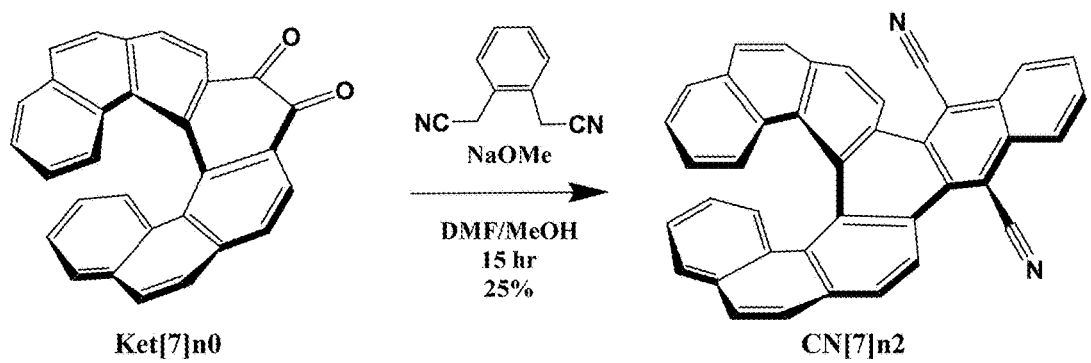
FIG. 21 illustrates an embodiment of synthesis of CN[7]n2.
Figure 22:
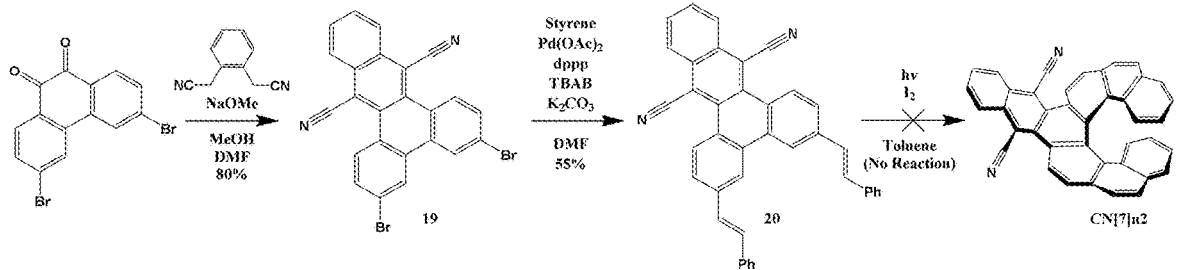
FIG. 22 illustrates an unsuccessful linear synthetic route to CN[7]n2.

CN[7]n2 was successfully synthesized using the reaction presented in FIG. 21. The starting material, Ket[7]n0, was synthesized as shown in FIG. 18. The attempted synthesis of CN[7]n2 via the linear pathway shown in FIG. 22 failed in the final step; the bis-Mallory photocyclization.

The condensation of o-dicyanomethylbenzene with Ket [7]n0 gave CN[7]n2 in 20% yield and in high purity. The reaction conditions for this condensation are not optimized. However, an alternative reaction pathway shown in FIG. 22 was devised to synthesize CN[7]n2. This route began with the condensation of o-dicyanomethylbenzene with 3,6-dibromophenanthrenequinone to give 3,6-dibromo-9,14-dicyanobenzo[f]tetraphene, 19, in good yield. This was followed by a Heck coupling to give the bis-styrenyl substrate 20 in moderate yield. Unfortunately, 20 was completely unreactive under the Mallory reaction conditions. This remained true despite the use of different solvents, reaction temperatures, and a quartz reaction vessel.

Both [7]n2 and CN[7]n2 have been fully characterized by $^1$H, $^{13}$C, proton-COSY, and HMQC NMR spectroscopy and their molecular weight was verified using high resolution mass spectrometry (HRMS). Also, their $^1$H chemical shifts have been calculated at the GIAO B3LYP/6-311+G(2d,p) level using an implicit solvation model with chloroform as the solvent.

Figure 23:
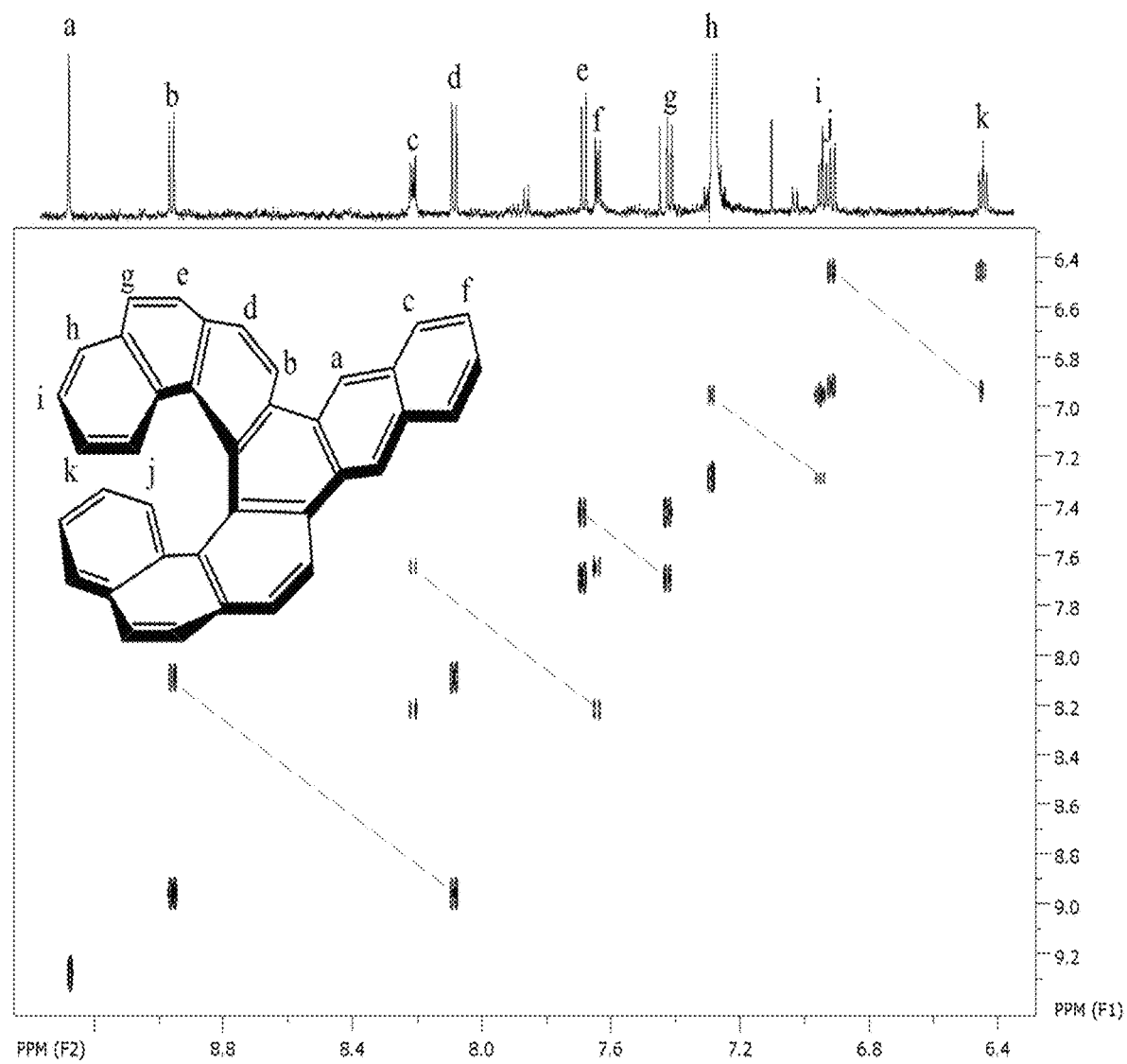
FIG. 23 shows the proton-proton COSY spectrum of [7]n2 with 1D $^1$H proton spectrum on top, and correct assignment of each resonance as indicated by lettering sequence.
Figure 24:
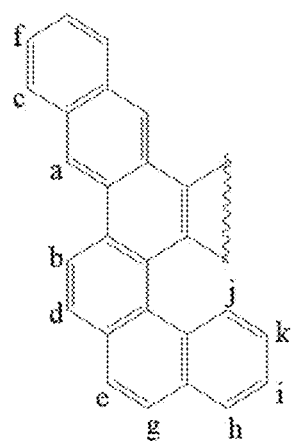
FIG. 24 is a structure that shows the resonance points of a [7]n2 structure with respect to Table 8.
Figure 25:
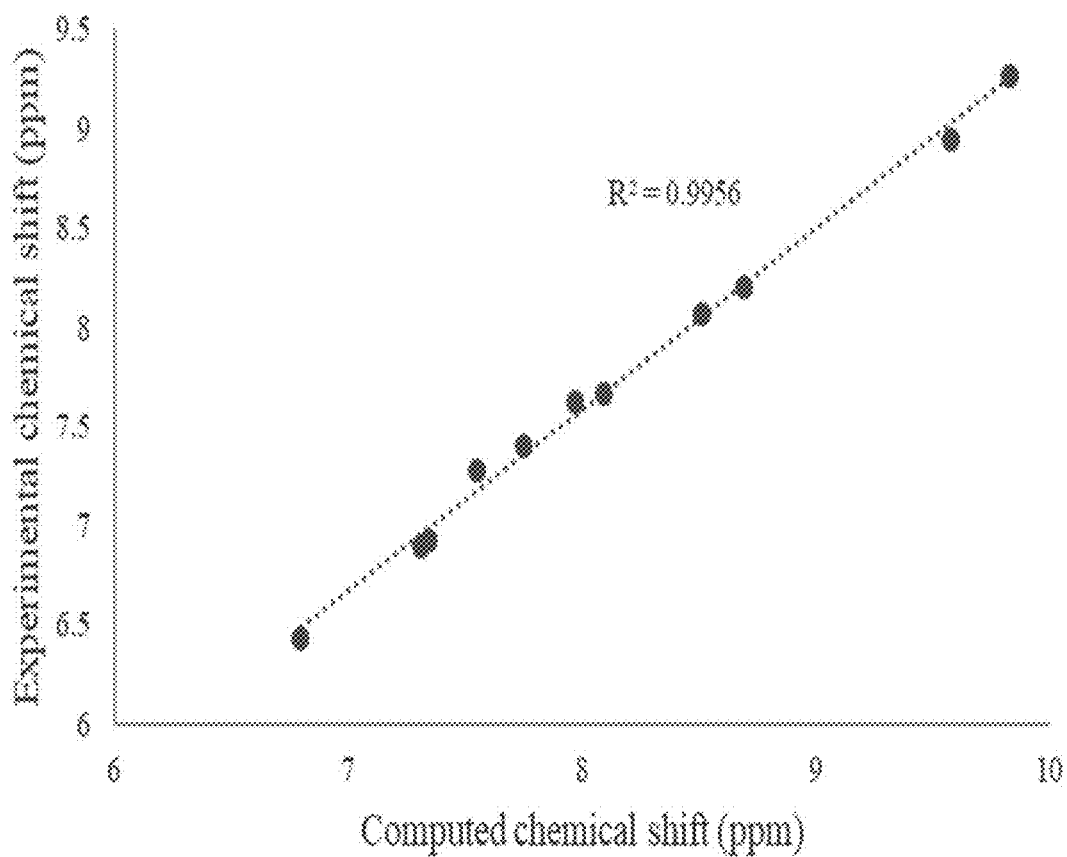
FIG. 25 show a mapping of a [7]n2 structure used to plot the experimental versus calculated chemical shifts shown in Table 8.

With respect to [7]n2, the 2D proton-proton COSY NMR spectrum of [7]n2 with the 1D spectrum overlaid on the F2 axis is presented in FIG. 23. A plot of the experimental versus computed chemical shifts shown in Table 8 for the corresponding [7]n2 structure shown in FIG. 24. An excellent linear correlation is observed ($R^2$=0.9956) although the calculated shifts are 0.43±0.19 ppm downfield of the experimental values.

TABLE 8

Experimental and calculated $^1$H chemical shifts of [7]n2.

| | $^1$H NMR chemical shifts | |
| --- | --- | --- |
| Resonance | Calculated* | Experimental |
| a | 9.83 | 9.27 |
| b | 9.57 | 8.95 |
| c | 8.69 | 8.20 |
| d | 8.51 | 8.07 |
| e | 8.09 | 7.67 |
| f | 7.97 | 7.62 |
| g | 7.75 | 7.40 |
| h | 7.55 | 7.77 |
| i | 7.34 | 6.93 |
| j | 7.31 | 6.89 |
| k | 6.80 | 6.43 |

*GIAO method at the B3LYP/6-311 + G(2d,p) level of theory, using an implicit solvation model for chloroform.

While resonances a, b, d, h, i, j, and k of [7]n2 could be assigned using the COSY spectrum in FIG. 23, the computational data in Table 8 is required to assign resonances c, e, f, and g unambiguously. In [7]n2, protons a and b are the most downfield resonances, while resonances i, j, and k are the most upfield. These groups of resonances with aberrant chemical shifts are the result of two distinct structural features of the [7]heliacenes. The first is the bay regions at the helicene acene junction. Steric compression of protons a and b in this region deshields these protons so that they appear 1.24 ppm and 0.88 ppm downfield of the chemical shift for proton c, respectively. The second unique structural feature of the heliacene, [7]n2 is the cofacial interaction between the two terminal helicene rings (rings A and A', FIG. 5A). In this "pi-sandwich" region, resonances h, i, and j reside in a shielding cone generated by the opposite cofacial ring. This causes these resonances to be uniquely up-field of the residual chloroform solvent signal (See $^1$H NMR spectrum in FIG. 23). The chemical shift assignments are also corroborated by their observed multiplicities. (FIG. 23)

Figure 26:
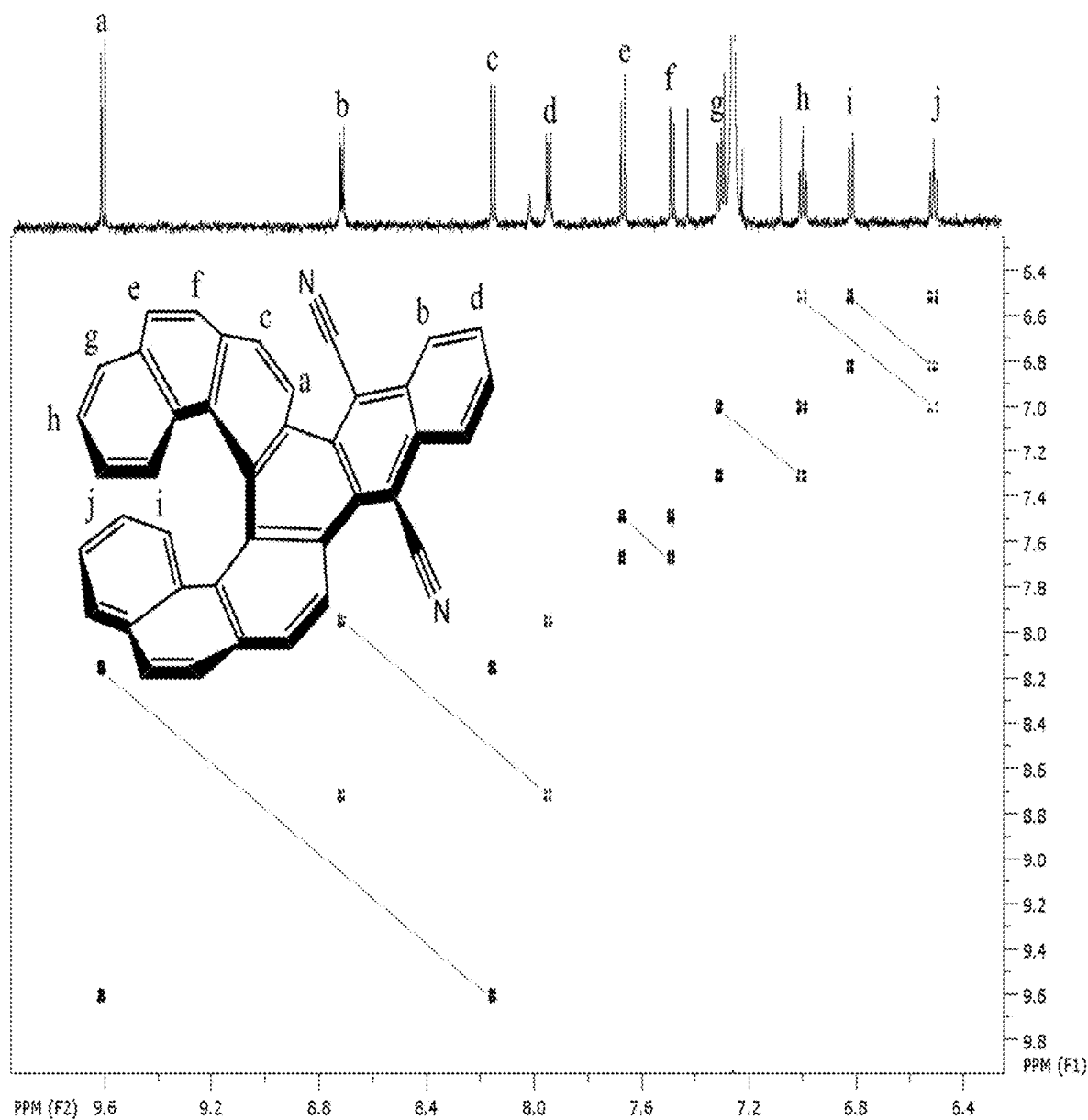
FIG. 26 shows the proton-proton COSY spectrum of CN[7]n2 with 1D $^1$H proton spectrum on top.
Figure 28:
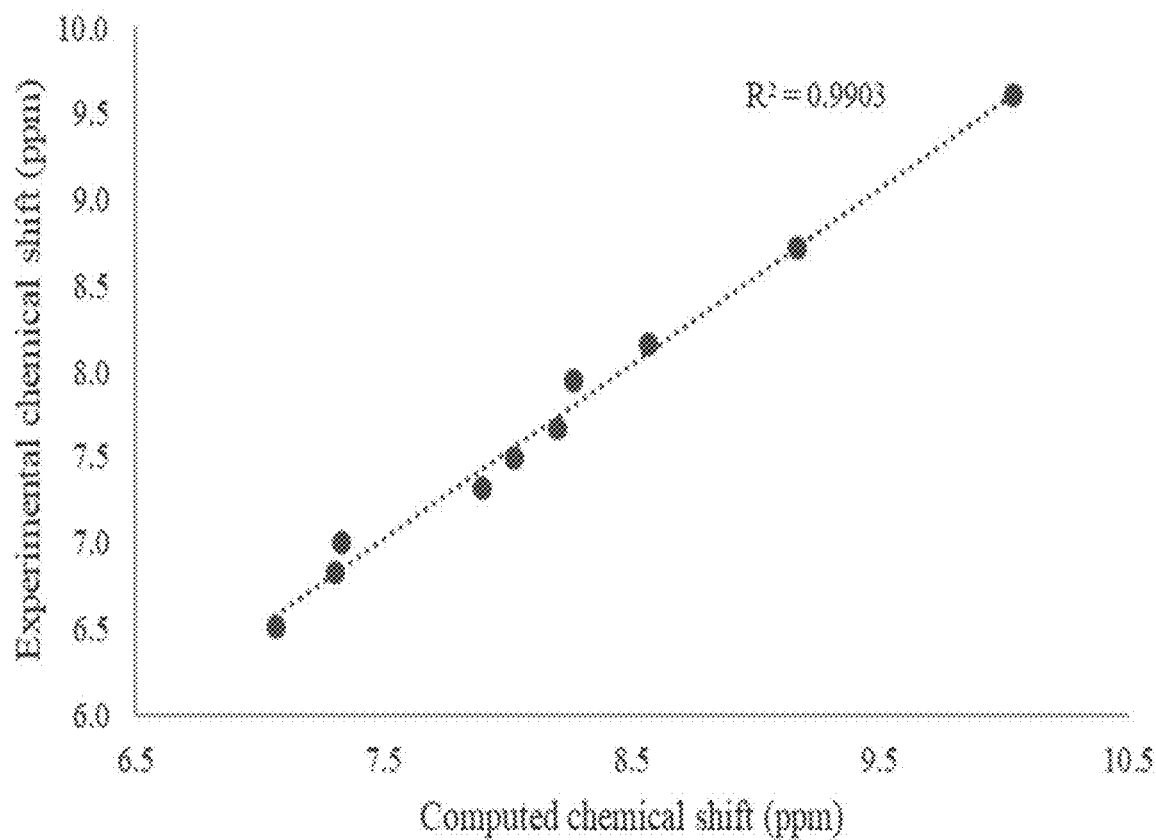
FIG. 28 show a mapping of a CN[7]n2 structure used to plot the experimental versus calculated chemical shifts shown in Table 9.

The 2D proton-proton COSY NMR spectrum of CN[7]n2 with the 1D $^1$H spectrum overlaid on the F2 axis is presented in FIG. 26. The calculated and experimentally determined chemical shifts are listed in Table 9 and a plot of the experimental values versus computational values is presented in FIG. 28. An excellent linear correlation is observed ($R^2$=0.9903) although the calculated shifts are 0.46±0.15 ppm downfield of the experimental values.

TABLE 9

Experimental and calculated $^1$H chemical shifts of CN[7]n2.

| | $^1$H NMR chemical shifts | |
| --- | --- | --- |
| Res:0mlice | Calculated | Experimental |
| a | 10.03 | 9.61 |
| b | 9.16 | 8.72 |
| c | 8.56 | 8.16 |
| d | 8.26 | 7.95 |
| e | 8.20 | 7.67 |
| f | 8.03 | 7.49 |
| g | 7.90 | 7.31 |
| h | 7.33 | 7.00 |
| i | 7.30 | 6.87 |
| j | 7.06 | 6.51 |

*Calculated using the GIAO method at the B3LYP/6-311 + G(2d,p) computational level, with an implicit solvation model for chloroform.

Figure 27:
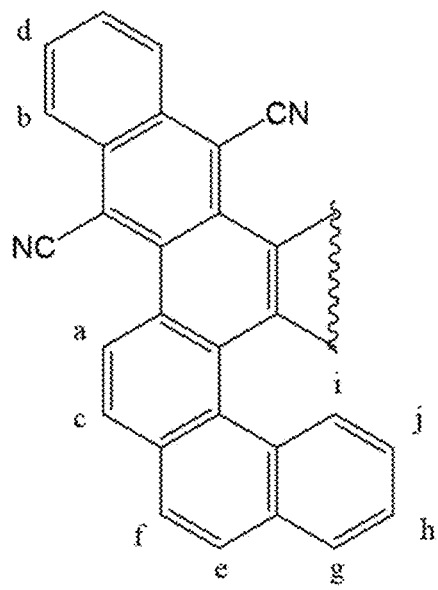
FIG. 27 is a structure that shows the resonance points of a CN[7]n2 structure with respect to Table 9.

The dual bay region and cofacial ring structural features in [7]n2 are also present in CN[7]n2 and consequently, the characteristic sets of protons responsible for the most downfield and upfield in [7]n2 are also found in CN[7]n2. (FIG. 27) In CN[7]n2 steric interactions between hydrogen b and the cyano carbon induce a 0.66 ppm downfield chemical shift in comparison to the analogous proton in [7]n2. This makes resonance b easily distinguishable from resonance d. Resonances e and f in CN[7]n2 are assigned with the assistance of the computational data shown in FIG. 28.

The unique/diagnostic up-field chemical shifts of hydrogens $H_1$, $H_2$, and $H_3$ in [7]n2 and CN[7]n2 provide an opportunity to use them to detect formation of other helicenes in complicated reaction mixtures. The ability of these resonances to function as indicators of [7]heliacene formation in the presence of starting material and other potential product found in a reaction mixture is illustrated by the stacked comparator $^1$H NMR plots for [7]n2 and CN[7]n2, respectively. These plots compare the $^1$H NMR spectra of [7]n2 and CN[7]n2 (top spectra) to their corresponding non-closed bis-styrenyl (middle spectra), and their nonstyrenylated (bottom spectra) precursors. The absence of [7]helicene functionality in 8, 17, 19, and 20 puts all of their chemical shifts up-field of the residual chloroform solvent peak. This leaves the unique up-field chemical shifts of $H_1$, $H_2$, and $H_3$ with their distinct splitting patterns in [7]n2 and CN[7]n2 as quick indicators of their presence, even in complex reaction mixtures. These diagnostic peaks are paramount to the analysis of the Mallory reaction for several species containing a [7]helicene structural domain.

Stacked comparator $^1$H NMR plots of CN[7]n2 (top), 9,14-dicyano-3,6-bis-styrylbenzo[f]tetraphene (20, middle), and 3,6-dibromo-9,14-dicyanobenzo[f]tetraphene (19, bottom). Diagnostic peaks of CN[7]n2 are indicated by *'s.

Figure 29A:
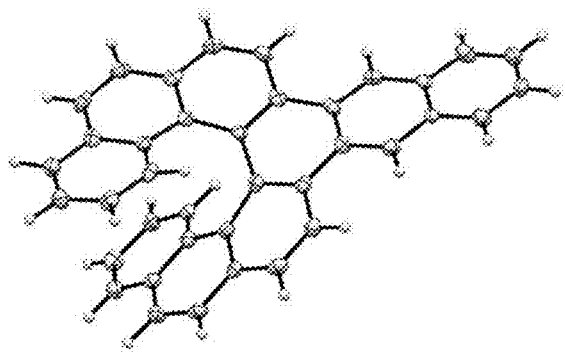
FIGS. 29A and 29B illustrates X-ray ORTEP representations of [7]n2 and CN[7]n2, respectively, at 50% thermal ellipsoid probability, and below each structure is a representative crystal from the batch of crystals that provided the X-ray diffraction results.
Figure 29B:
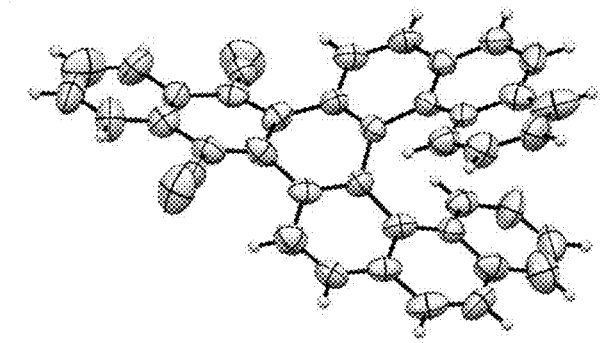

The structures of [7]n2 and CN[7]n2 were unambiguously elucidated through single crystal X-ray diffraction experiments. The X-ray ORTEP representations of each compound at 50% thermal ellipsoid probability are presented in FIGS. 29A and 29B, respectively.

Figure 30A:
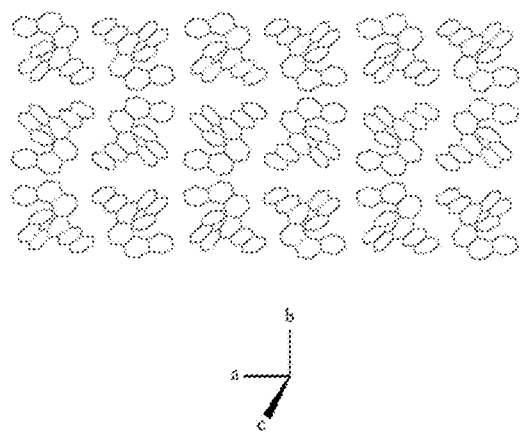
FIGS. 30A and 30B provide wire-frame depictions of the crystal lattice of [7]n2 viewed along the c-axis and the a-axis, respectively, and hydrogens are removed for clarity.
Figure 30B:
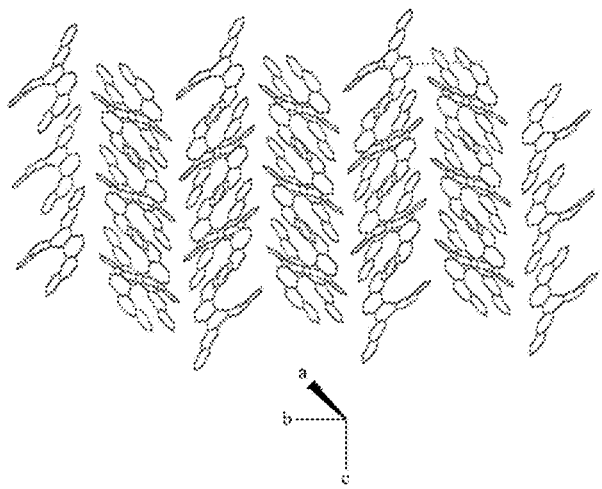

Yellow X-ray grade hexagonal prisms of [7]n2 (FIG. 29A, bottom) were grown from slow diffusion of EtOH into a solution of the [7]heliacene in toluene. These crystals are racemic, constructed by the self-assembly of [7]n2 into helical columns of each enantiomer. This generated a checker-board pattern of each enantiomer seen viewing the lattice down the c-axis in FIGS. 30A and 30B. In this figure, the P and M enantiomers are color coded green and red, respectively. These structures are tightly packed as evident by the space-fill view of the lattice along the c-axis, which also shows that no toluene co-crystallized with the [7]heliacene.

The closest approach distance between two molecules in the crystal lattice of [7]n2 is formed between two structures of the same configuration in the same column. The closest pi-stacking interaction for this approach is between ring A in one structure and ring E in the other, with a distance of 3.77 Å taken as the average distance between each heavy atom in ring A with the corresponding heavy atoms in ring E.

Orange X-ray grade rectangular crystals of CN[7]n2 (FIG. 29B) were grown from slow diffusion of EtOH into a solution of the [7]heliacene in $C_2D_2Cl_4$. The corresponding crystal lattice obtained through an X-ray diffraction experiment is generated. This lattice consists of alternating enantiomeric P/M sheets of CN[7]n2. The solvent, $C_2D_2Cl_4$, fills the void space between the helical jaws of two enantiomeric pairs in neighboring layers.

The closest approach distance between two CN[7]n2 molecules in its crystal lattice is between two structures of opposite configuration in neighboring sheets. The pi-stacking distance for this approach is achieved between helical ring B and acene ring E at 3.68 Å, taken as the average distance between heavy atoms in ring B and the corresponding heavy atoms in ring E.

The geometric parameters of [7]n2 and CN[7]n2 measured from their crystal structures are collected in Table 10 along with the experimental geometric parameters of [7]helicene ([7]n0) measured from data obtained by Fuchter.[43]

The acene twist of the embedded anthracene in [7]n2 is 32.5°. This twist is distributed in rings D, E, and F that have 23.5°, 6.1°, and 2.7° twists, respectfully. Despite having a helical core dihedral angle that is 5.1° greater in magnitude than that of [7]n0, [7]n2 has a helical pitch that is 0.12 Å less than [7]helicene. This is due to tighter packing in the crystal structure of [7]n2 compared to [7]n0. Alternatively, gas phase calculations predict that [7]n2 has a helical pitch that is 0.17 Å greater than that of [7]n0, while maintaining helical core dihedral angles that are about the same as found in the crystal structures (Table 1). This further exemplifies the geometric perturbations that can arise in these helical species due to crystallographic packing forces.

The acene twist of the embedded anthracene in CN[7]n2 is 38.0° distributed throughout the acene domain by twists of 28.8°, 10.5°, and −1.1° in rings D, E, and F, respectively. CN[7]n2 has a helical core dihedral angle and helical pitch that are 10.10 and 0.45 Å greater in magnitude compared to [7]n0.

The differences between the X-ray structural features of [7]n2 and CN[7]n2 are due to greater steric interactions between the helicene and acene domains of CN[7]n2, brought on by the bulk of the bay-region cyano groups. This increases the acene twist of CN[7]n2 by 5.5° compared to [7]n2, and also opens the helical jaws of CN[7]n2 relative to [7]n2 with a helical pitch and helical core dihedral angle that are 0.57 Å and 5.0° greater in magnitude, respectively.

Although crystallographic data is in accordance with the general findings of the calculated geometries of [7]n2 and CN[7]n2, there are some discrepancies between the theoretical and experimental structures. This is illustrated by the superposition of the X-ray crystal and B3LYP/6-311+G(2d, p) calculated structures of [7]n2 and CN[7]n2 in FIG. 31 and FIG. 32, respectively. The calculated and crystal structures are represented as red and green structures, respectively.

Figure 31:
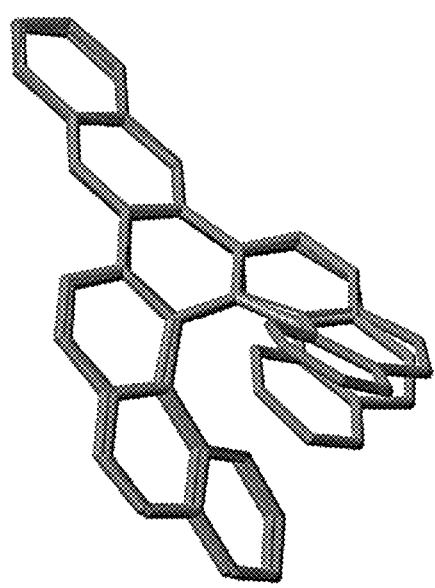
FIG. 31 depicts B3LYP/6-311+G(2d,p) calculated geometry and the crystal structure of [7]n2 with hydrogens omitted for clarity.
Figure 32:
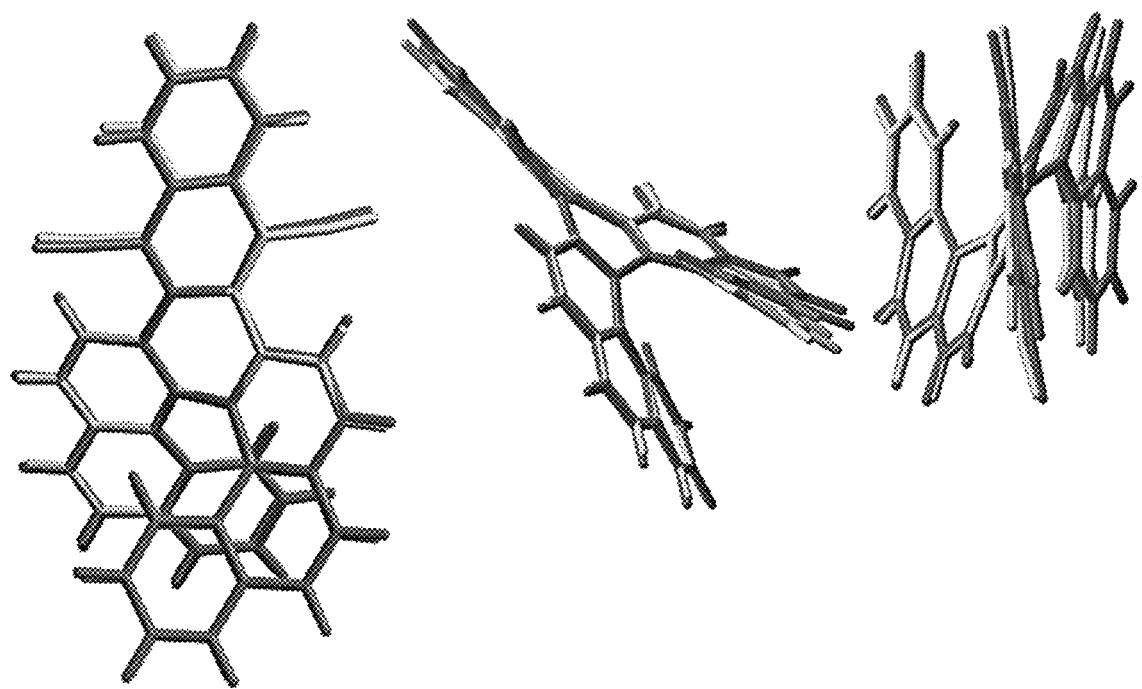
FIG. 32 depicts B3LYP/6-311+G(2d,p) calculated geometry and the crystal structure of CN[7]n2.

For the most part, the experimental structures of [7]n2 and CN[7]n2 were closely predicted by calculation, other than a grievous overestimate of the helical pitch of [7]n2 (FIG. 31). Another notable deficiency in the calculated structures is the under and over estimation of the acene twist angles of [7]n2 (24.6°, calculated; 32.5°, crystal) and CN[7]n2 (46.2°, calculated; 38.0°, crystal), respectively. These deviations are due to differences in crystal packing forces in the X-ray structures compared to calculations made in the gas phase.

CN[7]n2 is subjected to chiral HPLC on a Lux i-Cellulose-5 column to obtain enantiopure samples of (P)-(+)-CN7n2 and (M)-(−)-CN7n2. The carrier solvent is 100% acetonitrile at a flow rate of 1 ml/min. UV/Vis spectroscopy is used as the detection method, monitored at 360 nm. A resulting chromatogram of CN[7]n2 under these conditions is presented in FIG. 33. Each peak is collected and circular dichroism (CD) spectra are measured for each eluent. These spectra are presented in FIG. 34 along with the normalized UV-vis spectrum of the second eluent for comparison. The samples that produced these CD spectra are reinjected onto the chiral column, giving the chromatograms presented in

TABLE 10

| | Helical pitch (Å) | Helical core dihedral | Acene twist | Ring twist (D) | Ring twist (E) | Ring twist (F) | [7]Helicene configuration | Twisted acene configuration |
|---|---|---|---|---|---|---|---|---|
| [7]n2 | 4.02 | −29.5° | −32.5° | 23.5° | 6.1° | 2.7° | M | P |
| CN[7]n2 | 4.59 | −34.5° | −38.0° | 28.8° | 10.5° | −1.1° | M | P |
| [7]n0* | 4.14 | −24.4° | NA | 15.4° | NA | NA | M | NA |

*Geometric parameters measured from crystallographic data obtained by Fuchter.[43]

Figure 35:
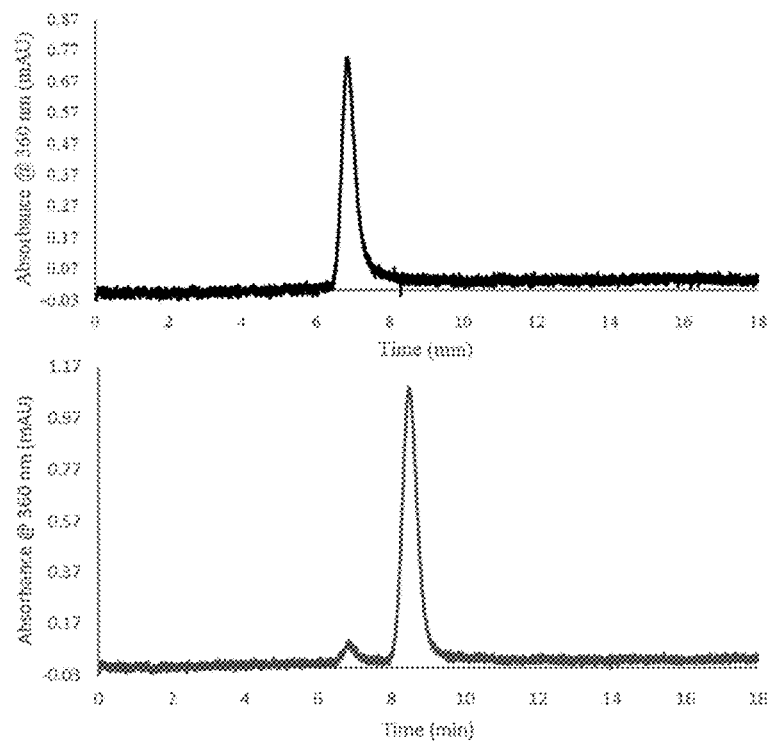
FIG. 35 shows HPLC chromatograms of the samples that produced the CD spectra in FIG. 4, where the color of each chromatogram correlates to the color of the CD spectrum that is produced by the injected sample.

FIG. 35. The units that make up the y-axis of the CD spectra in FIG. 33 (θ(mdeg)) can be related to the difference in absorbance of left ($A_l$) and right ($A_r$) circularly polarized light by the following equation EQ (1):

$$\theta(\deg) = \frac{(180\ln 10)\Delta A}{4\pi} \quad \text{EQ (1)}$$

The absorbance term follows Beer's law, Where ΔA (absorbance units)=$A_l-A_r$=(Δε)1c and Δε is the difference in the extinction coefficient for left and right circularly polarized light, and 1 and c are the path length and concentration, respectively.

Figure 34:
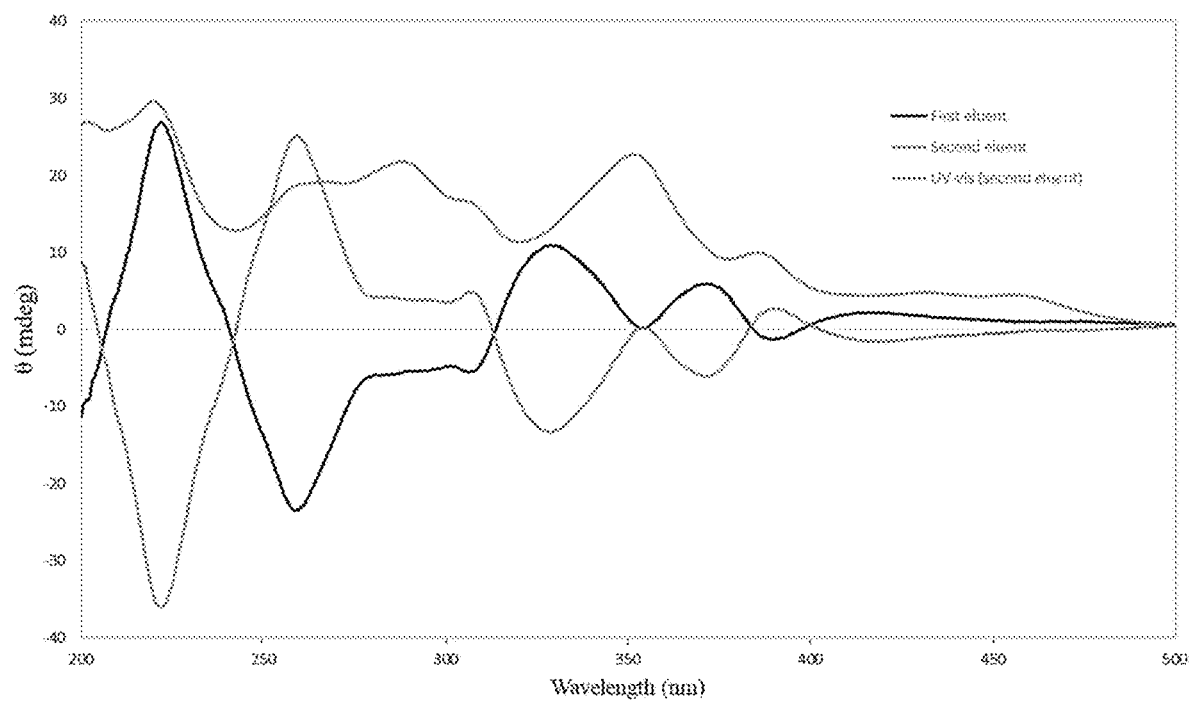
FIG. 34 shows a circular dichroism (CD) spectra of CN[7]n2.

Under the HPLC conditions the first eluent of CN[7]n2 began to come off the column at 6.15 minutes, with a base peak width of about 1 minute. The second eluent began to come off the column at 8 minutes, also with a base peak width of about 1 minute. The peak areas of the two enantiomers of CN[7]n2 in FIG. 34 are 5.17 mAU*min and 5.57 mAU*min for the first and second eluents, respectively. This is consistent with the resolution of a racemic mixture of CN[7]n2. Slight tailing of the first eluent is probably responsible for the 0.4 mAU*min difference in area between the two peaks.

Figure 33:
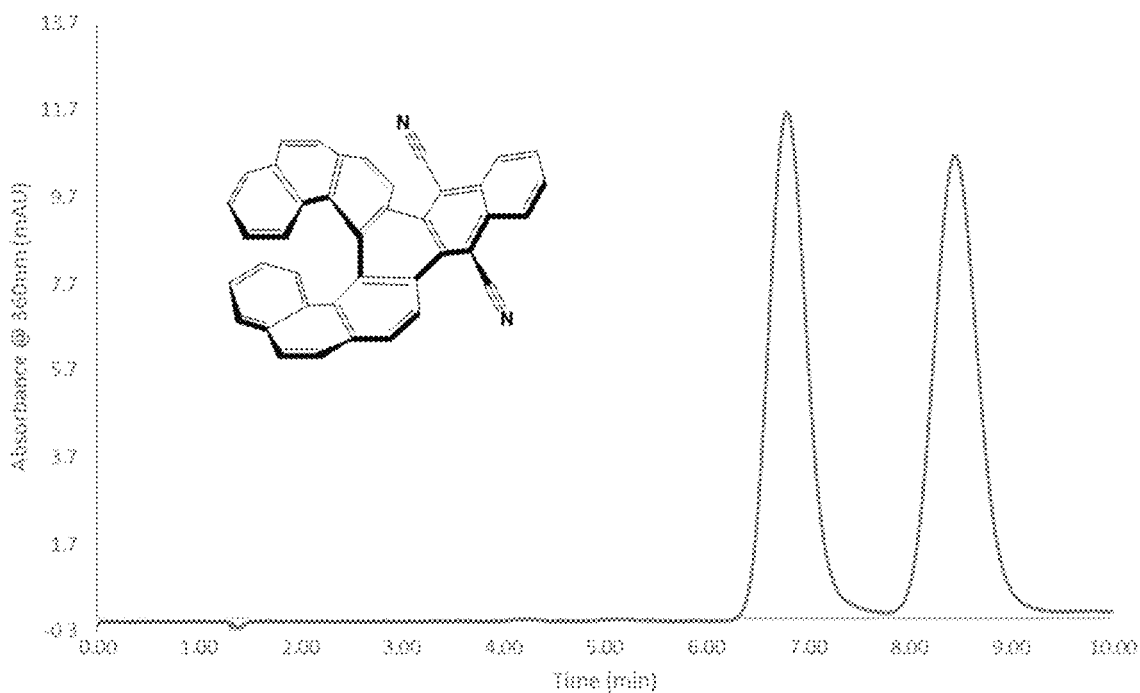
FIG. 33 is a HPLC chromatogram of CN[7]n2 showing chiral resolution, solvent: 100% acetonitrile, flow rate: 1 ml/min, injection volume: 5 µL of a saturated solution of CN[7]n2 in DCM, detection wavelength: 360 nm.

The CD spectra in FIG. 33 of the first and second eluents of the chiral resolution of CN[7]n2 are represented in black and blue, respectively. Two conclusions can be made based on these spectra:(i) The compounds that generated them are optically active, and (ii) they are enantiomers of one another, as evident by the mirror image nature of the spectra about the y=0 axis. Without further data, information like the assignment of each CD spectrum to an absolute configuration of CN[7]n2 is not possible. Fortunately, theoretical and experimental data for carbo[n]helicenes have been compiled, shedding light on some common trends in the CD spectra of these species.[58] A unique feature of the CD spectra of all carbohelicenes is a strong bisignate (change of sign within the peak/band) Cotton effect (CE) between 250-300 nm and 300-400 nm. The sign of these bisignate CEs can be used as a tool to assign the absolute configuration of the helicenes.[58] The (P)-(+) configuration of [5]helicene through [9]helicene is found to produce negative CEs between 250-300 nm and positive CEs between 300-400 nm. The first eluent of CN[7]n2 has a strong negative CE between 240-310 nm and several weaker bands which appear positive between 315-380 nm. Reinjection of the resolved enantiomers of CN[7]n2 (FIG. 35) demonstrated that (P)-(+)-CN[7]n2 is very pure (FIG. 35, top) but that the (P)-(+)-CN[7]n2 is contaminated with a trace amount of the first eluent (FIG. 35, bottom) due to a tailing first peak. Consequently, the configuration of the first eluent can be assigned as (P)-(+)-CN7n2, producing the black spectrum in FIG. 34, and the second eluent can be assigned with a moderate level of confidence as (M)-(−)-CN7n2, producing the blue spectrum in FIG. 34. Nevertheless, since the region between approximately 310 and 450 nm is significantly more complicated than observed with the carbo[n]helicenes, these assignments were verified with the computational studies described below.

Figure 36:
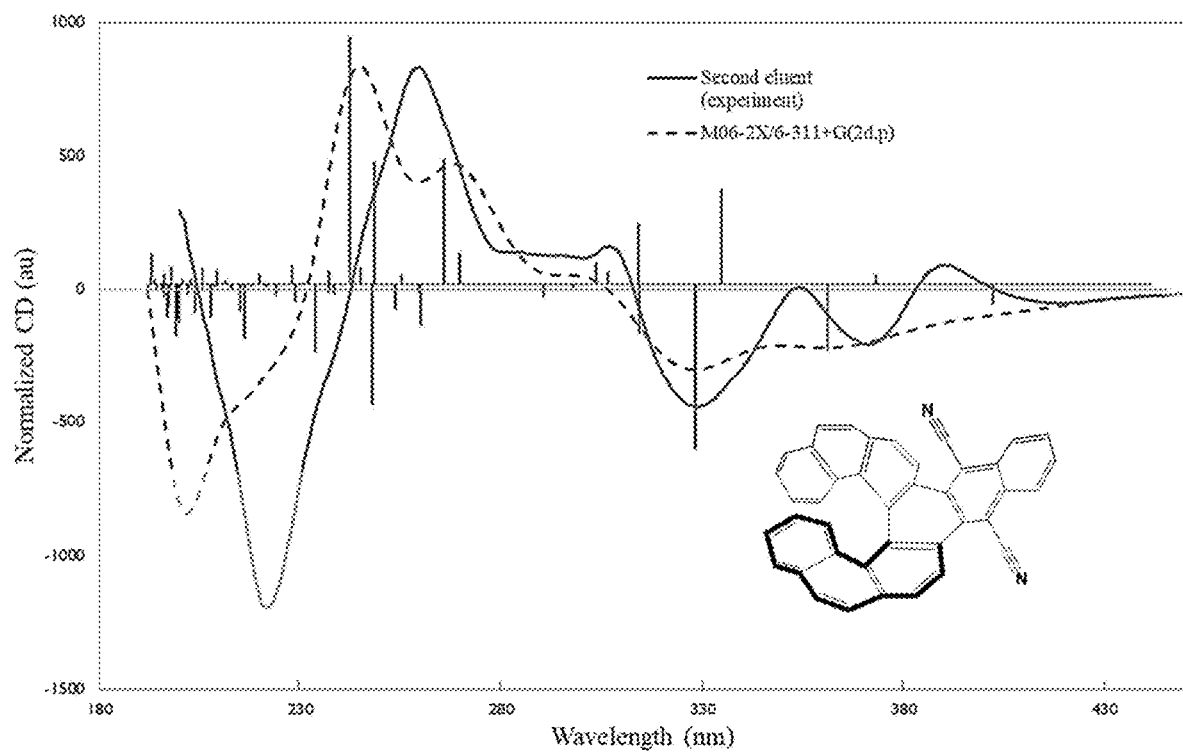
FIG. 36 illustrates experimental and M06-2X/6-311+G (2d,p) ECD spectra of (M)-(−)-CN[7]n2, where the vertical lines are the calculated TD-DFT states.

The electronic circular dichroism (ECD) spectrum of (M)-(−)-CN[7]n2 was calculated using several different functionals and basis sets. All of the calculations produced a reasonable fit to the experimental data for the second eluent in FIG. 34, however, the best fit is obtained using the M06-2X functional in conjunction with the 6-311+G(2d,p) basis set as shown in FIG. 36. The theoretical CD spectrum is produced by fitting the calculated TD-DFT states using the wavefunction analyzer software Multiwfn.[45]

The calculation shown in FIG. 36 provides a compelling case that the second eluent (blue CD spectrum, FIG. 33) is the (M)-CN[7]n2 enantiomer and that the first eluent (black CD spectrum) is the (P)-CN[7]n2 enantiomer. However, the calculation does not confirm that the rotation of the P enantiomer is (+) and the M enantiomer is (−) as is consistently observed in carbo[n]helicenes.

Figure 37:
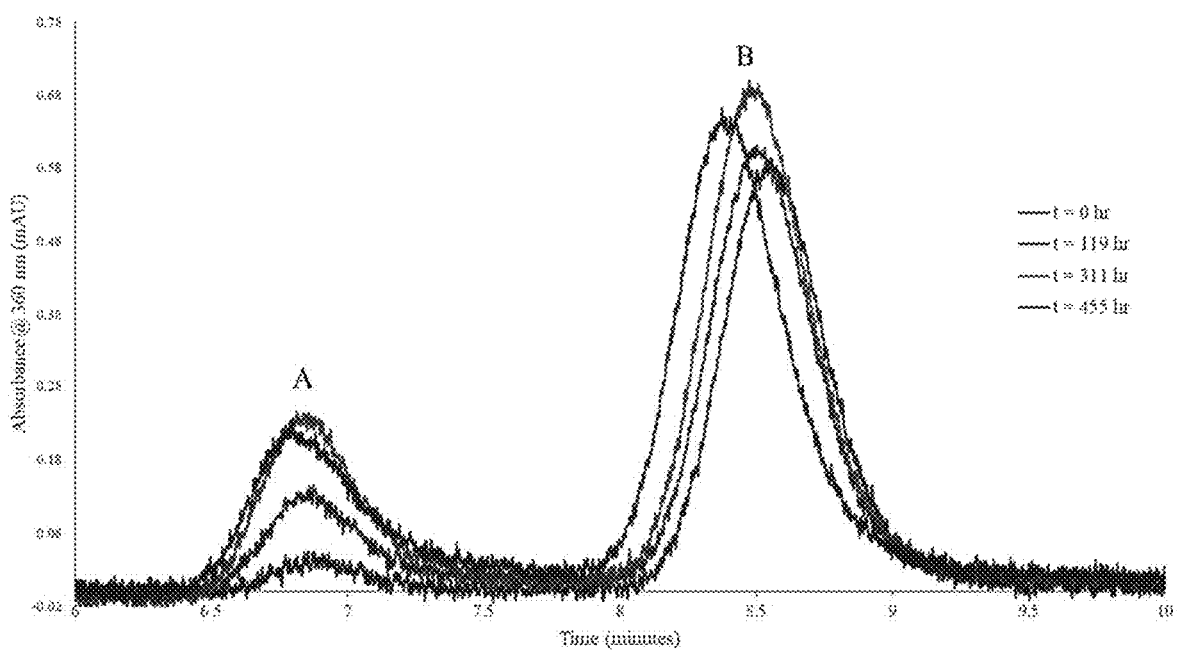
FIG. 37 shows chromatograms of 100 µL aliquots of an optically active sample of CN[7]n2 taken after heating in a 115° oil bath for 0, 119, 311, and 455 hours.
Figure 38:
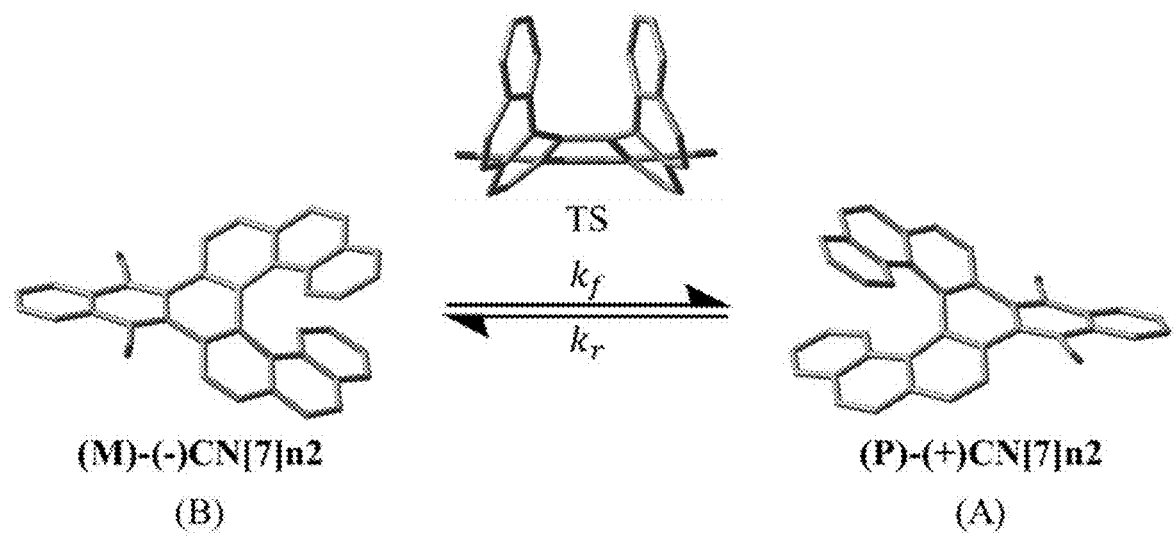
FIG. 38 illustrates the process of reversible interconversion of (M)-(−)-CN[7]n2 to (P)-(+)-CN[7]n2.

A sample containing 94% (M)-(−)-CN[7]n2 and 6% (P)-(+)-CN[7]n2 in acetonitrile was heated at 115° C. for several weeks in a pressure vessel. 100 μL aliquots of this sample were subjected to chiral chromatography after heating for 0, 119, 311, and 455 hours. An overlay of these chromatograms are presented in FIG. 37. Relative concentrations of the first (A) and second (B) eluents are obtained through the integration of these plots under the respective peaks. These values are listed in Table 11, using an arbitrarily chosen combined (A+B) concentration of 1.

TABLE 11

Relative concentrations of (P)-(+)-CN[7]n2 (A) and (M)-(−)-CN[7]n2 (B) at different time intervals at 115° C. in a pressure vessel. Calculated using the area under peaks A and B in the chromatograms of FIG. 37.

| time (hours) | [A] | [B] |
|---|---|---|
| 0 | 0.06 | 0.94 |
| 119 | 0.18 | 0.82 |
| 311 | 0.24 | 0.76 |
| 455 | 0.26 | 0.74 |

Figure 45:
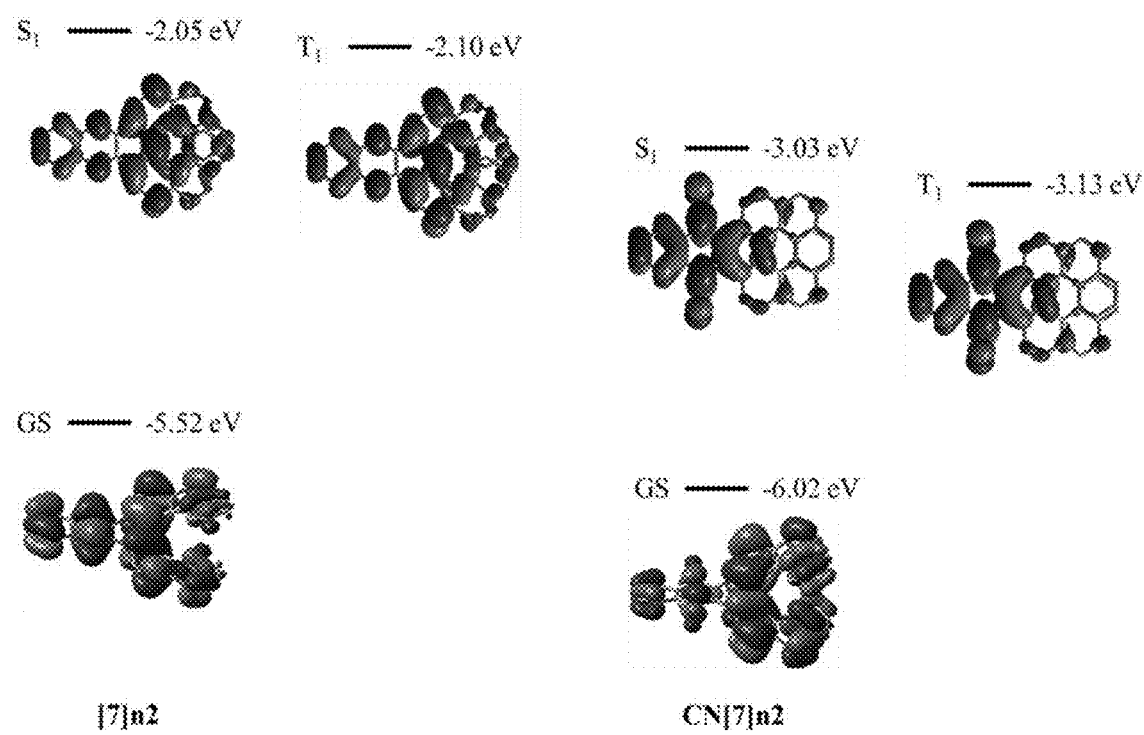
FIG. 45 is an orbital correlation diagram comparing the ground (GS), first excited singlet ($S_1$), and first excited triplet ($T_1$) states, as well as orbitals obtained through single point energy calculations performed on the corresponding optimized state at the B3LYP/6-31G(d) computational level.
Figure 46:
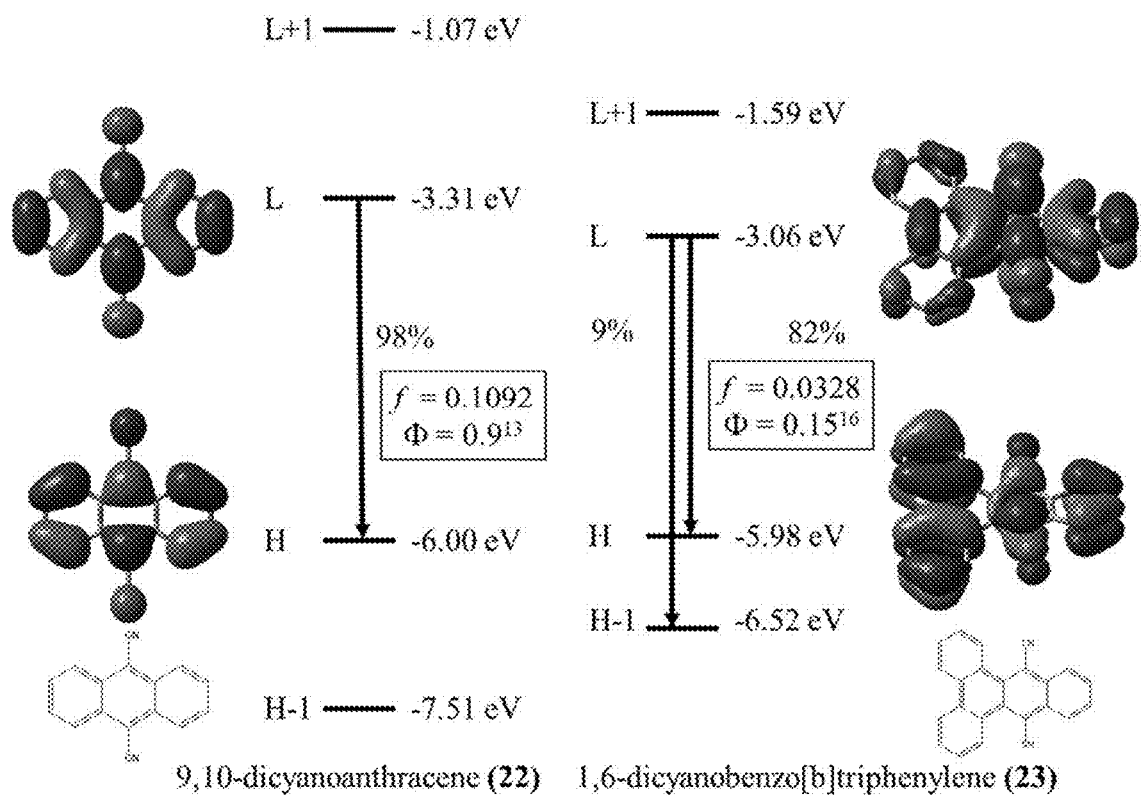
FIG. 46 is an orbital correlation diagram and composition of the $S_1 \rightarrow S_0$ transition for 9,10-dicyanoanthracene and 1,6-dicyanobenzo[b]triphenylene calculated at the RTD-B3LYP/6-31G(d) level of theory.

The data shown in Table 11 provided insight into the dynamic racemization process shown in FIG. 45, where (M)-(−)CN[7]n2 (B, second eluent) interconverts via the saddle-like TS to (P)-(+)CN[7]n2 (A, first eluent). This is a first-order equilibrium process. It is important to note that the dynamic interconversion of the twistomer, D/E-CN[7]n2 to CN[7]n2 (FIGS. 13A, 13B) has a prohibitively low barrier (≈0.5 kcal/mol, B3LYP/6-31G(d)) and can't possibly be the source of the data in FIG. 37.

Figure 39:
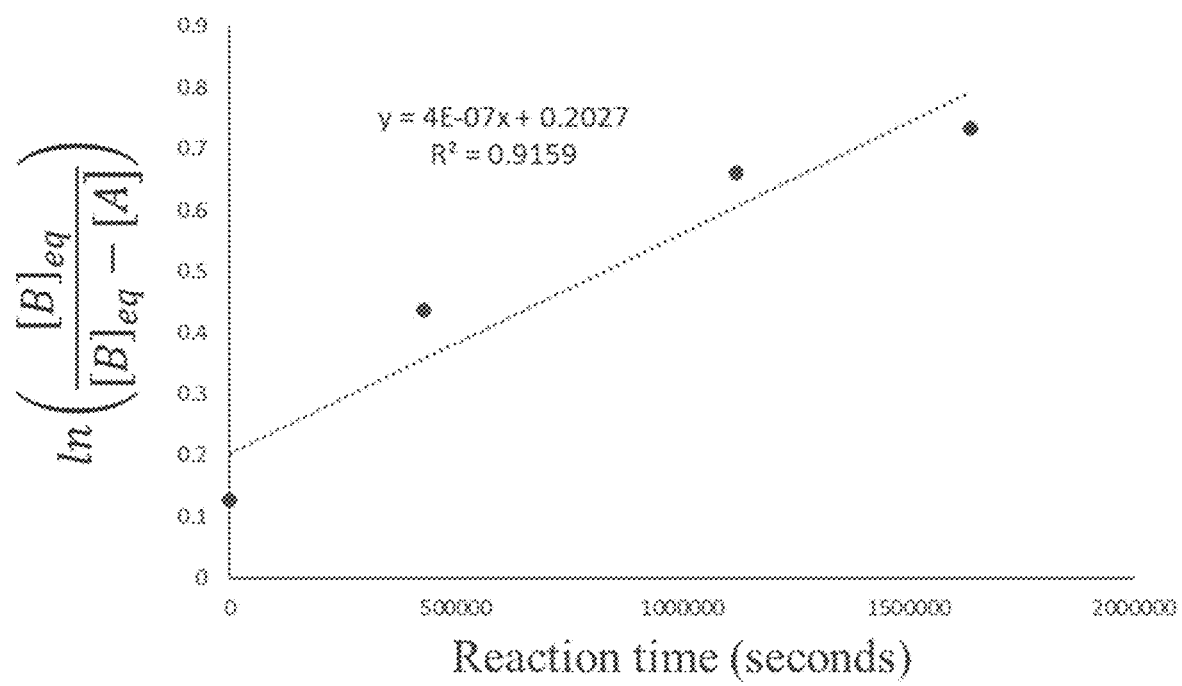
FIG. 39 is a plot of equation 2 with respect to reaction time using data from Table 11.

The forward and reverse rate constants ($k_f$ and $k_r$) in Scheme 2-5 can be related to concentration and time (t) by equation 2:

$$\ln\left(\frac{[B]_{eq}}{[B]_{eq}-[A]}\right) = (k_f + k_r)t \quad \text{EQ (2)}$$

where $[B]_{eq}$ is the concentration of (M)-(−)-CN[7]n2 at equilibrium (1:1, A:B) and [A] is the relative concentration of (P)-(+)CN[7]n2 at time t. [A] is equivalent to the relative concentration of B lost at time t. A plot of ln $$\left(\frac{[B]_{eq}}{[B]_{eq}-[A]}\right)$$

vs. t was generated for the data in Table 11. This plot is presented in FIG. 39. Linear regression gave a line with a slope of $4*10^{-7}$ and an $R^2$ value of 0.92. Equation 2 shows that $(k_f+k_r)=4*10^{-7}$ s$^{-1}$. Since $k_f=k_r$, then $k_f=2*10^{-7}$ s$^{-1}$. With this rate constant, the activation energy of racemization can be calculated using the Eyring equation (equation 3)

$$k_f = 2.083 \times 10^{10} Te^{\left(\frac{-\Delta G^{\ddagger}}{RT}\right)} \quad \text{EQ (3)}$$

where T is the reaction temperature and R is the ideal gas constant. Substituting 388 K (115° C.) for T yields an activation barrier of 34.8 kcal/mol for the racemization of CN[7]n2. This is remarkably close, especially for a single rate constant determination, to the calculated barrier of 34.1 kcal/mol, obtained at the B3LYP/6-31G(d) computational level for this compound.

The low boiling point of acetonitrile (82°) necessitated the use of a sealed vessel during these racemization experiments at 115° C. At this temperature the Antoine equation using NIST parameters extracted from the work of Dojcansky[45] suggest that the internal pressure only reached a value of approximately 2.5 atm. This is 1000 fold smaller than the kbar pressures reported in the extensive review by Eldik, Asano, and Noble needed to affect changes in equilibrium constants.[46] Consequently, the observed barrier of 34.8 kcal/mol is a reasonable estimate of the racemization barrier at 1 atmosphere. In addition, the calculated B3LYP/6-31G(d) volume of activation for the racemization process of CN[7]n2 is negative since starting material and TS for the CN[7]n2 racemization have molecular volumes of 686 Å$^3$ and 614 Å$^3$, respectively. Consequently, higher reaction pressures favors the racemization process and any barrier measured in a sealed vessel is a lower limit to the actual value at 1 atmosphere.

The ultraviolet-visible light (UV-vis) absorption, fluorescence, and phosphorescence spectra of [7]n2 and CN[7]n2 are measured in spectrophotometric grade toluene.

Figure 40:
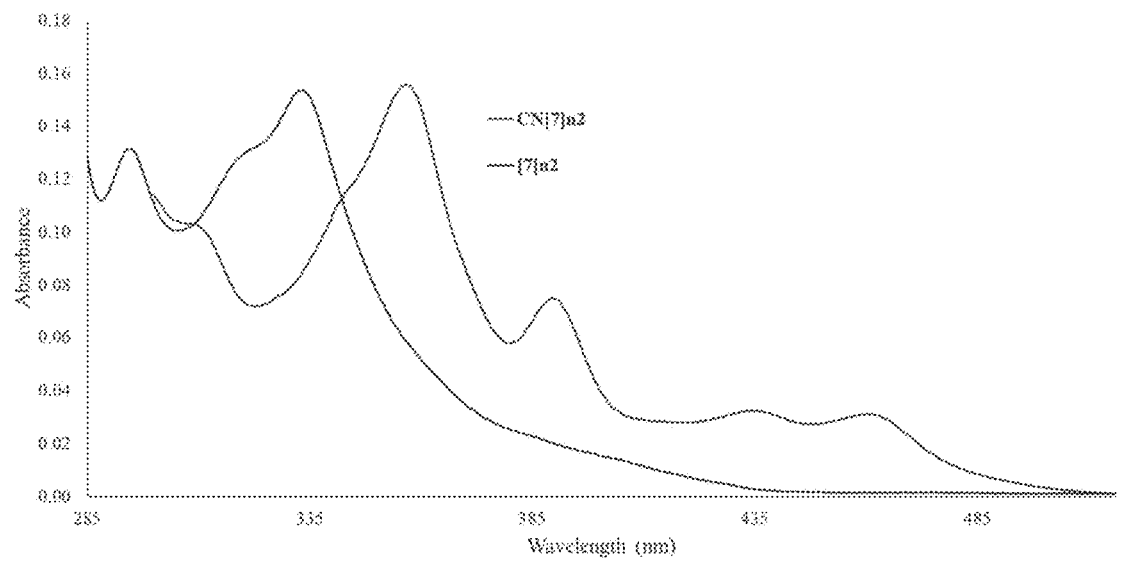
FIG. 40 is a plot of absorbance versus wavelength of normalized UV-Vis spectra of [7]n2 and CN[7]n2 in toluene.

FIG. 40 shows UV-vis spectra of [7]n2 and CN[7]n2. The lowest energy transitions of [7]n2 and CN[7]n2 are summarized in the orbital correlation diagram in FIG. 41.

The UV-Vis absorption spectra of [7]n2 and CN[7]n2 are shown in FIG. 40, depicted as blue and red lines, respectively. [7]n2 has a $\lambda_{max}$ at 333 nm with a featureless shoulder that extends into the visible region, falling to zero absorbance at around 435 nm consistent with its observed yellow color. The presence of the cyano groups bathochromically shifts the absorption spectrum of CN[7]n2 by 24 nm relative to [7]n2 to a $\lambda_{max}$ of 357 nm. The cyano groups also cause a much sharper $S_0 \rightarrow S_1$ transition to arise with peaks at 435 and 460 nm. These absorbances extend much further into the visible region relative to [7]n2, causing the observed deep orange color of CN[7]n2. The spacing of these peaks is consistent with their assignment as vibronic fine-structure in the $S_1$ excited state ($\Delta E$=1249.4 cm$^{-1}$, C=C aromatic).

Figure 41:
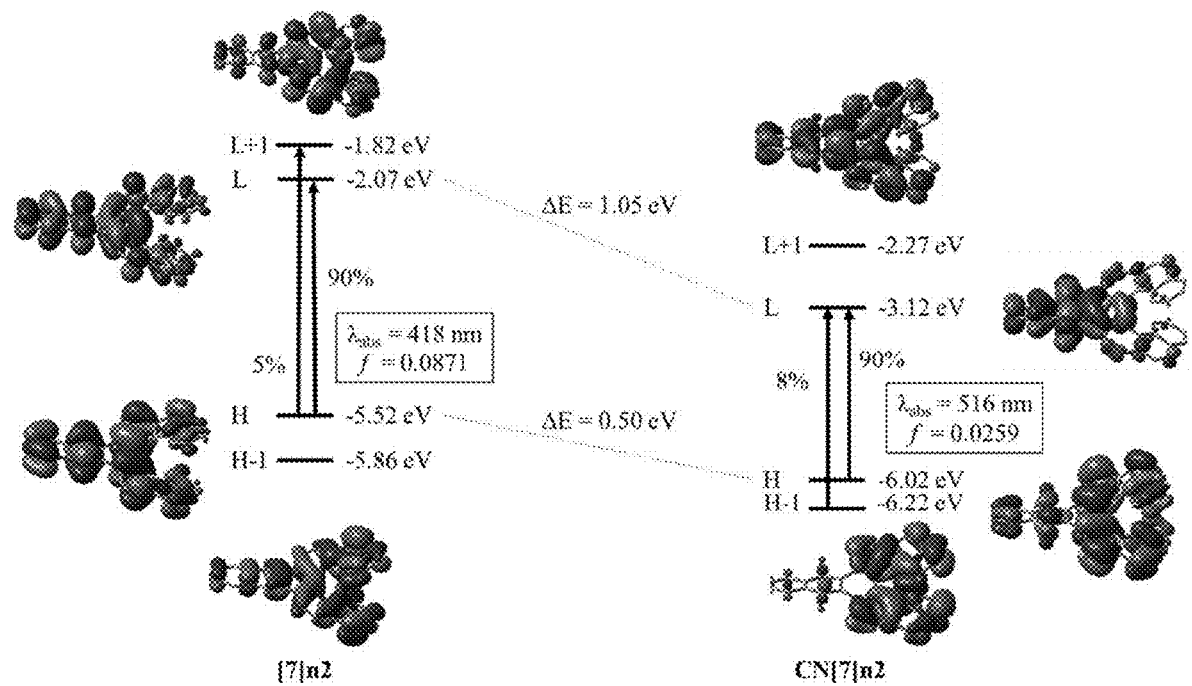
FIG. 41 is an orbital correlation diagram and composition of the $S_0 \rightarrow S_1$ transition for [7]n2 and CN[7]n2 calculated at the RTD-B3LYP/6-311+G(2d,p) level of theory in toluene.

The lowest energy transitions of both the cyanated and non-cyanated [7]heliacenes (FIG. 41) are almost purely HOMO/LUMO transitions with a 90% contribution from these orbitals, taken as the square of the coefficient in the configuration interaction (CI) expansion multiplied by 2 (B3LYP/6-311+G(2d,p)). In both cases, the HOMOs are $C_2$ symmetric and the LUMOs are $C_2$ anti-symmetric, making each transition symmetry allowed. The para-cyano groups in CN[7]n2 act to lower the energy of the frontier orbitals relative to those of [7]n2, with HOMO and LUMO energy levels that are 0.50 eV and 1.05 eV less than those of [7]n2, respectively. This is consistent with the observed bathochromic shift of CN[7]n2 and corroborates the prior discussion about the calculated band-gaps of these species. The HOMO to LUMO transition, which is the dominant contributor to the most bathochromic absorbance at (435+460)/2=448 nm in CN[7]n2, is clearly a charge transfer (CT) band as depicted in FIG. 41. Consequently, it is surprising that the TD-DFT calculated shift of this CT band is at 516 nm only 64 nm bathochromic of the observed value. B3LYP often does not do a good job predicting the position of charge transfer excitations and the better performing cam-B3LYP functional[47] which is corrected for the long-range orbital-orbital exchange interaction is often used in these situations.

Figure 42:
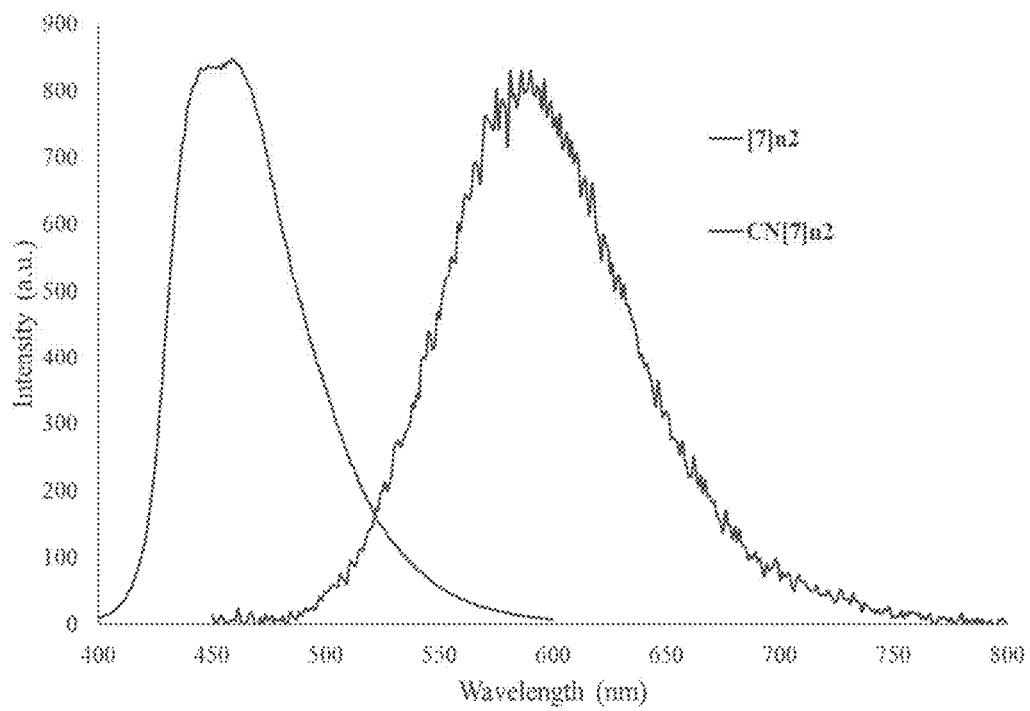
FIG. 42 illustrates fluorescence spectra of [7]n2 and CN[7]n2 in toluene, where $\lambda_{ex}$: [7]n2=333 nm, CN[7]n2=435 nm.

The fluorescence spectra of [7]n2 and CN[7]n2 are presented in FIG. 42. The $S_1 \rightarrow S_0$ transitions for [7]n2 and CN[7]n2 are summarized in the orbital correlation diagram in FIG. 43.

Figure 43:
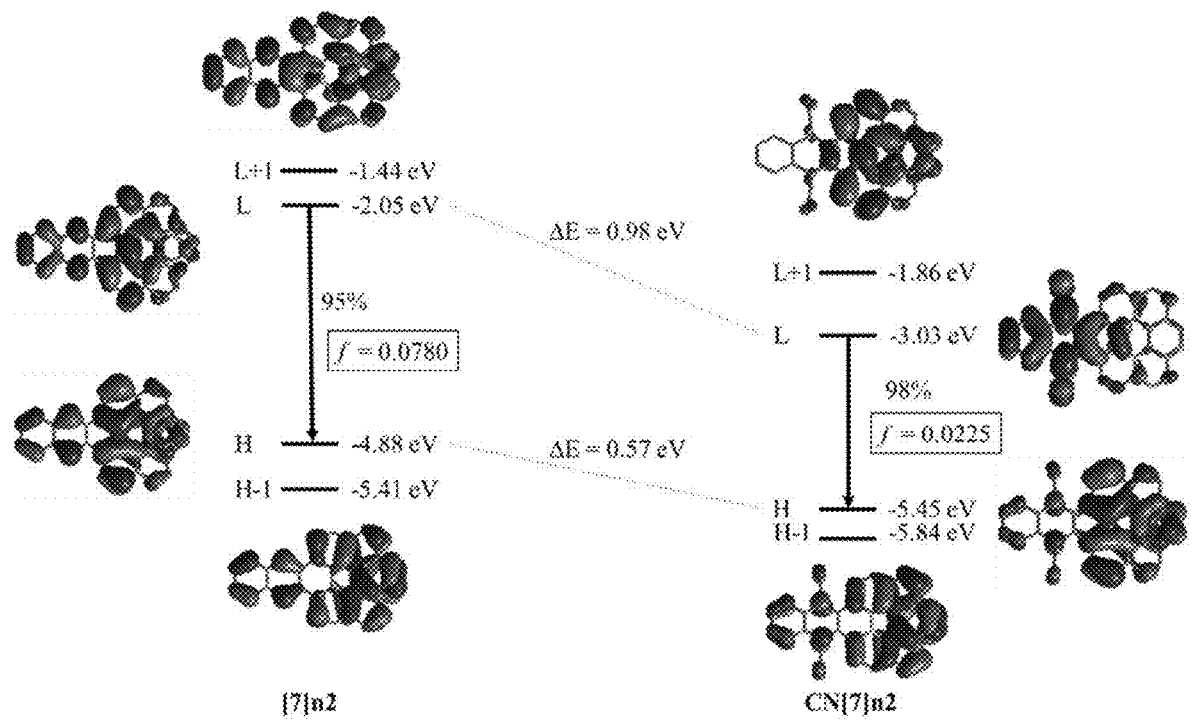
FIG. 43 is an orbital correlation diagram and composition of the $S_1 \rightarrow S_0$ transition for [7]n2 and CN[7]n2 calculated at the RTD-B3LYP/6-31G(d) level of theory.
Figure 44:
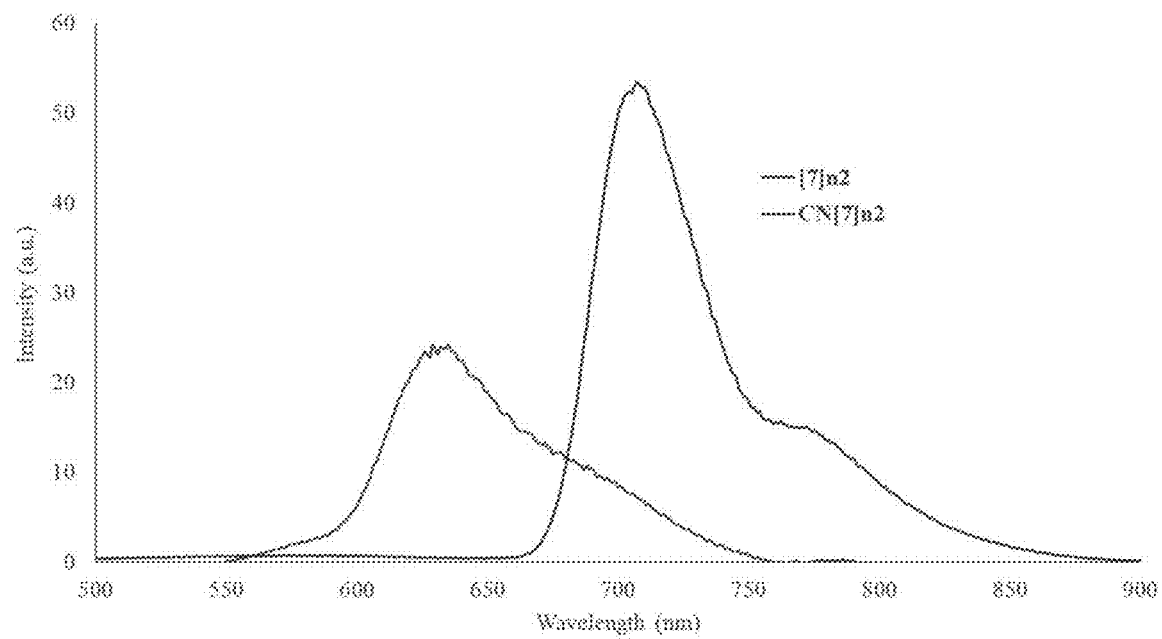
FIG. 44 shows the phosphorescence spectra of [7]n2 and CN[7]n2 in toluene glass, where $\lambda_{ex}$: [7]n2=333 nm, CN[7]n2=435 nm.

The fluorescence spectrum of CN[7]n2 is red-shifted by 135 nm relative to that of [7]n2 producing orange and blue emissive solutions under blacklight, respectively. (Table 12) The $S_1 \rightarrow S_0$ transitions of both species are purely HOMO/LUMO transitions with a >95% contribution from these orbitals and are orbital symmetry allowed with $C_2$ symmetric HOMOs and $C_2$ antisymmetric LUMOs. The bathochromic fluorescence shift of CN[7]n2 relative to [7]n2 is consistent with a 0.41 eV decrease in the HOMO-LUMO gap (FIG. 43). The RTD-B3LYP calculated fluorescence emissions are at 521 nm and 647 nm within 66 nm and 57 nm, respectively, for the observed emission maxima for [7]n2 and CN[7]n2.

The fluorescence quantum yields of [7]n2 and CN[7]n2 were measured using the comparative method of Williams,[48] with anthracene and 9-cyanoanthracene as the standards (Table 12). The fluorescence emission of CN[7]n2 was found to be weaker under both experimental ($\Phi$=0.054 vs. $\Phi$=0.078 for [7]n2) and theoretical (f=0.0225 vs. f=0.0780 for [7]n2) contexts. The biggest difference in the $S_1 \rightarrow S_0$ transition of CN[7]n2 in comparison to [7]n2 is the smaller spatial overlap of the HOMO and LUMO orbitals. In [7]n2 the HOMO/LUMO orbitals are distributed equally throughout the acene and helicene domains. Alternatively, in CN[7]n2 the LUMO resides almost entirely on the acene domain while the HOMO resides almost entirely on the helicene. The charge transfer nature of the orbitals involved in the $S_1 \rightarrow S_0$ transition of CN[7]n2 results in an electronic transition moment that is diminished due to the lack of orbital overlap in the initial and final states. This coincides with the lower oscillator strength and quantum yield observed for CN[7]n2 compared to [7]n2, which has a spatially allowed $S_1 \rightarrow S_0$ transition with full orbital overlap between its initial and final states.

The phosphorescence spectra of [7]n2 and CN[7]n2 were measured in toluene glass. These spectra are presented in FIG. 51. The ground (GS), first excited singlet ($S_1$), and first excited triplet ($T_1$) states of [7]n2 and CN[7]n2 are summarized in the orbital correlation diagram in FIG. 45.

The cyano groups act to red-shift the phosphorescence spectrum of CN[7]n2 relative to [7]n2, by about 100 nm. In both species vibronic fine-structure of the ground-state is evident, manifesting as a shoulder in [7]n2 and something that looks more like a peak in CN[7]n2. The difference in energy between $\kappa_{max}$ and the shoulder peak of CN[7]n2 is 1221 cm$^{-1}$ consistent with a C=C out of plane bending frequency.

The $T_1 \rightarrow S_1$ energy gap decreased from 3.42 eV in [7]n2 to 2.89 eV in CN[7]n2 consistent with the bathochromic shift in the phosphorescence spectrum of CN[7]n2. For both compounds the $T_1$ energy level was predicted to be very close to $S_1$ giving a $\Delta E_{T-S}$=1-2 kcal/mol, which is much smaller than the 20.7 kcal/mol and 14.7 kcal/mol $\Delta E_{T-S}$ values experimentally observed for [7]n2 and CN[7]n2, respectively. The large differences between the calculated and observed (Table 12) $\Delta E_{T-S}$ values for [7]n2 and CN[7]n2 are not too surprising given that the experimental triplet energy is determined in a toluene glass which is not modeled in the computational study.

The photophysical properties data of [7]n2 and CN[7]n2 related to their UV-Vis absorption, fluorescence, and phosphorescence spectra are presented in Table 12. Photophysical properties data of related compounds extracted from the literature are presented in Table 13.

TABLE 12

Photophysical properties data of [7]n2 and CN[7]n2.[a,b]

| | [7]n2 | CN[7]n2 |
|---|---|---|
| $\lambda_{max}$ {$\varepsilon$} (nm. $M^{-1}cm^{-1}$) | 333{46500 ± 100} | 460{10200 ± 100} 435{10700 ± 100} 390{26500 ± 100} 357{54800 ± 100} |
| $\lambda_F$ (nm) | 455 | 590 |
| $\lambda_P$ (nm) | 635 | 708 775 |
| Stokes shift (nm) | 122 | 130 |
| $E_S$ (kcal/mol) | 69.0 ± 0.1 | 57.5 ± 0.3 |
| $E_t$ (kcal/mol) | 48.3 ± 0.4 | 43.0 ± 0.3 |
| $E_{S-T}$ (kcal/mol) | 20.7 | 14.7 |
| $\Phi_F$ | 0.078 ± 0.001 | 0.054 ± 0.003 |
| $\tau_S$ (ns) | 6.0 ± 0.1 | 7.5 ± 0.3 |
| $\tau_T$ (ms) | 39.0 ± 0.9 | 25.0 ± 0.6 |

[a]In spectrophotometric grade toluene at room temperature.
[b]Fluorescence quantum yields determined using the comparative method of Williams[48] with anthracene and 9-cyanoanthracene as standards.

TABLE 13

Photophysical values of related compounds obtained from the literature.

| Compound | $E_g$ (kcal/mol) | $E_t$ (kcal/mol) | $E_{S-T}$ (kcal/mol) | $\Phi_F$ | $\tau_S$ (ns) | $\tau_T$ (μs) | ref. |
|---|---|---|---|---|---|---|---|
| [7]Helicene | 64.3 | 48.9 | 15.4 | 0.021 | 13.8 | 670000 | 14, 15 |
| Anthracene | 76 | 42.5 | 33.5 | 0.3 | 5.3 | 670 | 13 |
| Benzo[b]triphenylene | 76.2 | 12.8 | 63.4 | na | 53.5 | 0.09 | 13 |
| 9-Cyanoanthracene | 71 | na | na | 0.93 | 15.6 | 600 | 13 |
| 9,10-Dicyanoanthracene | 67.9 | 41.8 | 26.1 | 0.9 | 11.7 | 100 | 13 |
| 1,6-Dicyanobenzo[b]triphenylene | 68.8 | na | na | 0.15 | 5.4 | na | 16 |

All of the photophysical properties of [7]n2 were intermediate between those reported for anthracene and [7]helicene. The fluorescence quantum yield of [7]n2 is only slightly higher than the low values reported for the unsubstituted carbohelicenes that have $\Phi_f$<0.05 for [5]helicene through [14]helicene.[49] However, there was about a 4 fold increase in the fluorescence quantum yield of [7]n2 compared to [7]helicene, probably due to the anthracenyl contribution to the overall value. Although the photophysical properties of [7]n2 are intermediate between [7]helicene and anthracene, the values fall closer to those reported for [7]helicene, reflecting a large frontier orbital residence on the helicene domain with leakage onto the acene domain. The Stokes shift for [7]n2 of 122 nm (Table 12) is overestimated since the sharp absorbance at 333 nm was used for the calculation shown in Table 12. The lowest energy transition is embedded in a bathochromically shifted featureless shoulder. It is estimated that the real Stokes shift is as small as 55 nm (3000 $cm^{-1}$).

With the exceptions of the singlet energy and singlet-triplet energy gap, which are 6.8 kcal/mol and 0.7 kcal/mol lower in energy than what is reported for [7]helicene, CN[7]n2 has photophysical quantities that are intermediate between [7]helicene and anthracene. Addition of the cyano groups to [7]n2 to form CN[7]n2 lowers the quantum yield from 0.078 to 0.054. This is especially unexpected since addition of two cyano-groups to anthracene to form 9,10-dicyanoanthrene increases the quantum yield from 0.3 to 0.9. It is however, comforting to see that the addition of two rings to make 1,6-dicyanobenzo[b]triphenylene caused the quantum yield of fluorescence to decrease to 0.15[50] from 0.9 reported for 9,10-dicyanoanthracene. The Stoke's shift in CN[7]n2 is 4800 $cm^{-1}$ much larger than the 3000 $cm^{-1}$ estimate for [7]n2. The larger Stoke's shift in CN[7]n2 is attributed to the charge transfer character of its excited state that requires a greater solvent reorganization than is necessary in [7]n2 that has far less charge separation in its excited state.[51] The Stoke's shift for [7]helicene is approximately 800 $cm^{-1}$ It is tempting to suggest that the larger Stoke's shift in [7]n2 is a result of flattening of the acene domain in the optimized singlet excited state. (vide infra Table 15)

To gain insight into the lower than expected quantum yield of fluorescence of CN[7]n2, the $S_1 \rightarrow S_0$ transition for 9,10-dicyanoanthracene (22) and 1,6-dicyanobenzo[b]triphenylene (23) are examined at the B3LYP/6-31G(d) computational level. The orbital correlation diagrams for these transitions are presented in FIG. 53.

The inclusion of the phenanthrene motif onto 9,10-dicyanoanthracene (22) to form 1,6-dicyanobenzo[b]triphenylene (23) decreased the quantum yield of fluorescence by 0.75 and the calculated oscillator strength by 0.076. This is true despite a symmetry allowed $S_1 \rightarrow S_0$ transition for 23. This observation can arise from two factors that are reflected in the behavior of CN[7]n2 (FIG. 41). (i) It has been demonstrated that removal of degeneracy of the frontier orbitals of [5]helicene (i.e. increase ΔE, HOMO/HOMO−1 and ΔE, LUMO/LUMO+1) through functionalization increases fluorescence quantum yields.[52] Putting these three species in order of decreasing frontier orbital degeneracy yields CN[7]n2, 23, and 22. This ranking is congruent with increasing fluorescence quantum yields and calculated oscillator strengths with D=0.05, f=0.02; (=0.15, f=0.32; and D=0.9, f=0.11 for CN[7]n2, 23, and 22 respectively. (ii) There is less spatial overlap between the orbitals of $S_0$ and $S_1$ in 23 compared to 22, which has complete overlap between its HOMO and LUMO. In 23 heavy lobes reside on the phenanthrene motif of the HOMO, while the LUMO resides predominantly on the acene portion of the molecule leaving the two peripheral phenanthrene rings relatively empty in the excited state. The $S_1 \rightarrow S_0$ in CN[7]n2 is even more spatially disallowed, with a HOMO that resides entirely on the [7]helicene domain and a LUMO that is localized on the acene domain (FIG. 41). In addition, the HOMO-LUMO gap is larger in 22 leading to a decrease in the non-radiative decay, $k_{NR}$, of the excited state and an increase in the quantum yield of fluorescence (i.e. $\Phi_f = k_f/(k_f + k_{NR})$) With these considerations, the low fluorescence quantum yield observed for CN[7]n2 can be rationalized.

Figure 47:
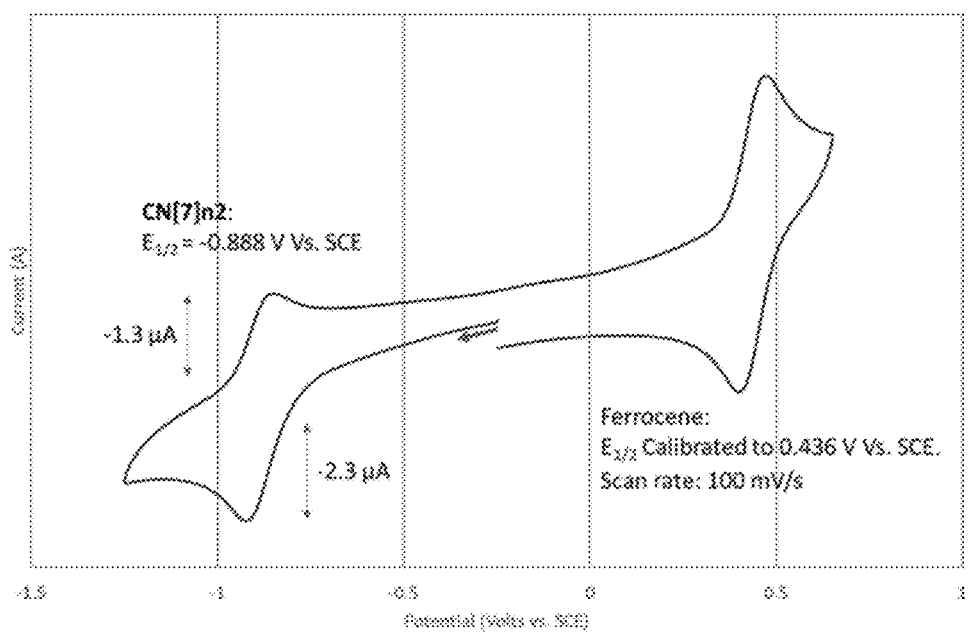
FIG. 47 show the cyclic voltammogram of CN[7]n2 with ferrocene as an internal standard at a platinum electrode.

The cyclic voltammogram of CN[7]n2 was measured in DMF in the presence of ferrocene as an internal standard and is presented in FIG. 47.

The reduction potential of CN[7]n2 in DMF ($E_{1/2}$ (Redn)= −0.89 V vs SCE) is given by the half-wave potential, ($E_{1/2}$ (Redn)=$[E_p$ (cathodic)+$E_p$(anodic)]/2), measured from a voltammogram at a platinum electrode using ferrocene as an internal standard calibrated vs. SCE. The voltammogram of CN[7]n2 is characterized by a one-electron quasi-reversible peak ($ip_c/ip_a$=−1.18; $\Delta E$=76 mV) The reduction potential at −0.89 V vs. SCE falls in close proximity to the reduction potentials reported for the related compounds 21 and 22.[50] The reduction potential of CN[7]n2 and these compounds are summarized in Table 14.

TABLE 14

Reduction potential of CN[7]n2 and the reported reduction potentials of 21 and 22.[50]

| Compound | $E_{red}$ (V vs. SCE) |
|---|---|
| CN[7]n2 | −0.89 |
| 9,10-dicyanoanthracene (21) | −0.92 |
| 1,6-diryanobenzo[b]triphenylene (22) | −0.83 |

The first electronic excited state, radical anion, and radical cation of [7]n2 and CN[7]n2 were optimized at the B3LYP/6-31G(d) computational level. Their geometric parameters are presented in Table 15 alongside those of the ground state of each [7]heliacene. The optimized geometries of the ground (green structures) and $S_1$ (red structures) states of [7]n2 and CN[7]n2 are compared in FIGS. 48A and 48B, respectively.

TABLE 15

Geometric parameters of the ground state, first excited electronic state, radical anion, and radical cation of [7]n2 and CN[7]n2 calculated at the B3LYP/6-31G(d) computational level.

| | | Helical pitch (Å) | Helical core dihedral | Acene twist | Ring twist (D) | Ring twist (E) | Ring twist (F) |
|---|---|---|---|---|---|---|---|
| [7]n2 | Ground state | 4.85 | −33.8° | 24.6° | 21.7° | 2.7° | 0.1° |
| | First excited electronic state($S_1$) | 4.77 | −19.7° | 10.4° | 12.6° | −1.8° | −0.5° |
| | Radical anion | 4.87 | −27.9° | 12.6° | 13.3° | −0.4° | −0.4° |
| | Radical cation | 4.96 | −30.0° | 22.5° | 21.2° | 1.2° | −0.04° |
| CN[7]n2 | Ground state | 4.94 | −39.6° | 46.2° | 31.9° | 12.5° | 1.5° |
| | First excited electronic state($S_1$) | 5.00 | −33.6° | 41.2° | 30.0° | 9.7° | 1.2° |
| | Radical anion | 4.93 | −38.2° | 42.7° | 29.8° | 11.4° | 1.3° |
| | Radical cation | 5.11 | −35.6° | 46.1° | 32.3° | 12.1° | 1.4° |

Time dependent density functional theory (TD-DFT) optimizations of CN[7]n2 and [7]n2 gave excited state geometries with reduced acene twists. The decrease in the acene twist is especially large for [7]n2 going from an twist angle of 24.6° in the ground-state to 10.4° in $S_1$. Interestingly, rings B and C are slightly twisted in the opposite direction in the excited state, opposing the overall longitudinal twist of the acene. This change in the structure of the acene domain was accompanied by a helical core dihedral angle in the excited-state that is 14.1 degrees less in magnitude compared to the ground-state of [7]n2. Although this is an indication of a dramatic change in the geometry of the [7]helicene motif, there was surprisingly little change in the helical pitch between the excited and ground states. All these geometric features are easily observed in FIG. 48A, where the optimized excited-state (red) of [7]n2 is superimposed with the ground-state (green) structure. The same structural trends were observed upon excitation of the ground state of CN[7]n2 to its $S_1$ excited state, albeit to a smaller extent than observed in [7]n2 in FIG. 48B.

A decrease in the acene twist angle was also observed for the radical anion and to a lesser extent the radical cation compared to the neutral closed-shell species of [7]n2 and CN[7]n2 structures. The difference was especially stark for the radical anion of [7]n2, with an acene twist angle 12° less than in the neutral species. The radical cation deviates much less, with an acene twist angle that is 1.9° smaller than in neutral [7]n2. The acene twist angle of CN[7]n2 deviates by no more than 5° in its $S_1$, radical cation, and radical anion. It is possible that the added bulk of the two nitrile groups in CN[7]n2 inhibits the flattening of the acene in the excited and radical anionic states through enhanced bay-region strain. The magnitude of geometric deviation from the neutral ground states of [7]n2 and CN[7]n2 follows the order: $S_1$>radical anion>radical cation.

It has been determined that the [7]heliacenes have acenes with twists that are of the opposite configuration and orthogonal to those of the [7]helicene cores. Functionalization of the acene tail with groups larger than hydrogen acts to propagate steric communication between the [7]helicene and acene motifs, enhancing the acene twist angle in most cases. However, the potential energy surface is dramatically complicated in the multi-functionalized species with the possible formation of a large number of twistomers. For the di-functionalized species these twistomers are expected to have a negligible contribution to the solution ensemble, but further functionalization to form the tetra-, hexa-, and octa-functionalized species opens the door to a new class of twistomers with no $C_2$-axis of symmetry. In the case of the cyano and methyl functionalized [7]heliacenes these twistomers are lower in energy compared to their fully twisted counterparts. Alternatively, only one $C_2$ symmetric twistomer is located for the phenylated species that is over 20 kcal/mol higher in energy than its fully twisted counterpart. This is true regardless of the extent of Ph-functionalization. Furthermore, the phenylated [7]heliacenes have the highest acene twists and multi-functionalization cause the racemization barrier to increase in these species relative to the parent helicene, [7]n0. This makes the multi-phenylated [7]heliacenes valuable synthetic targets that should exist as a single twistomers with exceptionally twisted acenes and racemization barriers that are more prohibitive to enantiomeric excess loss.

At least two novel [7]heliacenes, [7]n2 and CN[7]n2 were synthesized. Following the prediction, the embedded acene is twisted in these species. The para-cyano groups in the bay-regions of CN[7]n2 act to further twist the acene and lower the HOMO and LUMO energy levels compared to [7]n2, as demonstrated through single-crystal X-ray diffraction and photophysical studies, respectively. Chiral resolution of CN[7]n2 was performed followed by the acquisition and assignment of its CD spectra. The configurational stability of the [7]heliacenes was bolstered by the measurement of the racemization barrier of CN[7]n2, which indicates that it stays enantiomerically pure at room temperature indefinitely and at moderately high temperatures for hours. Thus, configurationally locked twisted acenes were synthesized.

The polycyclic aromatic hydrocarbons (PAHs) are well suited to the study of their properties as one advances through each homologues series. The helicenes and acenes are especially conducive to this treatment, since progression from one member to the next entails the annulation of only a single ring. These two classes of PAHs are combined, fusing an acene tail onto the fulcrum ring of [7]helicene, forming a novel homologues class of PAHs called the [7]heliacenes. Since the spring-like helicenes and planar acenes are divergent in their stability, solubility, chiroptical and electronic behavior, the extent that each structural domain is expressed becomes an important question; are the [7]heliacenes more acene-like or helicene-like? This question is answered in part by a rigorous computational study of these compounds, entailing quantum chemical calculations of thermodynamic, aromatic, and chiroptical properties as a function of acene elongation. As previously described the band-gap values of the [7]heliacenes are projected to become acene-like in the higher members. FIG. 49 illustrates examples of heliacenes to be discussed further below.

The acenes have been found to be experimentally less stable than their phenanthrene analogues.[53] Pentacene degrades in the presence of light through photooxidative[54] and Diels Alder[55] dimerization pathways. The instability of the higher members is further exacerbated by increasing open-shell, diradical behavior.[56] The stabilization energies of the acenes, [5]heliacenes, and [7]heliacenes were extracted through homodesmotic equations and compared, while the diradical nature of the higher members of the [7]heliacenes were analyzed. The distortion energy corresponding to longitudinally twisting the pentacene motif in [7]n4, along with opening the helical "jaws" of the [7]Series further described herein.

Figure 50:
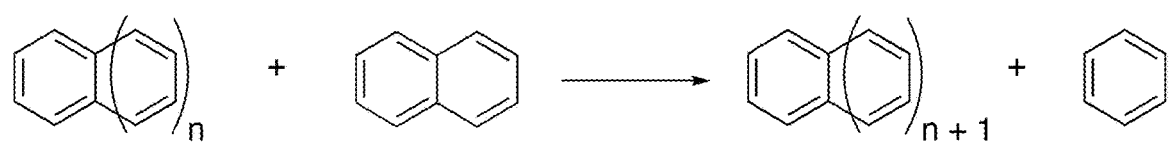
FIG. 50 shows an embodiment of a homodesmotic reaction used to extract stabilization energies of the acenes.
Figure 51A:
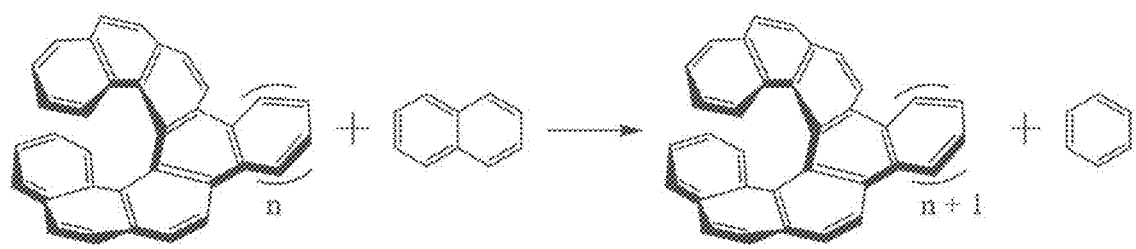
FIGS. 51A and 51B illustrate a homodesmotic equation-a (blue) and equation-b (red), respectively, used to extract the stabilization energy for the expansion through the [7]Series.
Figure 51B:
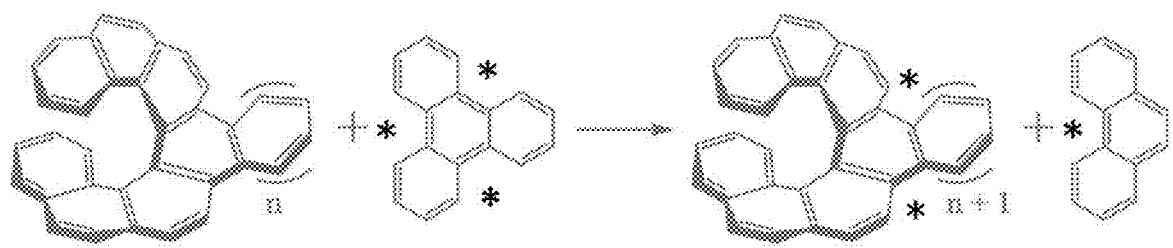

The stabilization energy (SE) of the acenes and the [7]heliacenes disclosed herein correspond to the free energy of the isodesmic (homodesmotic) reactions as shown in FIG. 50, FIG. 51A, and FIG. 51B respectively. These homodesmotic reactions involve reactions of the acenes and [7]heliacenes with a benzo-donor; naphthalene in the case of the acenes in FIG. 50 and both naphthalene (blue-equation in FIG. 51A) and triphenylene (red-equation In FIG. 51B) in the case of the [7]heliacenes. The SE's for these homodesmotic reactions are given by the mathematical equations for as follows (Equations 4 and 5):

$$SE_{n \to n+1} = (\Delta G°_{n+1} - \Delta G°_n) - (\Delta G°_{Benzene} - \Delta G°_{naphthalene}) \quad \text{EQ(4)}$$

$$SE_{n \to n+1} = (\Delta G°_{n+1} - \Delta G°_n) - (\Delta G°_{Phenanthrene} - \Delta G°_{triphenylene}) \quad \text{EQ(5)}$$

Figure 52:
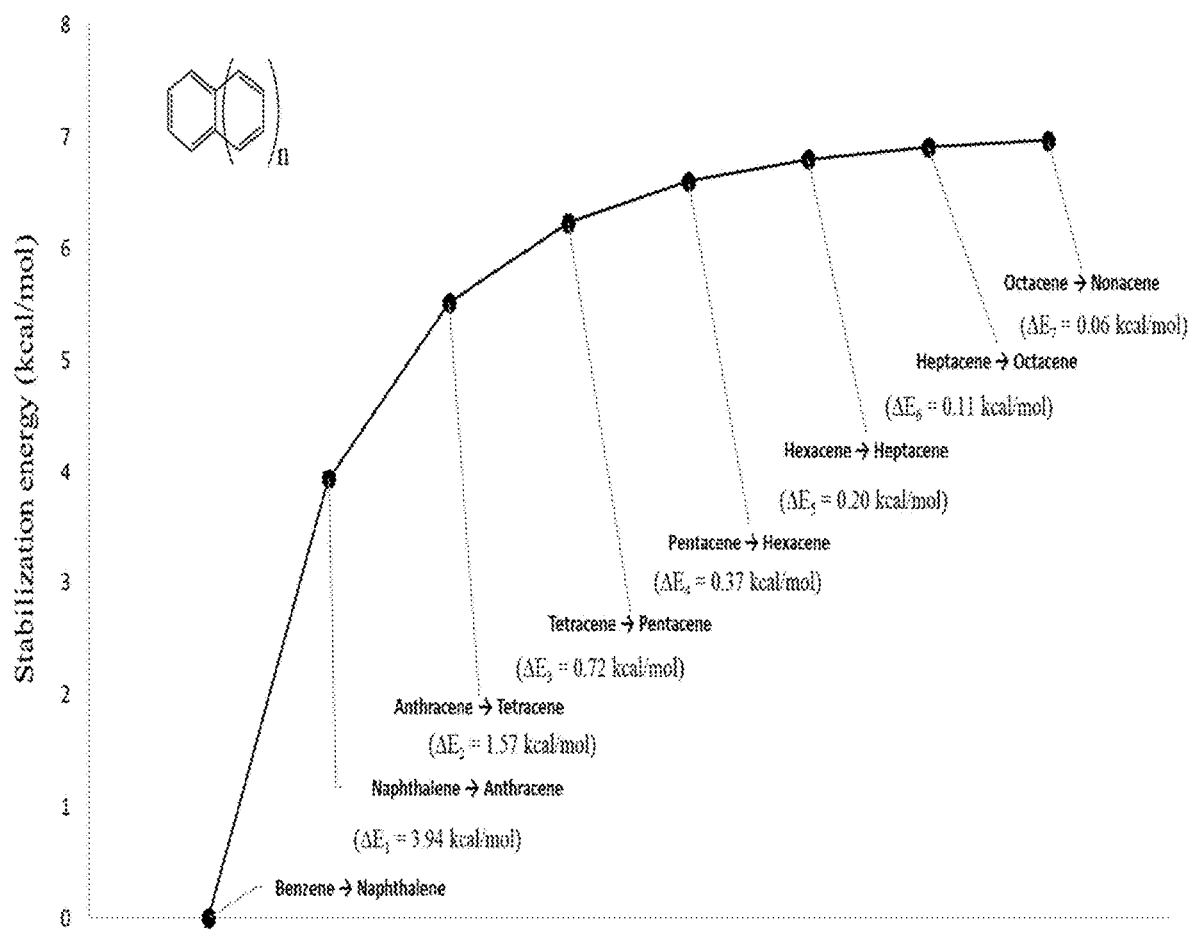
FIG. 52 is a graphical representation of stabilization energies of the acenes extracted using the homodesmotic reaction shown in FIG. 57, where geometries are optimized at the B3LYP/6-31G(d) computational level and shows total electronic energies used.
Figure 53:
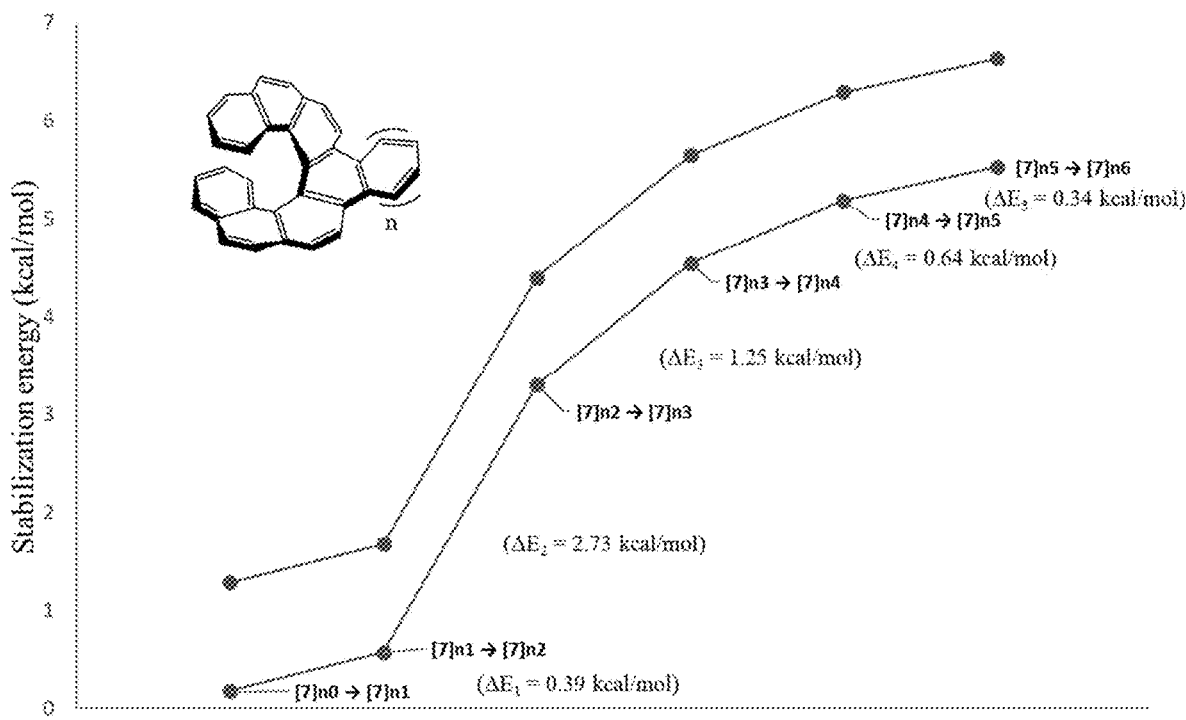
FIG. 53 illustrates stabilization energies of the [7]Series extracted using equation-a (blue line) and equation-b (red line)

FIG. 52 and FIG. 53 are graphical representations of the stabilization energies of the acenes and [7]heliacenes, respectively. Table 16 lists the SEs for all the homodesmotic reactions that are used to generate FIG. 52 and FIG. 53. The blue and red stabilization energy plots for the [7]heliacenes (FIG. 53) are identical but displaced vertically. This is understandable because the stabilization energies for the blue and red plots only differ in the magnitudes of the second term in the SE equation shown in equations EQ(3) and EQ(4) (i.e., ($\Delta G°_{BENZENE} - \Delta G°_{NAPHTHALENE}$) for the blue reaction and ($\Delta G°_{PHENANTHRENE} - \Delta G°_{TRIPHENYLENE}$) for the blue reaction).

TABLE 16

Stabilization energies of the acenes and [7]Series.

| The Acenes | Stabilization energy (kcal/mol) | Equation-a | Stabilization energy (kcal/mol) | Equation-b | Stabilization energy (kcal/mol) |
|---|---|---|---|---|---|
| Benzene → Naphthalene | 0.00 (1.20)* | [7]u0 → [7]n1 | 1.28 (−3.52)* | [7]n0 → [7]n1 | 0.18 |
| Naphthalene → Anthracene | 3.94 | [7]u1 → [7]n2 | 1.67 | [7]u1 → [7]n2 | 0.57 |
| Anthracene → Tetracene | 5.51 | [7]u2 → [7]n3 | 4.40 | [7]u2 → [7]n3 | 3.30 |
| Tetracene → Pentacene | 6.23 | [7]u3 → [7]n4 | 5.65 | [7]u3 → [7]n4 | 4.55 |
| Pentacene → Hexacene | 6.60 | [7]u4 → [7]n5 | 6.29 | [7]u4 → [7]n5 | 5.19 |
| Hexacene → Heptacene | 6.80 | [7]u5 → [7]n6 | 6.63 | [7]u5 → [7]n6 | 5.53 |
| Heptacene → Octacene | 6.91 | | | | |
| Octacene → Nonacene | 6.97 | | | | |

Figure 54:
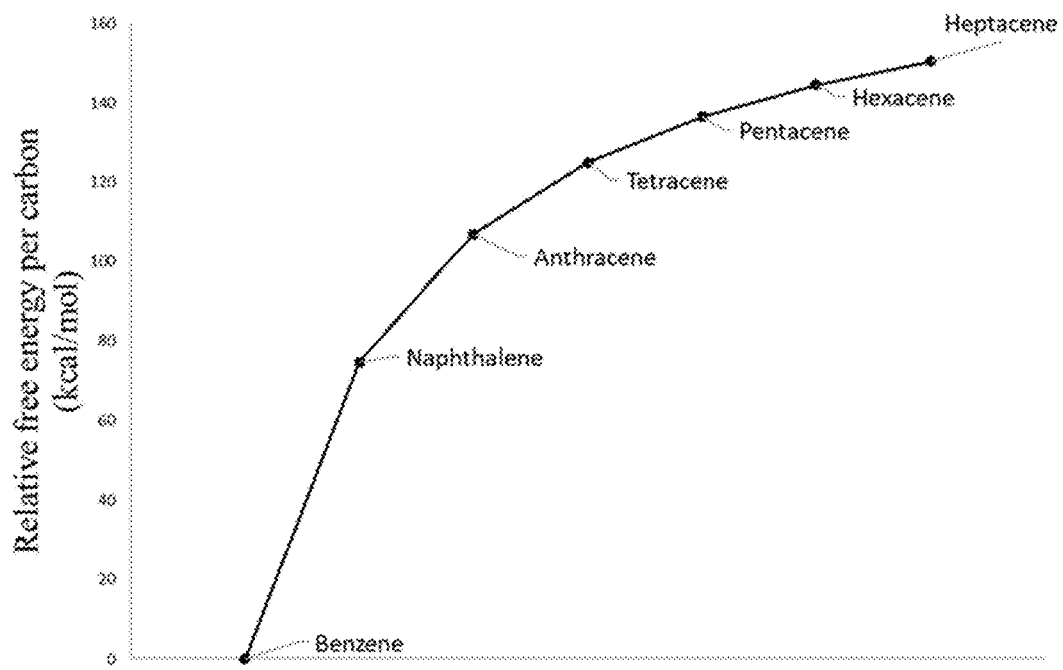
FIG. 54 is a graphical representation of relative free energies per carbon for the acene series, (B3LYP/6-311+G (2d,p))

The increasing stabilization energies from benzene to octacene in FIG. 52 reflect an increase in ($\Delta G°_{n+1} - \Delta G°_n$) because ($\Delta G°_{Benzene} - \Delta G°_{Naphthalene}$) remains constant for all the homodesmotic reactions. Consequently, the acenes become destabilized as they are elongated. This is in accord with incremental loss of benzenoid character through the series as predicted by Clar theory.[57] Interestingly, the magnitude of the destabilization energy increases rapidly up to pentacene, but slows until reaching a plateau around 7 kcal/mol for subsequent annulations in the higher members. This behavior is characterized by a decrease in $\Delta E$ from $\Delta E_1$ to $\Delta E_7$ in FIG. 52. This saturation-like behavior is intuitively anticipated since addition of a single benzo-ring to a large acene should have a smaller destabilizing effect than addition of a benzo-ring to benzene. The conclusion that benzo-annulation is destabilizing is corroborated by a plot of the B3LYP/6-311+G(2d,p) Free Energies of the acenes divided by the number of carbons they contain shown in FIG. 54.

The stabilization energy for the [7]heliacene are found to increase from [7]n0 to [7]n5 when calculations were made using equation-a with naphthalene or equation-b with triphenylene as a donor. (EQ(4) and EQ(5)) This means that elongation of the acene-domain is destabilizing for the [7]heliacenes. The destabilization energies appear to plateau as previously observed in the acenes (EQ(4) and EQ(5)) also indicating that the destabilizing effect of benzo-ring annulation exhibits a saturation effect. However, the differences in the adjacent destabilization energies, $\Delta E$'s in FIG. 53, do not decrease uniformly as you go from $\Delta E_1$ to $\Delta E_5$. $\Delta E_1$ is 0.39 kcal/mol only slightly larger than $\Delta E_5$ (0.34 kcal/ml) and does not fit into this trend established for $\Delta E_2$ to $\Delta E_5$, which does conform to the behavior observed for the acenes. The smaller $\Delta E_1$ corresponds to a larger than anticipated SE for the parent [7]helicene. It is tempting to attribute the larger SE for [7]helicene, [7]n0, to the introduction of two bay-region steric interactions that does not occur in the homodesmotic reactions of [7]n1 to [7]n5 using either naphthalene or triphenylene as the benzo-donor. However, the formation of an additional Clar sextet, is another unique feature of the homodesmotic reaction of [7]n0 that is not observed in the homodesmotic reactions of the other [7]heliacenes, but would lead to a lower than expected SE (i.e. smaller ($\Delta G^0_{n+1} - \Delta G^0_n$)) not the larger than expected SE that is observed.

Figure 55:
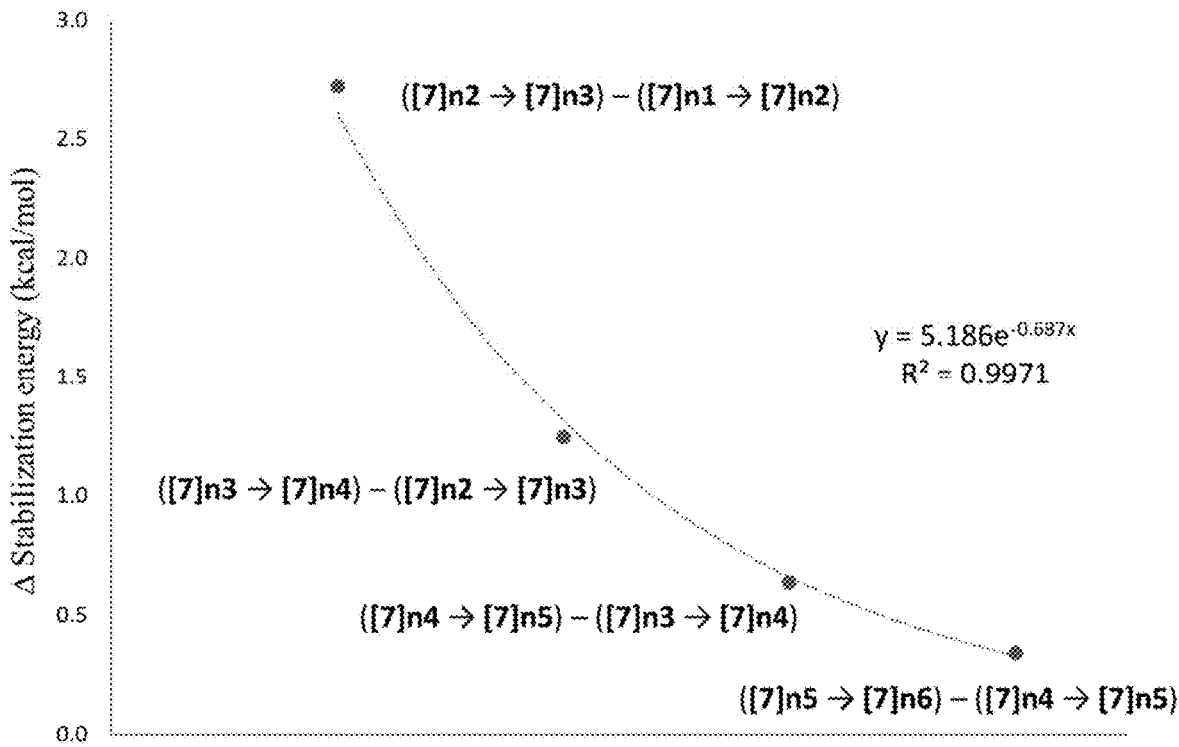
FIG. 55 is a plot that illustrates differences in stabilization energies (ΔSE) for the [7]Series.
Figure 62:
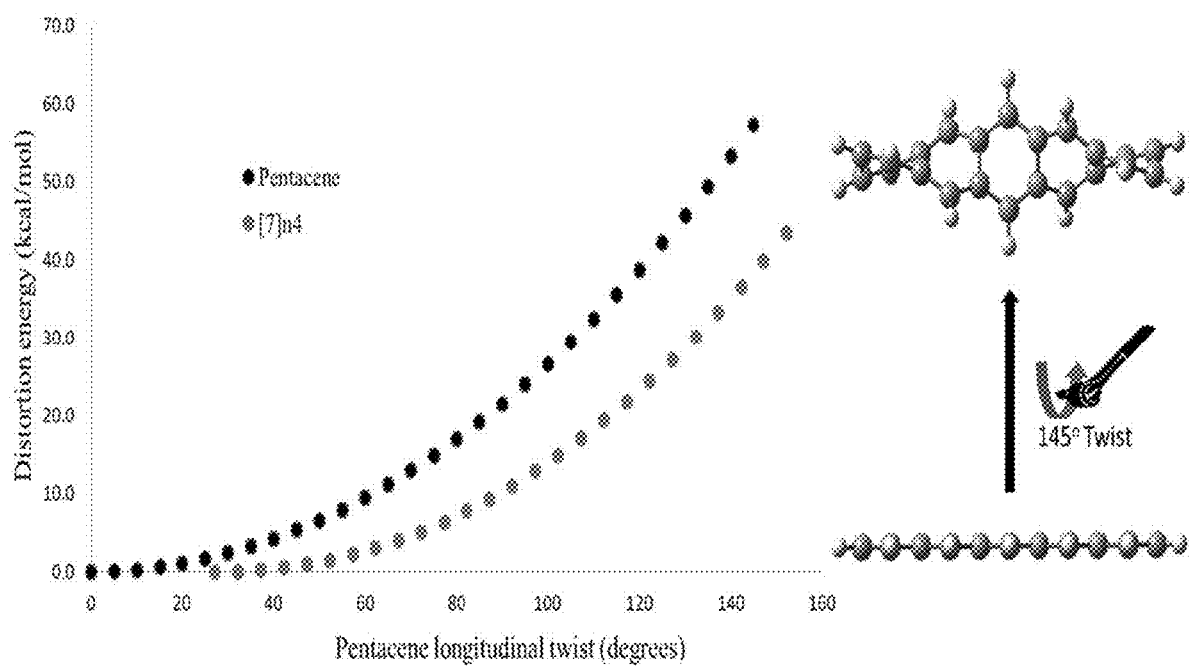
FIG. 62 is a graph of distortion energy as a function of pentacene longitudinal twist for the imbedded pentacene in [7]n4 (red) and free pentacene (black) as obtained from a relaxed scan calculated at the B3LYP/6-31G(d) computational level.

An interaction-free stabilization energy was determined for [7]n0 that eliminates the effect(s) that is(are) responsible for the decrease in $\Delta E_1$. This was accomplished by extrapolating the trend in stabilization energies established by the homodesmotic benzo-annulations of [7]n1 through [7]n5. This is done by plotting the change in the stabilization energies for the red reaction ($\Delta E$'s in FIG. 53) as shown in FIG. 55 (exponential fit $R^2=0.9971$) and extrapolating to determine $\Delta E_0$ (the difference in the destabilization energies of the ([7]n1 to [7]n2) and the ([7]n0 to [7]n1) homodesmotic reactions). This value, $\Delta E_1$, which is the intercept of the plot in FIG. 62 is 5.19 kcal/mol. Subtraction of $\Delta E_0$ from the 1.67 kcal/mol destabilization energy for [7]n1 (Table 16) gives an extrapolated value of −3.52 kcal/mol for the ([7]n0 to [7]n1) homodesmotic reaction.

Figure 56:
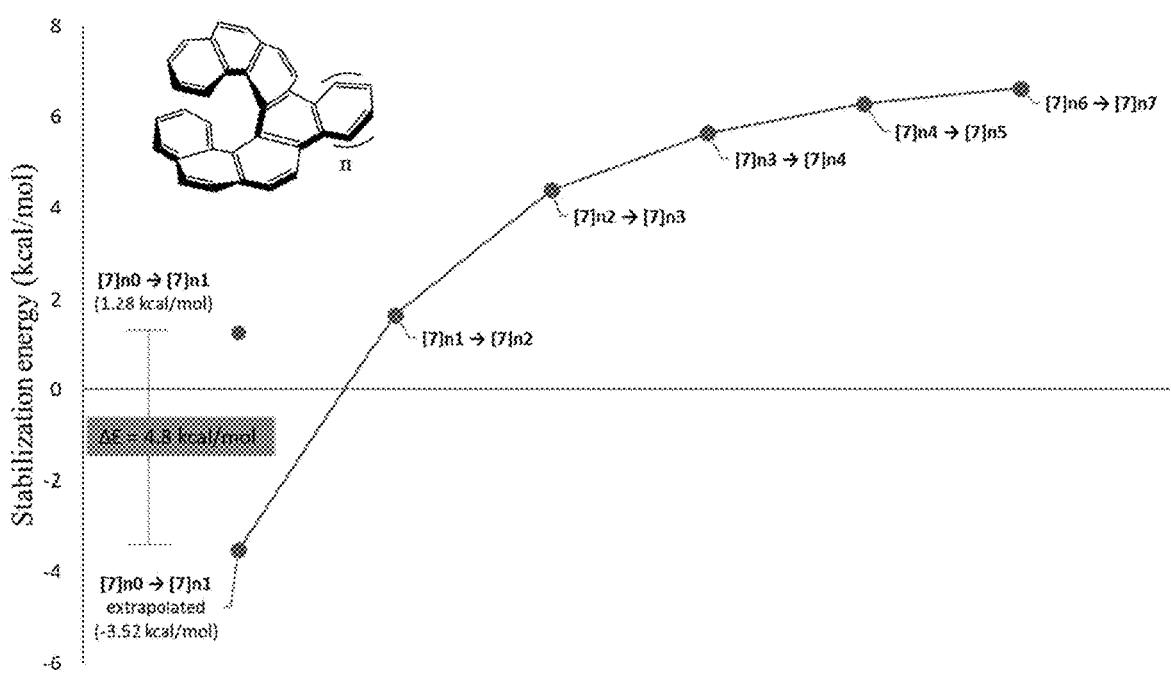
FIG. 56 is a plot that illustrates stabilization energies of the [7]Series including extrapolated electronic stabilization energy for progression from [7]n0 to [7]n1.
Figure 57:
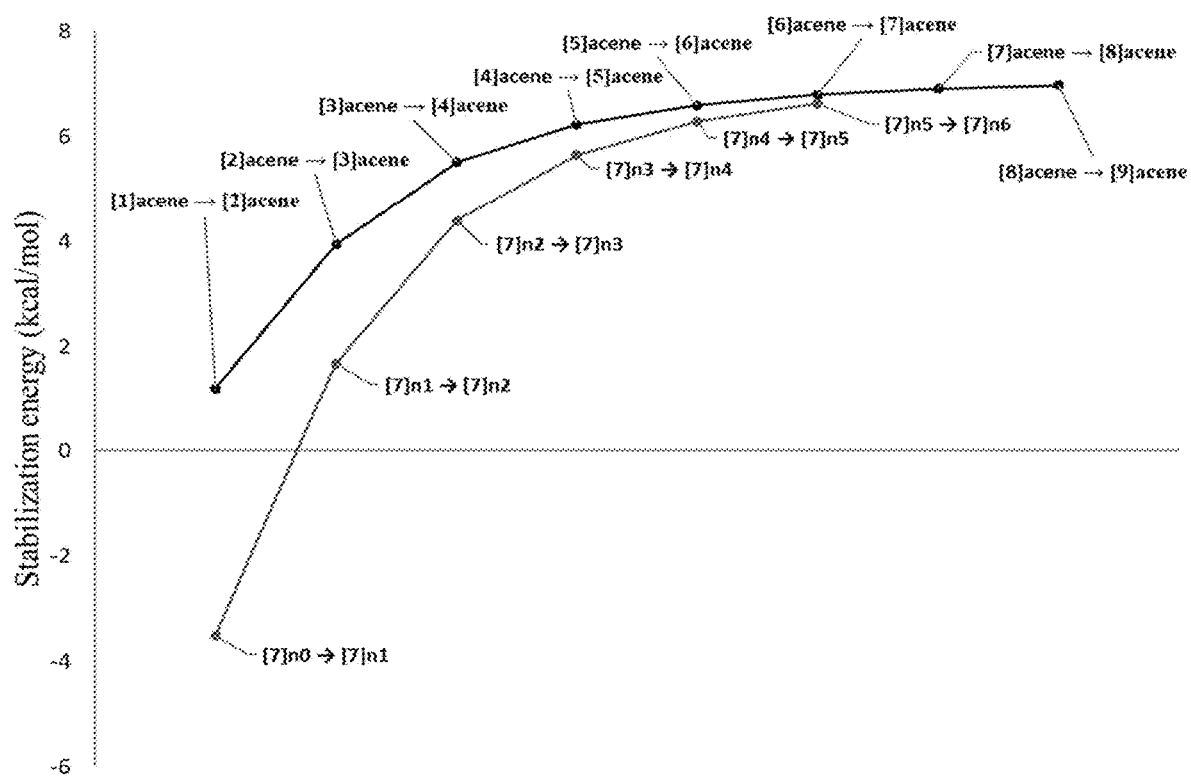
FIG. 57 is a plot that illustrates stabilization energies of the acenes and [7]Series with B3LYP/6-31G(d), total electronic energies used.

The difference between the two stabilization energies for [7]n0, the extrapolated interaction free value at −3.52 kcal/mol, and the calculated value at 1.28 kcal/mol, shown in FIG. 56, is 4.8 kcal/mol. This value was determined by the contributions from both the energy of the bay-region effect, $E_{bay-region}$, and the energy of the Clar effect as given by $4.8 = 2E_{bay-region} - E_{Clar}$. $E_{Clar}$ is very small since the additional Clar sextet only contributes to a small subset of the many resonance structures that determine the over-all energy of [7]n1 and that 4.8 kcal/mol is a reasonable estimate of the value of 2 bay-region interactions.

The stabilization energies of the [7]Series and the acenes are plotted in the same graph for comparison. The extrapolated values for the first transformation in each series are used, equation-a is used for the [7]Series.

Figures 58A, 58B:
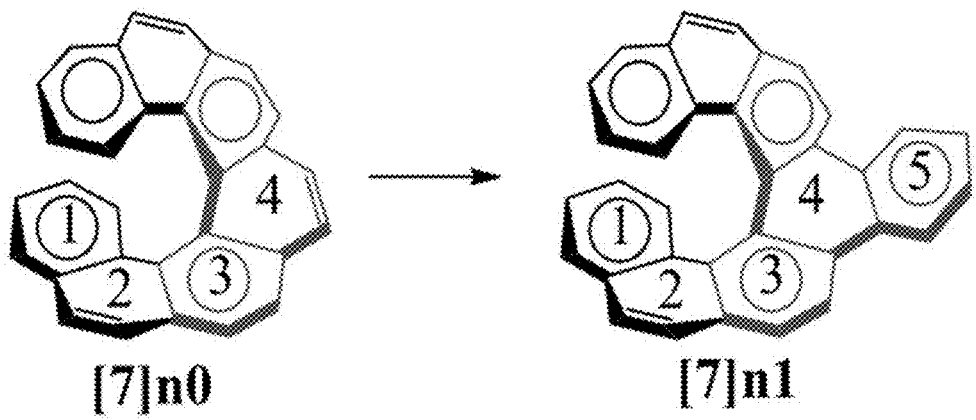
FIGS. 58A and 58B together illustrate transformation of [7]n0 to [7]n1 showing the phenanthrene (red) and triphenylene (blue) motifs in [7]n0 and [7]n1, respectively.
Figure 59:
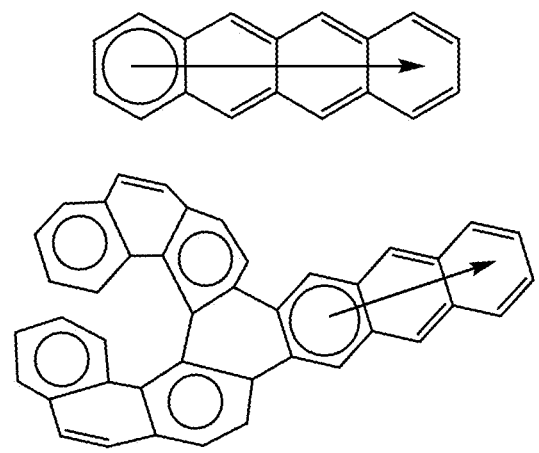
FIG. 59 illustrates a resonating sextet in tetracene and [7]n3.
Figure 60:
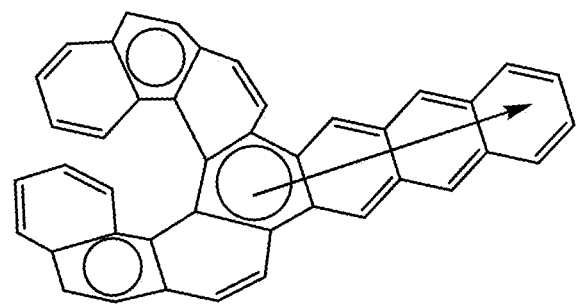
FIG. 60 a resonance form of [7]n4 with aromatic sextet in fulcrum ring.

Stabilization energies in the early members of the [7]Series are much smaller than in the early members of the corresponding free-acenes. However, the energetic response to acene elongation in the higher members of the [7]Series converge with their corresponding free-acenes. Both species approach a capped stabilization value that is approximately 7 kcal/mol. vs.: The first transformation in the [7]Series, [7]n0→[7]n1, is 4.72 kcal/mol more favorable than the corresponding transformation in the acenes, [1]acene→[2]acene. This large difference is easily explained under the context of Clar theory. The first transformation in the [7]Series entails progression from a partially filled phenanthrene motif in rings 3 and 4 (red rings, FIG. 58A) in [7]n0 to a fully benzenoid triphenylene motif in rings 3, 4, and 5 (blue rings, FIG. 58B) in [7]n1, corresponding to the acquisition of an additional Clar sextet. There is no change in the number of Clar sextets in the first or any of the homodesmotic transformation in the acene series. Beyond the first homodesmotic transformation, the stabilization energies remain less for subsequent transformations in the [7]Series compared to those of the corresponding free-acenes. This can also be amply explained under the context of Clar theory. The principle destabilizing event as progression is made through the acene series is loss of aromatic character as predicted by a single aromatic sextet being shared by an increasing number of rings. The same decrease in aromatic character occurs in the heliacenes as benzo-annulation is increased. However, the resonating sextet in tetracene, (FIG. 59) is shared equally by all four rings. In contrast, in [7]n4 the aromatic sextet is primarily shared by only the three terminal acene rings. Allowing the aromatic sextet to be shared with the fulcrum ring in the [7]heliacenes (FIG. 60) generates a resonance structure with only 3 Clar sextets rather than 5 Clar sextets in the other resonance forms shown in FIG. 59. Interestingly, the stabilization energies for homodesmotic transformations that form species that share the resonating sextet with the same number of rings in both the acene and heliacene series are very similar. (e.g. →Tetracene, 5.51 kcal/mol vs.→[7]n4, 5.65 kcal/mol; →Pentacene, 6.23 kcal/mol vs.→[7]n5, 6.29 kcal/mol)

Figure 61:
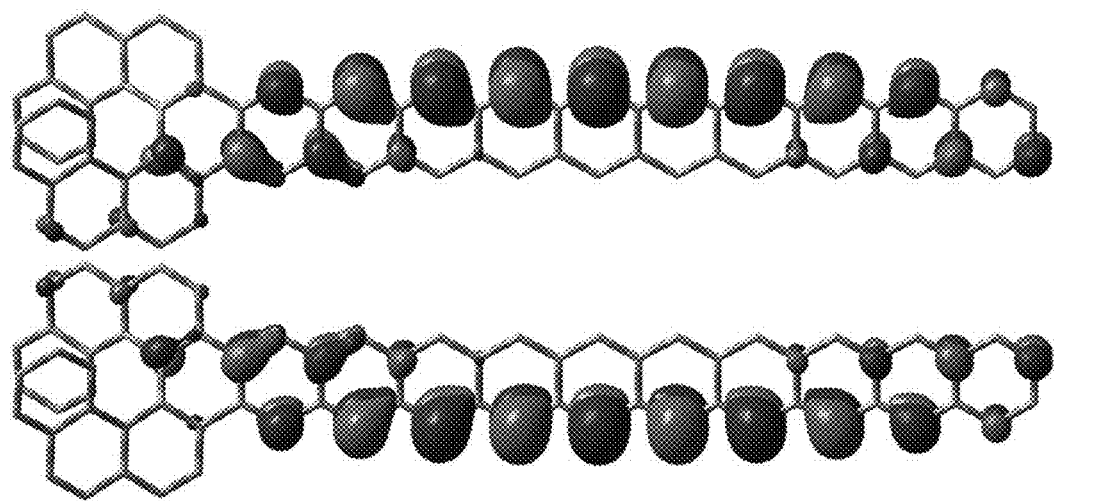
FIG. 61 illustrates singularly occupied orbitals of [7]n10.

The higher acenes have open-shell singlet, diradical ground states with degenerate SOMOs that reside on opposite edges of the linear structures.[56] Hexacene is the first acene to have an open-shell ground state at the UB3LYP/6-31G(d) computational level. Stability calculations of the [7]Series at the same computational level are conducted for comparison. For those compounds found to have a RHF→UHF instability, an unrestricted optimization is performed at the UB3LYP/6-31G(d) computational level. The SOMOs of [7]n10 are presented in FIG. 61.

Although the open-shell behavior of the acene-embedded [7]Series is similar to the free-acenes, they deviate in two ways. (i) As progression is made through the [7]Series, an open-shell singlet diradical ground state is not detected until [7]n6, which is the heptacene embedded species. This is one benzo-annulation longer than the point at which the acenes have an RHF→UHF instability. This is due to higher benzenoid character in the [7]heliacenes than the free-acenes (see FIG. 59). (ii) The SOMOs of the [7]Series do not reside entirely on the acene motif, with leakage of the radical-ribbon SOMOs onto the helical domain. The ability of the dual-domain nature of the [7]heliacenes to curb diradical behavior has important consequences related to their persistence, since open-shell arrangements open pathways to decomposition in the absence of light.

Houk has already studied the distortion energy for twisting the acenes longitudinally.[36] This experiment is reproduced with a relaxed scan, longitudinally twisting pentacene by 5° increments for 29 steps reaching an acene twist of 145° in the final structure. The 145° twisted pentacene is 57.3 kcal/mol higher in energy than planar pentacene in excellent agreement with the 60 kcal/mol value that Houk[36] reported for 144° twisted pentacene. For comparison, a relaxed scan is performed on [7]n4, increasing the longitudinal twist of the imbedded acene by 5° for 25 steps. This twisted the acene an additional 125° from a base value of 27°, reaching a final acene twist of 152°. The distortion energy as a function of acene longitudinal twist for both experiments are presented in the same graph in FIG. 62, while these energies and the corresponding scan coordinate and resulting acene twists are listed in Table 17.

TABLE 17

Figure 69:
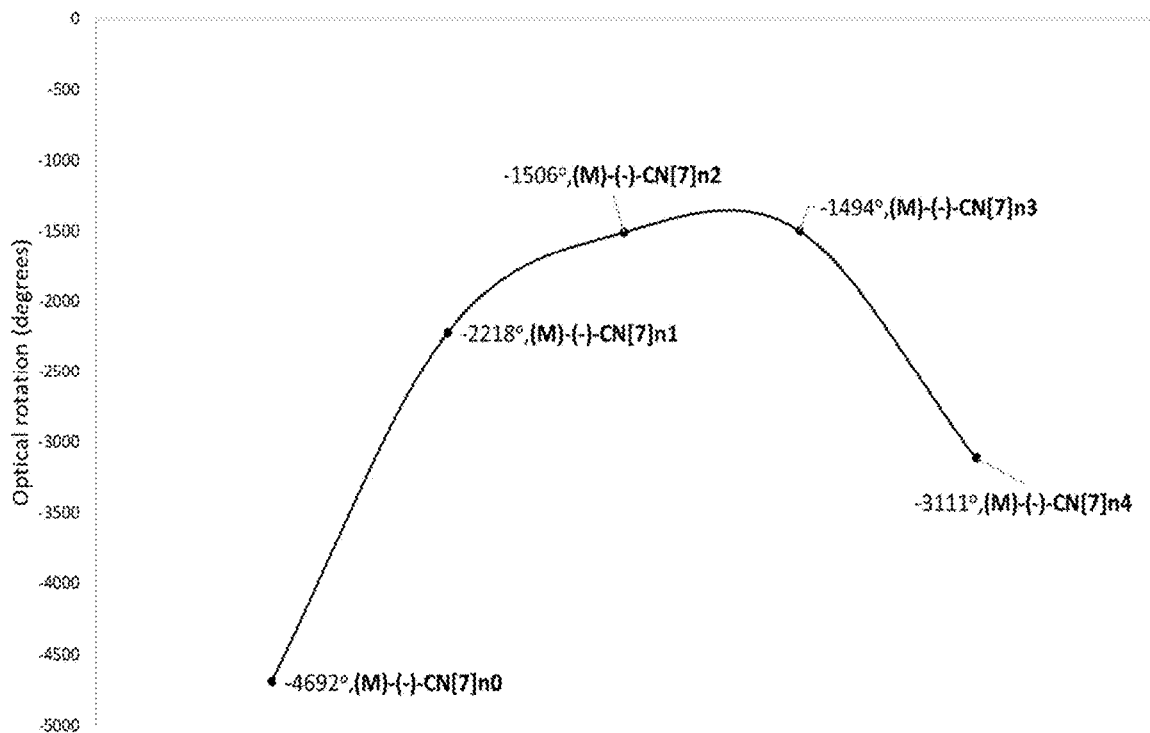
FIG. 69 is a graph that shows optical rotations of the (M)-(−)-CN[7]Series calculated at the M06-2X/6-31G(d) computational level.

Distortion energies, scan coordinates, and acene twist values for the relaxed scan experiments described for FIG. 69. (B3LYP/6-31G(d))

| Pentacene | | | [7]n4 | | |
| --- | --- | --- | --- | --- | --- |
| Acene Twist (degrees) | θ* (degrees) | Distortion energy (kcal/mol) | Acene Twist (degrees) | θ* (degrees) | Distortion energy (kcal/mol) |
| 0 | 0 | 0.00 | 27 | 0 | 0.00 |
| 5 | 5 | 0.07 | 32 | 5 | 0.06 |
| 10 | 10 | 0.27 | 37 | 10 | 0.26 |
| 15 | 15 | 0.60 | 42 | 15 | 0.57 |
| 20 | 20 | 1.06 | 47 | 20 | 0.99 |
| 25 | 25 | 1.66 | 52 | 25 | 1.53 |
| 30 | 30 | 2.39 | 57 | 30 | 2.22 |
| 35 | 35 | 3.25 | 62 | 35 | 3.04 |

TABLE 17-continued

Distortion energies, scan coordinates, and acene twist values for the relaxed scan experiments described for FIG. 69. (B3LYP/6-31G(d))

| Pentacene | | | [7]n4 | | |
|---|---|---|---|---|---|
| Acene Twist (degrees) | θ* (degrees) | Distortion energy (kcal/mol) | Acene Twist (degrees) | θ* (degrees) | Distortion energy (kcal/mol) |
| 40 | 40 | 4.23 | 67 | 40 | 4.01 |
| 45 | 45 | 5.33 | 72 | 45 | 5.11 |
| 50 | 50 | 6.57 | 77 | 50 | 6.36 |
| 55 | 55 | 7.95 | 82 | 55 | 7.76 |
| 60 | 60 | 9.48 | 87 | 60 | 9.32 |
| 65 | 65 | 11.15 | 92 | 65 | 11.02 |
| 70 | 70 | 12.96 | 97 | 70 | 12.87 |
| 75 | 75 | 14.89 | 102 | 75 | 14.88 |
| 80 | 80 | 16.96 | 107 | 80 | 17.04 |
| 85 | 85 | 19.17 | 112 | 85 | 19.35 |
| 90 | 90 | 21.53 | 117 | 90 | 21.83 |
| 95 | 95 | 24.04 | 122 | 95 | 24.46 |
| 100 | 100 | 26.69 | 127 | 100 | 27.21 |
| 105 | 105 | 29.50 | 132 | 105 | 30.14 |
| 110 | 110 | 32.45 | 137 | 110 | 33.24 |
| 115 | 115 | 35.55 | 142 | 115 | 36.51 |
| 120 | 120 | 38.80 | 147 | 120 | 39.92 |
| 125 | 125 | 42.20 | 152 | 125 | 43.49 |
| 130 | 130 | 45.75 | | | |
| 135 | 135 | 49.45 | | | |
| 140 | 140 | 53.31 | | | |
| 145 | 145 | 57.33 | | | |

*Scan coordinate

Figure 63:
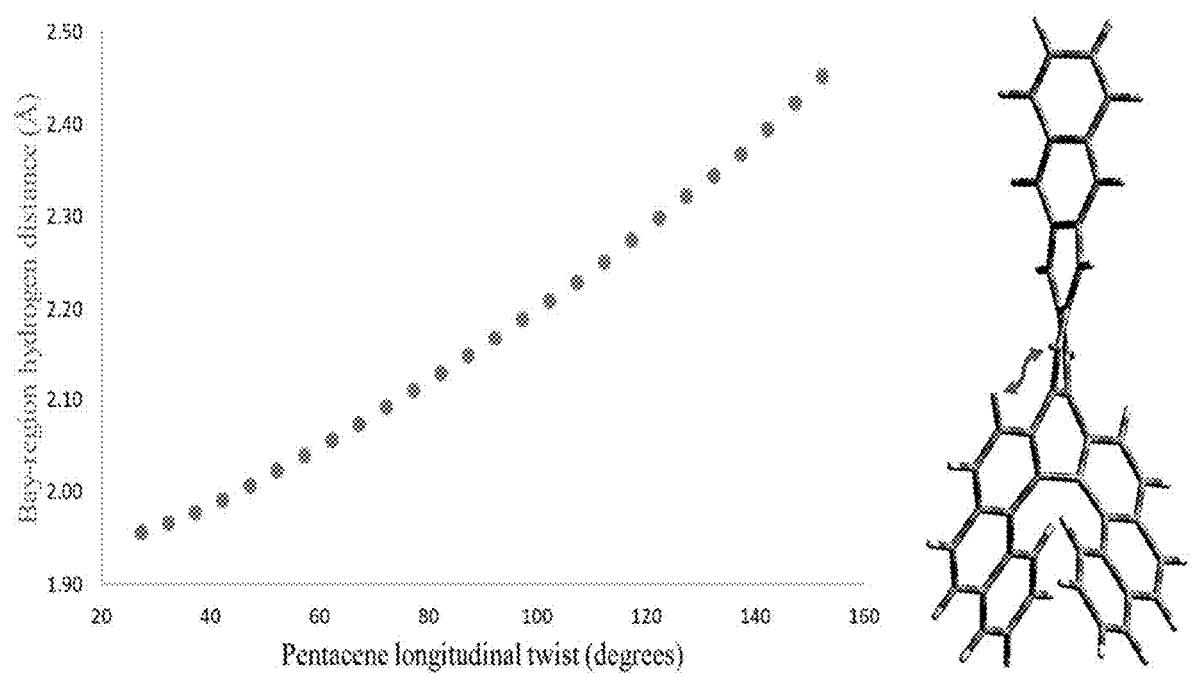
FIG. 63 is a plot of distance between the bay-region hydrogens (green) of [7]n4 as a function of pentacene longitudinal twist. (B3LYP/6-31G(d))

Pascal reported a distortion energy of only 3.2 kcal/mol for longitudinally twisting naphthalene by 20°.[42] This is one of the first indications that the acenes, a series of compounds traditionally thought of as rigid, have a much higher propensity to flex than originally anticipated. Pentacene can reach even higher twist values at lower distortion energies (20° pentacene twist=1.1 kcal/mol, Table 17) since each ring shares the overall acene twist. Small distortion energies for twisting 20° are indicative of minimal loss of orbital overlap. It has been noted that 97% overlap between adjacent p-orbitals is maintained when heptacene is subjected to an end-to-end twist of 24 to 27°.[36] The heliacene [7]n4 is significantly easier to twist about the longitudinal axis of the acene moiety than pentacene. (FIG. 62) For example, to access the 145° twisted structure in pentacene it costs approximately 57 kcal/mol (Table 17) but only 39 kcal/mol in [7]n4. Twisting in the heliacene [7]n4 is facilitated by a concomitant decrease in the two H/H bay-region interactions. The distance between the bay-region hydrogens increase from 1.96 Å to 2.45 Å (FIG. 63) as the acene twist angle is changed from 27° to 147°. This suggests that each bay-region H/H interaction contributes approximately 9 kcal/mol to the strain energy that is released upon twisting by 120° in [7]n4.

Figure 64A:
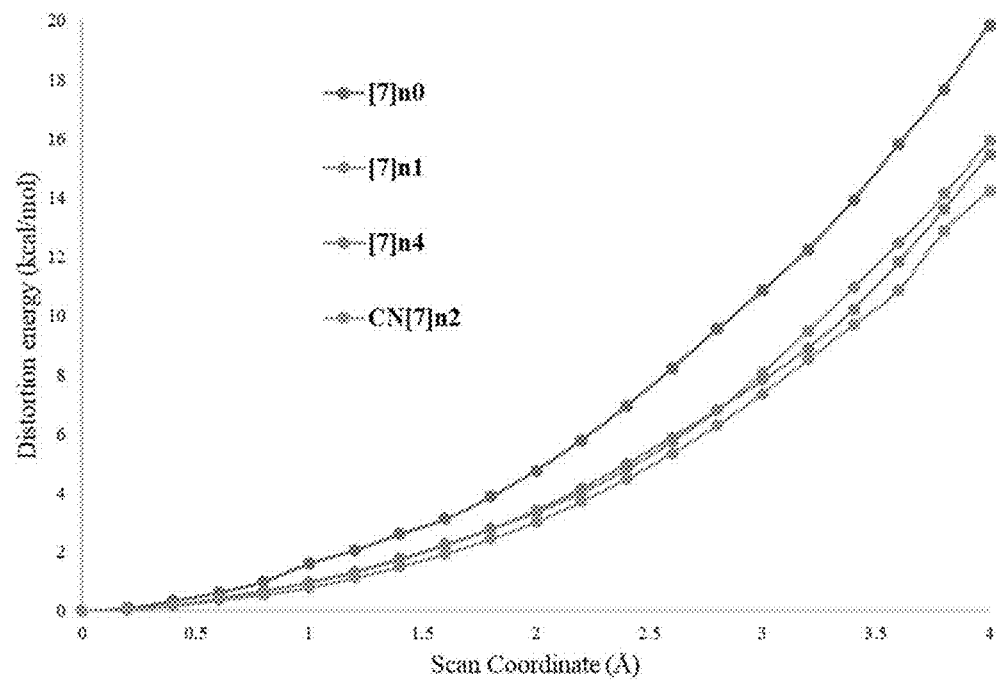
FIG. 64A is a plot of distortion energies of [7]n0, [7]n1, [7]n4, and CN[7]n4 as a function of increasing the helical pitch by 0.2 Å increments.
Figure 64B:
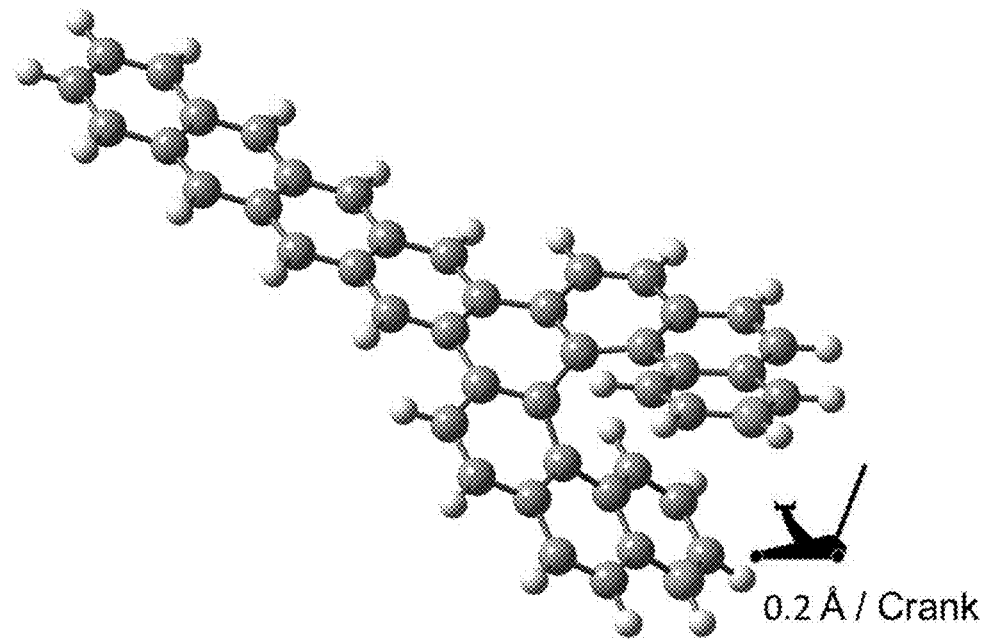
FIG. 64B illustrate the structure of [7]n4 with outer-rim carbons used in the scan coordinate color coded orange (M06-2X/6-31G(d))
Figure 65:
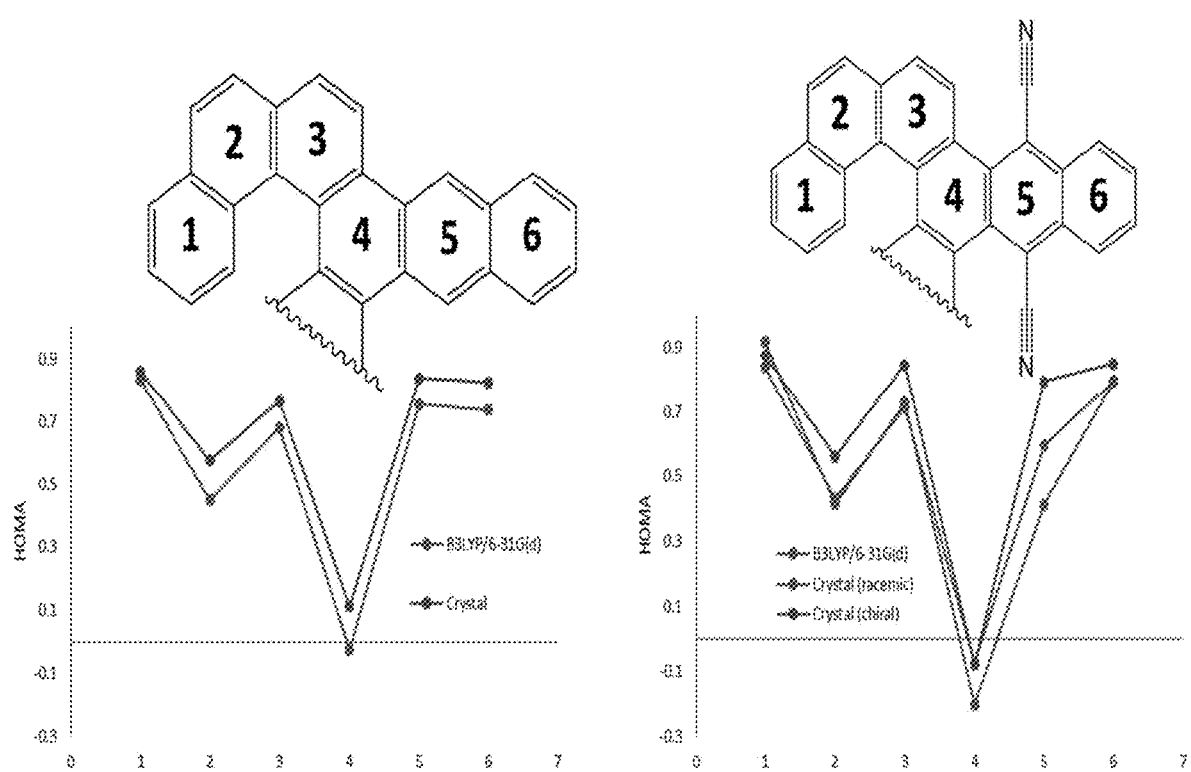
FIG. 65 illustrates HOMA values for the rings of [7]n2 (left) and CN[7]n2 (right), with bond lengths obtained from crystal structures and from B3LYP/6-31G(d) optimized structures for comparison.

The distortion energy related to opening the helical "jaws" of the [7]Series is calculated through a relaxed scan in which the bond distance between the two outer-rim carbons color coded orange in FIG. 64B is incrementally increased by 0.2 Å for 20 steps. This experiment is performed for the [7]Series and CN[7]n2. The distance between the orange carbons is 4.30 Å, 4.11 Å, 4.15 Å, and 4.14 Å at scan coordinate 0 for [7]n0, 7]n1, 7]n4, and CN[7]n2, respectively. The distortion energies as a function of scan coordinate are presented graphically in FIGS. 64A and 64B and listed in Table 18. To better account for the dispersion interactions between the terminal rings in the [7]helicene motifs, the Minnesota functional,[59] M06-2X, is used in conjunction with the 6-31G(d) basis set.

TABLE 18

Relaxed scan coordinates and corresponding distortion energies for FIGS. 64A and 64B;

| Scan Coordinate (Å) | Distortion Energy (kcal/mol) | | | | | |
|---|---|---|---|---|---|---|
| | [7]n0 | [7]n1 | [7]n2 | [7]n3 | [7]n4 | CN[7]n2 |
| 0.0 | 0.00 | 0.00 | 0.00 | 0.00 | 0.00 | 0.00 |
| 0.2 | 0.10 | 0.05 | 0.05 | 0.06 | 0.06 | 0.06 |
| 0.4 | 0.35 | 0.20 | 0.19 | 0.20 | 0.20 | 0.18 |
| 0.6 | 0.63 | 0.42 | 0.43 | 0.44 | 0.44 | 0.37 |
| 0.8 | 1.00 | 0.68 | 0.69 | 0.70 | 0.70 | 0.56 |
| 1.0 | 1.62 | 0.98 | 0.97 | 0.97 | 0.96 | 0.80 |
| 1.2 | 2.06 | 1.35 | 1.34 | 1.34 | 1.32 | 1.12 |
| 1.4 | 2.61 | 1.78 | 1.78 | 1.78 | 1.75 | 1.51 |
| 1.6 | 3.12 | 2.26 | 2.28 | 2.28 | 2.22 | 1.93 |
| 1.8 | 3.87 | 7.78 | 2.82 | 2.85 | 7.78 | 2.43 |
| 2.0 | 4.76 | 3.34 | 3.40 | 3.48 | 3.41 | 3.02 |
| 2.2 | 5.79 | 4.02 | 4.04 | 4.16 | 4.15 | 3.71 |
| 2.4 | 6.95 | 4.82 | 4.77 | 4.92 | 4.99 | 4.48 |
| 2.6 | 8.23 | 5.74 | 5.61 | 5.74 | 5.90 | 5.34 |
| 2.8 | 9.55 | 6.82 | 6.56 | 6.65 | 6.82 | 6.30 |
| 3.0 | 10.87 | 8.09 | 7.68 | 7.66 | 7.83 | 7.37 |
| 3.2 | 12.26 | 9.50 | 9.02 | 8.86 | 8.91 | 8.53 |
| 3.4 | 13.93 | 10.98 | 10.56 | 10.34 | 10.22 | 9.71 |
| 3.6 | 15.81 | 12.49 | 12.14 | 11.98 | 11.83 | 10.88 |
| 3.8 | 17.70 | 14.12 | 13.77 | 13.70 | 13.62 | 12.88 |
| 4.0 | 19.88 | 15.95 | 15.56 | 15.50 | 15.48 | 14.22 |

Three notable observations may be made from the information in FIGS. 64A and 64B and Table 18. (i) The energetics of all species studied are extremely resilient to geometric distortions of the helical pitch, indicated by distortion energies less than 5 kcal/mol for a 2 Å increase in helical pitch for each compound. This is an important finding for those who seek to engineer helicenes as molecular tweezers for cationic species, since a single geometry is not achieved in the helical domain, but rather a wide range of geometries are sampled even at room temperature. This also contradicts reports of inflexibility in the [7]helicene scaffold.[60] (ii) Compared to [7]helicene, the acene annulated species have lower distortion energies. This is caused by relief of strain associated with an increased distance between bay-region hydrogens with increasing scan coordinate. (iii) Finally, the distortion energies of the cyanated species, CN[7]n4, are only marginally less than those observed for the non-cyanated analogue, [7]n4.

The aromatic nature of the acenes and helicenes have previously been explored using the magnetic Nucleus Independent Chemical Shifts (NICS), the geometric Harmonic Oscillator Model of Aromaticity (HOMA), and the electronic Para Delocalized (PDI) indices of local aromaticity.[61] The respective NICS(0), HOMA, and PDI values of −9.67, 0.984, and 0.1047 originating from the archetypical aromatic compound, benzene, serve as a good points of reference for approximate values typically observed for fully aromatic rings. Values that are less negative for NICS(0) and smaller for HOMA and PDI are indicative of rings that have a lower expression of aromaticity compared to benzene. The local aromaticity of the acenes and helicenes are independently calculated using these widely used indices. These findings confirm those reported in the literature, but additional insight is obtained when the results of each corresponding homologue of the helicene and acene series areare plotted on the same graph. Without this correlation, plotting the aromaticity of the helicenes and the acenes can be misleading. Correlator plots of the local aromaticity of the (n)acenes and (n)helicenes are generated.

NICS(0) values greatly deviate from one ring to the next within each helicene and acene studied. This is consistent with the higher benzenoid character of the helicenes, with species containing localized aromatic sextets, but is inconsistent for the acenes, which have a single resonating aromatic sextet shared by each ring. Even more concerning, is the fact that NICS predicts local aromaticity values that fluctuate to a greater extent in the acenes compared to the helicenes. The HOMA and PDI indices agree with NICS(0) for the helicenes and match the expected aromaticity pattern for [5]helicene with only one optimal Clar resonance structure. However, these indices deviate dramatically from NICS in their assessment of the aromatic behavior of the acenes. Like NICS(0), these indices predict that the central rings of the acenes are more aromatic than the terminal rings, but values do not deviate by an appreciable amount. This is especially evident with a side-by-side comparison to the helicene isomers, with acene values forming relatively flat plots. This is much more congruent with chemical intuition and shines a light on a flaw of the NICS local aromaticity index.

The local assessment of aromaticity via the NICS technique is known to be perturbed by Global ring currents in PAHs.[62] For example, in pentacene there are benzene-, naphthalene-, anthracene-, and pentacene-motifs, each with their own ring current. It is impossible to get a NICS value that represents a single ring in the presence of these global ring-currents. To eliminate these global ring-currents each ring is "cut" out, replacing C—C bonds with C—H bonds when required, and separately analyzed their NICS values. This approach is called the Isolated Ring Nucleus Independent Chemical Shifts (IR-NICS) technique. The IR-NICS approach is desirable for two reasons: (i) NICS values cannot exceed those found for the archetypical aromatic ring, namely benzene (NICS(0)=−9.67 @ B3LYP/6-31G (d)). (ii) Only the local ring-current contribution to NICS is measured. The IR-NICS(0) values for the helicenes and acenes are measured.

The IR-NICS technique gives local aromaticity values that are much more constant through each ring of the acenes compared to traditional NICS, while the aromatic behavior of the helicenes remains the same. IR-NICS has a much stronger correlation with HOMA, PDI, and chemical intuition.

The local aromaticity values of the [7]heliacenes were assessed using the NICS(0), HOMA, and PDI indices. Included in these aromaticity studies are the structural components that make up the [7]heliacenes, such as [7]helicene, triphenylene and the corresponding free-acenes. Correlator plots of the local aromaticity values of the [7]Series and their structural components are part of the present invention.

There are three different types of rings in the [7]heliacenes. (i) Helicene-like (rings 1-3). (ii) Acene-like (rings 5-8). (iii) Ring 4 is the most unique, it is triphenylene-like, behaving in its aromatic expression as the empty ring in triphenylene. This indicates that there is minor contribution from resonance forms that contain an aromatic sextet in the fulcrum ring like the structure in FIG. 60. To reiterate, ring 4 remains empty through the series and rings 5 through 8 contain a resonating sextet. In [7]n1 ring 5 is fully benzenoid, but gradual loss in aromaticity is observed for this ring as the sextet is shared by more rings.

Detection of the aromatic nature of the transition state of the Diels-Alder cycloaddition has been used as a qualifying test for aromatic indices.[63] The local aromaticity of the transition states of racemization are assessed for the [7]Series.

The aromatic response of the transition states of racemization and the corresponding starting structures are very similar.

The NICS(0), HOMA, and PDI aromaticity values were calculated for the CN[7]Series.

Overall, there is not a marked difference in the aromaticity of the CN[7]Series compared to the [7]Series. As expected, ring 5 which contains two electron withdrawing para-nitrile groups is less aromatic than the non-cyanated counterparts in all instances for HOMA and PDI. This is not universally true for NICS(0), probably due to global ring perturbations.

Figure 77:
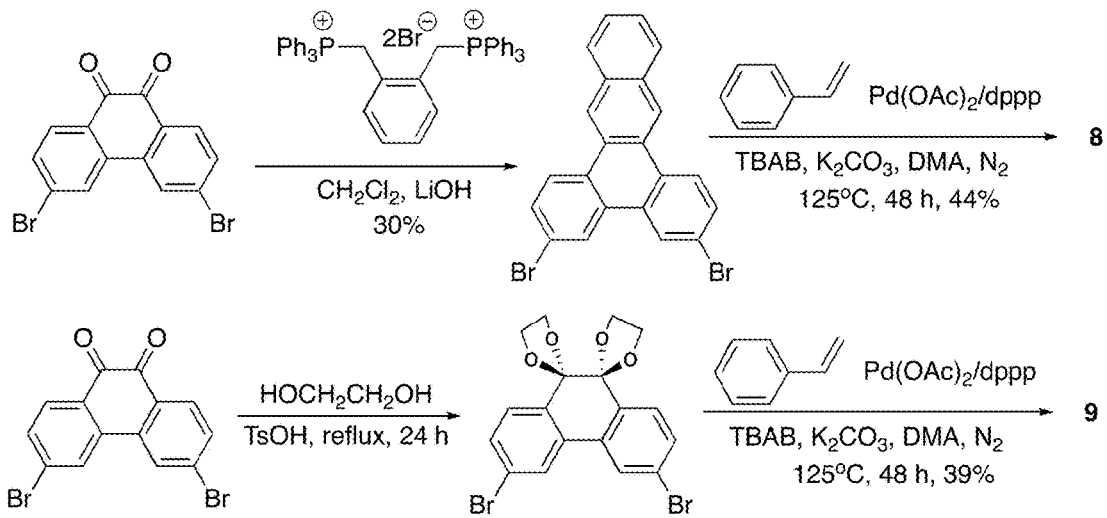
FIG. 77 illustrates the synthesis of bis-Mallory photocyclization substrates 8 and 9.

Structural elucidation is achieved for [7]n2 and CN[7]n2 through Single-crystal X-ray diffraction experiments. An additional structure is obtained for CN[7]n2 when a chiral crystal is analyzed. Bond lengths from these experimentally observed geometries are used to calculate local aromaticity through the HOMA index. These values are graphically presented in FIG. 77 for [7]n2 (left) and CN[7]n2 (right). For comparison, the HOMA values originating from the corresponding computer optimized structures are overlaid in each plot (B3LYP/6-31G(d)).

Experimental HOMA values of [7]n2 do not deviate much from those obtained computationally. This is true despite markedly different geometries in the crystal vs. the calculated structure (acene twist, 32.5° vs. 24.6°; Helical pitch, 4.02 Å vs. 4.84 Å; helical core dihedral, −29.5° vs. −33.8°). This is an indication that orbital overlap is maintained with moderate geometric, torsional changes. Bond-length equalization is maintained through longitudinal twisting.

Two distinct crystals were grown for CN[7]n2, one chiral and one racemic. Each of these crystals displayed different packing motifs and different geometric parameters. Despite these differences these compounds and the calculated structure presented very similar HOMA values.

How the chiroptical properties evolve through the [7]heliacenes as a function of acene elongation is of interest, since they have utility as chiroptical components in organic electronic devices. As already described, the chiral resolution of CN[7]n2 and the measurement of its circular dichroism (CD) spectra were presented. The CD spectra of CN[7]n2 is also computer fitted, assigning its absolute configuration. The evolution of the CD spectra and optical rotation through the [7]Series and CN[7]Series were computationally investigated as will now be described.

Figure 66A:
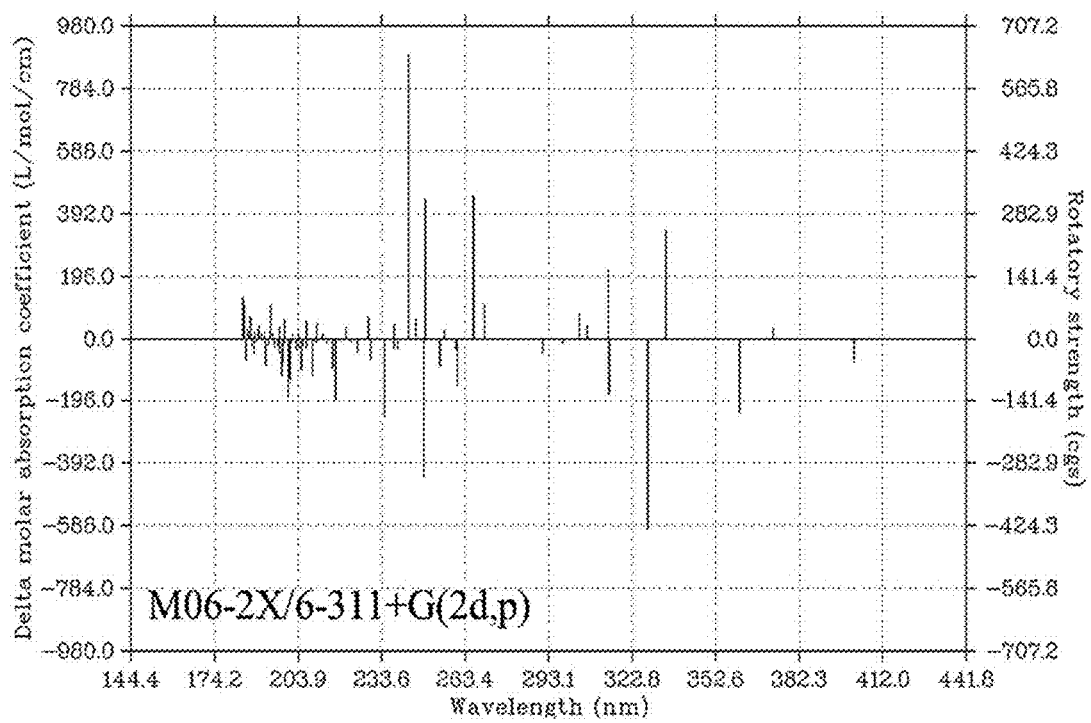
FIGS. 66A and 66B illustrate transitions and rotatory strengths of (M)-(−)-CN[7]n2 calculated using the TDM06-2X/6-31G(d) and TDM06-2X/6-311+G(2d,p) computational levels, respectively.
Figure 66B:
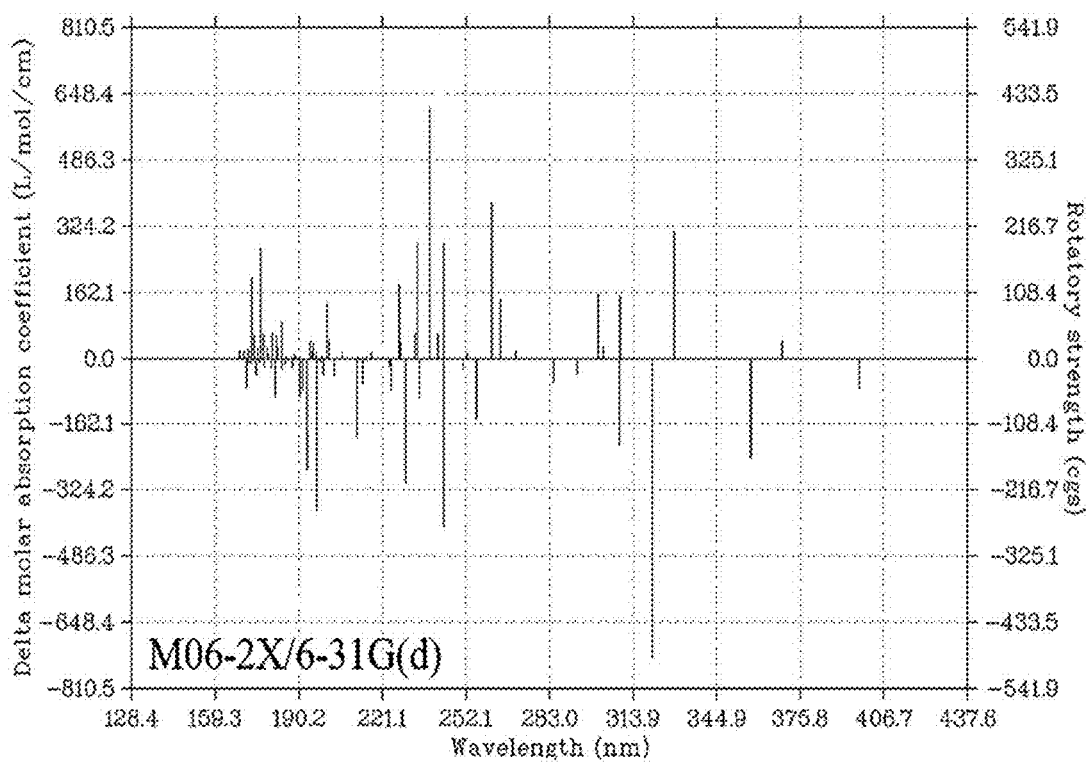

Previously, it has been found that the M06-2X functional best reproduced the bisignate nature of the experimental CD spectrum of (M)-(−)-CN[7]n2. This calculation is run using the computationally expensive 6-311+G(2d,p) basis set. To see how the much smaller 6-31G(d) basis set performed in conjunction with the M06-2X functional, a side-by-side comparison is performed between these two basis sets. The calculated transitions and rotatory strengths of (M)-(−)-CN [7]n2 using these different basis-sets while holding the functional constant (M06-2X) are presented in FIGS. 66A and 66B for TDM06-2X/6-311+G(2d,p) and TDM06-2X/6-31G(d), respectively.

Although the wavelengths of each transition are offset by a uniform amount between each basis set, the sign and intensity of the 10 most bathochromic transitions are identical. To save computational resources the M06-2X functional is used in conjunction with the smaller 6-31G(d) basis set to calculate the CD spectra of the (M)-(−)-[7]Series.

There are two primary trends in the CD spectra of the [7]Series as the acene domain is extended: (i) The bisignate strength between 300 and 350 nm gets incrementally weaker up to the anthracene embedded species (M)-(−)-[7]n2 and is close to non-existent for the tetracene and pentacene embedded species. This seems to be due to the sudden development of two transitions around 325 nm with approximately equal rotatory strengths and of the opposite sign. (ii) Weaker bathochromic transitions appear as the acene is extended. Longer acenes absorb at increasingly longer wavelengths. The weak rotatory strength of these acene transitions are indicative of the minimally twisted nature of the acenes in the non-substituted [7]Series.

The CD spectra were also calculated for the (M)-CN[7] Series. These spectra are calculated at the M06-2X/6-31G(d) computational level.

The CD behavior of the CN[7]Series is similar to that of the [7]Series. However, there are two noteworthy differences. (i) The CN[7]Series has lower energy transitions, coinciding with the experimentally observed bathochromic absorption of CN[7]n2 relative to [7]n2. (ii) These bathochromic transitions have higher rotatory strength in the CN[7]Series compared to the most bathochromic transitions of the [7]Series. This is consistent with the experimental and theoretical observation that the acene is more twisted in the cyanated [7]heliacenes, resulting in higher CD responses for the more twisted acene chromophore in the CN[7]Series.

The optical rotations of the (M)-[7]Series were calculated at the M06-2X/6-311++G(2d,p) computational level as a function of acene elongation. An incident light frequency of 579 nm was used for the electromagnetic field perturbation. This calculation is repeated for the (M)-[7]Series using the smaller 6-31G(d) basis set and an incident light frequency of 589 nm, which is the sodium D-line.

Figure 67:
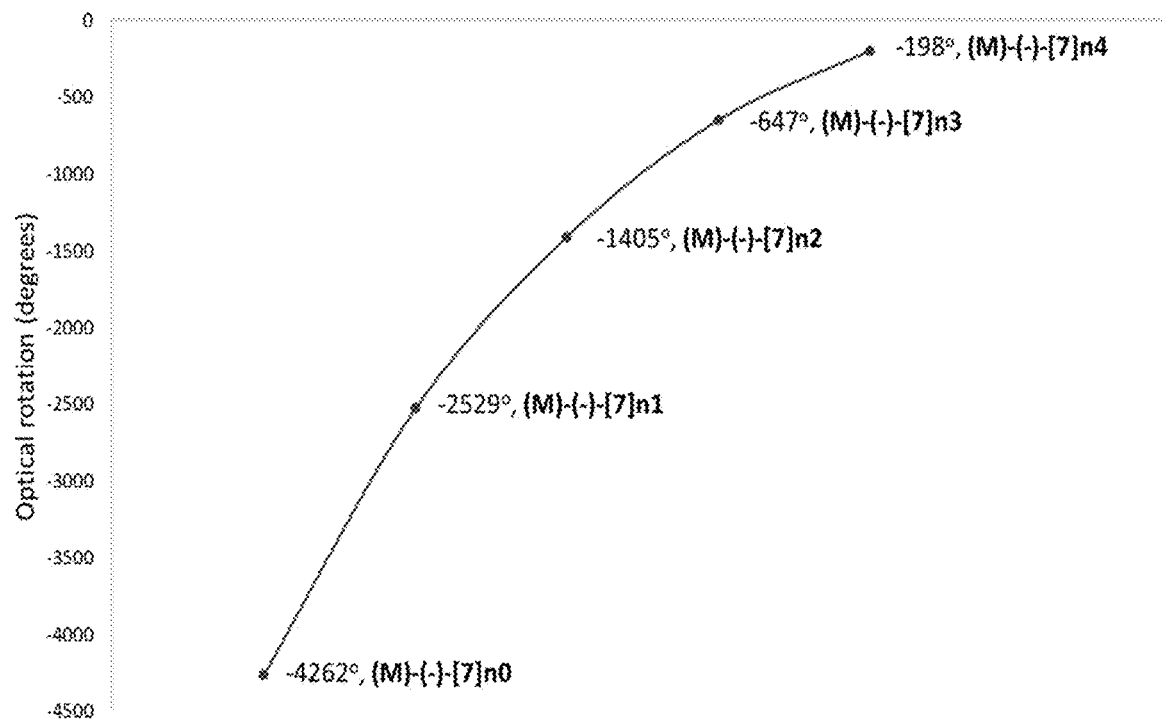
FIG. 67 is a graph that shows optical rotations of the (M)-(−)-[7]Series calculated at the M06-2X/6-311++G(2d, p) computational level.
Figure 68:
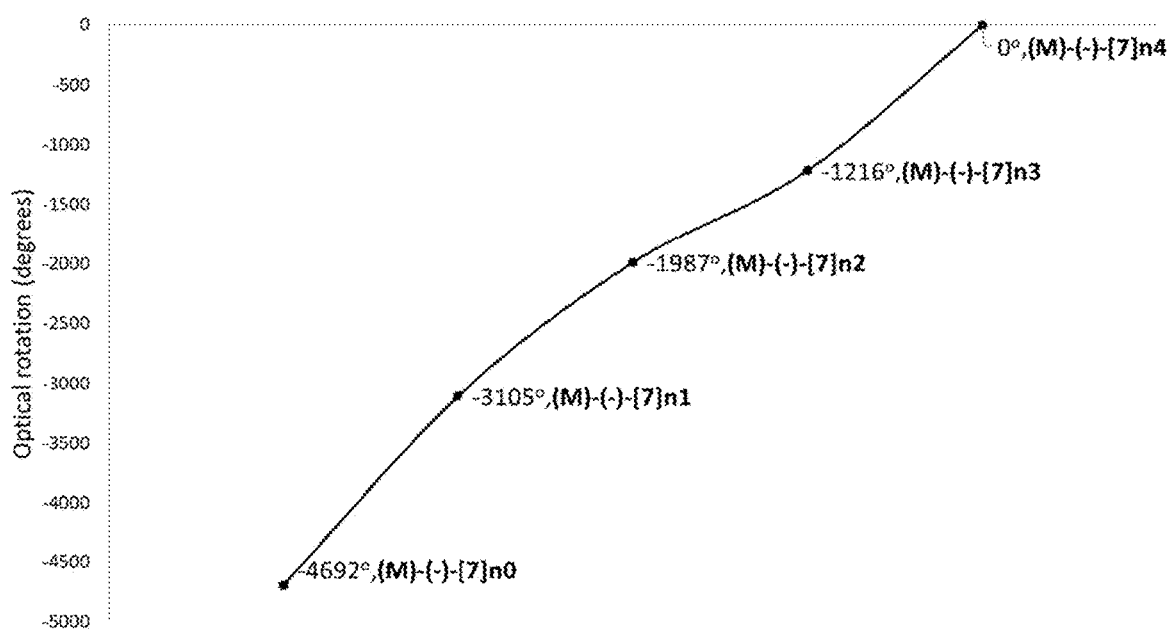
FIG. 68 is a graph that shows optical rotations of the (M)-(−)-[7]Series calculated at the M06-2X/6-31G(d) computational level.

Despite the difference in basis set, both plots in FIGS. 67 and 68 predict optical rotations that decrease through the [7]Series. A large value around 4500 for [7]helicene steadily decreases to a value close to 0° for the pentacene embedded species [7]n4. This is consistent with the incremental migration of the frontier orbitals onto the less optically active acene domain through the series. These results are also in accord with the experimental observation that benzo-annulation onto [7]helicene causes the optical rotation to decrease.[64]

The optical rotations of the (M)-(−)-CN[7]Series are calculated at the M06-2X/6-31G(d) computational level. These values are plotted in FIG. 69 as a function of acene elongation.

The optical rotations of the cyanated species respond to acene elongation in a similar fashion compared to their non-cyanated counterparts for the first few species. The optical activity decreases steadily, leveling off at around −1500° for (M)-(−)-CN[7]n3. However unexpectedly, the optical activity of (M)-(−)-CN[7]n4 increases dramatically reaching a rotation of −3111°.

It is noted that Mori et al.[65] have shown that dual helicenes can have enhanced chiroptical properties, depending on the orientation of each "chirophore" with respect to one another. This phenomenon is explained by the coupling, or vector addition of the electronic ($\mu_e$) and magnetic ($\mu_m$) transition dipole moments of each optical domain of the dual helicene structure. If the angle relating the summed electronic and magnetic transition dipole moments is close to zero, then enhanced chiroptical properties are observed. The X and S shaped dual helicenes studied by Mori's group had helicenes with the same configuration and helical axes oriented in the same general direction. The inventive systems differ from these X and S shaped dual helicenes, in that the two "chirophores" that make up the [7]heliacenes are of the opposite configuration and have helical axes that are orthogonal to one another. To investigate if constructive or deconstructive coupling is present between the two chiroptical components in the inventive [7]heliacenes systems, the optical rotation and CD spectra of each chiral component isolated is first separately analyzed and then compared to the results originating from the combined dual-domain species. In this investigation, octa-Ph[7]n4 is used as a model system, since it has large optical contributions from both the [7]helicene and the acene (158° longitudinal acene twist) domains. For ease of analysis and to cut down on computational time, the phenyl groups are removed (replaced by hydrogens) and the acene twist is frozen. Removal of Ph-groups from twisted acenes has been shown to have little effect on their electronic properties.[36] Under this constraint the structure is allowed to relax. To generate a series, the acene is incrementally shortened and the resulting acene twist is again frozen and each structure is optimized under this constraint. This generated a [7]heliacene series that is studied as a function of elongation of a fully twisted acene domain. For each of these structures, an optical rotation calculation is performed at the M06-2X/6-31G(d) computational level. These values are presented in FIG. 70. A comparable series without the helical domain is generated in the same fashion starting with pentacene frozen at 158°. Optical rotations for these structures calculated at the same level of theory are presented in FIG. 71.

Figure 70:
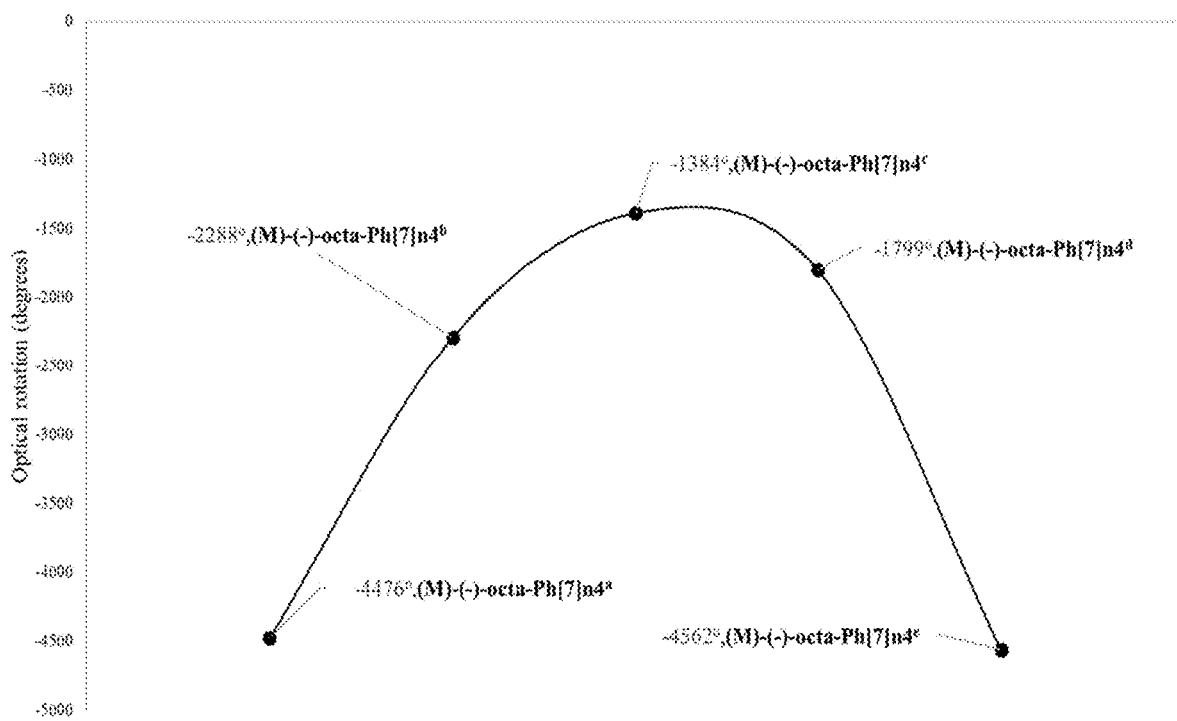
FIG. 70 is a graph that shows optical rotations of modified geometries of octa-Ph[7]n4, where all structures have Ph substituents replaced by hydrogens; a: rings E, F, G, and H removed; b: rings F, G, and H removed; c: rings G, and H removed; d: ring H removed; e: no rings removed; and each structures acene twist is frozen and reoptimized under this constraint.
Figure 71:
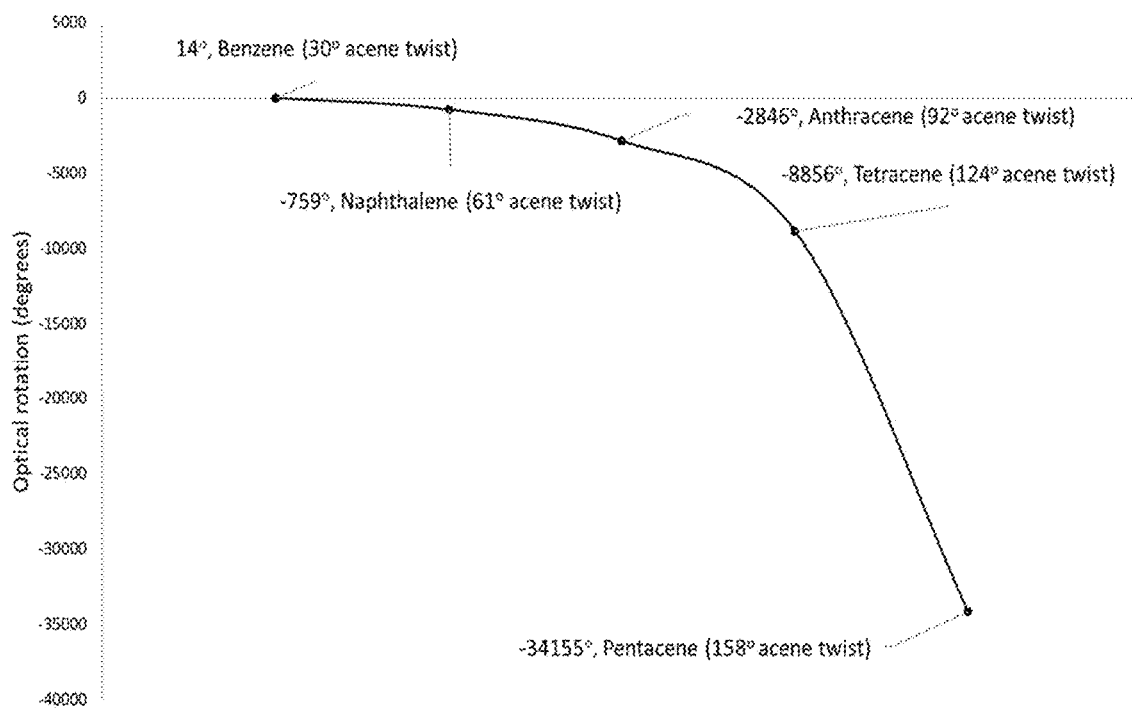
FIG. 71 is a graph that shows optical rotations of artificially twisted acenes, with accene twists frozen, and where accene twists are indicated in parentheses, as calculated at the M06-2X/6-31G(d) computational level.

FIGS. 70 and 71 indicate that there is non-additive coupling between the twisted acene and [7]helicene domains. [7]helicene and 158° twisted pentacene have optical rotations of −4476° and −34155°, respectively. When these two components are combined, the optical rotation is −4562°, giving an absolute value of rotation that is 34069° less than the sum of the two individual components.

Figure 72A:
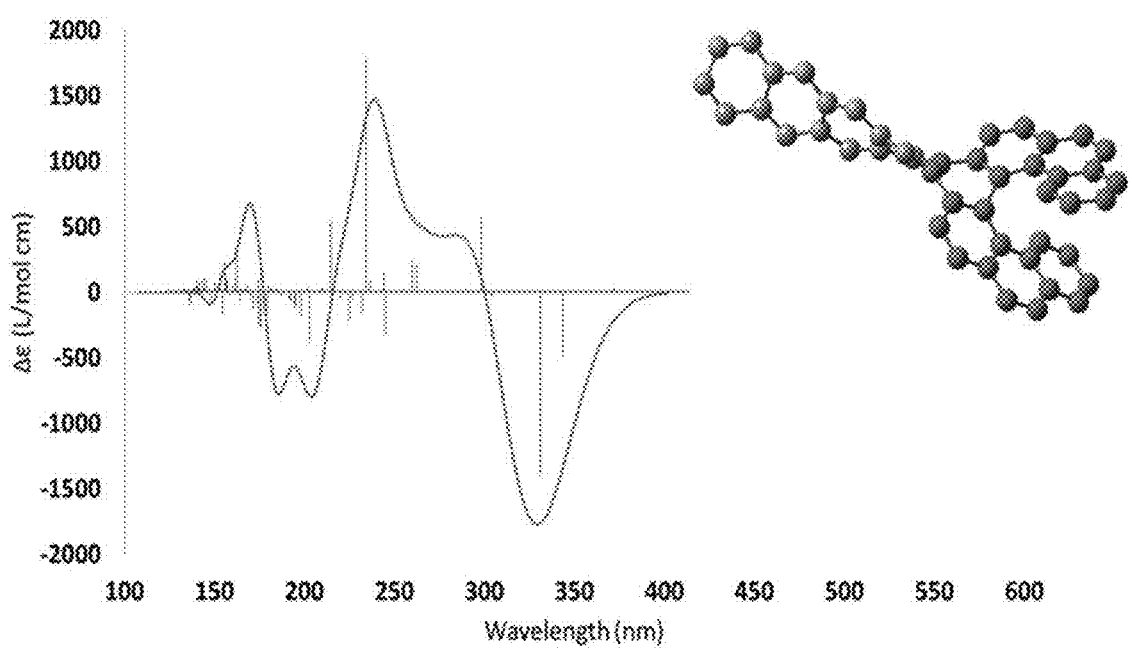
FIGS. 72A-72C illustrate the calculated CD spectra of modified octa-Ph[7]n4 with phenyl groups replaced by hydrogens and the acene twist frozen (FIG. 72C), the isolated twisted acene domain (FIG. 72B), and the isolated helical domain (FIG. 72A), which are calculated at the M06-2X/6-31G(d) computational level.
Figure 72B:
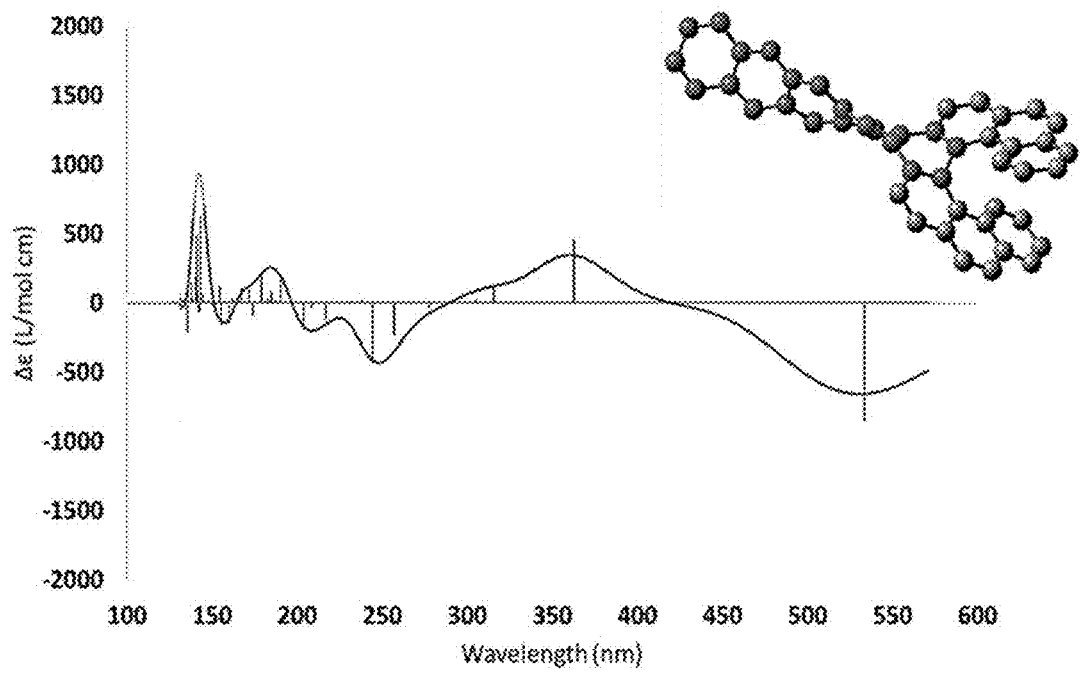
Figure 72C:
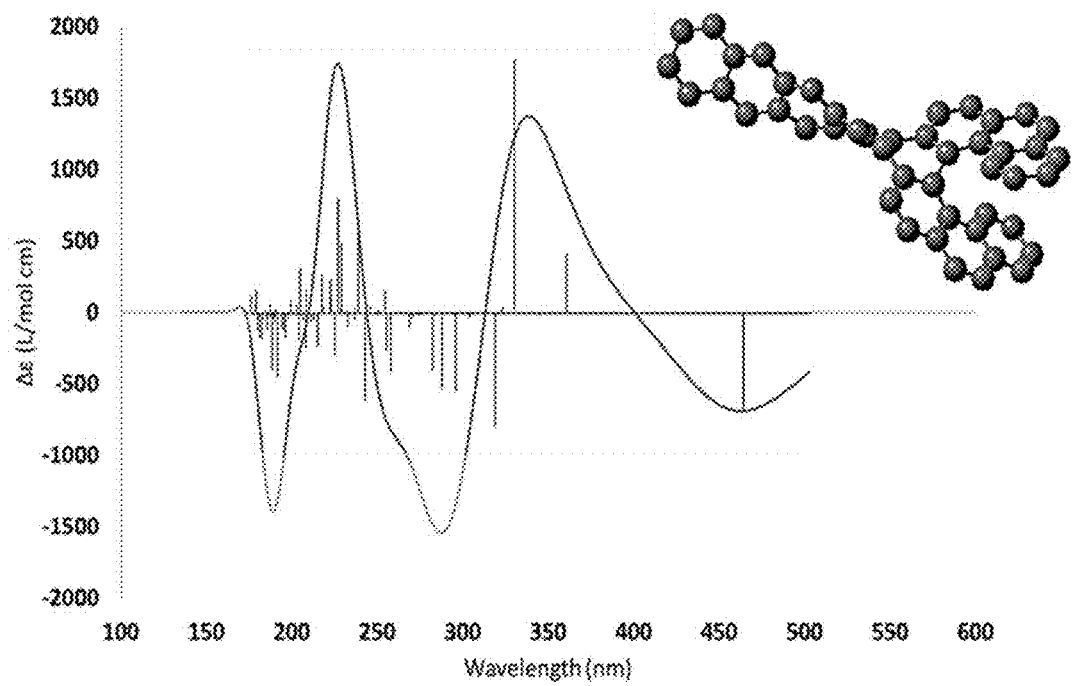

The effect of coupling [7]helicene and twisted acenes to make the [7]heliacenes on their CD spectra is probed. For this experiment, TD-DFT calculations are performed on the relaxed structure of octa-Ph[7]n4 with its phenyls removed and its acene twist frozen. This is repeated on relaxed pentacene with its longitudinal twist constrained to 158°, and on the isolated helical motif of octa-Ph[7]n4. These are the purple, blue, and red structures in FIGS. 72A-72C, respectively. To the left of these structures are the corresponding calculated CD spectra with the transitions and rotatory strengths, calculated at the M06-2X/6-31G(d) computational level.

The rotatory strength of the most bathochromic transition of the purple structure is much stronger than that produced by the dramatically less twisted acene in minimized [7]n4 (. Compared to the free helicene, the cotton effect sign is reversed between 300 and 350 nm for the dual-domain purple structure. Interestingly, the transition rotatory strengths are weaker in the free twisted acene, despite this structure producing a huge optical rotation of −34000°.

The rotatory strength of the most bathochromic transition of the purple structure is much stronger than that produced by the dramatically less twisted acene in minimized [7]n4. Compared to the free helicene, the cotton effect sign is reversed between 300 and 350 nm for the dual-domain purple structure. Interestingly, the transition rotatory strengths are weaker in the free twisted acene, despite this structure producing a huge optical rotation of −34000°.

Isodesmic treatment of the acenes and the [7]heliacenes show that the inventive dual-domain systems have a different energetic response to acene elongation for the first few members, but become acene-like in the higher members. For both species, an upper-limit of destabilization is approached.

This disclosure shows that it is energetically more favorable to longitudinally twist the acene in the hybrid systems compared to the free-acenes due to relief of bay-region strain.

Correlator plots of NICS, PDI, and HOMA highlighted a shortcoming in the NICS technique. The large fluctuations of aromaticity from one ring to the next for the acenes as predicted by NICS(0) is inconsistent with the geometric and electronic indices HOMA and PDI. This also contradicts expected results from a single resonating sextet under the context of Clar theory. A new index of aromaticity is provided that analyzes the NICS behavior of each ring independently. Removing global ring currents, this new index produced results for the acenes that correlates with HOMA, PDI, and chemical intuition. Application of the local indices of aromaticity toward the [7]heliacenes gave values that corresponded to rings that are helicene-, acene-, and triphenylene-like in their aromatic expression. The aromaticity of the fulcrum ring remained very low for the entire [7]Series, confirming that the migrating aromatic sextet does not reside on this ring to an appreciable extent.

Correlator plots of NICS, PDI, and HOMA highlighted a shortcoming in the NICS technique. The large fluctuations of aromaticity from one ring to the next for the acenes as predicted by NICS(0) is inconsistent with the geometric and electronic indices HOMA and PDI. This also contradicts expected results from a single resonating sextet under the context of Clar theory. A new index of aromaticity is provided that analyzes the NICS behavior of each ring independently. Removing global ring currents, this new index produced results for the acenes that correlates with HOMA, PDI, and chemical intuition. Application of the local indices of aromaticity toward the [7]heliacenes gave values that corresponded to rings that are helicene-, acene-, and triphenylene-like in their aromatic expression. The aromaticity of the fulcrum ring remained very low for the entire [7]Series, confirming that the migrating aromatic sextet does not reside on this ring to an appreciable extent.

The calculated CD spectra as a function acene elongation showed decreasing bisignate character between 300 and 350 nm, and the development of weak bathochromic transitions corresponding to the contribution of the less twisted acene domain. The rotatory strength of these bathochromic transitions is enhanced when the acene twist is enhanced. The optical rotation incrementally decreased through the [7]Series approaching a value of 0° in [7]n4. Unexpected results are observed when the optical rotation is analyzed for the CN[7]Series, where optical activity initially decreased but increased dramatically in CN[7]n4. To understand this behavior, the effect of coupling in the two chiral components was explored in a series of experiments.

The Mallory photocyclization dehydrogenation reaction is an important method for synthetically accessing large, strained polycyclic aromatic hydrocarbons. Concerning this valuable reaction, it was discovered that temperature can be used to select final regio-isomeric product distributions. This discovery coupled with a deeper computational investigation, has culminated into a satisfying rational for the confounding tendency of Mallory photocyclizations to often preferentially form helical products when less strained regioisomers are available. This discovery is the basis for a paper the inventors published in the Journal of Organic Chemistry titled: *Origin of the Preferential Formation or Helicenes in Mallory Photocyclizations. Temperature as a Tool to Influence Reaction Regiochemistry*[66] and is incorporated by reference herein in its entirety.

Figure 73:
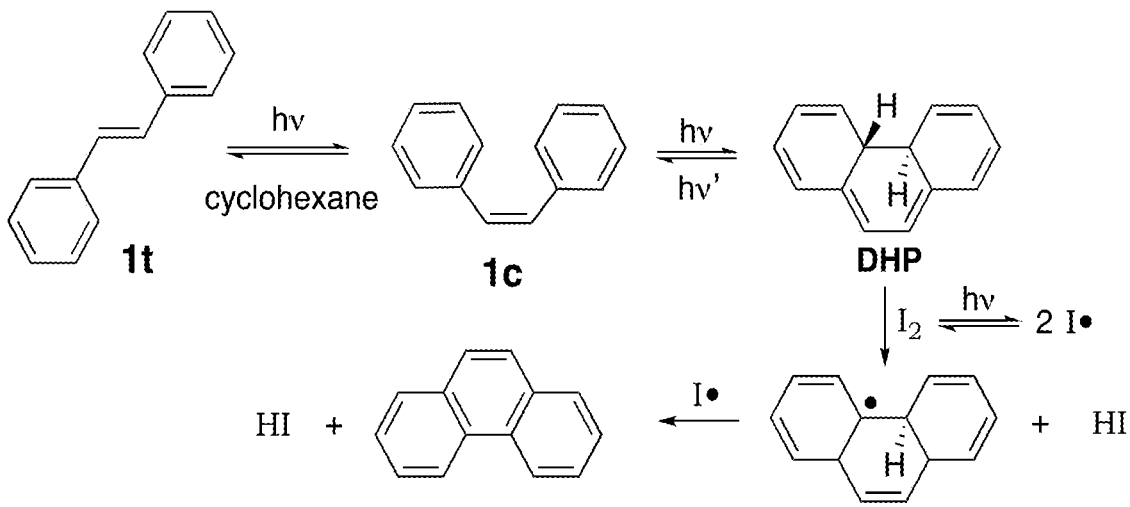
FIG. 73 illustrates the typical mechanism for the Mallory Photocyclization of trans-Stilbene.

The Mallory photocyclization as shown in FIG. 73 was first observed in 1934 and provided, at the time, an unknown by-product during the photochemically initiated cis-trans isomerization of stilbene, $1t \leftrightarrows 1c$.[67] This byproduct was subsequently identified by Parker and Spoerri[68] in 1950 as phenanthrene. This reaction, although studied sporadically, was more or less dormant until Mallory and coworkers[69] reported in 1962 its development into a preparatively useful oxidative photocyclization by the use of 12, rather than $O_2$, as the oxidant (Scheme 1). The key step in the mechanism of the Mallory photocyclization is the widely recognized formation of a trans-dihydrophenanthrene (DHP) intermediate[70-73] by an orbital symmetry allowed conrotatory electrocyclic closure. (FIG. 73) This skeletal rearrangement in many diaryl-ethylenes is photochromic and consequently has been utilized in the construction of a large number of photoswitching devices.[74] The dihydrophenanthrene, DHP, however, in the Mallory photocyclization is an intermediate, not an end-product, that is subsequently converted to the phenanthrene end-product by abstraction of hydrogen and formation of HI.

A Mallory photocyclization was used during the first synthesis of [7]helicene75 and opened the door for decades of study of these fascinating polycyclic aromatic hydrocarbons (PAHs).[76-79] In addition, the importance of the Mallory photocyclization has subsequently been amply demonstrated by the publication of several reviews,[80-85] by the development of useful modifications,[86-92] and most recently by its use in the construction of carbon nanomaterials.[93] The sentence that appears in the elegant review of Morin, Daigel, and Desroche;[93] "The photochemical dehydrogenation, or Mallory reaction, is probably the most widely spread photochemical method for the preparation of carbon nanomaterials and PAHs." is not hyperbole, and given the seemingly endless applications of PAHs (polycyclic aromatic hydrocarbons) underscores the value of further studies to understand the intimate details of this important reaction.

Figure 74:
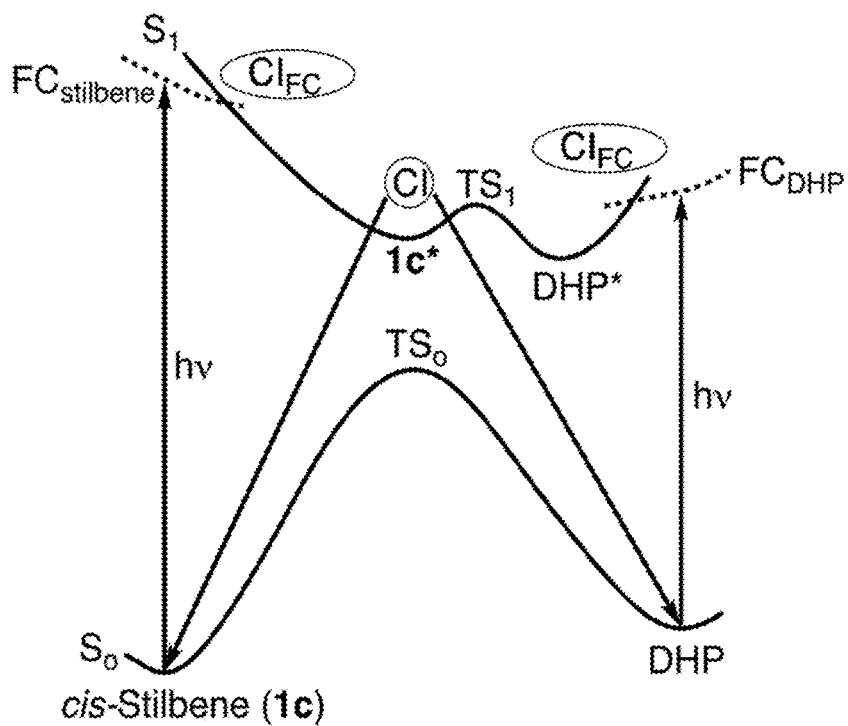
FIG. 74 illustrates potential energy surfaces involved in the reversible cis-Stilbene DHP interconversion.

The mechanistic details of the photochemical interconversion of the cis-stilbene, 1c, to the dihydrophenanthrene, DHP, (FIG. 73) step of the Mallory photocyclization has been extensively examined from both experimental[94-96] and theoretical[97-100] perspectives. A two-dimensional slice through the currently accepted potential energy surfaces (PES) for this reaction step is depicted in FIG. 74. Upon irradiation of either 1c or DHP an allowed transition to the corresponding Franck-Condon PES, $FC_{stilbene}$ or $FC_{DHP}$, occurs. Rapid movement on the Franck-Condon PES brings the vibrationally excited state into proximity to a conical intersection, $CI_{FC}$, where picosecond or sub-picosecond internal conversion to $S_1$ takes place. Finally, both vibrationally excited states move on the $S_1$ PES until they reach the critical conical intersection region, CI, where ultrafast deactivation forms either the cis-stilbene or the DHP on the $S_0$ PES. The activation barrier, $TS_1$ on the $S_1$ PES, which was predicted theoretically, provides an explanation for both the observed temperature,[101] and wavelength,[102] dependence of the cycloreversion quantum yield for the DHP.

Figure 75:
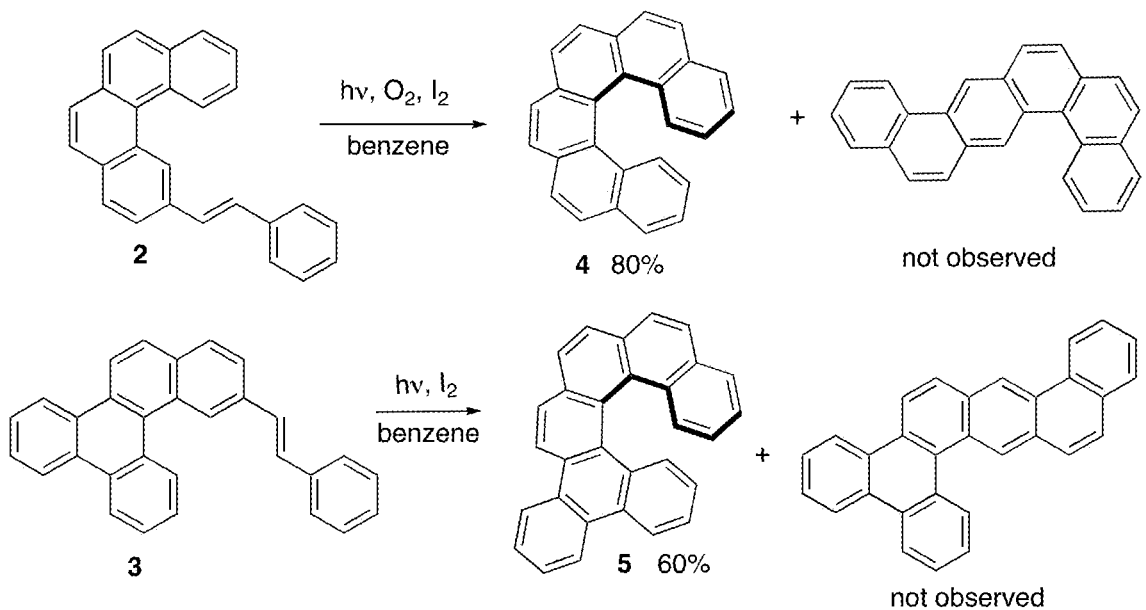
FIG. 75 illustrates regioselectivity in Mallory photocyclizations.

The detailed understanding of the cis-stilbene/DHP interconversion step of the Mallory photocyclization, however, stands in stark contrast to our fundamental lack of understanding, of perhaps the most unusual and distinguishing feature of the Mallory reaction, which is its propensity to form helicenes even when competing photocyclizations to form more thermodynamically stable, sterically less encumbered, planar PAHs are available. This phenomenon is illustrated in FIG. 75 with the reactions of 2,[103] and 3,[82]

which exclusively produced [6]helicene, 4, and benzo[b] hexahelicene, 5, without a trace of the alternative photocyclization products.

Laarhoven et al.[104,105] used the Coulson free valence numbers[106] to devise a set of rules to predict the regiochemical outcome of Mallory photocyclizations. These free valence numbers, $\Sigma F^*_{rs}$, are measures of the "residual affinity" for bond formation and are given by $\sqrt{3}$-$\Sigma$ P for aromatic carbons where $\Sigma$ P is the sum of the bond orders for the 3 bonds attached to the aromatic carbon in the excited state. According to the Laarhoven rules when the sum of the free valences of the two carbon atoms that form the new bond in the Mallory reaction are less than 1 (i.e. $\Sigma F^*_{rs}$<1.0) photocyclization does not occur. This reactivity parameter has been remarkably successful, however, other experimental parameters in addition to the identity of the substrate also influence the extent of regioselectivity including, the concentrations of the oxidant (e.g. $I_2$, $O_2$) and substrate, the identity of the solvent, and the temperature.[107] Despite the predictive power of the Laarhoven rules they do not provide a satisfying rationale or a framework to control the unusual regiochemistry observed in many of these important photocyclizations.

Figure 76:
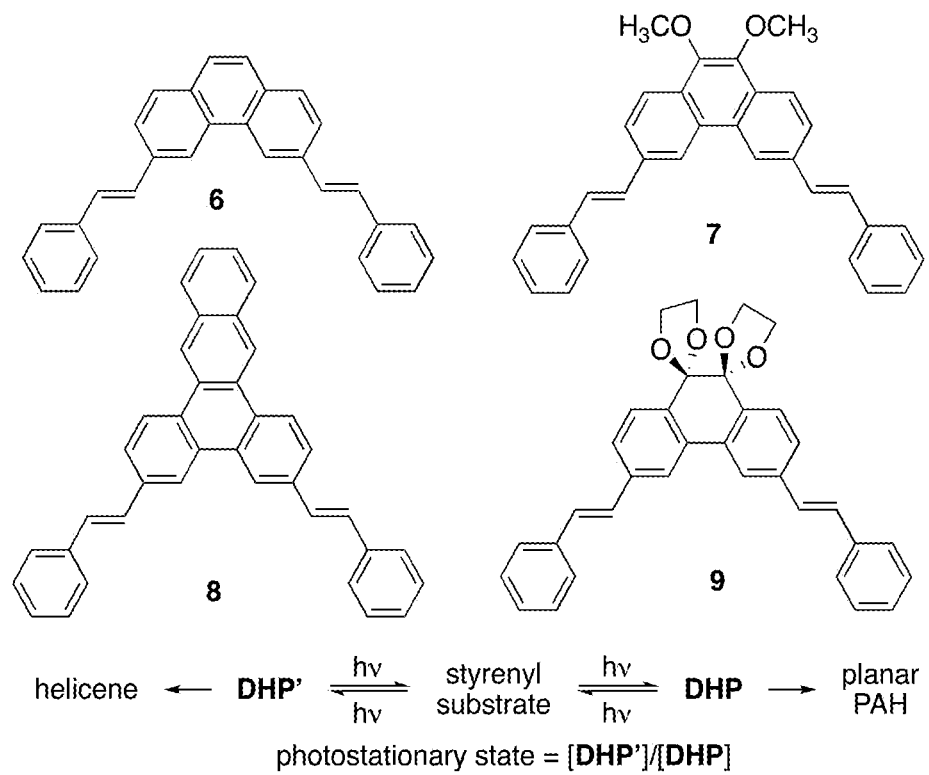
FIG. 76 illustrates the bis-Mallory photocyclizations of 6, 7, 8, and 9 focused on understanding the regioselectivity observed in these reactions.

An experimental and computational study was conducted of the bis-Mallory photocyclizations of 6, 7, 8, and 9 (FIG. 76) focused on understanding the regioselectivity observed in these reactions. The experimental study revealed that the product regiochemistry in the reactions of 6 and 9 responds very differently to changes in experimental conditions and that the Mallory photocyclizations of 7 and 8 are intermediate in their behavior. The computational results are used to argue that the photostationary state established between competing DHPs plays an important role in these reactions. In addition, in those reactions that produce the helicene as the major product the photostationary state lies on the side of the DHP precursor to the helicene (DHP' FIG. 76). These results provided valuable insight into Mallory photocyclizations that can be used to design new efficient photocyclization reactions.

Bis-Mallory photocyclization substrates 8 and 9 were synthesized from 3,6-dibromophenanthrenequinone in straightforward two-step procedures as outlined in Scheme 3. The key steps were the Mizoroki-Heck reactions[108] which had previously been successfully used with 3,6-dibromophenanthrene and 3,6-dibromo-9,10-dimethoxyphenanthrene to make 6 and 7, respectively.[109] Unfortunately, 3,6-bis-styrenylphenanthrene quinone, despite the fact that is readily accessible from a Mizoroki-Heck reaction, could not be used in this study. It is completely, unreactive under our Mallory photocyclization conditions.

Figure 78:
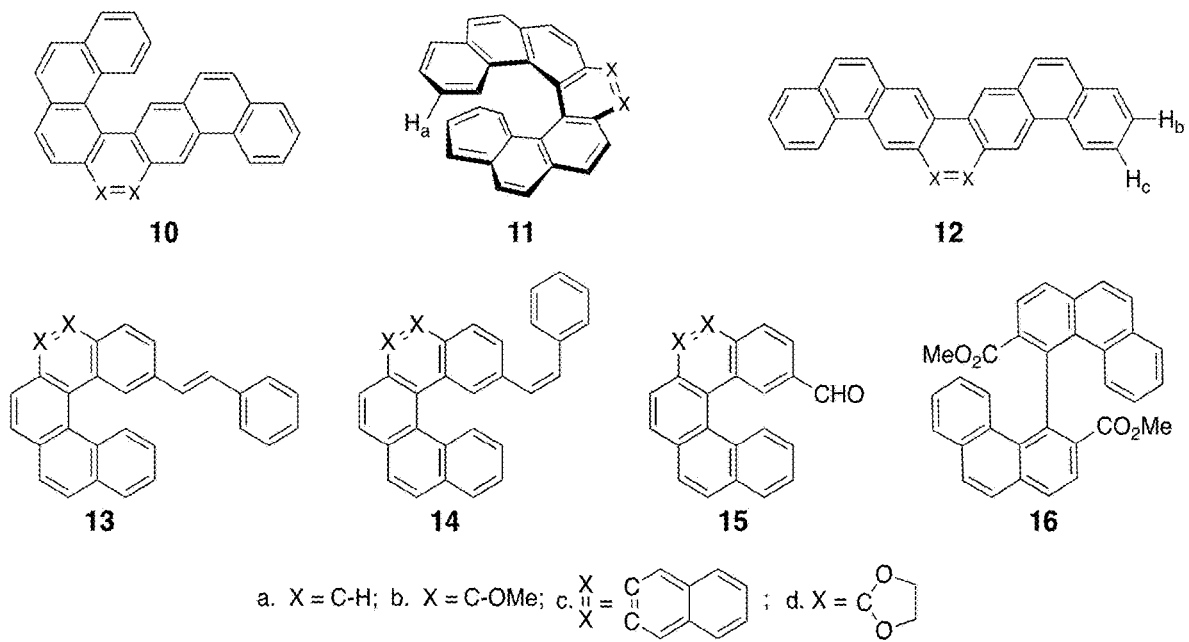
FIG. 78 illustrates reactions with 10, 11, 12, 13, 14, 15, 16.

The bis-Mallory photocyclizations were conducted by irradiation (600 W medium pressure mercury vapor lamp) of a 0.5 mM toluene solution of 6, 7, 8, or 9 through the walls of a Pyrex vessel containing 1.1 mM iodine, and 25 mM propylene oxide.[86] As shown in FIG. 78 at room temperature 9 reacts to give a mixture of all three Mallory photocyclization products, the benzo[k]naphtho[1,2-a]tetraphene, 10d, the [7]helicene, 11d, and the dibenzo[c,m]pentaphene, 12d. The benzo[k]naphtho[1,2-a]tetraphenes, 10a,b,c however, were conspicuously absent from room temperature irradiations of 6, 7 and 8. However, oxidation products 15b and 15c are formed in approximately 40% yield during bis-Mallory photocyclizations of substrates, 7 and 8, respectively.[110] In addition, di-ester, 16,[111] is also formed in approximately 5% yield in the reactions of 7. On the other hand, no oxidative cleavage of the styrenyl double bond was observed in any of the phenanthrenyl substrates, 6-9. This suggest that singlet oxygen formed by self-sensitization is involved in these reactions since the singlet triplet energy gap is 5.4 kcal/mol smaller[112] and the intersystem crossing rate constant[113] to the triplet nearly 3 times larger in the [5]helicene core[114] of 13b,c, that is oxidatively cleaved to form 15b,c, than in the phenanthrene core of 6-9, which are oxidatively inert. The formation of di-ester 16 can be attributed to the well-established enhanced reactivity of singlet oxygen[115,116] with electron rich enol ethers and to the even larger intersystem crossing rate constant of [7]helicene in comparison to [5]helicene.[113] The amount of these oxidation products, however, can be substantially reduced by exclusion of oxygen from the reaction mixtures. Products from further complications such as hydrogen shifts in the dihydrophenanthrene, DHP, and bis-dihydrophenanthrene, bis-DHP, intermediates, which have been observed in other systems were not detected in the reactions of 6-9.[82]

These reactions were typically conducted overnight and the crude product mixtures analyzed by NMR spectroscopy. Products 11a, 11b, and 16 are known, and products 10d, 11c, 12c, 12d, 15b, and 15c were isolated, purified, and fully characterized by $^1$H and $^{13}$C NMR spectroscopy (with the exception of 12c whose limited solubility precluded collection of its $^{13}$C NMR spectrum), and by high-resolution mass spectrometry. Diagnostic peaks in the NMR spectra of these conclusively identified products were then used to identify their homologues (11d, 12a, 12b, and 12c) formed in the other Mallory photocyclization reactions. Stacked comparator $^1$H NMR plots used in this analysis are provided in the Supporting Information for the 11, and 12 homologous series. A diagnostic ddd for proton $H_2$ (FIG. 78) showed up in the 11 comparator spectra at approximately 6.4 ppm in all of the [7]helicenes 11a, b, c, and d. This proton was upfield of all other peaks in the reaction mixtures because it is located in the shielding cone of the terminal ring on the other end of the helicene. The dibenzo[c,m]pentaphenes, 12, were also easily identified because Mallory photocyclization conditions (vide infra) are available where these compounds are the major or exclusive product of the reaction. Their most upfield peaks, between 7.6 and 7.7 ppm are also ddd's and are readily assigned to $H_4$ and $H_5$. The cis- and trans-3-strenyl[5]helicenes, 13 and 14, were identified as fleeting intermediates in the crude reaction mixtures by their characteristic doublet-of-doublets for the styrenyl double bond.

The product compositions at approximately 40° C. during Mallory photocyclizations of 6-9 as a function of irradiation time are determined. The mono-Mallory products 13 and 14 form rapidly followed by slower formation of the [7]helicenes 11. In addition, the yields of the [7]helicenes decrease in the order 6>7>8>9. The photocyclization of 9 was completed in approximately 5 h in comparison to the 10-12 hours of irradiation needed to produce the final products in the reactions of 6, 7, and 8. The photocyclization of 9 also produced 10d under these conditions as the dominant product in approximately 85% yield. In contrast, 10a,b,c were not observed at any point during the photocyclizations of 6, 7, or 8.

Figure 79:
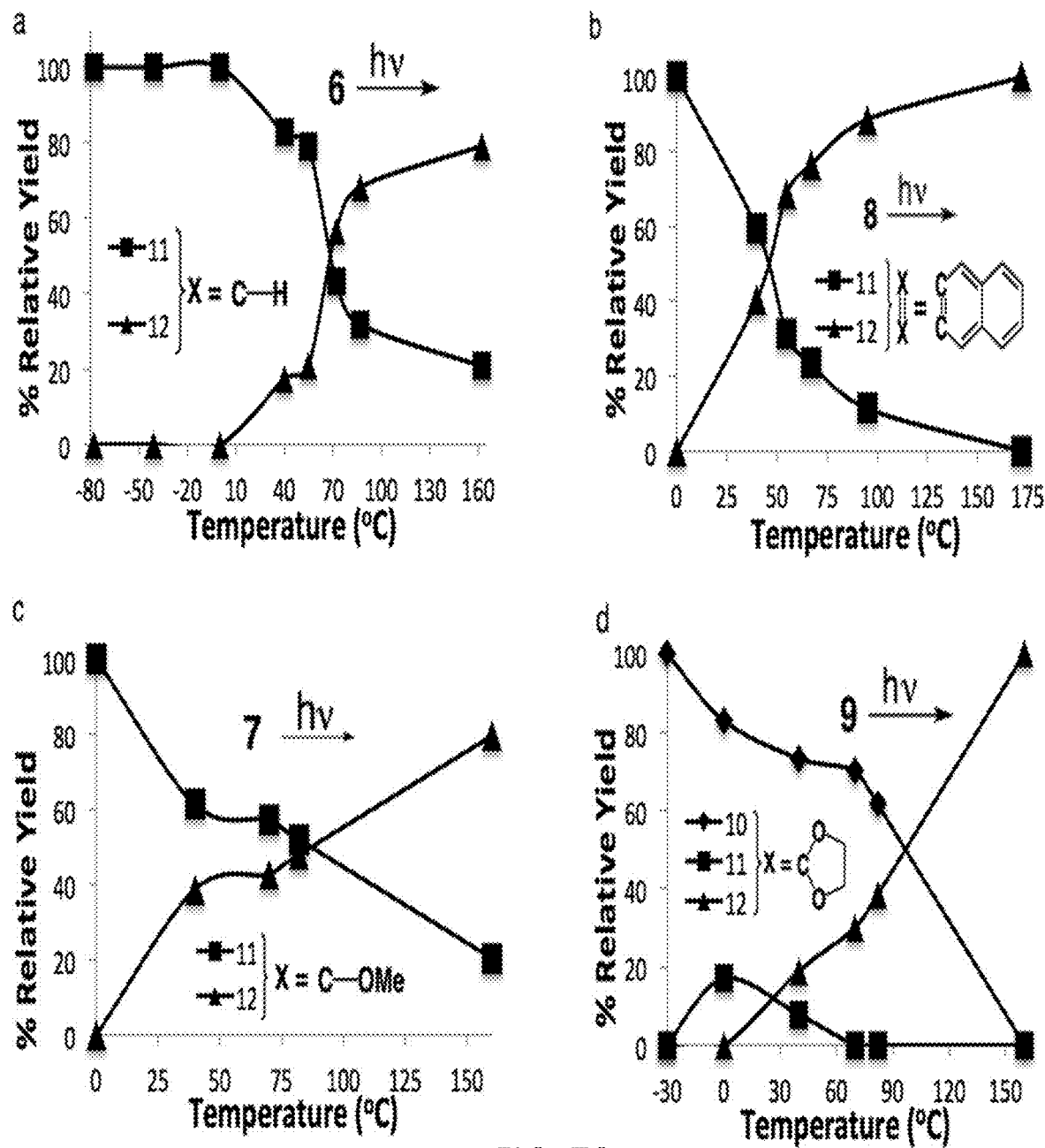
FIG. 79 are a set of plots that show relative product composition as a function of temperature for the Mallory photocyclizations of 6, 7, 8, and 9, wherer all reactions were run under an atmosphere of air, however, the oxygenated products are not included in the plots.

The effect of temperature on the Mallory photocyclizations was examined by running each of the reactions in a pyrex vessel submerged in an appropriate temperature-controlled bath. The products were then analyzed by NMR spectroscopy and their relative yields plotted versus temperature as depicted in FIG. 79. The [7]helicenes, 11a, 11b, and 11c were the exclusive products in the reactions of 6, 7, and 8 at low temperatures (<0° C.). On the other hand, the [7]helicene, 11d, is observed, but its % yield peaks at approximately 0° C. and never becomes the major product at any temperature between −30° C. and +150° C. In all four Mallory photocyclizations the thermodynamically most stable product (vide infra), the planar dibenzo[c,m]pentaphene, 12, is the dominant product at high temperature.

The mechanisms of the bis-Mallory photocyclizations of 6-9 are considerably more complex than the simple photocyclization of cis-stilbene shown in FIG. 73. The bis-Mallory substrates undergo two photocyclizations and each photocyclization can occur at two different sites on the phenanthrene core to give two different DHPs. This leads to eleven different possible closed shell intermediates on these very complicated reaction surfaces in addition to the three possible products, 10, 11, and 12.

Figure 80:
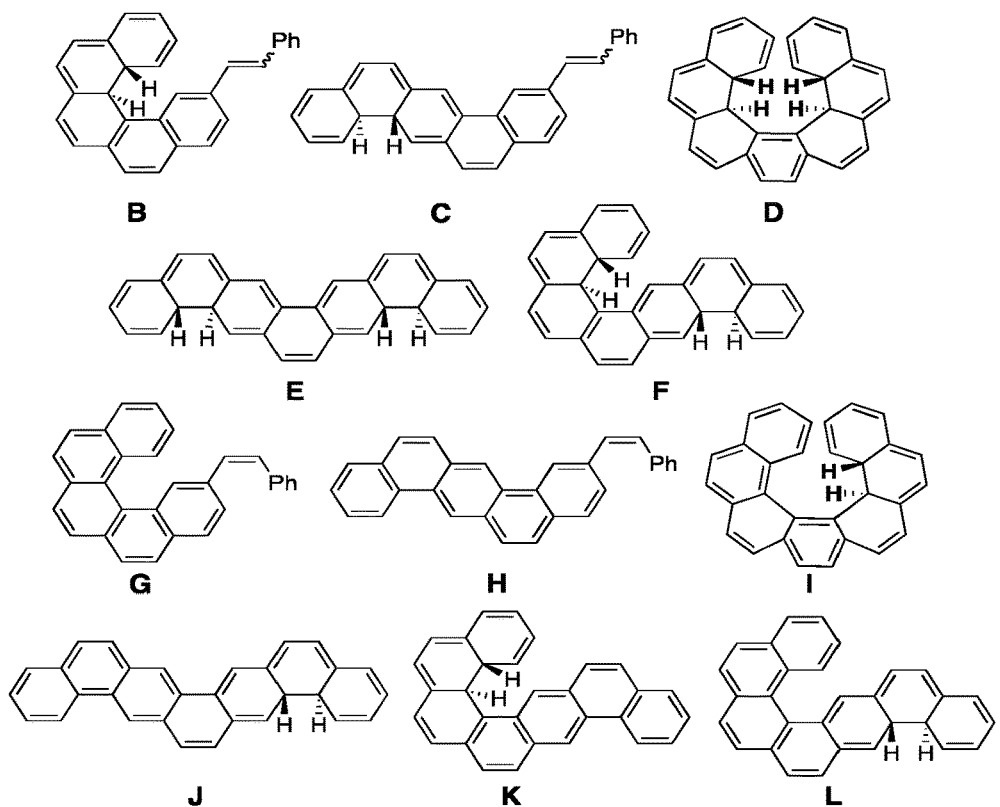
FIG. 80 illustratre potential intermediates in the Mallory bis-photocyclization of 6.

In order to facilitate the consideration of the computational results and the upcoming consideration of potential mechanisms in the discussion section of the manuscript, these intermediates are organized using the interconversion diagram shown in FIG. 81. However, it is important to recognize that this complicated interconversion diagram is itself a simplification of the actual potential energy surface. Both diastereomers of the DHP regioisomers depicted in FIG. 80, which are generated by competing clockwise and counterclockwise ring closures, are not explicitly included in the interconversion diagram. This is not a serious omission. A single diastereomer thermodynamically dominates in most cases (Table 1) but even in those cases where two stereoisomers might be simultaneously present (e.g. $E_{tct}$ and $E_{ttt}$ in Table 19; see Supporting Information for detailed structural information) it will not change the mechanistic conclusions discussed below. Consequently, all the Tables in this manuscript, except Table 19, contain only those values calculated using the thermodynamic data for the most stable diastereomer of each of the DHP regioisomers shown in FIG. 80.

TABLE 19

Relative Free Energies[a] of bis-Mallory Reaction Stationary Points with Zero Negative Frequencies.[a]

| | 6(parent) | 7(di-MeO) | 8(Naphtho) | 9(Bis-Ketal) |
|---|---|---|---|---|
| $C_XH_{Y+4}$ (Blue Region)[b] Bis-Mallory Reaction Intermediates[c] | | | | |
| A | 0 | 0 | 0 | 0 |
| B | 49.8 | 50.7 | 52.8 | 52.4 |
| Ba | 44.2 | 44.8 | 46.0 | 48.1 |
| C | 46.1 | 45.8 | 42.8 | 39.1 |
| Diooi | 101.7 | 102.8 | 105.5 | 107.4 |
| Doiio | 84.3 | 85.0 | 90.6 | 96.7 |
| Doioi | 89.9 | 90.7 | 97.0 | 101.3 |
| Etct | 85.9 | 85.6 | 84.1 | 78.7 |
| Ettt | 85.2 | 85.8 | 83.4 | 78.1 |
| Ftct | 93.7 | 93.9 | 89.4 | 85.2 |
| Ftcta | 97.1 | 97.5 | 93.7 | 88.7 |
| Fttt | 99.2 | 99.4 | 96.1 | 90.5 |
| Fttta | 92.3 | 92.1 | 89.0 | 85.5 |
| $C_XH_{Y+2}$ (Red/Green Region)[b] Bis-Mallory Reaction Intermediates[c] | | | | |
| G | 13.4 | 13.2 | 13.7 | 12.4 |
| H | 0 | 0 | 0 | 0 |
| I | 60.9 | 61.7 | 63.7 | 63.4 |
| Ia | 57.4 | 58.2 | 60.8 | 62.2 |
| J | 45.0 | 44.5 | 42.9 | 39.5 |
| K | 50.4 | 51.2 | 53.2 | 52.0 |
| Ka | 44.7 | 45.0 | 46.4 | 47.8 |
| L | 61.1 | 61.1 | 57.8 | 52.0 |
| La | 58.0 | 58.0 | 55.3 | 50.6 |

TABLE 19-continued

Relative Free Energies[a] of bis-Mallory Reaction Stationary Points with Zero Negative Frequencies.[a]

| | 6(parent) | 7(di-MeO) | 8(Naphtho) | 9(Bis-Ketal) |
|---|---|---|---|---|
| CxHy (Black)[b] Final Reaction Products[c] | | | | |
| 10 | 13.2 | 13.7 | 13.3 | 11.9 |
| 11 | 24.2 | 24.4 | 25.5 | 23.4 |
| 12 | 0 | 0 | 0 | 0 |

[a]B3LYP/6-311 + G(2d,p) sum of electronic and thermal Free Energies in kcal/mol.
[b]See Scheme 4 for region colors.
[c]X = number of carbons in 6-9; Y = number of hydrogens in the final reaction products, 10-12, of bis-Mallory photocyclization/oxidation of 6-9.

The A's in the interconversion diagram represent the cis-cis (cc), cis-trans (ct), and trans-trans (tt) isomers of the bis-styrenyl starting materials, 6-9, and the subscripts represent the total number of Clar sextets[117] (i.e., the number of six membered rings with a localized aromatic 6π cyclic array of electrons). The remaining letters (See FIGS. 80 and 81) represent either dihydrophenanthrenes, B, C, I, J, K, and L, each with 2 Clar sextets, or bis-dihydrophenanthrenes, D, E, and F, with 1, 0, and 0 Clar sextets, respectively, or mono-Mallory photocyclized intermediates, G and H, containing 4 Clar sextets. To the left, emanating from $A^{ct}$ is an identical interconversion diagram differing only from the one on the right by the trans-configuration of the styrenyl double bond in intermediates B, C, G and H. The mechanistic conclusions that can be deduced from either wing of the interconversion diagram are identical so we will use the expanded right hand wing for the remaining discussion. Intermediates in different colored regions of the diagram are not interconvertible, either thermally or photochemically, because it would require reversible loss of $H_2$, which is highly improbable. The *'s in the diagram are for microscopic steps that can occur either thermally by a stepwise, or concertedly by a controtatory photochemically allowed process.

DFT based-methods with large basis sets have been shown to perform well in thermochemical studies of large polyaromatic hydrocarbons and in studies of delocalized radicals.[118] Consequently, we used the B3LYP/6-311+G(2d, p) computational method to optimize and determine the energies of all the diastereomers for the regioisomeric intermediates located on the right hand side of FIG. 81, including the products 10, 11, and 12. The energies are given in Table 19 and the optimized geometries are provided in the supporting information.

The stabilities of the $C_{30}H_{22}$ isomers (for 6) in the blue region and the $C_{30}H_{20}$ isomers in the green/red regions decrease with the decreasing number of Clar sextets (blue: $A_4^{cc} > B_2 \cong C_2 > E_o \cong F_0$ and green/red: $H_4 \cong G_4 > I_2 \cong J_2 \cong K_2 \cong L_2$). Superimposed on these primarily aromaticity driven stability sequences there is also a strain/steric contribution. In the reactions of 6 and 7 this internal strain raises the energy of the most stable isomer of the tetrahydro[7]helicene D with one Clar sextet above that of both E and F with zero Clar sextets. In the reactions of all the bis-Mallory substrates, 6-9, the embedded [5]helical structure in F raises its energy by 6 or more kcal/mol above that of E despite the fact that both contain the same number of Clar sextets (zero). The internal strain energy imparted by the helical architecture, and the greater strain imparted by the [7]—relative to the [5]helical architecture, is also expressed in the relative energies of the final bis-Mallory products, (11>10>12) all of which can be drawn with 4 Clar sextets.

The dihydrophenanthrenes, B and C, are key intermediates in the blue region (FIG. 81) of the bis-Mallory photocyclizations of 6-9. The most stable isomers of the bis-dihydrophenanthrenes, D, E, and F, (Table 19) formed in the blue region are approximately 42.6±6.0, 36.6±6.6, and 43.2±5.8 kcal/mol higher in energy than the least stable dihydrophenanthrene and are unlikely to be involved in the reactions. The B3LYP/6-311+G(2d,p) optimized structures of B and C formed in the photocyclization of 6 are shown in Scheme 5 and have the trans-configuration of the hydrogens at the dihydrophenanthrene ring closure junctions as dictated by the allowed conrotatory closure. The two conrotatory closures in B lead to diastereomers B and Ba. Diastereomer B (PRR/MSS configuration) is 5.6 kcal/mol less stable than diastereomer Ba (PSS/MRR configuration) as a result of the 0.36 Å closer approach (1.765 Å vs. 2.128 Å). The two conrotatory closures to form the C intermediates are very close in energy at the B3LYP/6-31G(d) computational level ($\Delta\Delta G°$ (RB3LYP)=0.4 kcal/mol) so only the most stable diastereomer was optimized at the higher B3LYP/6-311+G (2d,p) computation level and included in Table 1.

The key dihydrophenanthrene intermediates in the red and green regions (FIG. 81) of the interconversion diagram, I, J, K, and L, which are formed in the photocyclization of 6. (P)-$18a$(S), $18b$(S)-Dihydro[7]helicene $I_a$ is 3.5 kcal/mol more stable than its isomer (P)-$18a$(R), $18b$(R)-dihydro[7]helicene I. Isomer $I_a$ is also likely to form faster because it is formed by photocyclization on the least hindered face of the [5]helicene intermediate, G. (P)-Naphtho[1,2,b]-$14a$(R), $14b$(R)-dihydro[5]helicene, K, is significantly destabilized, by 5.7 kcal/mol, relative to (P)-naphtho[1,2,b]-$14a$(S), $14b$(S)-dihydro[5]helicene, $K_a$, by the energetically costly 1.78 Å through space $H_1$-$H_{14a}$ distance, which is increased to a sterically more tolerable 2.23 Å $H_1$-$H_{14b}$ closest approach distance in $K_a$ ($H_1$ blue atom and $H_{14a,14b}$ red atoms in Scheme 6). (P)-1(R), $8a$(S)-dihydronaphtho[1,2,b]-[5]helicene, L, is 3.1 kcal/mol less stable than its isomer (P)-1(S), $8a$(R)-dihydronaphtho[1,2,b]-[5]helicene, La, due in part to the shorter $H_1$-$H_{14}$ through space distance (2.60 Å in L and 2.82 Å in La) and by the increased strain in the helical section of the intermediate as revealed by a 3.1° increase in the $C_{14a}$-$C_{14b}$-$C_{14c}$-$C_{14d}$ internal dihedral.

The DHPs are subsequently oxidized by stepwise removal of two hydrogen atoms with photochemically generated iodine atoms. Aromatic resonance energy is recovered as a result of the second hydrogen abstraction and as a result the first hydrogen abstraction is likely to be the rate determining step for formation of the fully polyaromatic hydrocarbon product. The initial hydrogen abstraction can occur from the terminal or internal ring of the DHP leading to two different radicals, the A* and B* series, respectively. The relative energies of these radicals generated by hydrogen abstraction from $B_a$, C, $I_a$, J, $K_a$, and $L_a$ in the reactions of 6 and 9 are given in Table 20. Hydrogen abstraction is prohibitively favored ($\Delta\Delta G° \geq 14.4$ kcal/mol) from the terminal ring to give the A* series when the DHP is part of the helical domain (i.e. $B_a$, $I_a$, and $K_a$). On the other hand, the energies of the A* and B* series radicals, formed by hydrogen abstraction from the DHPs that reside in the acene domain (i.e. C, J, and $L_a$), are nearly equal. Formation of the A* series radicals from the helical embedded DHPs open up the jaws of the helicene decreasing steric interactions while formation of the B* series radicals closes the jaws and increases the intra-helicene steric interactions. The formation of the A* series radicals in the helical domain embedded DHPs are also likely kinetically preferred since the hydrogen on the terminal ring is on the periphery of the helicene while the internal hydrogen is buried in the jaws of the helical clef.

TABLE 20

Relative Energies of Radicals formed in Mallory Cyclizations of 6 and 9.[a,b]

| | 6 | | $9^c$ | |
|---|---|---|---|---|
| | A* | B* | A* | B* |
| $B_a$ | 1.0 | 17.6 | 5.4 | 15.1 |
| C | 1.4 | 0 | 0 | 2.6 |
| $I_a$ | 14.2 | 28.6 | 19.8 | 27.6 |
| J | 0.6 | 0 | 0 | 2.83 |
| $K_a$ | 1.0 | 16.4 | 5.2 | 15.2 |
| $L_a$ | 12.1 | 12.6 | 11.3 | 14.9 |

[a]Relative B3LPY/6-311 + G(2d,p) sum of electronic and thermal Free Energies in kcal/mol for the radicals generated from the most stable DHP diastereomer (See Table 1).
[b]A*-radical formed by hydrogen abstraction from the terminal ring of DHP; B*-radical formed by hydrogen abstraction from internal ring of DHP.
[c]Calculated at the B3LYP/6-31G(d) level.

Figure 81A:
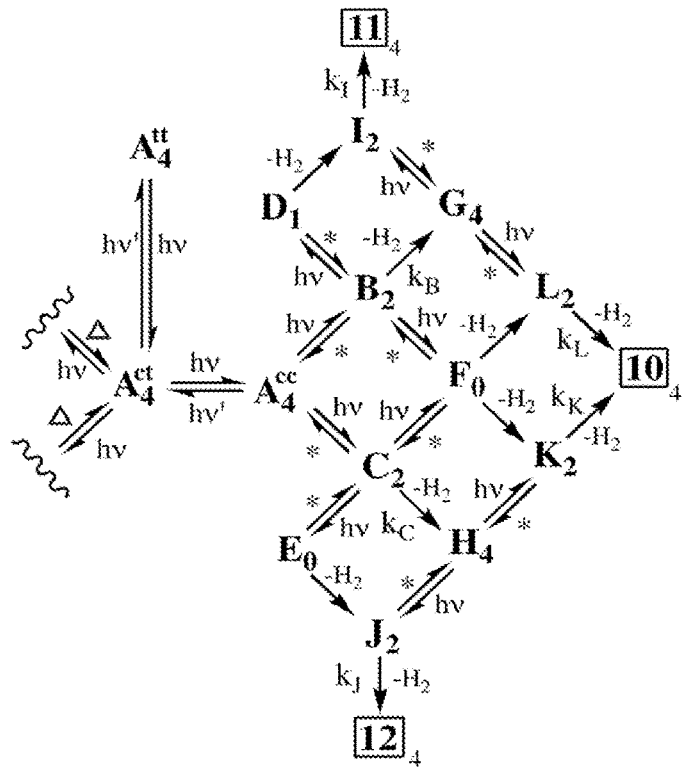
FIG. 81A is an interconversion diagram for intermediates in the Bis-Mallory photocyclizations of 6, 7, 8, and 9, where *hv or heat; cc cis-cis and ct cis-trans; subscripts on all numerical and letter compound designations refer to its number of Clar sextets.
Figure 81B:
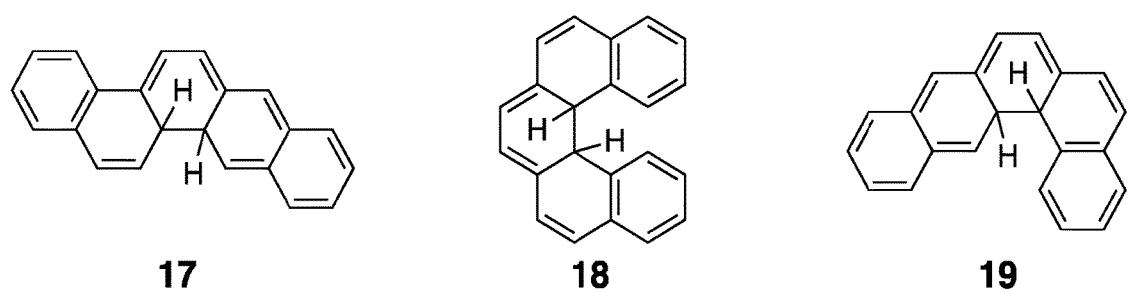
FIG. 81B are structures for DHPs 17, 18, and 19.
Figure 82:
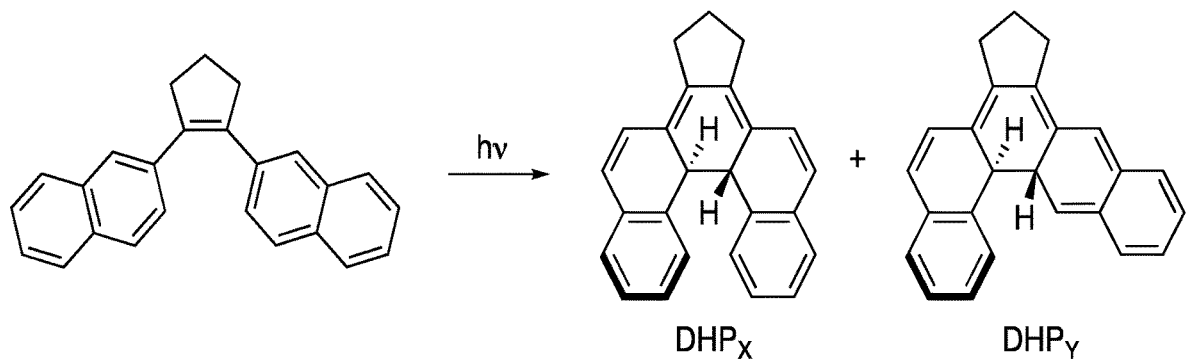
FIG. 82 illustrates DHP diastereomers formed during Mallory photocyclization of 1,2-di-(2-naphthyl)cyclopentene.

The UV-Vis spectra of the DHPs were calculated using the TD-DFT/6-311+G(2d,p) computational model. The lowest energy transitions are given in Table 21 along with their oscillator strengths. The DHPs (i.e. $B_a$ and C, $I_a$ and $L_a$, and $K_a$ and J) in the same colored region of FIG. 81A are thermally and photochemically interconvertible and are placed in the same rows of Table 21 for comparison. The HOMO-LUMO determinant in all cases was the ≥99% contributor to the excited-state wavefunction as determined by taking two times the square of the coefficient for the configuration interaction expansion. The absorbance maxima are all between 580 and 750 nm consistent with the transient formation of a colored intermediate noted in many Mallory photocyclizations.[119] For example, the bathochromic absorption maxima for DHPs 17, 18, and 19 are reported at 603 nm, 448 nm, and 530 nm, respectively, with extinction coefficients of approximately 10,000-12,000 $M^{-1}$ $cm^{+1}$.[120] The structures for DHPs 17, 18, and 19 are shown in FIG. 81B. The oscillator strengths (f) for the DHPs embedded in helical domains (column 3) were 5 to approximately 9 times smaller than those embedded in acene domains (column 6, Table 21).

TABLE 21

Wavelength Maxima and Oscillator Strengths of Low Energy DHP UV/Vis Absorbances.[a]

| | $\lambda_{MAX}^b$ | $f^c$ | | $\lambda_{MAX}^b$ | $f^c$ |
|---|---|---|---|---|---|
| 6 | | | | | |
| $B_a$ | 683 | 0.0622 | C | 663 | 0.3135 |
| $I_a$ | 689 | 0.0628 | $L_a$ | 704 | 0.3325 |
| $K_a$ | 727 | 0.0527 | J | 662 | 0.4857 |
| 7 | | | | | |
| $B_a$ | 688 | 0.0619 | C | 670 | 0.2946 |
| $I_a$ | 696 | 0.0631 | $L_a$ | 713 | 0.3154 |
| $K_a$ | 732 | 0.0514 | J | 670 | 0.4500 |
| 8 | | | | | |
| $B_a$ | 717 | 0.0617 | C | 624 | 0.4144 |
| $I_a$ | 730 | 0.0629 | $L_a$ | 667 | 0.4358 |
| $K_a$ | 743 | 0.0683 | J | 630 | 0.5821 |

TABLE 21-continued

Wavelength Maxima and Oscillator Strengths of Low Energy DHP UV/Vis Absorbances.[a]

| $\lambda_{MAX}$[b] | f[c] | | $\lambda_{MAX}$[b] | f[c] |
|---|---|---|---|---|
| 9 | | | | |
| $B_a$ 713 | 0.0877 | C | 585 | 0.4764 |
| $I_a$ 720 | 0.0888 | $L_a$ | 601 | 0.5019 |
| $K_a$ 730 | 0.1019 | J | 607 | 0.6746 |

[a]Calculated at the TD-DFT/6-311 + G(2d,p) level in toluene.
[b]Wavelength of lowest energy transition.
[c]Oscillator strength.

The yields of the three products formed in the bis-Mallory photocyclizations are sensitive functions of the concentrations of the DHPs ([B], [I], etc.) and of the rate constants for hydrogen abstraction, $k_{DHP}$ (e.g. $k_I$, $k_B$, etc.). This is expressed mathematically in Eqns. 1, 2, and 3. The yield of 11 for example is the product of the fraction of the precursor B formed in the blue region $\emptyset_B$ and the fraction of I formed in the red region $\emptyset_I$. The yield of 10 on the other hand has two terms since it can be formed in both the green and red region.

$$\%10 = [\emptyset_L\emptyset_B + \emptyset_K\emptyset_C] \times 100 \quad \text{EQ (6)}$$

$$\%11 = \emptyset_I\emptyset_B = \left(\frac{k_I[I]}{k_I[I] + k_L[L]}\right)\left(\frac{k_B[B]}{k_B[B] + k_C[C]}\right) \times 100 \quad \text{EQ (7)}$$

$$\%12 = \emptyset_J\emptyset_C = \left(\frac{k_J[J]}{k_J[J] + k_K[K]}\right)\left(\frac{k_C[C]}{k_B[B] + k_C[C]}\right) \times 100 \quad \text{EQ (8)}$$

Several experimental and structural variables can influence the concentrations of the DHPs and the rate constants of hydrogen abstraction, $k_{DHP}$, whose magnitudes dictate product formation (Eqns. 1, 2, and 3). These include: (1) The position of the photostationary state established between the two competing DHPs; (2) the relative stability of the competing DHPs; (3) the relative stabilities of DHP radicals (A*) produced during hydrogen abstraction from the competing DHPs; and (4) experimental variables such as reaction temperatures.

The photostationary states established between the two competing DHPs in the mutually inaccessible blue, red, and green regions of FIG. 81 are given by equations 9a, 9b, and 9c, respectively. These equations are analogous to the equation for the photostationary state reached upon irradiation of cis- and trans-alkenes[121] but differs because it is the product of two photostationary equilibria, for example L⇌G and G⇌I in the red region of FIG. 81. The ratio, of the extinction coefficients, $\varepsilon_L/\varepsilon_I$, at the $\lambda_{MAX}$ of the HOMO→LUMO absorption peaks for the DHPs shown in Table 21, are proportional to the ratio of oscillator strengths[122] (Table 21) when the band widths are the same. This relationship also implies that the ratio of DHP concentrations will change with changing irradiation wavelength. This is consistent with the observation of Fisher et al.[119] who observed a strong wavelength dependence on the ratio of $DHP_X/DHP_Y$ during the Mallory photocyclization of 1,2-di-(2-naphthyl) cyclopentene.

$$\frac{[B]}{[C]} = \frac{\varepsilon_C}{\varepsilon_B} \cdot \frac{(\phi_{A \to B})(\phi_{C \to A})}{(\phi_{B \to A})(\phi_{A \to C})} \quad \text{EQ (9a)}$$

$$\frac{[I]}{[L]} = \frac{\varepsilon_L}{\varepsilon_I} \cdot \frac{(\phi_{G \to I})(\phi_{L \to G})}{(\phi_{I \to G})(\phi_{G \to L})} \quad \text{EQ (9b)}$$

$$\frac{[K]}{[J]} = \frac{\varepsilon_J}{\varepsilon_K} \cdot \frac{(\phi_{H \to K})(\phi_{J \to H})}{(\phi_{K \to H})(\phi_{H \to J})} \quad \text{EQ (9c)}$$

The relative stabilities of the competing DHPs in the blue ($B_a$-C), red ($I_a$-$L_a$), and green ($K_a$-J) regions of the mechanism shown in FIG. 81 are compared in terms of both their free energies in Table 19 and enthalpies in Table 22. This data reveals that the DHPs in the reactions of 6 and 7 that are embedded in the helical domain, $B_a$, $I_a$, and $K_a$, and are the precursors for formation of a helical product, are equal or perhaps slightly more stable than the DHPs embedded in the acene domain, C, $L_a$, and J. (Columns 2 and 3 in Table 22). On the other hand Mallory substrates 8 and 9 exhibit the opposite behavior with their acene-embedded DHPs, C, $L_a$, and J, more stable than their helicene-embedded DHPs, $B_a$, $I_a$, and $K_a$. This stability preference for C, $L_a$, and J in 9 is especially large (7.0-10.1 kcal/mol) and essentially precludes all but a trace of $B_a$, $I_a$, and $K_a$ at thermodynamic equilibrium.

TABLE 22

Differences in Enthalpies and Free Energies of Formation and for Hydrogen Abstraction from DHPs with Iodine atom.[a]

| | $\Delta\Delta H_f^o$ (6)[b] | $\Delta\Delta H_f^o$ (7)[b] | $\Delta\Delta H_f^o$ (8)[b] | $\Delta\Delta H_f^o$ (9)[c] | $\Delta\Delta H_{Rxn}^o$ (6)[d] | $\Delta\Delta H_{Rxn}^o$ (9)[d] |
|---|---|---|---|---|---|---|
| ($B_a$-C) | -2.6(-1.9) | -1.9(-1.0) | +2.3(+3.2) | +7.8(+8.3) | +1.21(+1.61) | -2.29(-2.89) |
| ($I_a$-$L_a$) | -1.2(-0.6) | -0.6(+0.2) | +4.9(+5.5) | +10.1(+11.1) | +2.59(+2.72) | -2.58(-2.64) |
| ($K_a$-J) | -1.0(-0.3) | -0.3(+0.5) | +2.2(+3.5) | +7.0(+7.8) | +0.42(+0.63) | -2.62(-2.59) |

[a]$\Delta\Delta G_f^o$ in parenthesis.
[b]In kcal/mol calculated at the B3LYP/6-311 + G(2d, p), and,
[c]at the B3LYP/6-31G(d) computational level.
[d]Calculated using equation 10.

The relative stabilities of DHP radicals formed in reactions with the iodine atom/radical can also potentially play an important role in the rates of hydrogen abstraction. The relative stability's of radicals generated by abstraction of hydrogen from the terminal unsaturated ring of the DHPs (Series A* radicals) are given in Table 20. In the reaction of 6 the stability differences between radicals formed from competing DHPs, $B_a$-C, $I_a$-$L_a$, and J-$K_a$ are very small, -0.4, +2.1, and -0.4 kcal/mol respectively. In stark contrast, these energy differences, $B_a$-C, $I_a$-$L_a$, and J-$K_a$, +5.4, +8.5, and -5.2 kcal/mol respectively, are much larger in the reaction of 9. These values can be used in conjunction with equation 10 to generate the differences in the enthalpies of reaction for abstraction of the first hydrogen from the competing DHPs with the iodine atom (Table 22 columns 5 and 6). In 6 these endothermic hydrogen abstractions are energetically more favorable from its acene-embedded DHPs, C, $L_a$, and J, while in substrate 9 they are more favorable from their helicene-embedded DHPs (Table 22 columns 6 and 7). In both cases, hydrogen abstraction is enthalpically more favorable from the least stable set of DHPs.

Equation 10 to determine $\Delta\Delta H°_{Rxn}$ for 6 and 9 of Table 22.

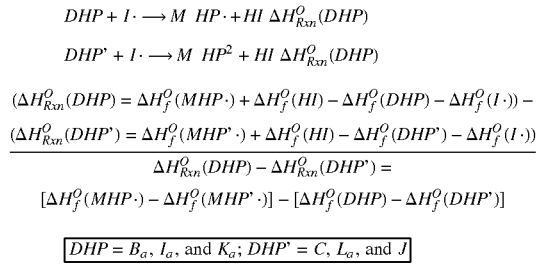

Increasing temperature can: (a) enhance the rate of passage over the $TS_1$ barrier on the Mallory photocyclization $S_1$ PES, (b) it can increase the rate of thermal decompositions of the DHPs, and (c) it can increase the rate of hydrogen abstraction by iodine atom from the DHPs.

Dulić et al.[101] have examined the temperature dependence of passage over the $TS_1$ barrier for a series of cis-stilbene photochromic switches. The rate of approach to the open/closed photostationary state is temperature independent at temperatures above 0° C. where most Mallory photocyclizations are conducted. At temperatures below 0° C. the quantum yields (e.g., $\phi A \rightarrow B$, $\phi_I \rightarrow H$, etc.) may exhibit small changes as a function of temperature, however, to a large extent these changes are likely to cancel each other in the quantum yield ratios (e.g., $[(\phi A \rightarrow B)(\phi C \rightarrow A)]/[(\phi B \rightarrow A)(\phi A \rightarrow C)]$, etc.) that are directly proportional to the steady state concentrations of the competing DHPs (Eqns. 9a, 9b, and 9c). trans-Stilbene but not cis-stilbene also encounters an activation barrier on the way to the twisted phantom intermediate on its geometric isomerization energy surface and as a result competitive fluorescence is observed in solution for the trans- but not the cis-isomer.[123] This barrier, however, is only 3.5 kcal/mol[124] and, consequently, unlikely to influence the cis-/trans-stilbene photostationary state at temperatures used for Mallory photocyclizations. It is also worthwhile to note that the 13/14 cis/trans photostationary state is established early on the bis-Mallory photocyclization PES and is maintained throughout the reaction.

DHPs have been directly observed and their thermal decompositions have been monitored.[120] Lifetimes of the DHPs have also been measured but their accuracy, and what is really being measured, is debatable because of the wide range of processes including oxidation and rearrangements that contribute to their decompositions. Nevertheless, the thermal decompositions of the competing DHP isomers in the blue, red, and green regions of the interconversion diagram (FIG. 81) with the greatest internal energy are expected to be more facile. The concerted thermal conrotatory openings of the DHPs reported here are not allowed, however, their high-energy content (>39 kcal/mol relative to their styrenyl precursor; Table 19) provides a driving force for their homolytic cleavage initiated decompositions to regenerate the Mallory substrates.

In DHPs $B_a$, $I_a$, and $K_a$ the two hydrogens available for abstraction differ in their accessibility to the iodine atom and lead to radicals of very different thermodynamic stabilities (Table 20). In contrast, both hydrogens in DHPs C, J, and $L_a$ are equally accessible for abstraction and lead to nearly iso-energetic radicals. Consequently, the rate constants for hydrogen abstraction will increase with increasing temperature more rapidly for DHPs C, J, and $L_a$ than for DHPs $B_a$, $I_a$, and $K_a$ since they enjoy an Rln2 symmetry contribution to the entropy of activation.

The bis-Mallory photocyclizations of 6, 7, 8, and 9 are very complex reactions, (FIG. 81) and as discussed above, depend upon a myriad of experimental conditions and substrate structural features that can influence their choice of reaction pathway. Detailed photophysical studies will be required to unravel the precise mechanistic details for each of these bis-Mallory substrates. Nevertheless, it is useful to qualitatively examine how the factors discussed above can influence the reaction pathways and product distributions in these substrates.

At 0° C. and below Mallory substrates 6 and 7 exclusively produce the helicene products 11a and 11b, respectively (FIG. 81). This is consistent with preferential photostationary formations of B and I, since the ratio $\varepsilon_C/\varepsilon_B$ and $\varepsilon_L/\varepsilon_I$ for 6 and 7, respectively, are equal to the ratios of the oscillator strengths and the smaller oscillator strength of the DHP precursor to 11a and 11b (e.g. $f_C/f_B(6)=(0.3135/0.0622)=5.04$ and $f_C/f_B(7)$ $(0.2946/0.0619)=4.76$; Table 21) means that their concentrations build-up because they absorbs less light. However, in order to attain [B]/[C] and [I]/[L] ratios of 20 or greater (i.e. exclusive detection of 11a and 11b), it would also require that $[(\phi_{A \rightarrow B})(\phi_{C \rightarrow A})]/[(\phi_{B \rightarrow A})(\phi_{A \rightarrow C})]$ and $[(\phi_{G \rightarrow I})(\phi_{L \rightarrow G})]/[(\phi_{I \rightarrow G})(\phi_{G \rightarrow L})]$ (See Eqn. 9a,b) have values of approximately 4 to 5. We argue that values of 4 to 5 are reasonable and are consistent with the Laarhoven effect that suggests (vide supra) that bonding occurs between carbon atoms where the "residual affinity" for bond formation is the greatest, which in many cases leads to preferential helicene formation. Consequently, the Laarhoven (kinetic) effect in the photocyclizations of 6 and 7 requires the blue quantum yields, $(\phi_{A \rightarrow B})$ and $(\phi_{G \rightarrow I})$, involving formation or extension of a helical structure to be larger than the red quantum yields, $(\phi_{B \rightarrow A})$ and $(\phi_{I \rightarrow G})$ that involve loss or decrease of helical structure. This observation, coupled with the fact that the black quantum yields for the photo-reversible formation of DHPs, that do not involve formation, extension, loss, or decrease in helical structure, are more comparable in magnitude, $(\phi_{C \rightarrow A}) \approx (\phi_{A \rightarrow C})$ and $(\phi_{L \rightarrow G}) \approx (\phi_{G \rightarrow L})$ support our contention that values of 4 to 5 for the ratio of quantum yields in equations 4a and 4b are reasonable. As the temperature is raised the photostationary state favoring helicene formation is not established, instead, for example, in the case of 6, the 3.65 kcal/mol and 1.94 kcal/mol (Table 4) energetically preferred hydrogen abstractions from DHPs C and J, respectively, serve to shift the $B \leftrightarrows C$ and $K \leftrightarrows J$ equilibrium towards these more stable DHPs and ultimately produce the high temperature products 12a and 12b.

At 0° C. the helicene, 11c, is the exclusive product of the Mallory photocyclization of 8. However, the concentration of the dibenzopentaphene product, 12c, becomes approximately equal to the concentration of 11c at 30° C. to 40° C. at lower temperatures than observed for 6 and 7 (FIG. 79). This is consistent with the observation that DHPs, C and J, on the way to 12c are 3.2 and 3.5 kcal/mol more stable than their competitively formed DHPs $B_a$ and $K_a$, respectively (Tables 19 and 22). Consequently, the rates of hydrogen abstraction, $k_C[C][I^·]$ and $k_J[J][I^·]$, because of the higher concentrations of C and J, can more effectively compete with establishment of the photostationary state and enhance the amount of 12c formed in the photocyclization. In comparison, in the reactions of 6 and 7, DHPs, C and J, on the way to 12a and 12b, respectively, are far less stable relative to their competitively formed DHPs $B_a$ and $K_a$ (Tables 19 and 22). As a consequence formation of 12a and 12b do not compete as effectively with formation of 11a and 11b and a higher temperature is required for their concentrations to become equal (i.e., [12a]=[11a] and [12b]=[11b]).

Photocyclization of 9 at −30° C. unexpectedly generated benzo[k]naphtho[1,2-a]tetraphene, 10d, as the only product (FIG. 79-d). In contrast to the other two possible regioisomers, 11d and 12d, it can form either in the red or green regions. However, irradiation of 9 is anticipated to predominantly generate DHP C because it is 9 kcal/mol more stable than $B_a$ (Table 19). Nevertheless, at −30° C. hydrogen abstraction from DHP C does not enjoy as large a symmetry advantage (T$\Delta$S=Tln2) as it would have at higher temperatures, and its lifetime is extended sufficiently to allow formation of the photostationary state and DHP $B_a$. Hydrogen abstraction to form G followed by exclusive photocyclization to form $L_a$, driven by its very large thermodynamic stability (11.6 kcal/mol) relative to $I_a$, (Table 19) subsequently generates the observed product, 10d. (Note: for comparison $I_a$ and $L_a$ formed in the photocyclizations of 6 and 7 (Table 19) are nearly identical in energy) This scenario is supported by the fact that at slightly higher temperatures the less stable $I_a$ is increasingly populated and 11d forms but then decreases as it succumbs to the thermodynamic stability's of DHPs C, and J on the way to the thermodynamically most stable regioisomer 12d.

It has been determined that Mallory substrates, 6, 7, and 8, react at low temperatures to exclusively produce their helicene products, 11a, 11b, and 11c, despite the fact that their regioisomers, 10a, 10b, and 10c, that can form competitively are 11.0, 10.7, and 12.2 kcal/mol more stable. This unusual, and synthetically useful, observation may be attributed to three effects: (1) the energies of the DHP precursors to these two sets of regioisomers are much closer in energy (≤5.5 kcal/mol) than the 10.7-12.2 kcal/mol separating the energies of the final regioisomeric products; (2) the extinction coefficients of the DHP precursors to the helicenes are smaller than the extinction coefficients of DHP precursors to their regioisomers by a factor of 4.8 to 9.2; and (3) at low temperatures thermal decompositions of intermediates are suppressed. Consequently, these effects allow attainment of the photostationary state while suppressing thermal decomposition of the DHPs and simultaneously bias the photostationary state towards population of the DHP precursor to the helicene product. This provides a satisfying and compelling rationale for what many feel is the most bizarre feature of Mallory photocyclization reactions; the preferential formation of the thermodynamically least stable helicene regioisomer.

As disclosed herein a method for unparalleled control over product regiochemistry in Mallory photocyclizations is now available by rationale design of substrates to influence dihydrophenanthrene (DHP) intermediate stability and the magnitudes of their extinction coefficients. These structural controls coupled with the ability to use temperature to influence approach to the DHP photostationary state enhances the utility of one of the most widely used photochemical methods for formation of polycyclic aromatic hydrocarbons.

Examples

Instruments and General Methods
Materials
Ferrocene was obtained from Sigma-Aldrich, Inc. and recrystallized from absolute ethanol. Anthracene was obtained from Sigma-Aldrich, Inc. and purified via sublimation. 9-Cyanoanthracene was obtained from Sigma-Aldrich, Inc. and used as is. Tetrabutylammonium perchlorate was obtained from Fluka Division of Honeywell, Inc. and was twice recrystallized from absolute ethanol. HPLC grade acetonitrile was used from Sigma-Aldrich, Inc. as received for chiral separation and circular dichroism spectroscopy experiments. Spectrophotometric grade toluene was received from Alfa Aesar of Thermo Fisher Scientific, Inc. and used as is. All other reagents and solvents were received from Sigma-Aldrich, Inc. and used without purification.

UV-Vis
UV-Vis spectra were collected on a Jasco V-670 Spectrophotometer. The lamps were preheated for at least 20 minutes prior to use to prevent baseline shift. A square quartz cuvette with a path length of 1 cm is used. A baseline was applied with the spectrophotometric grade solvent used to dissolve each corresponding analyte.

Fluorescence, Fluorescence Quantum Yield, and Fluorescence Lifetime
Fluorescence spectra were recorded on a Cary Eclipse Fluorescence Spectrophotometer. A square quartz cuvette with a path length of 1 cm was used. A blank sample consisting of the spectrophotometric grade solvent used to dissolve each corresponding analyte was checked prior to analysis. Excitation and emission slit widths were held at 5 nm for all fluorescence experiments.

Fluorescence quantum yields of [7]n2 and CN[7]n2 were determined using the comparative method of Williams[48] with anthracene ($\Phi_F$=0.27) and 9-cyanoanthracene ($\Phi_F$=0.93) as standards. These standards were cross-checked with each other to demonstrate the accuracy of the inventive method.[125] The fluorescence quantum yield of anthracene obtained using 9-cyanoanthracene as the standard is 0.29, acceptably close to the literature value of 0.27.[126] Spectrophotometric grade toluene (f=1.497) was used for all quantum yield of fluorescence experiments. Excitation wavelengths of 360 and 380 nm were used for anthracene and 9-cyanoanthracene, respectively. Excitation wavelengths of 333 and 356 nm are used for [7]n2 and CN[7]n2, respectively. The fluorescence quantum yield protocol used was as follows:

1. The UV-Vis absorbance spectra of samples and the standard were measured. These experiments were collected at a series of concentrations that gave absorbances at the excitation wavelengths that are approximately 0.02, 0.04, 0.06, 0.08, and 0.1. These low absorbances were chosen to insure that reabsorption effects were minimized.[127]
2. Fluorescence spectra were recorded using these same solutions, keeping the instrument settings the same between sample and standard measurements. The areas under the emission bands were then determined using MATLAB.
3. Graphs of integrated fluorescence intensity vs. absorbance were plotted for the sample and the standard. Using the slopes from these plots (m), the quantum yields were calculated as follows:

$$\Phi_X = \Phi_{ST}\left(\frac{m_X}{m_{ST}}\right)\left(\frac{\eta_X^2}{\eta_{ST}^2}\right)$$

Where η is the solvent refractive index, Φ is the fluorescence quantum yield, m is the slope from the integrated fluorescence intensity plot and the subscripts X and ST indicate values for the sample and the standard, respectively.

Fluorescence lifetimes were determined on an Optical Building Blocks Co. Easylife X Instrument. The instrument response factor (IRF) was collected on a dilute colloidal silica solution. A 375 nm LED was used as the excitation source for all samples.

Phosphorescence and Phosphorescence Lifetime

Phosphorescence spectra and phosphorescence lifetimes were recorded on a Cary Eclipse Fluorescence Spectrophotometer. The samples were dissolved in spectrophotometric grade toluene prior to introduction to a 3 mm quartz tube. This sample was then submerged in a glass dewar containing liquid nitrogen, forming a toluene glass. Phosphorescence spectra and lifetimes were then recorded at −196° C.

Cyclic Voltammetry

Cyclic voltammograms (CVs) were collected with a CH Instruments CHI600C Electrochemical Analyzer. All CV were collected using a three-electrode system consisting of a platinum working electrode, a silver wire reference electrode, and a silver wire auxiliary electrode. After an electrochemical response was observed for a sample, ferrocene was spiked with the sample as an internal standard. Tetrabutylammonium perchlorate (TBAP, 0.1 M) was used as the supporting electrolyte. Sample solutions were saturated with argon prior to analysis.

Circular Dichroism (CD)

CD spectra were recorded at 20° C. using a Jasco CD J-815 spectropolarimeter equipped with a Peltier temperature control system. The conditions were as follows: scanning speed 50 nm/min, data pitch 0.5 nm, DIT 1 s, and bandwidth 4 nm. A quartz cuvette with a 1 cm path length was used for CD experiments.

NMR $^1$H NMR and $^{13}$C NMR spectra were obtained on either a Bruker Advance 400 or 600 MHz NMR and referenced to TMS or the residual solvent signal.

X-ray

All X-ray experiments were carried out and analyzed on a Bruker SMART APEX II CCD by Dr. Arulsamy Navamoney. A molybdenum X-ray source was used.

High Pressure Liquid Chromatography (HPLC)

Chiral resolution of CN[7]n2 was performed on a Thermo Scientific Ultimate 3000 HPLC, with a LUX i-Cellulose-5 column. The carrier solvent was 100% HPLC grade acetonitrile.

Light source Mallory photocyclizations were performed using a 600 W medium-pressure mercury-vapor Hanovia UV lamp, with Pyrex as a filter.

Computations

All computational calculations were made using the Gaussian 09 software package produced by Gaussian, Inc. of Wallingford, Conn. Para-delocalized index of aromaticity (PDI) calculations are made using the third party program, Multiwfn[44] version 3.3.8. The protocol for obtaining PDI values are as follows:

1. The polycyclic aromatic hydrocarbon (PAH) of interest is optimized using Gaussian 09 and a formatted checkpoint (fchk) file is created.
2. The fchk file is opened with the Multiwfn software and a basin analysis is performed. The electron density is chosen as the real space function to be integrated. A medium quality grid with 0.1 Bohr spacing is then chosen.
3. Once basins are generated, the localization index (LI) and delocalization index (DI) are calculated for the basins. Finally, the PDI value for each ring is calculated by taking the average DI value of each para-related set of carbons in each six-membered ring.

The circular dichroism (CD) spectra are calculated using Multiwfn version 3.6. The protocol for calculating CD using this software is as follows:

1. A TD-DFT calculation is performed on the optimized structure of the system of interest using Gaussian 09.
2. The output file (log) from this calculation is opened with the Multiwfn software and the electronic circular dichroism (ECD) spectrum is plotted using the velocity representation. For each plot, the full width at half maximum is set to 0.5 eV.

Synthesis—FIG. 20

3,6-Dibromo-9,14-dicyanobenzo[f]tetraphene (19)

A solution of 3,6-dibromophenanthrene-9,10-dione (0.22 g, $6.01\times10^{-4}$ mol) in DMF (5 ml) was added drop-wise to a stirred solution of o-dicyanomethylbenzene (0.17 g, 2 eq) and NaOMe (0.13 g, 4 eq) in methanol (5 ml). This was stirred at room temperature overnight. The resulting precipitate was filtered and washed with EtOH yielding a yellow solid. (0.25 g, 80% yield) $^1$H NMR (400 MHz, CDCl$_3$): δ 9.25 (d, 2H, J=8.9 Hz), 8.65 (dd, 2H, J=6.5, 3.2 Hz), 8.59 (d, 2H, J=2.0 Hz), 7.81 (dd, 2H, J 6.5, 3.2 Hz), 7.86 (dd, 2H, J=8.9, 2.0 Hz). HRMS (MALDI-TOF) m/z: [M]$^+$ Calcd for $C_{24}H_{11}N_2Br_2$ 484.9290; Found 484.9219.

9,14-dicyano-3,6-di((E)-styryl)benzo[f]tetraphene (20)

A mixture of 19 (30 mg, 0.06 mmol), tetra-nbutylammonium bromide (46 mg, 0.144 mmol), and $K_2CO_3$ (9.95 mg, 0.072 mmol) in 3 mL of DMA was stirred and heated to 120° C. under nitrogen. When 60° C. was reached, the reaction mixture was charged with styrene (18.7 mg, 0.18 mmol). When 90° C. was reached, a prepared palladium catalyst solution was added dropwise (Pd(OAc)$_2$ (2.7 mg, 12 µmol), 1,3-bis(diphenylphosphino)propane (6.6 mg, 16 µmol) in 2 mL of DMA). This reaction was then stirred at 120° C. for 48 h and then allowed to cool to room temperature. The reaction mixture was reduced in a vacuum oven and the reaction product was washed with methylene chloride and then ethanol to give the product as a yellow solid. (14.7 mg, 46%) $^1$H NMR (400 MHz, CDCl$_3$): δ 9.36 (d, 2H, j=8.6 Hz), 8.64 (dd, 2H, J=6.8, 3.3 Hz), 8.63 (s, 2H), 7.94 (d, 2H, J=8.51 Hz), 7.91 (dd 2H, J=6.4, 3.1 Hz), 7.66 (d, 4H, J=7.5 Hz), 7.46-7.33 (m, 10H). $^{13}$C NMR (400 MHz, CDCl$_3$): δ 139.9 (2C), 137.0 (2C), 133.7 (2C), 132.3 (2C), 132.1 (2C), 131.9 (2C), 129.9 (2C), 128.9 (4C), 128.5 (2), 128.4 (2C), 127.8 (2C), 127.0 (4), 126.5 (2C), 1264 (2C), 125.5 (2C), 121.2 (2C), 118.6 (2C), 107.9 (2C). HRMS (MALDI-TOF) m/z: [M]$^+$ Calcd for $C_{40}$-$C_{25}N_2$ 533.2018; Found 533.2029.

9,14-Dicyanonaphtho[2,3-L]heptahelicene (CN[7]n2)

A solution of Ket[7]n0 (17.3 mg, $4.24\times10^{-5}$ mol) in DMF (1.5 ml) was added drop-wise to a stirred solution of o-dicyanomethylbenzene (6.6 mg, 1 eq) and NaOMe (9.2 mg, 4 eq) in methanol (1 ml). This was stirred at room temperature overnight. Reaction product added to water (10 ml) and extracted with toluene (3×'s 10 ml). The organic layer was dried over MgSO$_4$, filtered and reduced yielding an orange-yellow solid. The crude reaction product was purified by triturating in acetonitrile to give a deep orange solid (5.6 mg, 25%). $^1$H NMR (600 MHz, C$_2$D$_2$Cl$_2$, δ): 6.53 (ddd, J=1.3 Hz, 6.9 Hz, 8.3 Hz, 2H), 6.80 (d, J=8.4 Hz, 2H), 7.02 (ddd, J=1.0 Hz, J=7.0 Hz, J=7.9 Hz, 2H), 7.32 (d, 7.9 Hz, 2H), 7.50 (d, J=8.5 Hz, 2H), 7.69 (d, J=8.5 Hz, 2H), 7.97-7.98 (m, 2H), 8.18 (d, 8.6 Hz, 2H), 8.70-8.71 (m, 2H), 9.57 (d, J=8.5 Hz, 2H). $^{13}$C NMR (100 MHz, C$_2$D$_2$Cl$_2$, δ): 106.7 (2C), 118.7 (2C), 122.8 (2C), 124.0 (2C), 125.0 (2C), 125.1 (2C), 125.9 (2C), 126.0 (2C), 126.2 (2C), 126.9 (2C), 127.5 (2C), 128.7 (4C), 128.8 (2C), 129.3 (2C), 129.9 (2C), 131.7 (2C), 131.9 (2C), 133.7 (2C), 134.1 (2C). HRMS (MALDI-TOF) m/z calculated for C$_{40}$H$_{20}$N$_2$ [M]$^+$, 528.1626, found 528.1634.

3,6-Di((E)-styryl)-9,10-bis-methoxyphenanthrene (7)

A mixture of 3,6-dibromo-9,10-bis-methoxyphenanthrene (306.3 mg, 0.77 mmol), tetra-n-butylammonium bromide (99.7 mg, 0.3 mmol), and K$_2$CO$_3$ (534 mg, 3.9 mmol) in 3 mL of DMA was stirred and heated up to 120° C. under nitrogen. When 60° C. was reached, the reaction mixture was charged with styrene (241 mg, 2.3 mmol). When 90° C. was reached, a prepared palladium catalyst solution was added dropwise (Pd(OAc)$_2$ (3.5 mg, 0.015 mmol), 1,3-bis(diphenylphosphino)propane (7.7 mg, 0.019 mmol) in 1 mL of DMA). This reaction was then stirred at 120° C. for 48 h and then allowed to cool to room temperature and transferred to a separatory funnel along with 25 mL of 6 N HCl. The reaction product was extracted with CH$_2$Cl$_2$ and washed with 6 N HCl and water. Removal of the solvent produced a yellow-brown film (342 mg, 87%). $^1$H NMR chemical shifts are consistent with literature values.[128]

Heptahelicene-9,10-dione (Ket[7]n0)

MeO[7]n0 (49.8 mg, 114 μmol) in acetonitrile (10 ml) was combined with a solution of ceric ammonium nitrate (CAN) (155.7 mg, 284 μmol) in acetonitrile (10 ml) and hand-shaken for 5 minutes. This was then poured into 20 ml of water and extracted with toluene (3×'s 20 ml). The crude reaction mixture was reduced and purified by silica gel chromatography (1:9 EtOAc:hexanes) giving a red solid (17.3, 37%). $^1$H NMR chemical shifts are consistent with literature values.[129]

3,6-dibromobenzo[f]tetraphene

A CH$_2$Cl$_2$ (32 mL) suspension of 3,6-dibromophenanthrenequinone (0.25 g, 0.68 mmol) and o-xylylenebis(triphenylphosphonium bromide) (0.625 g, 0.79 mmol) was stirred until homogenous. The stir bar was removed and 15 ml of freshly prepared LiOH solution (3.36 M, 0.35 g Li metal in 15 ml water) was added. The two-phase mixture was sonicated for 80 min. The reaction product was extracted with CH$_2$Cl$_2$ and washed with water. The crude product was purified by silica gel chromatography (toluene) and was finally recrystallized from the eluent to give (90 mg, 30%) of 2, 13-dibromobenzo[b]triphenylene as colorless needles. $^1$H NMR (400 MHz, CDCl$_3$, δ): 7.58-7.60 (m, 2H), 7.76 (dd, J=1.9 Hz, 8.7 Hz, 2H), 8.05-8.07 (m, 2H), 8.55 (d, J=1.9 Hz, 2H), 8.58 (d, J=8.8 Hz, 2H), 8.97 (s, 2H). $^{13}$C{$^1$H} NMR (100 MHz, CDCl$_3$, δ): 122.4 (2C), 122.4 (2C), 125.7 (2C), 126.6 (2C), 126.8 (2C), 127.6 (2C), 128.3 (2C), 129.5 (2C), 130.8 (2C), 131.3 (2C), 132.6 (2C). See the Supporting information on the details of the X-ray structure of 2,13-dibrombenzo[b]triphenylene.

3,6-di((E)-styryl)benzo[f]tetraphene (8)

A mixture of 2,13-dibromobenzo[b]triphenylene (66.5 mg, 0.14 mmol), tetra-n-butylammonium bromide (108 mg, 0.34 mmol), and K$_2$CO$_3$ (84.4 mg, 0.61 mmol) in 4 ml DMA was stirred and heated to 120° C. under nitrogen. When 60° C. was reached, the reaction mixture was charged with styrene (47.5 mg, 0.46 mmol). When 90° C. was reached a prepared palladium catalyst solution was added drop-wise (Pd(OAc)$_2$ (0.7 mg, 3 μmol), 1,3-bis(diphenylphosphino)propane (1.9 mg, 4.6 μmol) in 4 ml DMA). This reaction was then stirred at 120° C. for 48 h and then allowed to cool to room temperature and transferred to a separatory funnel along with 25 ml of 6 N HCl. The reaction product was extracted with CH$_2$Cl$_2$ and washed with 6N HCl and water. Removal of the solvent produced an off-white solid in nearly quantitative yield that was used in the next step without purification. An analytically pure sample for characterization was obtained by washing with acetone to give a white solid. (30 mg, 44%) $^1$H NMR (400 MHz, CDCl$_3$, δ): 7.32-7.48 (m, 10H), 7.58-7.61 (m, 2H), 7.68 (d, J=8.1 Hz, 4H), 7.93 (d, J=1.4 Hz, 8.5 Hz, 2H), 8.11-8.13 (m, 2H), 8.71 (d, J=1.5 Hz, 2H), 8.79 (d, J=8.6 Hz, 2H), 9.09 (s, 2H). $^{13}$C{$^1$H} NMR (100 MHz, CDCl$_3$, δ): 122.2 (2C), 122.2 (2C), 122.3 (2C), 124.3 (2C), 125.2 (2C), 126.2 (2C), 126.7 (4C), 127.9 (2C), 128.2 (2C), 128.4 (2C), 128.8 (4C), 128.8 (2C), 128.9 (2C), 129.6 (2C), 129.9 (2C), 132.4 (2C), 136.7 (2C). HRMS (MALDI-TOF) m/z calculated for C$_{38}$H$_{27}$ [M+H]$^+$, 483.2113, found 483.2144.

3,6-di((E)-styryl)-9,10-bis-ethyleneketal-phenanthrene (9)

A mixture of 3,6-dibromo-9,10-bis-ethyleneketal-phenanthrene (280 mg, 0.62 mmol), tetra-n-butylammonium bromide (480 mg, 1.49 mmol), and K$_2$CO$_3$ (103 mg, 0.74 mmol) in 6 ml DMA was stirred and heated up to 120° C. under nitrogen. When 60° C. was reached, the reaction mixture was charged with styrene (193 mg, 1.86 mmol). When 90° C. was reached a prepared palladium catalyst solution was added drop-wise (Pd(OAc)$_2$ (28 mg, 0.12 mmol), 1,3-bis(diphenylphosphino)propane (77 mg, 0.19 mmol) in 6 ml DMA). This reaction mixture was then allowed to stir at 120° C. for 48 h followed by removal of the DMA using a vacuum oven. The residue was then treated with hot ethanol and filtered. Recrystalization in EtOH gave 9 (120 mg, 39%) as off-white crystals. $^1$H NMR (400 MHz, CDCl$_3$, δ): 3.69 (broad s, 4H), 4.22 (broad s, 4H), 7.27-7.41 (m, 8H), 7.57-7.62 (m, 8H), 7.76 (d, J=8.0 Hz, 2H), 8.06 (s, 2H). $^{13}$C{$^1$H} NMR (100 MHz, CDCl$_3$, δ): 61.7 (broad, 4C), 92.9 (2C), 122.5 (2C), 126.7 (2C), 126.9 (2C), 126.9 (4C), 128.1 (2C), 128.4 (2C), 129.0 (4C), 130.1 (2C), 132.5 (4C), 133.5 (2C), 137.3 (2C), 139.2 (2C). HRMS(MALDI-TOF) m/z calculated for C$_{34}$H$_{28}$O$_4$ [M]$^+$500.1988, found 500.1984.

General procedure for Mallory bis-photocyclization-dehydrogenation

A solution of the bisstyrylphenanthrene substrate (0.5 mM), I$_2$ (2.2 molar equivalent), and propylene oxide (50 molar equivalent) in toluene was heated or cooled to the desired temperature and subsequently irradiated overnight in a Pyrex vessel with a 600 W medium pressure mercury vapor lamp. The reaction mixture was allowed to cool or warm to room temperature and was washed with sodium thiosulfate 3×'s and DI water 3×'s and finally with brine. The toluene was removed and the sample was dried in a vacuum oven overnight prior to NMR analysis. No precipitate was visible in any of the NMR samples.

5,6-Bis-ethyleneketal-naphtho[2,1-b]pentahelicene (10d)

A solution of 9 (100 ml, 0.5 mM), $I_2$ (1.1 mM), and propylene oxide (25 mM) in toluene was placed in an ice-bath. The reaction mixture temperature was maintained at 0° C. and irradiated for 13 hours with a 600 W medium pressure mercury vapor lamp. The organic reaction product was washed with sodium thiosulfate 3×'s and water 3×'s and dried over $MgSO_4$. The solvent was removed at reduced pressure and the crude product was purified by silica gel chromatography (1:4 EtOAc: hexanes) to give 10d as a colorless solid. $^1$H NMR (600 MHz, $CDCl_3$, δ): 3.40 (d, J=11.1 Hz, 1H), 3.53 (dd, J=2.3 Hz, 11.1 Hz, 1H), 3.79 (td, J=2.5 Hz, 12.3 Hz, 1H), 3.94 (dd, J=2.1 Hz, 12.0 Hz, 1H), 4.11 (d, J=7.3 Hz, 2H), 4.60-4.68 (m, 2H), 7.0 (t, J=7.7 Hz, 1H), 7.34 (d, J=8.9 Hz, 1H), 7.42 (t, J=7.0 Hz, 1H), 7.61 (t, J=7.2 Hz, 1H), 7.63 (d, 8.7 Hz, 1H), 7.69 (t, J=7.7, 1H), 7.73 (d, J=8.7 Hz, 1H), 7.80 (d, J=8.8 Hz, 1H), 7.85 (d, J=8.4 Hz, 1H), 7.87 (s, 2H), 8.14 (s, 1H), 8.36 (d, J=8.6 Hz, 1H), 8.81 (d, J=8.3 Hz, 1H), 9.09 (s, 1H). $^{13}$C{H} NMR (100 MHz, $CDCl_3$, δ): 59.1 (1C), 59.4 (1C), 63.5 (1C), 63.9 (1C), 92.7 (1C), 93.2 (1C), 120.4 (1C), 123.0 (1C), 123.6 (1C), 124.1 (1C), 126.5 (1C), 126.7 (1C), 126.8 (1C), 126.9 (1C), 126.9 (1C), 127.7 (1C), 127.8 (1C), 128.0 (1C), 128.0 (1C), 128.6 (1C), 129.5 (1C), 129.5 (1C), 129.6 (1C), 129.6 (1C), 130.3 (1C), 130.4 (1C), 130.8 (1C), 131.9 (1C), 132.3 (1C), 132.4 (1C), 132.7 (1C), 133.1 (1C), 133.3 (1C), 134.8 (1C). HRMS (MALDI-TOF) m/z calculated for $C_{34}H_{24}O_4$ [M]$^+$, 496.1675, found 496.1680.

Naphtho[2,3-1]heptahelicene (11c)

To a solution of 9,10-[7]helicenequinone (6.2 mg, 15.2 μmol), O-xylenebis(triphenylphosphonium bromide) (21.5 mg, 27.4 μmol), and tetra-n-butylammonium perchlorate (3 mg, 8.8 μmol) in $CH_2Cl_2$ (2 ml) 2 ml of freshly prepared LiOH solution (0.5 M, 7 mg Li metal in 2 ml water) was added. The two-phase mixture was sonicated for 90 min. The reaction product was extracted with toluene and washed with water. The crude product was purified by silica gel chromatography (100% hexanes) to give 11c (1.3 mg, 18%) as a pale yellow solid. $^1$H NMR (600 MHz, $CDCl_3$, δ): 6.43 (ddd, J=1.3 Hz, 6.8 Hz, 8.3 Hz, 2H), 6.89 (d, J=8.5, 2H), 6.93 (ddd, J=1.1 Hz, 6.8 Hz, 7.87 Hz, 2H), 7.27 (d, J=7.9 Hz, 2H), 7.40 (d, J=8.5 Hz, 2H), 7.62-7.63 (m, 2H), 7.67 (d, J=8.5 Hz, 2H), 8.07 (d, J=8.4 Hz, 2H), 8.19-8.21 (m, 2H), 8.95 (d, J=8.6 Hz, 2H), 9.27 (s, 2H). $^{13}$C{$^1$H} NMR (100 MHz, $CDCl_3$, δ): 121.2 (2C), 122.3 (2C), 123.6 (2C), 125.0 (2C), 125.4 (2C), 125.4 (2C), 126.0 (2C), 126.1 (2C), 126.5 (2C), 127.2 (2C), 127.9 (2C), 128.3 (2C), 129.0 (2C), 129.6 (2C), 129.7 (2C), 129.8 (2C), 131.7 (2C), 131.8 (2C), 132.4 (2C). HRMS (MALDI-TOF) m/z calculated for $C_{38}H_{22}$ [M]$^+$, 478.1722, found 478.1717.

Dibenzo[c,m]-naphtho[2,3,h]pentaphene (12c)

A solution of crude 8 (100 mg, 0.21 mmol), $I_2$ (116 mg, 0.46 mmol), and propylene oxide (725 μL, 103.6 mmol) in toluene (420 ml) was heated up to 95° C. in a 500 ml Pyrex flask. Once the target temperature was reached, the sample was irradiated with a 600 W medium pressure mercury vapor lamp for 20 hours. The reaction solution was allowed to cool to room temperature and then washed with sodium thiosulfate to remove unreacted iodine and subsequently washed with water. The reaction product was passed through a silica gel plug using toluene to give 12c (57.2 mg, 58%) as a yellow solid. $^1$H NMR (400 MHz, $CDCl_3$, δ): 7.61 (dd, J=7.8 Hz, 7.8 Hz, 2H), 7.69 (dd, J=7.7 Hz, 7.7 Hz, 2H), 7.72-7.73 (m, 2H), 7.87 (d, J=7.6 HZ, 2H), 8.36-8.37 (m, 2H), 8.59-8.66 (m, 4H), 8.77 (d, J=8.5 Hz, 2H), 8.82 (d, J=8.82 Hz, 2H), 9.67 (dd, J=3 Hz, 8.7 Hz, 2H), 9.78 (d, J=5.6 Hz, 2H). HRMS (MALDI-TOF) m/z calculated for $C_{38}H_{22}$ [M]$^+$, 478.1722, found 478.1714.

7,8-bis-ethyleneketal-dibenzo[c,m]pentaphene (12d)

A solution of 9 (100 ml, 0.5 mM), 12 (1.1 mM), and propylene oxide (25 mM) in toluene was prepared in a 250 ml Pyrex glass pressure vessel. The reaction mixture was heated to 157° C. and subsequently irradiated for 18 hours with a 600 W medium pressure mercury vapor lamp. The reaction mixture was washed with sodium thiosulfate 3×'s and water 3×'s and dried over $MgSO_4$. The solvent was removed at reduced pressure and the reaction product was purified by recrystallization in toluene/EtOH to afford 12d as a colorless solid. $^1$H NMR (600 MHz, $CDCl_3$, δ): 3.84 (Broad s, 4H), 4.41 (Broad s, 4H), 7.64 (ddd, J=1.0 Hz, 7.1 Hz, 7.9 Hz, 2H), 7.70 (ddd, J=1.3 Hz, 7.1 Hz, 8.2 Hz, 2H), 7.82 (d, J=8.8 Hz, 2H), 7.89 (d, J=8.8 Hz, 2H), 7.92 (d, 7.8 Hz, 2H), 8.62 (s, 2H), 8.82 (d, 8.3 Hz, 2H), 9.14 (s, 2H). $^{13}$C{H} NMR (100 MHz, $CDCl_3$, δ): 93.3 (2C), 121.1 (2C), 123.1 (2C), 124.2 (2C), 126.8 (2C), 126.9 (2C), 127.0 (2C), 128.3 (2C), 128.7 (2C), 130.4 (2C), 130.6 (2C), 131.3 (2C), 131.3 (2C), 132.2 (2C), 133.2 (2C). HRMS (MALDI-TOF) m/z calculated for $C_{34}H_{24}O_4$ [M]$^+$, 496.1675, found 496.1676.

3,6-Bis-styrylphenanthrenequinone

A mixture of 3,6-dibromophenanthrenequinone (100 mg, 0.27 mmol), tetra-nbutylammonium bromide (35 mg, 0.11 mmol), and $K_2CO_3$ (189 mg, 1.37 mmol) in 1.5 ml DMA was stirred and heated up to 120° C. under nitrogen for 48 hours. When 60° C. was reached, the reaction mixture was charged with styrene (85 mg, 0.82 mmol). When 90° C. was reached a prepared palladium catalyst solution was added drop-wise (Pd(OAc)$_2$ (0.6 mg, 2.7 μmol), 1,3-Bis(diphenylphosphino)propane (1.4 mg, 3.28 μmol) in 1.5 ml DMA). The DMA was removed using a vacuum oven. The reaction product was purified by silica gel chromatography (3:2 Hexanes: Ethyl acetate) to afford 3,6-bis-styrylphenanthrenequinone (20.8 mg, 19%) as a red film. $^1$H NMR (400 MHz, $CDCl_3$, δ): 7.26 (d, J=7.8 Hz, 16.0 Hz, 2H), 7.34-7.45 (m, 8H), 7.62 (d, J=7.7 Hz, 4H), 7.67 (d, 8 Hz, 2H), 8.15 (s, 2H), 8.23 (d, J=8.1 Hz, 2H).

5,6-Dimethoxy-2-pentahelicenecarboxaldehyde (15b)

A solution of 7 (100 ml, 0.5 mM), $I_2$ (2.2 molar equivalent), and propylene oxide (50 molar equivalent) in toluene was irradiated overnight with a 600 W medium pressure mercury vapor lamp. The organic reaction product was washed with sodium thiosulfate 3×'s and water 3×'s and dried over $MgSO_4$. The toluene was filtered and removed under reduced pressure and the crude reaction product was purified by slilica gel chromatography (1% EtOAc in hexanes) to afford 15b as a yellow solid. $^1$H NMR (600 MHz, $CDCl_3$, δ): 4.20 (s, 3H), 4.21 (s, 3H), 7.24 (ddd, J=1.4

Hz, 7.0 Hz, 8.3 Hz, 1H), 7.53 (ddd, J=1.0 Hz, 7.0 Hz, 7.9 Hz, 1H), 7.91 (d, J=8.5 Hz, 1H), 7.96-7.99 (m, 3H), 8.02 (dd, J=1.5 Hz, 8.6 Hz, 1H), 8.31 (d, 8.5 Hz, 1H), 8.39 (d, 8.4 Hz, 1H), 8.40 (d, 8.5 Hz, 1H), 8.92 (s, 1H), 9.72 (s, 1H). $^{13}C\{H\}$ NMR (100 MHz, CDCl$_3$, δ): 61.5 (1C), 61.5 (1C), 121.1 (1C), 122.9 (1C), 123.5 (1C), 124.9 (1C), 125.8 (1C), 126.5 (1C), 126.9 (1C), 127.0 (1C), 128.1 (1C), 128.3 (1C), 128.4 (1C), 128.6 (1C), 128.7 (1C), 130.0 (1C), 130.7 (1C), 132.0 (1C), 132.3 (1C), 132.7 (1C), 133.1 (1C), 135.9 (1C), 144.4 (1C), 146.9 (1C), 192.6 (1C). HRMS (MALDI-TOF) m/z calculated for $C_{25}H_{18}O_3$ [M]$^+$, 366.1256, found 366.1257.

Naphtho[2,3-f]-2-pentahelicenecarboxylaldehyde (15c)

A solution of 8 (100 ml, 0.5 mM), I$_2$ (2.2 molar equivalent), and propylene oxide (50 molar equivalent) in toluene was placed in an ice-bath and irradiated for 14 hours with a 600 W medium pressure mercury vapor lamp. The organic reaction product was washed with sodium thiosulfate 3×'s and water 3×'s and dried over MgSO$_4$. The toluene was filtered and removed under reduced pressure and the reaction product was purified by slilica gel chromatography (1% EtOAc in hexanes) to afford (15c) as a yellow solid. $^1$H NMR (600 MHz, CDCl$_3$, δ): 7.21 (ddd, J=1.3 Hz, 6.8 Hz, 8.3 Hz, 1H), 7.51 (ddd, J=1.0 Hz, 6.8 Hz, 7.9 Hz, 1H), 7.63-7.65 (m, 2H), 7.89 (d, 8.5 Hz, 1H), 7.92 (d, 8.6 Hz, 1H), 7.95 (dd, J=1.0 Hz, 8.0 Hz, 1H), 8.05 (d, 8.3 Hz, 1H), 8.06 (dd, J=1.6 Hz, 8.3 Hz, 1H), 8.14-8.19 (m, 2H), 8.38 (d, 8.4 Hz, 1H), 8.73 (d, 1.2 Hz, 1H), 8.74 (d, 8.6 Hz, 1H), 8.80 (d, 8.3 Hz, 1H), 9.07 (s, 1H), 9.19 (s, 1H), 9.73 (s, 1H). $^{13}C\{H\}$ NMR (100 MHz, CDCl$_3$, δ): 121.5 (1C), 123.1 (1C), 123.4 (1C), 124.8 (1C), 124.9 (1C), 125.2 (1C), 126.2 (1C), 126.6 (1C), 126.8 (1C), 126.9 (1C), 126.9 (1C), 127.5 (1C), 128.0 (1C), 128.2 (1C), 128.3 (1C), 128.4 (1C), 128.4 (1C), 128.7 (1C), 129.0 (1C), 129.3 (1C), 130.5 (1C), 131.2 (1C), 131.4 (1C), 132.2 (1C), 132.9 (1C), 133.1 (1C), 133.2 (1C), 133.4 (1C), 134.9 (1C), 135.6 (1C), 192.1 (1C). HRMS (MALDI-TOF) m/z calculated for $C_{31}H_{18}O$ [M]$^+$, 406.1358, found 406.1358.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

CITED REFERENCES (1) Clennan, E. L.; Liao, C. Synthesis, Characterization, Photophysics and Photochemistry of Pyrylogen Electron Transfer Sensitizers. *Photochem. Photobiol.* 2014, 90, 344-357.
(2) Bakupog, T.; Clennan, E. L.; Zhang, X. Viologen embedded polyaromatic hydrocarbons (VPAH2+): synthesis, computational, photophysical, and electrochemical characterizations of 3,8-diazaphenanthrenyl viologens. *Tetrahedron Lett.* 2015, 56, 5591-5594.
(3) Clennan, E. L.; Welch, W.; El-Idreesy, T. T.; Arulsamy, N. Regiochemistry and substituent effects on pyrylogen and thiopyrylogen stability and electronic character. *Can. J. Chem.* 2014, 93, 414-421.
(4) Clennan, E. L.; Zhang, X.; Petek, T. Synthesis, Reactivity, and Sulfide Quenching of Helical Viologens. *Phos. Sulfur and Silicon* 2017, 191, 222-226.
(5) Zhang, X.; Clennan, E. L.; Arulsamy, N.; Weber, R.; Weber, J. Synthesis, Structure, and Photochemical Behavior of [5]Heli-viologen Isomers. *J. Org. Chem.* 2016, 81, 5474-5486.
(6) Zhang, X.; Clennan, E. L.; Petek, T.; Weber, J. Synthesis, computation, and photophysical characterization of diaza-embedded [4]helicenes and pseudo[4]helicenes and their pyridinium and viologen homologues. *Tetrahedron* 2016, 72, Under Review.
(7) Johnson II, C. A.; Haley, M. M.: Pioneers of Carbon-rich Compounds. In *Carbon-Rich Compounds. From Molecules to Materials*; Haley, M. M., Tykwinski, R. R., Eds.; Wiley-VCH Verlag GmbH & Co. KGaA: Weinheim, 2006; pp 1-25.
(8) Randic, M. Aromaticity of Polycyclic Conjugated Hydrocarbons. *Chem. Rev.* 2003, 103, 3449-3606.
(9) Kekulé, A. Carboxytartronic acid. The constitution of benzene. *Liebigs Annalen* 1883, 221, 230-260.
(10) Pauling, L.: *The Nature of the Chemical Bond;* 3rd ed.; Cornell University Press: Ithaca, N.Y., 1960. pp. 644.
(11) Clar, E.: *The Aromatic Sextet*; John Wiley & Sons: London, 1972.
(12) Krätschmer, W.; Lamb, L. D.; Fostiropoulos, K.; Huffman, D. R. Solid C$_{60}$: a new form of carbon. *Nature* 1990, 347, 354-358.
(13) Kroto, H. W.; Heath, J. R.; O'Brien, S. C.; Curl, R. F.; Smalley, R. E. C$_{60}$: Buckminsterfullerene. *Nature* 1985, 318, 162-163.
(14) Novoselov, K. S.; Geim, A. K.; Morozov, S. V.; Jiang, D.; Zhang, Y.; Dubonos, S. V.; Grigorieva, I. V.; Firsov, A. A. Electric Field Effect in Atomically Thin Carbon Films. *Science* 2004, 306, 666-669.
(15) Anthony, J. E. Organic electronics: Addressing challenges. *Nature Materials* 2014, 13, 773-775.
(16) Rieger, R.; Müllen, K. Forever young: polycyclic aromatic hydrocarbons as model cases for structural and optical studies. *J. Phys. Org. Chem.* 2010, 23, 315-325.
(17) Gingras, M. One hundred years of helicene chemistry. Part 3: applications and properties of carbohelicenes. *Chem. Soc. Rev.* 2013, 42, 1051-1095.
(18) Gingras, M. One hundred years of helicene chemistry. Part 1: non-stereoselective syntheses of carbohelicenes. *Chem. Soc. Rev.* 2013, 42, 968-1006.
(19) Gingras, M.; Felix, G.; Peresutti, R. One hundred years of helicene chemistry. Part 2: stereoselective synthesis and chiral separations of carbohelicenes. *Chem. Soc. Rev.* 2013, 42, 1007-1050.
(20) Shen, Y.; Chen, C.-F. Helicenes: Synthesis and Applications. *Chem. Rev.* 2012, 112, 1463-1535.
(21) Yang, Y.; Da Costa, R. C.; Fuchter, M. J.; Campbell, A. J. Circularly polarized light detection by a chiral organic semiconductor transistor. *Nat. Photonics* 2013, 7, 634-638.
(22) Yang, Y.; da Costa, R. C.; Smilgies, D.-M.; Campbell, A. J.; Fuchter, M. J. Induction of Circularly Polarized Electroluminescence from an Achiral Light-Emitting Polymer via a Chiral Small-Molecule Dopant. *Adv. Mater.* 2013, 25, 2624-2628.
(23) Pospisil, L.; Bednarova, L.; Stepanek, P.; Slavicek, P.; Vavra, J.; Hromadova, M.; Dlouha, H.; Tarabek, J.; Teply, F. Intense chiroptical switching in a dicationic helicene-like derivative: exploration of a viologen-type redox manifold of a non-racemic helquat. *J. Am. Chem. Soc.* 2014, 136, 10826-10829.

(24) Zhou, L.-L.; Li, M.; Lu, H.-Y.; Chen, C.-F. Benzo[5]helicene-based conjugated polymers: synthesis, photophysical properties, and application for the detection of nitroaromatic explosives. *Polymer Chem.* 2016, 7, 310-318.

(25) Kiran, V.; Mathew, S. P.; Cohen, S. R.; Hernindez Delgado, I.; Lacour, J.; Naaman, R. Helicenes—A New Class of Organic Spin Filter. *Adv. Mater.* 2016, 28, 1957-1962.

(26) Delgado, I. H.; Pascal, S.; Wallabregue, A.; Duwald, R.; Besnard, C.; Guenee, L.; Nancoz, C.; Vauthey, E.; Tovar, R. C.; Lunkley, J. L.; Muller, G.; Lacour, J. Functionalized cationic [4]helicenes with unique tuning of absorption, fluorescence and chiroptical properties up to the far-red range. Chem. Sci. 2016, 7, 4685-4693

(27) Xiao, J.; Divayana, Y.; Zhang, Q.; Doung, H. M.; Zhang, H.; Boey, F.; Sun, X. W.; Wudl, F., Synthesis, structure, and optoelectronic properties of a new twistacene 1,2,3,4,6,13-hexaphenyl-7: 8, 11:12-bisbenzo-pentacene. Journal of Materials Chemistry 2010, 20 (37), 8167-8170.

(28) Xiao, J.; Liu, S.; Liu, Y.; Ji, L.; Liu, X.; Zhang, H.; Sun, X.; Zhang, Q., Synthesis, Structure, and Physical Properties of 5,7,14,16-Tetraphenyl-8:9,12:13-bisbenzo-hexatwistacene. 2012, 7 (3), 561-564.

(29) Liu, Z.; Xiao, J.; Fu, Q.; Feng, H.; Zhang, X.; Ren, T.; Wang, S.; Ma, D.; Wang, X.; Chen, H., Synthesis and Physical Properties of the Conjugated Dendrons Bearing Twisted Acenes Used in Solution Processing of Organic Light-Emitting Diodes. ACS Applied Materials & Interfaces 2013, 5 (21), 11136-11141.

(30) Duong, H. M.; Bendikov, M.; Steiger, D.; Zhang, Q.; Sonmez, G.; Yamada, J.; Wudl, F., Efficient Synthesis of a Novel, Twisted and Stable, Electroluminescent "Twistacene". Organic Letters 2003, 5 (23), 4433-4436.

(31) Anthony, J. E., The Larger Acenes: Versatile Organic Semiconductors. 2008, 47 (3), 452-483.

(32) Bendikov, M.; Wudl, F.; Perepichka, D. F., Tetrathiafulvalenes, Oligoacenenes, and Their Buckminsterfullerene Derivatives: The Brick and Mortar of Organic Electronics. Chemical Reviews 2004, 104 (11), 4891-4946.

(33) Thorley, K. J., The Electronic Nature and Reactivity of the Larger Acenes. Israel journal of chemistry 2014, 54 (5-6), 642-649.

(34) Lu, J.; Ho, D. M.; Vogelaar, N. J.; Kraml, C. M.; Pascal, R. A., A Pentacene with a 144° Twist. Journal of the American Chemical Society 2004, 126 (36), 11168-11169.

(35) Duong, H. M.; Bendikov, M.; Steiger, D.; Zhang, Q.; Sonmez, G.; Yamada, J.; Wudl, F., Efficient Synthesis of a Novel, Twisted and Stable, Electroluminescent "Twistacene". *Organic Letters* 2003, 5 (23), 4433-4436.

(36) Norton, J. E.; Houk, K. N., Electronic Structures and Properties of Twisted Polyacenes. Journal of the American Chemical Society 2005, 127 (12), 4162-4163.

(37) Lu, J.; Ho, D. M.; Vogelaar, N. J.; Kraml, C. M.; Bernhard, S.; Byrne, N.; Kim, L. R.; Pascal, R. A., Synthesis, Structure, and Resolution of Exceptionally Twisted Pentacenes. Journal of the American Chemical Society 2006, 128 (51), 17043-17050.

(38) Pascal, R. A.; McMillan, W. D.; Van Engen, D., 9,18-Diphenyltetrabenz[a,c,h,j]anthracene: a remarkably twisted polycyclic aromatic hydrocarbon. Journal of the American Chemical Society 1986, 108 (18), 5652-5653.

(39) Bondi, A., van der Waals Volumes and Radii. The Journal of Physical Chemistry 1964, 68 (3), 441-451.

(40) Martin, R. H.; Marchant, M. J., Thermal racemisation of hepta-, octa-, and nonahelicene: Kinetic results, reaction path and experimental proofs that the racemisation of hexa- and heptahelicene does not involve an intramolecular double diels-alder reaction. Tetrahedron 1974, 30 (2), 347-349.

(41) Barroso, J.; Cabellos, J. L.; Pan, S.; Murillo, F.; Zarate, X.; Fernandez-Herrera, M. A.; Merino, G., Revisiting the racemization mechanism of helicenes. Chemical Communications 2018, 54 (2), 188-191.

(42) Pascal, R. A., Twisted Acenes. Chemical Reviews 2006, 106 (12), 4809-4819.

(43) Fuchter, M. J.; Weimar, M.; Yang, X.; Judge, D. K.; White, A. J. P., An unusual oxidative rearrangement of [7]-helicene. Tetrahedron Letters 2012, 53 (9), 1108-1111.

(44) Lu, T.; Chen, F., Multiwfn: A multifunctional wavefunction analyzer. J. Comput. Chem. 2012, 33 (5), 580-592.

(45) Dojcansky, Saturated vapor pressure of acetonitrile. Chemical Papers 1974, 28 (2), 157-159.

(46) Van Eldik, R.; Asano, T.; Le Noble, W. J., Activation and reaction volumes in solution. 2. Chemical Reviews 1989, 89 (3), 549-688.

(47) Yanai, T.; Tew, D. P.; Handy, N. C., A new hybrid exchange-correlation functional using the Coulomb-attenuating method (CAM-B3LYP). Chemical Physics Letters 2004, 393 (1), 51-57.

(48) Williams, A. T. R.; Winfield, S. A.; Miller, J. N., Relative fluorescence quantum yields using a computer-controlled luminescence spectrometer. Analyst 1983, 108 (1290), 1067-1071.

(49) Birks, J. B.; Birch, D. J. S.; Cordemans, E.; Vander Donckt, E., Fluorescence of the higher helicenes. Chemical Physics Letters 1976, 43 (1), 33-36.

(50) Blanc, S.; Pigot, T.; Cugnet, C.; Brown, R.; Lacombe, S., A new cyanoaromatic photosensitizer vs. 9,10-dicyanoanthracene: systematic comparison of the photophysical properties. Physical Chemistry Chemical Physics 2010, 12 (37), 11280-11290.

(51) Li, Y.; Ren, T.; Dong, W.-J., Tuning photophysical properties of triphenylamine and aromatic cyano conjugate-based wavelength-shifting compounds by manipulating intramolecular charge transfer strength. Journal of Photochemistry and Photobiology A: Chemistry 2013, 251, 1-9.

(52) Kubo, H.; Hirose, T.; Matsuda, K., Control over the Emission Properties of [5]Helicenes Based on the Symmetry and Energy Levels of Their Molecular Orbitals. Organic Letters 2017, 19 (7), 1776-1779.

(53) Fradera, X.; Austen, M. A.; Bader, R. F. W., The Lewis Model and Beyond. The Journal of Physical Chemistry A 1999, 103 (2), 304-314.

(54) Fudickar, W.; Linker, T., Why Triple Bonds Protect Acenes from Oxidation and Decomposition. Journal of the American Chemical Society 2012, 134 (36), 15071-15082.

(55) Herndon, W. C.; Ellzey, M. L., Resonance theory. V. Resonance energies of benzenoid and nonbenzenoid .pi. systems. Journal of the American Chemical Society 1974, 96 (21), 6631-6642.

(56) Bendikov, M.; Duong, H. M.; Starkey, K.; Houk, K. N.; Carter, E. A.; Wudl, F., Oligoacenes: Theoretical Prediction of Open-Shell Singlet Diradical Ground States. Journal of the American Chemical Society 2004, 126 (24), 7416-7417.

(57) Clar, The Aromatic Sextet. Wiley: 1972; pp 128-pp.
(58) Nakai, Y.; Mori, T.; Inoue, Y., Theoretical and Experimental Studies on Circular Dichroism of Carbo[n]helicenes. The Journal of Physical Chemistry A 2012, 116 (27), 7372-7385.
(59) Zhao, Y.; Truhlar, D. G., Density Functionals with Broad Applicability in Chemistry. Accounts of Chemical Research 2008, 41 (2), 157-167.
(60) Fuchter, M. J.; Schaefer, J.; Judge, D. K.; Wardzinski, B.; Weimar, M.; Krossing, I., [7]-Helicene: a chiral molecular tweezer for silver(i) salts. Dalton Transactions 2012, 41(27), 8238-8241.
(61) Portella, G.; Poater, J.; Bofill, J. M.; Alemany, P.; Solà, M., Local Aromaticity of [n]Acenes, [n]Phenacenes, and [n]Helicenes (n=1-9). The Journal of Organic Chemistry 2005, 70(7), 2509-2521.
(62) Gershoni-Poranne, R.; Stanger, A., The NICS—XY-Scan: Identification of Local and Global Ring Currents in Multi-Ring Systems. 2014, 20 (19), 5673-5688.
(63) Feixas, F.; Matito, E.; Poater, J.; Solà, M., Quantifying aromaticity with electron delocalisation measures. Chemical Society Reviews 2015, 44 (18), 6434-6451.
(64) Buchta, M.; Rybáček, J.; Jančařík, A.; Kudale, A. A.; Buděšínský, M.; Chocholoušová, J. V.; Vacek, J.; Bednárová, L.; Císařová, I.; Bodwell, G. J.; Starý, I.; Stará, I. G., Chimerical Pyrene-Based [7]Helicenes as Twisted Polycondensed Aromatics. 2015, 21 (24), 8910-8917.
(65) Tanaka, H.; Ikenosako, M.; Kato, Y.; Fujiki, M.; Inoue, Y.; Mori, T., Symmetry-based rational design for boosting chiroptical responses. Communications Chemistry 2018, 1 (1), 38.
(66) Weber, J.; Clennan, E. L., Origin of the Preferential Formation of Helicenes in Mallory Photocyclizations. Temperature as a Tool to Influence Reaction Regiochemistry. The Journal of Organic Chemistry 2019, 84 (2), 817-830.
(67) Smakula, A. The photochemical transformation of trans-stilbene. Z. Physik. Chem. 1934, B25, 90-98.
(68) Parker, C. O.; Spoerri, P. E. Photochemical Conversion of Stilbene to Phenanthrene. Nature 1950, 166, 603.
(69) Mallory, F. B.; Wood, C. S.; Gordon, J. T.; Lindquist, L. C.; Savitz, M. L. Photochemistry of Stilbenes. I. J. Am. Chem. Soc. 1962, 84, 4361-4362.
(70) Moore, W. M.; Morgan, D. D.; Stermitz, F. R. The Photochemical Conversion of Stilbene to Phenanthrene. The Nature of the Intermediate. J. Am. Chem. Soc. 1963, 85, 829-830.
(71) Doyle, T. D.; Filipescu, N.; Benson, W. R.; Banes, D. Photocyclization of a, a'-Diethyl-4,4'-stilbenediol. Isolation of a Stable Tautomer of the Elusive Dihydrophenanthrenes. J. Am. Chem. Soc. 1970, 92, 6371-6372.
(72) Doyle, T. D.; Benson, W. R.; Filipescu, N. Photocyclization of Diethylstilbestrol. Isolation of a Stable, Self-Trapping Dihydrophenanthrene Intermediate. J. Am. Chem. Soc. 1976, 98, 3262-3267.
(73) Cuppen, J. H. M.; Laarhoven, W. H. Photodehydrocyclizations of Stilbene-Like Compounds. VI. Chemical Evidence of an Excited State Mechanism. J. Am. Chem. Soc. 1972, 94, 5914-5915.
(74) Irie, M.; Fukaminato, T.; Matsuda, K.; Kobatake, S. Photochromism of Diarylethene Molecules and Crystals: Memories, Switches, and Actuators. *Chem. Rev.* 2014, 114, 12174-12277.
(75) Flammang-Barbieux, M.; Nasielski, J.; Martin, R. H. Synthesis of heptahelicene (1) benzo [c] phenanthro [4,3-g]phenanthrene. Tetrahedron Lett. 1967, 8, 743-744.
(76) Martin, R. H. The Helicenes. Angew. Chem. Int. Ed. Engl. 1974, 13, 649-660.
(77) Gingras, M. One hundred years of helicene chemistry. Part 3: applications and properties of carbohelicenes. Chem. Soc. Rev. 2013, 42, 1051-1095.
(78) Gingras, M. One hundred years of helicene chemistry. Part 1: non-stereoselective syntheses of carbohelicenes. Chem. Soc. Rev. 2013, 42, 968-1006.
(79) Gingras, M.; Felix, G.; Peresutti, R. One hundred years of helicene chemistry. Part 2: stereoselective synthesis and chiral separations of carbohelicenes. Chem. Soc. Rev. 2013, 42, 1007-1050.
(80) Laarhoven, W. H. Photochemical cyclizations and intramolecular cycloadditions of conjugated aryl olefins. Part I. Photocyclization with dehydrogenation. Rec. Trav. Chim.-J. Roy. Neth. Chem. 1983, 102, 185-204.
(81) Mallory, F. B.; Mallory, C. W.: Photocyclization of Stilbenes and Related Molecules. In Organic Reactions; Dauben, W. G., Ed.; John Wiley & Sons: New York, N.Y., 1984; Vol. 30; pp 1-456.
(82) Laarhoven, W. H. Photocyclizations and Intramolecular Photocycloadditions of Conjugated Arylolefins and Related Compounds. Org. Photochem. 1989, 10, 163-308.
(83) Meier, H. The Photochemistry of Stilbenoid Compounds and Their Role in Materials Technology. Angew. Chem. Int. Ed. 1992, 31, 1399-1420.
(84) Tominaga, Y.; Castle, R. N. Photocyclization of aryl- and heteroaryl-2-propenoic acid derivatives. Synthesis of polycyclic heterocycles. J. Heterocycl. Chem. 1996, 33, 523-538.
(85) Hagen, S.; Hopf, H.: Modern routes to extended aromatic compounds. In Topics in Current Chemistry; de Meijere, A., Ed.; Carbon Rich Compounds I; Springer-Verlag: Berlin Heidelberg, 1998; Vol. 196; pp 45-89.
(86) Liu, L.; Yang, B.; Katz, T. J.; Poindexter, M. K. Improved methodology for photocyclization reactions. J. Org. Chem. 1991, 56, 3769-3775.
(87) Sudhakar, A.; Katz, T. J.; Yang, B. W. Synthesis of a helical metallocene oligomer. J. Am. Chem. Soc. 1986, 108, 2790-2791.
(88) Sudhakar, A.; Katz, T. J. Directive effect of bromine on stilbene photocyclizations. an improved synthesis of [7]helicene. Tetrahedron Lett. 1986, 27, 2231-2234.
(89) Liu, L.; Katz, T. J. Bromine auxiliaries in photosyntheses of [5]helicenes. Tetrahedron Lett. 1991, 32, 6831-6834.
(90) Finnie, A. A.; Hill, R. A. The synthesis of 1,5,7,10-tetraoxygenated 3-methylphenanthrenes. J. Chem. Res. Synop. 1987, 78-79.
(91) Mallory, F. B.; Rudolph, M. J.; Oh, S. M. Photochemistry of stilbenes. 8. Eliminative photocyclization of o-methoxystilbenes. J. Org. Chem. 1989, 54, 4619-4626.
(92) Li, Z.; Twieg, R. J. Photocyclodehydrofluorination. Chem.—European J. 2015, 21, 15534-15539.
(93) Morin, J.-F.: Photochemical and Direct C—H Arylation Routes toward Carbon Nanomaterials. In Synthetic Methods for Conjugated Polymers and Carbon Materials; 1st ed.; Leclerc, M., Morin, J.-F., Eds.; Wiley-VCH Verlag GmbH & Co. KGaA, 2017; pp 229-253.
(94) Ern, J.; Bens, A. T.; Martin, H. D.; Mukamel, S.; Schmid, D.; Tretiak, S.; Tsiper, E.; Kryschi, C. Reaction dynamics of photochromic dithienylethene derivatives. Chem. Phys. 1999, 246, 115-125.

(95) Bens, A. T.; Ern, J.; Kuldova, K.; Trommsdorff, H. P.; Kryschi, C. Reaction and excited state relaxation dynamics of photochromic dithienylethene derivatives. J. Luminescence 2001, 94-95, 51-54.

(96) Hania, P. R.; Telesca, R.; Lucas, L. N.; Pugzlys, A.; van Esch, J.; Feringa, B. L.; Snijders, J. G.; Duppen, K. An Optical and Theoretical Investigation of the Ultrafast Dynamics of a Bisthienylethene-Based Photochromic Switch. J. Phys. Chem. A 2002, 106, 8498-8507.

(97) Bearpark, M. J.; Bernardi, F.; Clifford, S.; Olivucci, M.; Robb, M. A.; Vreven, T. Cooperating Rings in cis-Stilbene Lead to an S0/S1 Conical Intersection. J. Phys. Chem. A 1997, 101, 3841-3847.

(98) Dou, Y.; Allen, R. E. Dynamics of the photocyclization of cis-stilbene to dihydrophenanthrene. J. Mod. Optics 2004, 51, 2485-2491.

(99) Harabuchi, Y.; Keipert, K.; Zahariev, F.; Taketsugu, T.; Gordon, M. S. Dynamics Simulations with Spin-Flip Time-Dependent Density Functional Theory: Photoisomerization and Photocyclization Mechanisms of cis-Stilbene in $\pi\pi^*$ States. The J. Phys. Chem. A 2014, 118, 11987-11998.

(100) Ioffe, I. N.; Granovsky, A. A. Photoisomerization of Stilbene: The Detailed XMCQDPT2 Treatment. J. Chem. Theory Computation 2013, 9, 4973-4990.

(101) Dulić, D.; Kudernac, T.; Pužys, A.; Feringa, B. L.; van Wees, B. J. Temperature Gating of the Ring-Opening Process in Diarylethene Molecular Switches. Adv. Mater. 2007, 19, 2898-2902.

(102) Sumi, T.; Takagi, Y.; Yagi, A.; Morimoto, M.; Irie, M. Photoirradiation wavelength dependence of cycloreversion quantum yields of diarylethenes. Chem. Commun. 2014, 50, 3928-3930.

(103) Martin, R. H.; Flammang-Barbieux, M.; Cosyn, J. P.; Gelbcke, M. 1-Synthesis of octa- and nonahelicenes. 2-New syntheses of hexa- and heptahelicenes. 3-Optical rotation and O.R.D. of heptahelicene. Tetrahedron Lett. 1968, 9, 3507-3510.

(104) Laarhoven, W. H.; Cuppen, T. H. J. H. M.; Nivard, R. J. F. Photodehydrocyclizations in stilbene-like compounds-III: Effect of steric factors. Tetrahedron 1970, 26, 4865-4881.

(105) Laarhoven, W. H.; Cuppen, T. J. H. M.; Nivard, R. J. F. Photodehydrocyclizations in stilbene-like compounds. Rec. Trav. Chim. 1968, 87, 687-698.

(106) Burkitt, F. H.; Coulson, C. A.; Longuet-Higgins, H. C. Free valence in unsaturated hydrocarbons. Trans. Faraday Soc. 1951, 47, 553-564.

(107) Yuan, Z.; Xiao, Y.; Qian, X. A design concept of planar conjugated ladder oligomers of perylene bisimides and efficient synthetic strategy via regioselective photocyclization. Chem. Commun. 2010, 46, 2772-2774.

(108) Shi, S.; Nawaz, K. S.; Zaman, M. K.; Sun, Z. Advances in Enantioselective C—H Activation/Mizoroki-Heck Reaction and Suzuki Reaction. Catalysts 2018, 8, 90.

(109) Talele, H. R.; Chaudhary, A. R.; Patel, P. R.; Bedekar, A. V. Expeditious synthesis of helicenes using an improved protocol of photocyclodehydration of stilbenes. ARKIVOC 2011, ix, 15-37.

(110) Ben Hassine, B.; Gorsane, M.; Pecher, J.; Martin, R. H. Diastereoselective NaBH4 Reductions of (dl) a-Keto Esters. Bull. Soc. Chim. Belg. 1985, 94, 597-603.

(111) Grandbois, A.; Collins, S. K. Enantioselective Synthesis of [7]Helicene: Dramatic Effects of Olefin Additives and Aromatic Solvents in Asymmetric Olefin Metathesis. Chem.—Euro. J. 2008, 14, 9323-9329.

(112) Sapir, M.; Vander Donckt, E. Intersystem Crossing in the Helicenes. Chem. Phys. Lett. 1975, 36, 108-110.

(113) Birks, J. B.; Birch, D. J. S.; Cordemans, E.; Vander Donckt, E. Fluorescence of the higher helicenes. Chem. Phys. Lett. 1976, 43, 33-36.

(114) Grellmann, K.-H.; Hentzschel, P.; Wismontski-Knittel, T.; Fischer, E. The photophysics and photochemistry of pentahelicene. J. Photochem. 1979, 11, 197-213.

(115) Wilkinson, F.; Helman, W. P.; Ross, A. B. J. Phys. Chem. Ref. Data 1993, 22, 113-262.

(116) Gorman, A. A.; Gould, I. R.; Hamblett, I. Time-Resolved Study of the Solvent and Temperature Dependence of Singlet Oxygen (1Δg) Reactivity toward Enol Ethers: Reactivity Parameters Typical of Rapid Reversible Exciplex Formation. J. Am. Chem. Soc. 1982, 104, 7098-7104.

(117) Clar, E.: The Aromatic Sextet; John Wiley & Sons: London, 1972.

(118) Hemelsoet, K.; De Vleeschouwer, F.; Van Speybroeck, V.; De Proft, F.; Geerlings, P.; Waroquier, M. Validation of DFT-Based Methods for Predicting Qualitative Thermochemistry of Large Polyaromatics. ChemPhysChem 2011, 12, 1100-1108.

(119) Wismontski-Knittel, T.; Kaganowitch, M.; Seger, G.; Fischer, E. The reversible photochemistry of 1,2-di-(2-naphthyl)cyclopentene. Rec. Trav. Chim. 1979, 98, 114-117.

(120) Muszkat, K. A. The 4a, 4b-Dihydrophenanthrenes. Topics Curr. Chem. 1980, 38, 89-143.

(121) Hammond, G. S.; Saltiel, J.; Lamola, A. A.; Turro, N. J.; Bradshaw, J. S.; Cowan, D. O.; Counsell, R. C.; Vogt, V.; Dalton, C. Mechanisms of Photochemical Reactions in Solution. XXII.1 Photochemical cis-trans Isomerization. J. Am. Chem. Soc. 1964, 86, 3197-3217.

(122) Klan, P.; Wirz, J.: Photochemistry of Organic Compounds. From Concepts to Practice.; John Wiley & Sons Ltd.: UK, 2009.

(123) Saltiel, J.; Charlton, J. L.: Rearrangements in Ground and Excited States; Academic Press: New York, 1980; Vol. 42/43.

(124) Fleming, G. R. Subpicosecond Spectroscopy. Ann. Rev. Phys. Chem. 1986, 37, 81-104.

(125) Melhuish, W. H., QUANTUM EFFICIENCIES OF FLUORESCENCE OF ORGANIC SUBSTANCES: EFFECT OF SOLVENT AND CONCENTRATION OF THE FLUORESCENT SOLUTE1. The Journal of Physical Chemistry 1961, 65 (2), 229-235.

(126) Montalti, M., Handbook of Photochemistry—Third Edition. CRC Press LLC: 2006; pp 650-pp.

(127) Dhami, S.; Mello, A. J. D.; Rumbles, G.; Bishop, S. M.; Phillips, D.; Beeby, A., PHTHALOCYANINE FLUORESCENCE AT HIGH CONCENTRATION: DIMERS OR REABSORPTION EFFECT? 1995, 61 (4), 341-346.

(128) Talele, H. R., Expeditious synthesis of helicenes using an improved protocol of photocyclodehydrogenation of stilbenes. Arkivoc 2011, 2011 (9), 15-37.

(129) Sakai, H.; Shinto, S.; Araki, Y.; Wada, T.; Sakanoue, T.; Takenobu, T.; Hasobe, T., Formation of One-Dimensional Helical Columns and Excimerlike Excited States by Racemic Quinoxaline-Fused [7]Carbohelicenes in the Crystal. 2014, 20 (32), 10099-10109.

The invention claimed is:
1. A heli-twisted acene selected from the group consisting of:

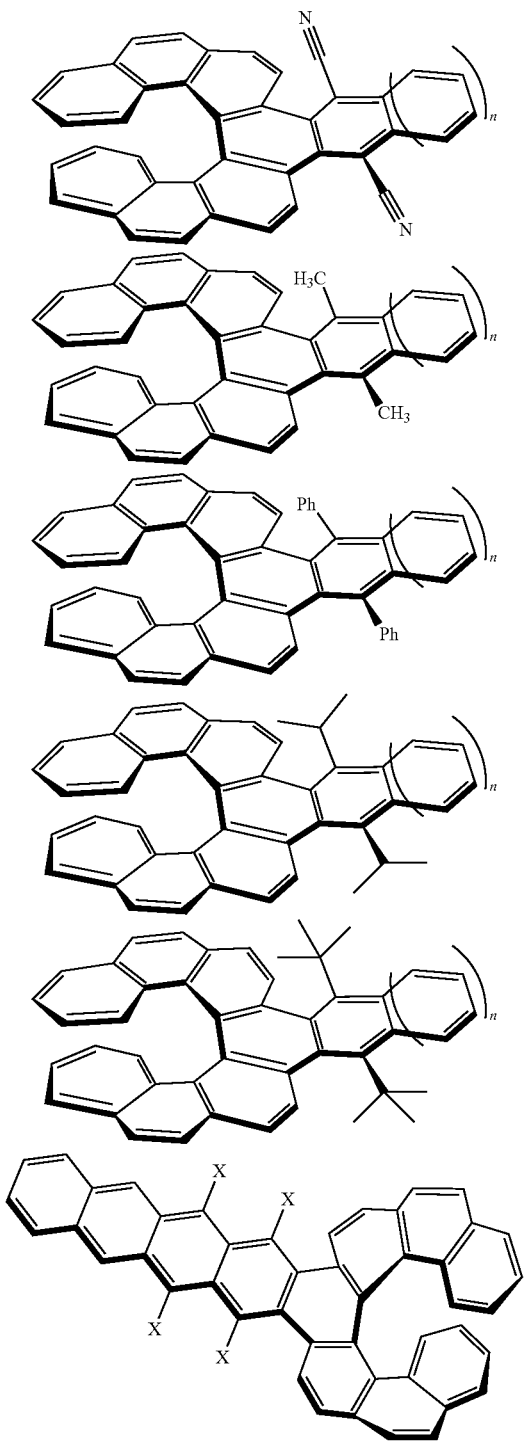

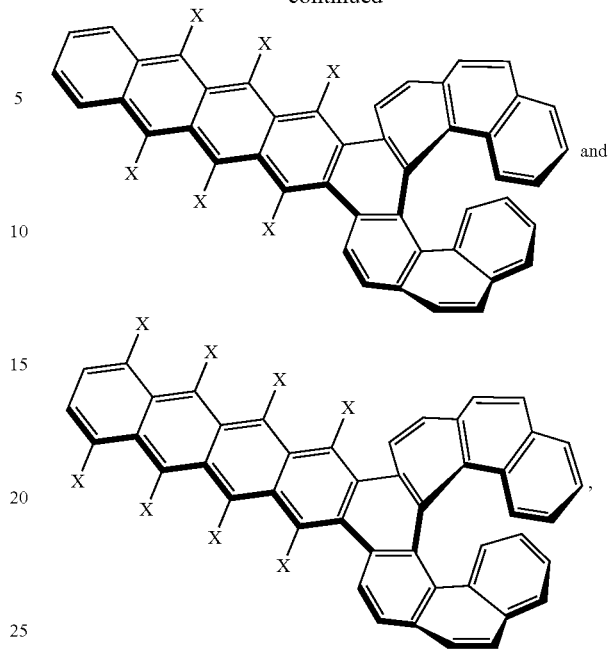

wherein n is 1-3, and X is simultaneously CN, Me or Ph.

2. The heli-twisted acene of claim 1 wherein the heli-twisted acene is at least one of a hole transport layer and an emissive layer of a mulit-layer organic light emitting diode (OLED).

3. The heli-twisted acene of claim 2 wherein the OLED is a circularly polarized OLED.

4. The heli-twisted acene of claim 2 wherein the OLED is a biomedical device.

5. The heli-twisted acene of claim 1 wherein the acene core is highly flurorescent.

6. The heli-twisted acene of claim 1 wherein the acene core has an end to end twist of any of 30°, 60°, and 144°.

7. The heli-twisted acene of claim 1 wherein the acene core has a specific rotation $[\alpha]_n^{35}$ 32 7400°.

8. The heli-twisted acene of claim 2 wherein the acene core is longitudinally twisted.

9. The heli-twisted acene of claim 2 wherein the heli-twisted acene is a carbocyclic heli-acene.

10. The heli-twisted acene of claim 1 wherein X in every instance is cyano.

11. The heli-twisted acene of claim 1 wherein X in every instance is methyl.

12. The heli-twisted acene of claim 1 wherein X in every instance is phenyl.

13. A process for synthesizing the heli-twisted acene of claim 2, the process comprising:
performing a bis-Wittig reaction with a 2,8-dibromophenanthrene-5,6-dione to form an intermediate; and then reacting the intermediate with styene in the presence of a Pd catalysis to synthesize the heli-twisted acene.

* * * * *